(12) United States Patent
Stasko et al.

(10) Patent No.: US 12,109,429 B2
(45) Date of Patent: *Oct. 8, 2024

(54) PHOTOTHERAPEUTIC LIGHT FOR TREATMENT OF PATHOGENS

(71) Applicant: KNOW Bio, LLC, Durham, NC (US)

(72) Inventors: Nathan Stasko, Chapel Hill, NC (US); David T. Emerson, Durham, NC (US); Adam Cockrell, Durham, NC (US); F. Neal Hunter, Durham, NC (US); Michael John Bergmann, Atlanta, GA (US); Rebecca McDonald, Chapel Hill, NC (US); Nicholas William Medendorp, Jr., Raleigh, NC (US); Gerald H. Negley, Chapel Hill, NC (US); Katelyn P. Reighard, Durham, NC (US)

(73) Assignee: KNOW Bio, LLC, Morrisville, NC (US)

( * ) Notice: Subject to any disclaimer, the term of this patent is extended or adjusted under 35 U.S.C. 154(b) by 781 days.

This patent is subject to a terminal disclaimer.

(21) Appl. No.: 17/117,858

(22) Filed: Dec. 10, 2020

(65) Prior Publication Data
US 2021/0128935 A1    May 6, 2021

Related U.S. Application Data

(63) Continuation-in-part of application No. 16/898,385, filed on Jun. 10, 2020, now Pat. No. 11,617,895,
(Continued)

(51) Int. Cl.
*A61N 5/06*   (2006.01)
*H01L 27/15*  (2006.01)

(52) U.S. Cl.
CPC ......... *A61N 5/0613* (2013.01); *A61N 5/0601* (2013.01); *A61N 5/0603* (2013.01);
(Continued)

(58) Field of Classification Search
None
See application file for complete search history.

(56) References Cited

U.S. PATENT DOCUMENTS 1,244,819 A    10/1917  Young
2,884,926 A     5/1959  Grasso
(Continued)

FOREIGN PATENT DOCUMENTS

AU    2016100390 A4    7/2016
CN      101687101 A    3/2010
(Continued)

OTHER PUBLICATIONS

Abeyakirthi, Sharnika, "Nitric oxide," DermNet NZ, 2009, 4 pages, www.dermnetnz.org/topics/nitric-oxide/.
(Continued)

*Primary Examiner* — Michael W Kahelin
(74) *Attorney, Agent, or Firm* — Withrow & Terranova, P.L.L.C.

(57) ABSTRACT

Methods and related devices for impinging light on tissue, for example within a body of a patient, to induce various biological effects are disclosed. Biological effects may include at least one of inactivating and/or inhibiting growth of one or more pathogens, upregulating a local immune response, stimulating enzymatic generation of nitric oxide to increase endogenous stores of nitric oxide, releasing nitric oxide from endogenous stores of nitric oxide, and inducing an anti-inflammatory effect. Wavelengths of light are selected based on intended biological effects for one or more of targeted tissue types and targeted pathogens. Light treat-
(Continued)

ments may provide multiple pathogenic biological effects, either with light of a single wavelength or with light having multiple wavelengths. Devices and methods for light treatments are disclosed that provide light doses for inducing biological effects on various targeted pathogens and targeted tissues with increased efficacy and reduced cytotoxicity.

34 Claims, 95 Drawing Sheets

Related U.S. Application Data which is a continuation of application No. 16/709,550, filed on Dec. 10, 2019, now Pat. No. 11,524,173, which is a continuation of application No. 15/222,199, filed on Jul. 28, 2016, now Pat. No. 10,525,275.

(60) Provisional application No. 63/123,631, filed on Dec. 10, 2020, provisional application No. 63/084,802, filed on Sep. 29, 2020, provisional application No. 63/074,800, filed on Sep. 4, 2020, provisional application No. 62/987,318, filed on Mar. 9, 2020, provisional application No. 62/197,746, filed on Jul. 28, 2015.

(52) U.S. Cl.
CPC ............ *A61N 5/0624* (2013.01); *H01L 27/15* (2013.01); *A61N 2005/0611* (2013.01); *A61N 2005/0626* (2013.01); *A61N 2005/0647* (2013.01); *A61N 2005/0652* (2013.01); *A61N 2005/0653* (2013.01); *A61N 2005/0661* (2013.01); *A61N 2005/0662* (2013.01); *A61N 2005/0663* (2013.01)

(56) References Cited

U.S. PATENT DOCUMENTS

| | | |
|---|---|---|
| 4,466,434 A | 8/1984 | Brownstein |
| 4,493,796 A * | 1/1985 | Rinehart, Jr. .......... C07K 11/00 930/20 |
| 4,736,745 A | 4/1988 | Gluckman |
| 5,074,295 A | 12/1991 | Willis |
| 5,228,431 A | 7/1993 | Giarretto |
| 5,282,462 A | 2/1994 | Kudo |
| 5,292,346 A | 3/1994 | Ceravolo |
| 5,541,822 A | 7/1996 | Bamber |
| 5,549,639 A | 8/1996 | Ross |
| 5,611,793 A | 3/1997 | Wilson et al. |
| 5,616,140 A | 4/1997 | Prescott |
| 5,634,711 A | 6/1997 | Kennedy et al. |
| 5,658,148 A | 8/1997 | Neuberger et al. |
| 5,683,436 A | 11/1997 | Mendes et al. |
| 6,026,828 A | 2/2000 | Altshuler |
| 6,045,499 A | 4/2000 | Pitesky |
| 6,096,066 A | 8/2000 | Chen et al. |
| 6,171,332 B1 | 1/2001 | Whitehurst |
| 6,201,764 B1 | 3/2001 | Rice et al. |
| 6,211,626 B1 | 4/2001 | Lys et al. |
| 6,244,865 B1 | 6/2001 | Nelson et al. |
| 6,251,127 B1 | 6/2001 | Biel |
| 6,283,956 B1 | 9/2001 | McDaniel |
| 6,290,496 B1 | 9/2001 | Azar et al. |
| 6,290,713 B1 | 9/2001 | Russell |
| 6,379,376 B1 | 4/2002 | Lubart |
| 6,443,978 B1 | 9/2002 | Zharov |
| 6,462,070 B1 | 10/2002 | Hasan et al. |
| 6,471,716 B1 | 10/2002 | Pecukonis |
| 6,491,618 B1 | 12/2002 | Ganz |
| 6,497,719 B2 | 12/2002 | Pearl et al. |
| 6,551,346 B2 | 4/2003 | Crossley |
| 6,561,808 B2 | 5/2003 | Neuberger |
| 6,623,513 B2 | 9/2003 | Biel |
| 6,645,230 B2 | 11/2003 | Whitehurst |
| 6,663,659 B2 | 12/2003 | McDaniel |
| 6,676,655 B2 | 1/2004 | McDaniel |
| 6,887,260 B1 | 5/2005 | McDaniel |
| 6,890,346 B2 | 5/2005 | Ganz et al. |
| 6,902,397 B2 | 6/2005 | Farrell et al. |
| 6,918,922 B2 | 7/2005 | Oron |
| 6,936,044 B2 | 8/2005 | McDaniel |
| 6,955,684 B2 | 10/2005 | Savage, Jr. et al. |
| 6,977,075 B2 | 12/2005 | Hasan et al. |
| 6,989,023 B2 | 1/2006 | Black |
| 7,090,497 B1 | 8/2006 | Harris |
| 7,107,996 B2 | 9/2006 | Ganz et al. |
| 7,144,248 B2 | 12/2006 | Irwin |
| 7,159,590 B2 | 1/2007 | Rife |
| 7,201,764 B2 | 4/2007 | Pearl et al. |
| 7,201,765 B2 | 4/2007 | McDaniel |
| 7,223,270 B2 | 5/2007 | Altshuler et al. |
| 7,223,281 B2 | 5/2007 | Altshuler et al. |
| 7,226,470 B2 | 6/2007 | Kemeny et al. |
| 7,267,673 B2 | 9/2007 | Pilcher et al. |
| 7,303,578 B2 | 12/2007 | De Taboada et al. |
| 7,304,201 B2 | 12/2007 | Holloway et al. |
| 7,309,348 B2 | 12/2007 | Streeter et al. |
| 7,329,273 B2 | 2/2008 | Altshuler et al. |
| 7,329,274 B2 | 2/2008 | Altshuler et al. |
| 7,422,598 B2 | 9/2008 | Altshuler et al. |
| 7,435,252 B2 | 10/2008 | Krespi et al. |
| 7,467,946 B2 | 12/2008 | Rizoiu et al. |
| 7,494,503 B2 | 2/2009 | McDaniel |
| 7,544,204 B2 | 6/2009 | Krespi et al. |
| D599,954 S | 9/2009 | Michaels et al. |
| 7,763,058 B2 | 7/2010 | Sterenborg et al. |
| D631,604 S | 1/2011 | Michaels et al. |
| D635,686 S | 4/2011 | Tucker et al. |
| 7,918,229 B2 | 4/2011 | Cumbie et al. |
| 7,950,396 B2 | 5/2011 | Rose et al. |
| D639,751 S | 6/2011 | Tucker et al. |
| D640,793 S | 6/2011 | Britt |
| 8,021,148 B2 | 9/2011 | Goodson et al. |
| 8,021,405 B2 | 9/2011 | White |
| 8,025,686 B2 | 9/2011 | Morgan |
| 8,029,278 B1 | 10/2011 | Levine |
| 8,053,977 B2 | 11/2011 | Lifka et al. |
| 8,088,122 B2 | 1/2012 | Li et al. |
| 8,109,981 B2 | 2/2012 | Gertner et al. |
| 8,146,607 B2 | 4/2012 | Rabin et al. |
| 8,186,997 B2 | 5/2012 | Binner et al. |
| 8,192,473 B2 | 6/2012 | Tucker et al. |
| 8,214,958 B2 | 7/2012 | Pinyayev et al. |
| 8,240,312 B2 | 8/2012 | Feuerstein et al. |
| 8,252,033 B2 | 8/2012 | Tucker et al. |
| 8,398,264 B2 | 3/2013 | Anderson et al. |
| 8,435,273 B2 | 5/2013 | Lum et al. |
| 8,486,123 B2 | 7/2013 | Vizethum et al. |
| 8,518,029 B2 | 8/2013 | Birmingham et al. |
| 8,535,361 B2 | 9/2013 | Lim et al. |
| 8,556,951 B2 | 10/2013 | Witt et al. |
| 8,641,702 B2 | 2/2014 | Pilcher et al. |
| 8,651,111 B2 | 2/2014 | McDaniel |
| 8,668,727 B2 | 3/2014 | Natale et al. |
| 8,684,577 B2 | 4/2014 | Vayser |
| 8,685,466 B2 | 4/2014 | Piergallini et al. |
| 8,690,933 B2 | 4/2014 | Mitchell |
| 8,710,460 B2 | 4/2014 | Dayton |
| 8,721,696 B2 | 5/2014 | Krespi et al. |
| 8,747,446 B2 | 6/2014 | Chen et al. |
| 8,758,215 B2 | 6/2014 | Legendre et al. |
| 8,771,327 B2 | 7/2014 | Pearl et al. |
| 8,790,381 B2 | 7/2014 | Pierce |
| 8,815,931 B2 | 8/2014 | Grafe et al. |
| D712,561 S | 9/2014 | Hagenauer |
| 8,838,228 B2 | 9/2014 | Beisang, III et al. |
| 8,845,704 B2 | 9/2014 | Dunning et al. |
| D716,493 S | 10/2014 | Michaels et al. |
| 8,858,607 B1 | 10/2014 | Jones |
| 8,900,282 B2 | 12/2014 | Brawn |
| 8,900,283 B2 | 12/2014 | Johnson et al. |

(56) References Cited

U.S. PATENT DOCUMENTS

| | | |
|---|---|---|
| 8,940,775 B2 | 1/2015 | Fedele et al. |
| 9,017,391 B2 | 4/2015 | McDaniel |
| 9,039,966 B2 | 5/2015 | Anderson et al. |
| 9,040,103 B2 | 5/2015 | Marrot et al. |
| 9,095,704 B2 | 8/2015 | McGuire |
| 9,132,279 B2 | 9/2015 | Roersma et al. |
| 9,144,690 B2 | 9/2015 | McDaniel |
| 9,149,348 B2 | 10/2015 | Wu et al. |
| 9,162,001 B2 | 10/2015 | Sunkara et al. |
| 9,180,308 B1 | 11/2015 | Frost |
| 9,192,780 B2 | 11/2015 | McDaniel |
| 9,198,502 B2 | 12/2015 | Barnes et al. |
| 9,211,420 B2 | 12/2015 | Patel et al. |
| 9,215,921 B2 | 12/2015 | Thiebaut et al. |
| 9,227,082 B2 | 1/2016 | McDaniel |
| D754,897 S | 4/2016 | Michaels et al. |
| 9,308,389 B2 | 4/2016 | Brawn |
| 9,333,274 B2 | 5/2016 | Peterson et al. |
| 9,415,237 B2 | 8/2016 | Wagenaar Cacciola et al. |
| 9,439,989 B2 | 9/2016 | Lalicki et al. |
| 9,474,811 B2 | 10/2016 | Sharma |
| 9,504,752 B2 | 11/2016 | Kanno et al. |
| 9,504,847 B2 | 11/2016 | Pryor et al. |
| D777,339 S | 1/2017 | Chen |
| 9,545,524 B2 | 1/2017 | Maass et al. |
| 9,554,963 B2 | 1/2017 | Pilcher et al. |
| 9,561,077 B2 | 2/2017 | Alfano |
| 9,561,386 B2 | 2/2017 | Pearl et al. |
| 9,616,013 B2 | 4/2017 | Casasanta, III et al. |
| 9,636,522 B2 | 5/2017 | Oversluizen et al. |
| 9,700,641 B2 | 7/2017 | Hawkins et al. |
| 9,724,536 B1 | 8/2017 | Rabin et al. |
| 9,730,780 B2 | 8/2017 | Brawn et al. |
| 9,744,375 B2 | 8/2017 | Oberreiter et al. |
| D804,047 S | 11/2017 | Michaels et al. |
| 9,808,646 B2 | 11/2017 | Piergallini et al. |
| 9,808,647 B2 | 11/2017 | Rhodes et al. |
| 9,901,747 B2 | 2/2018 | Gamelin et al. |
| 9,907,976 B2 | 3/2018 | Bourke, Jr. et al. |
| 9,913,994 B2 | 3/2018 | Marchese et al. |
| 10,010,718 B2 | 7/2018 | Basiony |
| 10,220,221 B2 | 3/2019 | Wu |
| 10,258,442 B2 | 4/2019 | Snyder et al. |
| 10,272,262 B2 | 4/2019 | Bourke, Jr. et al. |
| 10,328,276 B2 | 6/2019 | Williams et al. |
| 10,357,661 B2 | 7/2019 | Hellstrom et al. |
| 10,406,379 B2 | 9/2019 | Sentis et al. |
| 10,416,366 B2 | 9/2019 | Rose et al. |
| 10,463,873 B1 | 11/2019 | Yang et al. |
| 10,525,275 B2 | 1/2020 | Stasko et al. |
| 10,561,854 B2 | 2/2020 | Kim et al. |
| 10,569,097 B2 | 2/2020 | Medendorp, Jr. et al. |
| 10,639,498 B2 | 5/2020 | Enwemeka et al. |
| 10,682,203 B2 | 6/2020 | Vazales |
| 10,729,524 B2 | 8/2020 | Brawn et al. |
| 10,780,189 B2 | 9/2020 | Randers-Pehrson et al. |
| 10,981,017 B2 | 4/2021 | Enwemeka et al. |
| 11,058,888 B1 | 7/2021 | Steier et al. |
| 11,147,984 B2 | 10/2021 | Emerson et al. |
| 11,266,855 B2 | 3/2022 | Enwemeka et al. |
| 11,318,325 B2 | 5/2022 | Rezaie et al. |
| 2002/0029071 A1 | 3/2002 | Whitehurst |
| 2002/0128648 A1 | 9/2002 | Weber et al. |
| 2002/0135763 A1 | 9/2002 | MacKinnon et al. |
| 2002/0151941 A1 | 10/2002 | Okawa et al. |
| 2002/0173833 A1 | 11/2002 | Korman et al. |
| 2003/0009205 A1 | 1/2003 | Biel |
| 2003/0023284 A1* | 1/2003 | Gartstein ............. A61N 5/0624 606/2 |
| 2003/0045778 A1 | 3/2003 | Ohline et al. |
| 2003/0076281 A1 | 4/2003 | Morgan et al. |
| 2003/0130709 A1 | 7/2003 | D.C. et al. |
| 2003/0153825 A1 | 8/2003 | Mooradian et al. |
| 2003/0167080 A1 | 9/2003 | Hart et al. |
| 2003/0233138 A1 | 12/2003 | Spooner |
| 2003/0236487 A1 | 12/2003 | Knowlton |
| 2004/0032750 A1 | 2/2004 | Watts et al. |
| 2004/0039242 A1* | 2/2004 | Tolkoff ............... A61N 5/0624 600/9 |
| 2004/0044384 A1 | 3/2004 | Leber et al. |
| 2004/0052798 A1 | 3/2004 | Neuberger |
| 2004/0073079 A1 | 4/2004 | Altshuler et al. |
| 2004/0073278 A1 | 4/2004 | Pachys |
| 2004/0162596 A1 | 8/2004 | Altshuler et al. |
| 2004/0193235 A1 | 9/2004 | Altshuler et al. |
| 2004/0193236 A1 | 9/2004 | Altshuler et al. |
| 2004/0199227 A1 | 10/2004 | Altshuler et al. |
| 2005/0024853 A1 | 2/2005 | Thomas-Benedict |
| 2005/0045189 A1 | 3/2005 | Jay |
| 2005/0055070 A1 | 3/2005 | Jones et al. |
| 2005/0059731 A1 | 3/2005 | Albrecht et al. |
| 2005/0064371 A1* | 3/2005 | Soukos ............... A61N 5/0601 433/29 |
| 2005/0107853 A1 | 5/2005 | Krespi et al. |
| 2005/0231983 A1 | 10/2005 | Dahm |
| 2005/0256553 A1 | 11/2005 | Strisower |
| 2006/0019220 A1 | 1/2006 | Loebel et al. |
| 2006/0085052 A1* | 4/2006 | Feuerstein ............ A61L 2/0082 607/90 |
| 2006/0093561 A1 | 5/2006 | Kennedy |
| 2006/0167531 A1 | 7/2006 | Gertner et al. |
| 2006/0183071 A1 | 8/2006 | Hsuch |
| 2006/0194164 A1 | 8/2006 | Altshuler et al. |
| 2006/0239921 A1 | 10/2006 | Mangat et al. |
| 2006/0258896 A1 | 11/2006 | Haber et al. |
| 2006/0287696 A1 | 12/2006 | Wright et al. |
| 2007/0038272 A1 | 2/2007 | Liu |
| 2007/0060819 A1 | 3/2007 | Altshuler et al. |
| 2007/0099154 A1 | 5/2007 | Johnson |
| 2007/0100254 A1 | 5/2007 | Murakami et al. |
| 2007/0105063 A1 | 5/2007 | Pinyayev et al. |
| 2007/0106856 A1 | 5/2007 | Nomura et al. |
| 2007/0135874 A1 | 6/2007 | Bala |
| 2007/0149868 A1 | 6/2007 | Blank et al. |
| 2007/0185553 A1 | 8/2007 | Kennedy |
| 2007/0208396 A1 | 9/2007 | Whatcott et al. |
| 2007/0213792 A1 | 9/2007 | Yaroslavsky et al. |
| 2007/0219600 A1 | 9/2007 | Gertner et al. |
| 2007/0233208 A1 | 10/2007 | Kurtz et al. |
| 2007/0259310 A1 | 11/2007 | Goodson et al. |
| 2007/0260231 A1 | 11/2007 | Rose et al. |
| 2007/0270650 A1 | 11/2007 | Eno et al. |
| 2008/0021370 A1 | 1/2008 | Bornstein |
| 2008/0032252 A1 | 2/2008 | Hayman et al. |
| 2008/0033516 A1 | 2/2008 | Altshuler et al. |
| 2008/0038685 A1 | 2/2008 | Sakaguchi et al. |
| 2008/0065175 A1 | 3/2008 | Redmond et al. |
| 2008/0096156 A1 | 4/2008 | Rose et al. |
| 2008/0097414 A1 | 4/2008 | Li et al. |
| 2008/0145813 A1 | 6/2008 | Crohn |
| 2008/0161748 A1 | 7/2008 | Tolkoff et al. |
| 2008/0210233 A1 | 9/2008 | McCarthy |
| 2008/0214530 A1 | 9/2008 | Colles |
| 2008/0245371 A1 | 10/2008 | Gruber |
| 2008/0254405 A1 | 10/2008 | Montgomery et al. |
| 2008/0269849 A1 | 10/2008 | Lewis |
| 2008/0280260 A1 | 11/2008 | Belikov et al. |
| 2008/0319430 A1 | 12/2008 | Zenzie et al. |
| 2009/0035725 A1 | 2/2009 | Loebel et al. |
| 2009/0093865 A1 | 4/2009 | Krespi et al. |
| 2009/0132011 A1 | 5/2009 | Altshuler et al. |
| 2009/0143842 A1 | 6/2009 | Cumbie et al. |
| 2009/0148808 A1 | 6/2009 | Alexander et al. |
| 2009/0254156 A1 | 10/2009 | Powell et al. |
| 2009/0318802 A1 | 12/2009 | Boyden et al. |
| 2009/0323370 A1 | 12/2009 | Koo |
| 2010/0004645 A1 | 1/2010 | Jeong et al. |
| 2010/0042040 A1 | 2/2010 | Arentz |
| 2010/0049180 A1 | 2/2010 | Wells et al. |
| 2010/0063565 A1 | 3/2010 | Beerwerth et al. |
| 2010/0076526 A1 | 3/2010 | Krespi et al. |
| 2010/0076529 A1 | 3/2010 | Tucker et al. |
| 2010/0106077 A1 | 4/2010 | Rabin et al. |
| 2010/0121131 A1 | 5/2010 | Mathes |

(56) References Cited

U.S. PATENT DOCUMENTS

| | | |
|---|---|---|
| 2010/0136646 A1 | 6/2010 | Tsen et al. |
| 2010/0160838 A1 | 6/2010 | Krespi |
| 2010/0204762 A1 | 8/2010 | De Taboada et al. |
| 2010/0222852 A1 | 9/2010 | Vasily et al. |
| 2010/0239998 A1* | 9/2010 | Snyder .................. A61C 19/06 433/29 |
| 2010/0242155 A1 | 9/2010 | Carullo, Jr. |
| 2010/0286673 A1 | 11/2010 | Altshuler et al. |
| 2010/0331928 A1 | 12/2010 | Dunning et al. |
| 2011/0015707 A1 | 1/2011 | Tucker et al. |
| 2011/0020173 A1 | 1/2011 | Pryor et al. |
| 2011/0054573 A1 | 3/2011 | Mitchell |
| 2011/0054574 A1 | 3/2011 | Felix |
| 2011/0125229 A1 | 5/2011 | Lytle et al. |
| 2011/0144410 A1 | 6/2011 | Kennedy |
| 2011/0144727 A1 | 6/2011 | Benedict |
| 2011/0160814 A2 | 6/2011 | Tucker et al. |
| 2011/0162155 A1 | 7/2011 | Wai |
| 2011/0215261 A1 | 9/2011 | Lyslo et al. |
| 2011/0264174 A1 | 10/2011 | McNeill et al. |
| 2011/0301673 A1 | 12/2011 | Hoffer et al. |
| 2012/0045738 A1 | 2/2012 | Ho et al. |
| 2012/0059440 A1 | 3/2012 | Hamid |
| 2012/0065709 A1 | 3/2012 | Dunning et al. |
| 2012/0088204 A1 | 4/2012 | Ho et al. |
| 2012/0096657 A1 | 4/2012 | So et al. |
| 2012/0126134 A1 | 5/2012 | Deal et al. |
| 2012/0191162 A1 | 7/2012 | Villa |
| 2012/0209359 A1 | 8/2012 | Chen et al. |
| 2012/0215292 A1 | 8/2012 | Gustavsson |
| 2012/0223216 A1 | 9/2012 | Flaherty et al. |
| 2012/0263625 A1 | 10/2012 | Aicher et al. |
| 2012/0270183 A1 | 10/2012 | Patel et al. |
| 2012/0310307 A1 | 12/2012 | Zhou |
| 2012/0322018 A1 | 12/2012 | Lowe et al. |
| 2013/0006119 A1 | 1/2013 | Pan et al. |
| 2013/0041432 A1 | 2/2013 | Tucker et al. |
| 2013/0089829 A1 | 4/2013 | Boutoussov et al. |
| 2013/0103120 A1 | 4/2013 | Salteri |
| 2013/0131762 A1 | 5/2013 | Oversluizen et al. |
| 2013/0144364 A1 | 6/2013 | Wagenaar Cacciola et al. |
| 2013/0158358 A1 | 6/2013 | Holland |
| 2013/0172959 A1 | 7/2013 | Azoulay |
| 2013/0196284 A1 | 8/2013 | Brawn |
| 2013/0197495 A1 | 8/2013 | Koifman et al. |
| 2013/0245417 A1 | 9/2013 | Spector |
| 2013/0280671 A1 | 10/2013 | Brawn et al. |
| 2014/0023983 A1 | 1/2014 | Lowe et al. |
| 2014/0067024 A1 | 3/2014 | Jones et al. |
| 2014/0128941 A1 | 5/2014 | Williams |
| 2014/0128942 A1 | 5/2014 | Bembridge et al. |
| 2014/0148879 A1 | 5/2014 | Mersch |
| 2014/0163218 A1 | 6/2014 | Dei et al. |
| 2014/0171926 A1 | 6/2014 | Depfenhart |
| 2014/0194955 A1 | 7/2014 | Povolosky et al. |
| 2014/0243933 A1 | 8/2014 | Ginggen |
| 2014/0267662 A1 | 9/2014 | Lampo |
| 2014/0276247 A1 | 9/2014 | Hall et al. |
| 2014/0276248 A1 | 9/2014 | Hall et al. |
| 2014/0288351 A1 | 9/2014 | Jones |
| 2014/0296524 A1 | 10/2014 | Jones et al. |
| 2014/0303693 A1 | 10/2014 | Haarlander et al. |
| 2014/0323946 A1 | 10/2014 | Bourke, Jr. et al. |
| 2014/0350643 A1 | 11/2014 | Pepitone et al. |
| 2015/0005854 A1 | 1/2015 | Said |
| 2015/0030989 A1 | 1/2015 | Soukos et al. |
| 2015/0045720 A1 | 2/2015 | Kanno et al. |
| 2015/0112411 A1 | 4/2015 | Beckman et al. |
| 2015/0164618 A1 | 6/2015 | Heacock et al. |
| 2015/0217130 A1 | 8/2015 | Gross et al. |
| 2015/0265353 A1 | 9/2015 | Andrews et al. |
| 2015/0297914 A1 | 10/2015 | Hamid et al. |
| 2016/0000214 A1 | 1/2016 | Kim |
| 2016/0015840 A1 | 1/2016 | Gordon |
| 2016/0016001 A1* | 1/2016 | Loupis .................. H05B 45/20 604/20 |
| 2016/0039854 A1 | 2/2016 | McFarland |
| 2016/0051835 A1 | 2/2016 | Tapper et al. |
| 2016/0059031 A1 | 3/2016 | Wescott et al. |
| 2016/0106999 A1 | 4/2016 | Michaels et al. |
| 2016/0114185 A1 | 4/2016 | Mankin |
| 2016/0129278 A1 | 5/2016 | Mayer |
| 2016/0151639 A1* | 6/2016 | Scharf .................. A61N 5/0624 607/92 |
| 2016/0271415 A1 | 9/2016 | Min |
| 2016/0271420 A1 | 9/2016 | Pina |
| 2016/0317832 A1 | 11/2016 | Barneck et al. |
| 2017/0027432 A1 | 2/2017 | Wachs |
| 2017/0028215 A1 | 2/2017 | Medendorp, Jr. et al. |
| 2017/0028216 A1 | 2/2017 | Medendorp, Jr. et al. |
| 2017/0165499 A1 | 6/2017 | Blanche et al. |
| 2017/0173358 A1 | 6/2017 | Demarest et al. |
| 2017/0203132 A1 | 7/2017 | Luttrull et al. |
| 2017/0224206 A1 | 8/2017 | Vayser |
| 2017/0225011 A1 | 8/2017 | Frost |
| 2017/0290648 A1 | 10/2017 | Kuo |
| 2017/0333728 A1 | 11/2017 | Sentis et al. |
| 2017/0340898 A1 | 11/2017 | Moor et al. |
| 2018/0008847 A1 | 1/2018 | Key |
| 2018/0014777 A1 | 1/2018 | Amir et al. |
| 2018/0036554 A1 | 2/2018 | Krespi |
| 2018/0111003 A1 | 4/2018 | Hewitson |
| 2018/0117355 A1 | 5/2018 | Loupis et al. |
| 2018/0146520 A1 | 5/2018 | Williams |
| 2018/0178027 A1 | 6/2018 | Shang |
| 2018/0256916 A1 | 9/2018 | Kothari et al. |
| 2018/0264282 A1 | 9/2018 | Bornstein |
| 2018/0289940 A1 | 10/2018 | Spotnitz et al. |
| 2019/0014901 A1 | 1/2019 | Xi et al. |
| 2019/0030359 A1 | 1/2019 | Dijkstra et al. |
| 2019/0124888 A1 | 5/2019 | Coyle |
| 2019/0134419 A1 | 5/2019 | Bourke, Jr. et al. |
| 2019/0142516 A1 | 5/2019 | Boutoussov et al. |
| 2019/0175938 A1 | 6/2019 | Rezaie et al. |
| 2019/0201711 A1 | 7/2019 | Brawn et al. |
| 2019/0209857 A1 | 7/2019 | Brawn et al. |
| 2020/0101315 A1 | 4/2020 | Reinhardt |
| 2020/0114171 A1 | 4/2020 | Tortora |
| 2020/0155350 A1 | 5/2020 | Neev |
| 2020/0222714 A1 | 7/2020 | Stasko et al. |
| 2020/0261608 A1 | 8/2020 | Crosby et al. |
| 2020/0298014 A1 | 9/2020 | Stasko et al. |
| 2020/0298016 A1 | 9/2020 | Yoon et al. |
| 2020/0330186 A1 | 10/2020 | Barros et al. |
| 2020/0353112 A1 | 11/2020 | Randers-Pehrson et al. |
| 2020/0360124 A1 | 11/2020 | Woo et al. |
| 2021/0008384 A1 | 1/2021 | Lee |
| 2021/0128936 A1 | 5/2021 | Stasko et al. |
| 2021/0128937 A1 | 5/2021 | Stasko et al. |
| 2021/0128938 A1 | 5/2021 | Stasko et al. |
| 2021/0138259 A1 | 5/2021 | Stasko et al. |
| 2021/0138260 A1 | 5/2021 | Park et al. |
| 2021/0196977 A1 | 7/2021 | Zhang |
| 2021/0205487 A1 | 7/2021 | Balme et al. |
| 2021/0228900 A1 | 7/2021 | Kothari et al. |
| 2021/0260398 A1 | 8/2021 | Bilston et al. |
| 2021/0267738 A1 | 9/2021 | Mackie |
| 2021/0283490 A1 | 9/2021 | Lin |
| 2021/0290970 A1 | 9/2021 | Hunter et al. |
| 2021/0290971 A1 | 9/2021 | Cockrell et al. |
| 2021/0290975 A1 | 9/2021 | Hunter et al. |
| 2021/0346500 A1 | 11/2021 | Schikora |
| 2021/0379400 A1 | 12/2021 | Emerson et al. |
| 2021/0402212 A1 | 12/2021 | Schupp et al. |
| 2022/0023660 A1 | 1/2022 | Emerson et al. |
| 2022/0040495 A1 | 2/2022 | Hwang et al. |
| 2022/0088409 A1 | 3/2022 | Dombrowski et al. |
| 2022/0168586 A1 | 6/2022 | Kothari et al. |

(56) References Cited

U.S. PATENT DOCUMENTS

| | | |
|---|---|---|
| 2022/0226667 A1 | 7/2022 | Kothari et al. |
| 2023/0149735 A1 | 5/2023 | Miskin |

FOREIGN PATENT DOCUMENTS

| | | |
|---|---|---|
| CN | 102247656 A | 11/2011 |
| CN | 102348425 A | 2/2012 |
| CN | 102380169 A | 3/2012 |
| CN | 102731405 A | 10/2012 |
| CN | 102802694 A | 11/2012 |
| CN | 103143015 A | 6/2013 |
| CN | 203169848 U | 9/2013 |
| CN | 103601727 A | 2/2014 |
| CN | 103610464 A | 3/2014 |
| CN | 103724356 A | 4/2014 |
| CN | 103930162 A | 7/2014 |
| CN | 104667432 A | 6/2015 |
| CN | 105664367 A | 6/2016 |
| CN | 108371756 A | 8/2018 |
| DE | 102010010763 A1 | 9/2011 |
| DE | 102013202122 A1 | 6/2014 |
| DE | 102012224183 A1 | 7/2014 |
| EP | 2368598 A1 | 9/2011 |
| EP | 2508229 A1 | 10/2012 |
| EP | 3069762 A1 | 9/2016 |
| EP | 3108931 A1 | 12/2016 |
| GB | 2499921 A | 9/2013 |
| KR | 20100124083 A | 11/2010 |
| KR | 20120090317 A | 8/2012 |
| KR | 101349157 B1 | 1/2014 |
| KR | 20140014689 A | 2/2014 |
| KR | 20190063041 A | 6/2019 |
| WO | 1995010243 A1 | 4/1995 |
| WO | 2004033040 A1 | 4/2004 |
| WO | 2004084752 A2 | 10/2004 |
| WO | 2006047868 A1 | 5/2006 |
| WO | 2006063318 A1 | 6/2006 |
| WO | 2006130340 A2 | 12/2006 |
| WO | 2008024414 A1 | 2/2008 |
| WO | 2008041296 A1 | 4/2008 |
| WO | 2008051918 A2 | 5/2008 |
| WO | 2008066943 A2 | 6/2008 |
| WO | 2008131343 A1 | 10/2008 |
| WO | 2008144157 A1 | 11/2008 |
| WO | 2009047669 A2 | 4/2009 |
| WO | 2010098761 A1 | 9/2010 |
| WO | 2011083378 A1 | 7/2011 |
| WO | 2011083381 A1 | 7/2011 |
| WO | 2012001194 A1 | 1/2012 |
| WO | 2013036558 A1 | 3/2013 |
| WO | 2014021557 A1 | 2/2014 |
| WO | 2014089552 A1 | 6/2014 |
| WO | 2014116659 A1 | 7/2014 |
| WO | 2014136255 A1 | 9/2014 |
| WO | 2014146029 A1 | 9/2014 |
| WO | 2015006309 A1 | 1/2015 |
| WO | 2015134204 A1 | 9/2015 |
| WO | 2016039812 A1 | 3/2016 |
| WO | 2016078603 A1 | 5/2016 |
| WO | 2016081594 A1 | 5/2016 |
| WO | 2016116859 A1 | 7/2016 |
| WO | 2016178472 A1 | 11/2016 |
| WO | 2017019836 A1 | 2/2017 |
| WO | 2017044931 A1 | 3/2017 |
| WO | 2017070155 A1 | 4/2017 |
| WO | 2018026892 A1 | 2/2018 |
| WO | 2019022275 A1 | 1/2019 |
| WO | 2019127427 A1 | 7/2019 |
| WO | 2019145519 A1 | 8/2019 |
| WO | 2019156921 A1 | 8/2019 |
| WO | 2019191820 A1 | 10/2019 |
| WO | 2019234308 A1 | 12/2019 |
| WO | 2020006048 A1 | 1/2020 |
| WO | 2020047659 A1 | 3/2020 |
| WO | 2020081910 A1 | 4/2020 |
| WO | 2021178655 A1 | 9/2021 |

OTHER PUBLICATIONS

Adamskaya, Natalia et al., "Light therapy by blue LED improves wound healing in an excision model in rats," Injury, 2010, 5 pages.

Adusumilli, Nagasai, et al., "Harnessing nitric oxide for preventing, limiting and treating the severe pulmonary consequences of COVID-19," Nitric Oxide, vol. 103, Jul. 2020, Elsevier Inc., 5 pages.

Akerstrom, Sara, et al., "Nitric Oxide Inhibits the Replication Cycle of Severe Acute Respiratory Syndrome Coronavirus," Journal of Virology, vol. 79, Issue 3, Feb. 2005, pp. 1966-1969.

Akerstrom, Sara, et al., "Dual effect of nitric oxide on SARS-CoV replication: Viral RNA production and palmitoylation of the S protein are affected," Virology, vol. 395, Oct. 2009, Elsevier Inc., 9 pages.

Andrew, Penelope J. et al., "Enzymatic function of nitric oxide synthases," Cardiovascular Research, vol. 43, No. 3, Aug. 15, 1999, pp. 521-531.

Author Unknown, "Brilliant Light Therapy," In Light Wellness Systems, eBrochure, Date Unknown, 5 pages.

Author Unkown, "dpl Oral Care—For Healthy Teeth & Gums," Product Brief, Revive Light Therapy, revivelighttherapy.com/product/dpl-oral-care-light-therapy-system-teeth-whitening/, accessed Jan. 31, 2021, 5 pages.

Author Unknown, "Healed by Light," Digi-Key Electronics, Jul. 1, 2014, 4 pages, www.digikey.com/es/articles/techzone/2014/jul/healed-by-light.

Author Unknown, "illuMask," La Lumière, Date Unknown, 2 pages, http://www.illumask.com/dimming/.

Author Unknown, "IPL Hair Removal," Spectrum Science & Beauty, Spectrum Blog, Sep. 16, 2014, 3 pages, www.spectrumsciencebeauty.com.au/ipl-hair-removal/#prettyPhoto.

Author Unknown, "Near—IR Photoluminescent Dyes for Molecular Labeling," NanoQuantum, Technology, 2013, 7 pages, www.nanoquantum.com/Technology.html.

Author Unknown, "Philips Blue Touch," Koninklijke Philips N.V., Version 1.0.1, Sep. 1, 2013, 2 pages.

Author Unknown, "Safety and Efficacy of UVC to Fight Covid-19," Gilbert W. Beebe Webinar Series, Program Agenda, Sep. 16, 2020, 6 pages.

Author Unknown, "Theradome Laser Helmet Review—A 120 Day Continuous Journal," Prevent Hair Loss Products, Jan. 14, 2014, retrieved Jun. 27, 2017, web.archive.org/web/20140610024017/http://preventhairlossproducts.com:80/theradome-laser-helmet-review-120-day-continuous-journal/, pp. 1-4.

Author Unknown, "Ultraviolet Light Therapy," Wound Care Centers, Date Unknown, 3 pages, www.woundcarecenters.org/article/wound-therapies/ultraviolet-light-therapy.

Author Unknown, "Vio Orb—Antimicrobial Light Ball," Product Brief, Revive Light Therapy, revivelighttherapy.com/product/envirohygiene-orb-antimicrobial-light-ball/, accessed Jan. 31, 2021, 6 pages.

Author Unknown, "What is Light Therapy used for?" Rio, The Dezac Group, Ltd, Date Unknown, 4 pages, www.lightmask.com/uses_for_It.htm#top.

Avci, Pinar et al., "Low-Level Laser (Light) Therapy (LLLT) for Treatment of Hair Loss," Lasers in Surgery and Medicine, vol. 46, 2014, pp. 144-151.

Avci, Pinar et al., "Low-Level Laser (Light) Therapy (LLLT) in Skin: Stimulating, Healing, Restoring," Seminars in Cutaneous Medicine and Surgery, vol. 32, No. 1, 2013, pp. 41-52.

Ball, Kerri A. et al., "Low intensity light stimulates nitrite-dependent nitric oxide synthesis but not oxygen consumption by cytochrome c oxidase: Implications for phototherapy," Journal of Photochemistry and Photobiology B, vol. 102, No. 3, 2011, pp. 182-191.

Barolet, Daniel, "Light-Emitting Diodes (LEDs) in Dermatology," Seminars in Cutaneous Medicine and Surgery, vol. 27, No. 4, Dec. 1, 2008, pp. 227-238.

(56) References Cited

OTHER PUBLICATIONS

Bashkatov et al., "Optical properties of human skin, subcutaneous and mucous tissues in the wavelength range from 400-2000 nm," Journal of Physics D: Applied Physics, vol. 38, Jul. 2005, IOP Publishing Ltd, pp. 2543-2555.
Beck, Sara, et al., "Comparison of UV-Induced Inactivation and RNA Damage in MS2 Phage across the Germicidal UV Spectrum," Applied and Environmental Microbiology, vol. 82, Issue 5, Mar. 2016, pp. 1468-1474.
Beigel, JH, et al., "Remdesivir for the Treatment of Covid-19—Final Report," New England Journal of Medicine, vol. 383, Issue 19, Nov. 5, 2020, pp. 1813-1826.
Besaratinia, Ahmad, et al., "DNA lesions induced by UV A1 and B radiation in human cells: Comparative analyses in the overall genome and in the p53 tumor suppressor gene," PNAS, vol. 102, Issue 29, Jul. 2005, pp. 10058-10063.
Buonnano, Manuela, et al., "Far-UVC light (222 nm) efficiently and safely inactivates airborne human coronaviruses," Scientific Reports, Jun. 24, 2020, 8 pages.
Buonnano, Manuela, et al., "Germicidal Efficacy and Mammalian Skin Safety of 222-nm UV Light," Radiation Research, vol. 187, 2017, Radiation Research Society, 2017, pp. 493-501.
Cals-Grierson, M.-M. et al., "Nitric oxide function in the skin," Nitric Oxide, vol. 10, No. 4, Jun. 2004, pp. 179-193.
Chaves, Maria Emília De Abreu et al., "Effects of low-power light therapy on wound healing: Laser × LED," Anais Brasileiros de Dermatologia, vol. 89, No. 4, Jul./Aug. 2014, pp. 616-623.
Chen, Luni, et al., "Inhalation of Nitric Oxide in the Treatment of Severe Acute Respiratory Syndrome: A Rescue Trial in Beijing," Brief Report, Clinical Infectious Diseases, vol. 39, Oct. 2004, pp. 1531-1535.
Creagh-Brown, Benedict, et al., "Bench-to-bedside review: Inhaled nitric oxide therapy in adults," Critical Care, vol. 13, Issue 3, May 2009, BioMed Central Ltd, 8 pages.
Dai, Tianhong, et al., "Blue light for infectious diseases: Propionibacterium acnes, Helicobacter pylori, and beyond?," NIH-PA, Author Manuscript, 2012, Elsevier Ltd., 31 pages.
Darnelll, Miriam, et al., "Evaluation of inactivation methods for severe acute respiratory syndrome coronavirus in noncellular blood products," Transfusion, vol. 46, Oct. 2006, 8 pages.
De Marco, Federico, "Oxidative Stress and HPV Carcinogenesis," Viruses, vol. 5, Feb. 2013, pp. 708-731.
Donnarumma, G., et al., "Inhibition of HSV-1 Replication by Laser Diode-Irradiation: Possible Mechanism of Action," Journal of Immunopathology and Pharmacology, vol. 23, Issue 4, 2010, Biolife, pp. 1167-1176.
Dorrington, Michael, et al., "NF-KB Signaling in Macrophages: Dynamics, Crosstalk, and Signal Integration," Frontiers in Immunology, vol. 10, Apr. 9, 2019, 12 pages.
Eadie, Ewan, et al., "Extreme Exposure to Filtered Far-UVC: A Case Study," Ninewells Hospital and Medical School, Sep. 25, 2020, 14 pages.
Enwemeka, Chukuka, et al., "Blue 470-nm Light Kills Methicillin-Resistant *Staphylococcus aureus* (MRSA) in Vitro," Photomedicine and Laser Surgery, vol. 27, Issue 2, 2009, 6 pages.
Enwemeka, Chukuka, et al., "Light as a potential treatment for pandemic coronavirus infections: A perspective," Journal of Photochemistry & Photobiology, B: Biology, vol. 207, May 2020, 7 pages.
Enwemeka, Chukuka, et al., "Visible 405 nm SLD Light Photo-Destroys Methicillin-Resistant *Staphylococcus aureus* (MRSA) In Vitro," Lasers in Surgery and Medicine, vol. 40, 2008, pp. 734-737.
Farivar, Shirin et al., "Biological Effects of Low Level Laser Therapy," Journal of Lasers in Medical Sciences, vol. 5, No. 2, Spring 2014, pp. 58-62.
Feelisch, Martin et al., "Concomitant S-, N-, and heme-nitrosis(yl)ation in biological tissues and fluids: implications for the fate of NO in vivo," FASEB, vol. 16, No. 13, Nov. 2002, pp. 1775-1785.

Ferrari-Light, Dana, et al., "The Utility of Near-Infrared Fluorescence and Indocyanine Green During Robotic Pulmonary Resection," Frontiers in Surgery, Review, vol. 6, Aug. 2019, 7 pages.
Finsen, Niels, "The Red Light Treatment of Small-Pox," The British Medical Journal, Dec. 7, 1895, pp. 1412-1414.
Garza, Felix, et al., "Visible Blue Light Therapy: Molecular Mechanisms and Therapeutic Opportunities," Current Medical Chemistry, 2018, vol. 25, Bentham Science Publishers, pp. 5564-5577.
Glazer-Hockstein, "Could Blue Light-Blocking Lenses Decrease the Risk of Age-Related Macular Degeneration," Retina, vol. 26, 2006, 4 pages.
Gupta, Asheesh et al., "History and Fundamentals of Low-Level Laser (Light) Therapy," Handbook of Photomedicine, Chapter 5, CRC Press, 2014, pp. 43-52.
Hamblin, Michael, et al., "Can light-based approaches overcome antimicrobial resistance?," Drug Development Research, Jul. 2018, Wiley Periodicals, Inc., 20 pages.
Hamblin, Michael, et al., "Mechanisms of Low Level Light Therapy," Proceedings of the SPIE, vol. 6140, Feb. 10, 2006, pp. 614001-1 to 641001-12.
International Search Report and Written Opinion for International Patent Application No. PCT/US2022/019428, mailed Jun. 14, 2022, 16 pages.
Examination Report for European Patent Application No. 16831333.6, mailed May 20, 2022, 6 pages.
Advisory Action and Examiner-Initiated Interview Summary for U.S. Appl. No. 17/410,154, mailed Jul. 5, 2022, 4 pages.
Final Office Action for U.S. Appl. No. 17/410,166, mailed Jul. 1, 2022, 16 pages.
Non-Final Office Action for U.S. Appl. No. 17/162,259, mailed Jul. 6, 2022, 17 pages.
Non-Final Office Action for U.S. Appl. No. 17/410,154, mailed Jul. 28, 2022, 21 pages.
Notice of Allowance for Brazilian Patent Application No. BR112018001874-0, mailed Aug. 28, 2022, 6 pages.
Corrected Notice of Allowability for U.S. Appl. No. 16/709,550, mailed Sep. 21, 2022, 5 pages.
Non-Final Office Action for U.S. Appl. No. 17/148,124, mailed Oct. 13, 2022, 21 pages.
Final Office Action for U.S. Appl. No. 17/410,154, mailed Oct. 11, 2022, 20 pages.
Non-Final Office Action for U.S. Appl. No. 17/410,166, mailed Oct. 18, 2022, 11 pages.
Final Office Action for U.S. Appl. No. 17/162,259, mailed Oct. 19, 2022, 19 pages.
Non-Final Office Action for U.S. Appl. No. 17/162,283, mailed Nov. 8, 2022, 12 pages.
Non-Final Office Action for U.S. Appl. No. 17/173,457, mailed Oct. 17, 2022, 15 pages.
Technical Examination Report for Brazilian Patent Application No. 122020024964-1, mailed Nov. 29, 2022, 6 pages.
Advisory Action and Examiner-Initiated Interview Summary for U.S. Appl. No. 17/410,154, mailed Jan. 10, 2023, 4 pages.
Notice of Allowance for U.S. Appl. No. 17/410,166, mailed Feb. 15, 2023, 8 pages.
Advisory Action for U.S. Appl. No. 17/162,259, mailed Jan. 9, 2023, 3 pages.
Final Office Action for U.S. Appl. No. 17/173,457, mailed Feb. 23, 2023, 9 pages.
Notice of Allowance and Examiner-Initiated Interview Summary for U.S. Appl. No. 17/201,120, mailed Jan. 19, 2023, 21 pages.
Ankhzaya, "Airway management," slideshow, www.slideshare.net/gasilu/airway-management-111268937, Aug. 24, 2018, 87 pages.
Liu, et al., "Creation of a standardized geometry of the human nasal cavity," Journal of Applied Physiology, vol. 106, Jan. 2009, pp. 784-795.
International Search Report and Written Opinion for International Patent Application No. PCT/US2021/019785, mailed Jun. 15, 2021, 18 pages.
Advisory Action for U.S. Appl. No. 17/117,889, mailed Jun. 4, 2021, 3 pages.
Final Office Action for U.S. Appl. No. 16/709,550, mailed Feb. 17, 2021, 12 pages.

(56) References Cited

OTHER PUBLICATIONS

Second Office Action for Chinese Patent Application No. 202010561507.X, mailed Jul. 15, 2022, 33 pages.
Advisory Action for U.S. Appl. No. 17/410,166, mailed Sep. 7, 2022, 3 pages.
Final Office Action for U.S. Appl. No. 17/201,120, mailed Sep. 23, 2022, 34 pages.
Final Office Action for U.S. Appl. No. 17/148,124, mailed Mar. 13, 2023, 29 pages.
Notice of Allowance and Examiner-Initiated Interview Summary for U.S. Appl. No. 17/410,154, mailed Mar. 9, 2023, 14 pages.
Non-Final Office Action for U.S. Appl. No. 17/162,259, mailed Apr. 7, 2023, 18 pages.
Final Office Action for U.S. Appl. No. 17/162,283, mailed Apr. 10, 2023, 10 pages.
Advisory Action for U.S. Appl. No. 17/173,457, mailed May 1, 2023, 3 pages.
Non-Final Office Action for U.S. Appl. No. 17/201,061, mailed Apr. 20, 2023, 19 pages.
Notice of Allowance for U.S. Appl. No. 16/709,550, mailed Feb. 24, 2022, 8 pages.
Corrected Notice of Allowability for U.S. Appl. No. 16/709,550, mailed Mar. 25, 2022, 5 pages.
Corrected Notice of Allowability for U.S. Appl. No. 16/709,550, mailed Apr. 15, 2022, 5 pages.
Final Office Action for U.S. Appl. No. 16/898,385, mailed Feb. 15, 2022, 13 pages.
Advisory Action for U.S. Appl. No. 16/898,385, mailed Apr. 20, 2022, 4 pages.
Non-Final Office Action for U.S. Appl. No. 17/410,154, mailed Feb. 24, 2022, 21 pages.
Final Office Action for U.S. Appl. No. 17/410,154, mailed May 13, 2022, 18 pages.
Final Office Action for U.S. Appl. No. 17/410,166, mailed Mar. 14, 2022, 13 pages.
Advisory Action for U.S. Appl. No. 17/410,166, mailed May 11, 2022, 3 pages.
Non-Final Office Action for U.S. Appl. No. 17/201,120, mailed Apr. 15, 2022, 23 pages.
Notification of Reasons for Rejection for Japanese Patent Application No. 2021-518715, mailed Apr. 26, 2022, 9 pages.
Ahmed, Imran, et al., "Recent Patents on Light-Based Anti-Infective Approaches," Author Manuscript, Recent Patents on Anti-Infective Drug Discovery, vol. 13, Issue 1, 2018, 28 pages.
Akaberi, Dario, et al., "Mitigation of the replication of SARS-CoV-2 by nitric oxide in vitro," Redox Biology, vol. 37, Sep. 21, 2020, Elsevier B.V., 5 pages.
Author Unknown, "Assessing COVID-19-Related Symptoms in Outpatient Adult and Adolescent Subjects in Clinical Trials of Drugs and Biological Products for Covid-19 Prevention or Treatment," Guidance for Industry, US Department of Health and Human Services, Sep. 2020, 14 pages.
Baric, Ralph, "Emergence of a Highly Fit SARS-CoV-2 Variant," New England Journal of Medicine, vol. 383, Issue 27, Dec. 31, 2020, pp. 2684-2686.
Fajnzylber, Jesse, et al., "SARS-CoV-2 viral load is associated with increased disease severity and mortality," Nature Communications, vol. 11, Issue 1, Oct. 30, 2020, 9 pages.
Hamblin, Michael, "Mechanisms and Mitochondrial Redox Signaling in Photobiomodulation," Author Manuscript, Photochemistry and Photobiology, vol. 94, Issue 2, Mar. 2018, 31 pages.
Huang, Ni, et al., "Integrated Single-Cell Atlases Reveal an Oral SARS-CoV-2 Infection and Transmission Axis," medrXiv, Oct. 29, 2020, 22 pages.
Kim, Peter, et al., "Therapy for Early COVID-19: A Critical Need," JAMA, vol. 324, Issue 21, Nov. 11, 2020, American Medical Association, pp. 2149-2150.
Quirk, Brendan, et al., "What Lies at the Heart of Photobiomodulation: Light, Cytochrome C Oxidase, and Nitric Oxide—Review of the Evidence," Photobiomodulation, Photomedicine, and Laser Surgery, vol. 38, Issue 9, Jul. 2020, pp. 527-530.
To, KK, et al., "Temporal profiles of viral load in posterior oropharyngeal saliva samples and serum antibody responses during infection by SARS-CoV-2: an observational cohort study," Lancet Infectious Diseases, vol. 20, Issue 5, Mar. 23, 2020, 11 pages.
Wyllie, Anne, et al., "Saliva or nasopharyngeal swab specimens for detection of SARS-Cov-2," New England Journal of Medicine, vol. 383, Issue 13, Sep. 24, 2020, 4 pages.
Xu, Hao, et al., "High expression of ACE2 receptor of 2019-nCoV on the epithelial cells of oral mucosa," International Journal of Oral Science, vol. 12, Issue 8, Feb. 24, 2020, 5 pages.
Author Unknown, "Scientific Breakthrough: Phototherapy Device," Facebook Timeline Photo, medicsBLU, Oct. 1, 2020, facebook.com/medicsblu/, 4 pages.
Soukos, Nikolaos, et al., "Phototargeting Oral Black-Pigmented Bacteria," Antimicrobial Agents and Chemotherapy, Apr. 2005, vol. 49, Issue 4, pp. 1391-1396.
Advisory Action and Examiner-Initiated Interview Summary for U.S. Appl. No. 17/117,889, mailed May 19, 2021, 5 pages.
Non-Final Office Action for U.S. Appl. No. 17/117,889, mailed Mar. 19, 2021, 17 pages.
Applicant-Initiated Interview Summary for U.S. Appl. No. 17/117,889, mailed Apr. 19, 2021, 2 pages.
Final Office Action for U.S. Appl. No. 17/117,889, mailed Apr. 30, 2021, 19 pages.
Zein, Randa, et al., "Review of light parameters and photobiomodulation efficacy: dive into complexity," Journal of Biomedical Optics, vol. 23, Issue 12, Dec. 2018, 17 pages.
Zupin, Luisa, et al., "Antiviral properties of blue laser in an in vitro model of HSV-1 infection," Microbial Immunal, Letter to the Editor, vol. 62, 2018, pp. 477-479.
Zupin, Luisa, et al., "Photobiomodulation therapy reduces viral load and cell death in ZIKV-infected glioblastoma cell line," Lasers in Medical Science, vol. 33, Jul. 2018, Springer Nature, pp. 2011-2013.
International Search Report and Written Opinion for PCT/US2016/044400, mailed Oct. 4, 2016, 8 pages.
International Preliminary Report on Patentability for PCT/US2016/044400, mailed Feb. 8, 2018, 7 pages.
Non-Final Office Action for U.S. Appl. No. 15/222,199, mailed Jan. 11, 2019, 9 pages.
Non-Final Office Action for U.S. Appl. No. 15/222,243, mailed Jan. 11, 2019, 10 pages.
International Preliminary Report on Patentability for PCT/US2016/044403, mailed Feb. 8, 2018, 7 pages.
Final Office Action for U.S. Appl. No. 15/222,199, mailed Jul. 29, 2019, 9 pages.
Notice of Allowance and Applicant-Initiated Interview Summary for U.S. Appl. No. 15/222,199, mailed Sep. 18, 2019, 11 pages.
Final Office Action for U.S. Appl. No. 15/222,243, mailed Jul. 29, 2019, 12 pages.
Notice of Allowance and Applicant-Initiated Interview Summary for U.S. Appl. No. 15/222,243, mailed Dec. 19, 2019, 11 pages.
Non-Final Office Action for U.S. Appl. No. 16/709,550, mailed Apr. 30, 2020, 13 pages.
Arora, Prerna, et al., "B.1.617.2 enters and fuses lung cells with increased efficiency and evades antibodies induced by infection and vaccination," Cell Reports, vol. 37, Oct. 12, 2021, 12 pages.
Caly, Leon, et al., "The FDA-approved drug ivermectin inhibits the replication of SARS-CoV-2 in vitro," Antiviral Research, vol. 178, Apr. 3, 2020, Elsevier B.V., 4 pages.
Cele, Sandile, et al., "Escape of SARS-CoV-2 501Y.V2 from neutralization by convalescent plasma," Nature, vol. 593, May 6, 2021, 18 pages.
Cheng, Ya-Wen, et al., "D614G Substitution of SARS-CoV-2 Spike Protein Increases Syncytium Formation and Virus Titer via Enhanced Furin-Mediated Spike Cleavage," mBio, vol. 12, Issue 4, Jul. 27, 2021, 11 pages.
Do, et al., "A robust SARS-CoV-2 replication model in primary human epithelial cells at the air liquid interface to assess antiviral agents," Antiviral Research, vol. 192, Jun. 26, 2021, Elsevier, B.V., 8 pages.

(56) References Cited

OTHER PUBLICATIONS

Fulcher, et al., "Human Nasal and Tracheo-Bronchial Respiratory Epithelial Cell Culture," Methods in Molecular Biology, vol. 945, Chapter 8, 2012, pp. 109-121.
Gong, et al., "Contribution of single mutations to selected SARS-CoV-2 emerging variants spike antigenicity," Virology, vol. 563, Sep. 11, 2021, Elsevier Inc., 12 pages.
Good, Steven, et al., "AT-527 a Double Prodrug of a Guanosine Nucleotide Analog, Is a Potent Inhibitor of SARS-CoV-2 In Vitro and a Promising Oral Antiviral for Treatment of Covid-19," Antimicrobial Agents and Chemotherapy, vol. 65, Issue 4, Apr. 2021, 12 pages.
Harvey, William, et al., "SARS-CoV-2 variants, spike mutations and immune escape," Nature Reviews: Microbiology, vol. 19, Jul. 2021, pp. 409-424.
Heinen, Natalie, et al., "In Vitro Lung Models and Their Application to Study SARS-CoV-2 Pathogenesis and Disease," Viruses, vol. 13, Apr. 28, 2021, 17 pages.
Hou, Yixuan, et al., "SARS-CoV-2 Reverse Genetics Reveals a Variable Infection Gradient in the Respiratory Tract," Cell, vol. 182, Jul. 23, 2020, Elsevier Inc., 32 pages.
Huang, Ni, et al., "SARS-CoV-2 infection of the oral cavity and saliva," Nature Medicine, vol. 27, May 2021, 27 pages.
Krause, Philip, et al., "SARS-CoV-2 Variants and Vaccines," New England Journal of Medicine, vol. 385, Issue 2, Jul. 8, 2021, Massachusetts Medical Society, pp. 179-186.
Kumar, Sanjeev, et al., "Current status of therapeutic monoclonal antibodies against SARS-CoV-2," PLOS Pathogens, Sep. 3, 2021, 8 pages.
Levin, "Waning Immune Humoral Response to BNT162b2 Covid-19 Vaccine over 6 Months," New England Journal of Medicine, Oct. 6, 2021, Massachusetts Medical Society, 11 pages.
Liu, Haolin, et al., "The Lambda variant of SARS-CoV-2 has a better chance than the Delta variant to escape vaccines," Aug. 26, 2021, bioRxiv, 26 pages.
Liu, Jia, et al., "Hydroxychloroquine, a less toxic derivative of chloroquine, is effective in inhibiting SARS-CoV-2 infection in vitro," Cell Discovery, vol. 6, Issue 16, Mar. 18, 2020, 4 pages.
Liu, Yang, "Delta spike P681R mutation enhances SARS-CoV-2 fitness over Alpha variant," Sep. 5, 2021, bioRxiv, 29 pages.
Marchesan, et al., "The 'oral' history of COVID-19: Primary infection, salivary transmission, and post-acute implications," Journal of Periodontology, vol. 92, American Academy of Periodontology, Jul. 2021, pp. 1357-1367.
McCullough, Peter, et al., "Pathophysiological Basis and Rationale for Early Outpatient Treatment of SARS-CoV-2 (COVID-19) Infection," The American Journal of Medicine, Review, vol. 134, Issue 1, Jan. 2021, Elsevier Inc., pp. 16-22.
Motozono, Chihiro, et al., "SARS-CoV-2 spike L452R variant evades cellular immunity and increases infectivity," Cell Host and Microbe, vol. 29, Jul. 14, 2021, Elsevier Inc., 24 pages.
Naaber, Paul, et al., "Dynamics of antibody response to BNT162b2 vaccine after six months: a longitudinal prospective study," The Lancet Regional Health—Europe, Sep. 6, 2021, 9 pages.
Planas, Delphine, et al., "Reduced sensitivity of SARS-CoV-2 variant Delta to antibody neutralization," Nature, vol. 596, Jul. 8, 2021, 20 pages.
Plante, Jessica, et al., "Spike mutation D614G alters SARS-CoV-2 fitness," Nature, vol. 592, Oct. 26, 2020, 22 pages.
Pouwels, Koen, et al., "Effect of Delta variant on viral burden and vaccine effectiveness against new SARS-CoV-2 infections in the UK," Nature Medicine, Oct. 14, 2021, 25 pages.
Pruijssers, Andrea, et al., "Remdesivir Inhibits SARS-CoV-2 in Human Lung Cells and Chimeric SARS-CoV Expressing the SARS-CoV-2 RNA Polymerase in Mice," Cell Reports, vol. 32, Jul. 21, 2020, 15 pages.
Sellgren, et al., "A biomimetic multicellular model of the airways using primary human cells," Lab on a Chip, Jun. 2014, The Royal Society of Chemistry, 10 pages.

Sheahan, Timothy, et al., "An orally bioavailable broad-spectrum antiviral inhibits SARS-CoV-2 in human airway epithelial cell cultures and multiple coronaviruses in mice," Science Translational Medicine, Research Article, vol. 12, Apr. 29, 2020, 16 pages.
Stasko, Nathan, et al., "A randomized, controlled, feasibility study of RD-X19 in patients with mild-to-moderate COVID-19 in the outpatient setting," Oct. 25, 2021, medRxiv, 30 pages.
Stasko, Nathan, et al., "Visible blue light inhibits infection and replication of SARS-CoV-2 at doses that are well-tolerated by human respiratory tissue," Scientific Reports, vol. 11, Oct. 18, 2021, 14 pages.
Touret, Franck, et al., "Preclinical evaluation of Imatinib does not support its use as an antiviral drug against SARS-CoV-2," Antiviral Research, vol. 193, Jul. 12, 2021, 8 pages.
Touret, Franck, et al., "Replicative Fitness of a SARS-CoV-2 201/501Y.V1 Variant from Lineage B.1.1.7 in Human Reconstituted Bronchial Epithelium," mBio, vol. 12, Issue 4, Jul. 2021, 4 pages.
Wang, Pengfei, et al., "Antibody resistance of SARS-CoV-2 variants B.1.351 and B.1.1.7," Nature, vol. 593, May 6, 2021, 18 pages.
Wildera, Marek, et al., "Limited Neutralization of Authentic Severe Acute Respiratory Syndrome Coronavirus 2 Variants Carrying E484K In Vitro," The Journal of Infectious Diseases, Jul. 5, 2021, pp. 1109-1114.
Final Office Action for U.S. Appl. No. 16/709,550, mailed Dec. 27, 2021, 9 pages.
Advisory Action for U.S. Appl. No. 17/410,154, mailed Jan. 25, 2022, 3 pages.
Non-Final Office Action for U.S. Appl. No. 17/410,166, mailed Jan. 12, 2022, 12 pages.
Hamblin, Michael, "Mechanisms of Low Level Light Therapy," Aug. 14, 2008, 22 pages, photobiology.info/Hamblin.html.
Hamblin, Michael R., "The Role of Nitric Oxide in Low Level Light Therapy," Proceedings of SPIE, vol. 6846, 2008, pp. 684602-1 to 684602-14.
Hessling, Martin, et al., "Selection of parameters for thermal coronavirus inactivation—a data-based recommendation," GMS Hygiene and Infection Control, vol. 15, 2020, 7 pages.
Horby, Peter, et al., "Dexamethasone in Hospitalized Patients with Covid-19—Preliminary Report," New England Journal of Medicine, Jul. 17, 2020, 11 pages.
Jackson, George, et al., "Prevalidation of an Acute Inhalation Toxicity Test Using the EpiAirway In Vitro Human Airway Model," Applied In Vitro Toxicology, vol. 4, Issue 2, 2018, Mary Ann Liebert, Inc., pp. 149-158.
Jensen, Caleb, et al., "Is it Time to Start Transitioning From 2D to 3D Cell Culture," Frontiers in Molecular Biosciences, Review, vol. 7, Mar. 2020, 15 pages.
Jin, Jin, et al., "Noncanonical NF-KB Pathway Controls the Production of Type I Interferons in Antiviral Innate Immunity," Immunity, vol. 40, Mar. 2014, Elsevier Inc., pp. 342-354.
Karu, Tiina I., "Low-Power Laser Therapy," Biomedical Photonics Handbook, Chapter 48, CRC Press, 2003, pp. 48-1 to 48-25.
Kelm, Malte, "Nitric oxide metabolism and breakdown," Review, Biochimica et Biophysica Acta, vol. 1411, 1999, Elsevier Science B.V., pp. 273-289.
Kingsley, David, et al., "Oxygen-dependent laser inactivation of murine norovirus using visible light lasers," Virology Journal, Jul. 31, 2018, 8 pages.
Kirima, Kazuyoshi et al., "Evaluation of systemic blood NO dynamics by EPR spectroscopy: HbNO as an endogenous index of NO," American Journal of Physiology Heart and Circulatory Physiology, vol. 285, No. 2, Aug. 2003, pp. H589-H596.
Kitchel, Elaine, "The Effects of Blue Light on Ocular Health," Journal of Visual Impairment and Blindness, Jun. 2000, AFB, pp. 399-403.
Klein, Eili, et al., "The frequency of influenza and bacterial coinfection: a systematic review and meta-analysis," Influenza and Other Respiratory Viruses, vol. 10, Issue 5, May 2016, John Wiley & Sons Ltd., pp. 394-403.
Kovacs, Izabella et al., "Nitric oxide-based protein modification: formation and site-specificity of protein S-nitrosylation," Frontiers in Plant Science, vol. 4, Article 137, May 14, 2013, 10 pages.

(56) References Cited

OTHER PUBLICATIONS

Leong, Mimi, "Effects of Light-Emitting Diode Photostimulation on Burn Wound Healing," Thesis, The University of Texas Graduate School of Biomedical Sciences at Galveston, May 2006, 92 pages.
Li, Jie, et al., "Involvement of the Toll-Like Receptor/Nitric Oxide Signaling Pathway in the Pathogenesis of Cervical Cancer Caused by High-Risk Human Papillomavirus Infection," Biomed Research International, 2017, Hindawi, 9 pages.
Lubart, et al., "A Possible Mechanism for the Bactericidal Effect of Visible Light," Review Article, Laser Therapy, vol. 20, 2011, pp. 17-22.
Mandel, Arkady, et al., "A renaissance in low-level laser (light) therapy—LLLT," Photonics and Lasers in Medicine, vol. 1, No. 4, Nov. 2012, pp. 231-234.
Martin, Richard, "Laser-Accelerated Inflammation/Pain Reduction and Healing," Practical Pain Management, vol. 3, No. 6, Nov./Dec. 2003, pp. 20-25.
Marullo, Rosella, et al., "HPV16 E6 and E7 proteins induce a chronic oxidative stress response via NOX2 that causes genomic instability and increased susceptibility to DNA damage in head and neck cancer cells," Carcinogenesis, vol. 36, Issue 11, 2015, Oxford University Press, pp. 1397-1406.
Moseley, Harry, et al., "Population reference intervals for minimal erythemal doses in monochromator phototesting," Photodermatology, Photoimmunology & Photomedicine, vol. 25, 2009, pp. 8-11.
Narita, Kouji, et al., "Chronic irradiation with 222-nm UVC light induces neither DNA damage nor epidermal lesions in mouse skin, even at high doses," Research Article, PLOS One, doi.org/10.1371/journal.pone.0201259, Jul. 25, 2018, 9 pages.
Narita, Kouji, et al., "Disinfection and healing effects of 222-nm UVC light on methicillin-resistant *Staphylococcus aureus* infection in mouse wounds," Dissertation, Hirosaki University Graduate School of Medicine, 2017, Elsevier, 36 pages.
Narita, Kouji, et al., "Ultraviolet C light with wavelength of 222 nm inactivates a wide spectrum of microbial pathogens," Journal of Hospital Infection, vol. 105, Mar. 31, 2020, Elsevier Ltd., pp. 459-467.
Perdiz, Daniel, et al., "Distribution and Repair of Bipyrimidine Photoproducts in Solar UV-irradiated Mammalian Cells," Journal of Biological Chemistry, vol. 275, Issue 35, Sep. 2000, pp. 26732-26742.
Pfeifer, Gerd, et al., "UV wavelength-dependent DNA damage and human non-melanoma and melanoma skin cancer," Author Manuscript, Journal of Photochemistry and Photobiology, vol. 11, Issue 1, Jan. 2012, 14 pages.
Phurrough, Steve et al., "Decision Memo for Infrared Therapy Devices (CAG-00291N)," Centers for Medicare & Medicaid Services, Oct. 24, 2006, 37 pages.
Poyton, Robert O. et al., "Therapeutic Photobiomodulation: Nitric Oxide and a Novel Function of Mitochondrial Cytochrome C Oxidase," Discovery Medicine, Feb. 20, 2011, 11 pages.
Ramakrishnan, Praveen, et al., "Cytotoxic responses to 405 nm light exposure in mammalian and bacterial cells: Involvement of reactive oxygen species," Toxicology in Vitro, vol. 33, Feb. 2016, Elsevier B.V., pp. 54-62.
Ravanant, Jean-Luc, et al., "Direct and indirect effects of UV radiation on DNA and its components," Journal of Photochemistry and Photobiology, vol. 63, 2001, pp. 88-102.
Richardson, Tobias, et al., "Inactivation of murine leukaemia virus by exposure to visible light," Virology, vol. 341, 2005, Elsevier Inc., pp. 321-329.
Sabino, Caetano, et al., "Light-based technologies for management of COVID-19 pandemic crisis," Journal of Photochemistry and Photobiology, Aug. 2020, Elsevier B.V., 8 pages.
Sarti, Paolo et al., "The Chemical Interplay between Nitric Oxide and Mitochondrial Cytochrome c Oxidase: Reactions, Effectors and Pathophysiology," International Journal of Cell Biology, vol. 2012, Article 571067, 2012, 11 pages.
Saura, Marta, et al., "An Antiviral Mechanism of Nitric Oxide: Inhibition of a Viral Protease," Immunity, vol. 10, Jan. 1999, Cell Press, 8 pages.
Serrage, Hannah, et al., "Under the spotlight: mechanisms of photobiomodulation concentrating on blue and green light," Photochemical and Photobiological Sciences, Jun. 2019, 43 pages.
St. Denis, Tyler, et al., "Killing Bacterial Spores with Blue Light: When Innate Resistance Meets the Power of Light," Photochemistry and Photobiology, vol. 89, Issue 1, Sep. 2012, Wiley Preiodicals, Inc., 7 pages.
Tomb, Rachael, et al., "Inactivation of Streptomyces phage $\phi$C31 by 405 nm light," Bacteriophage, vol. 4, Jul. 2014, Landes Bioscience, 7 pages.
Tomb, Rachael, et al., "New Proof-of-Concept in Viral Inactivation: Virucidal Efficacy of 405 nm Light Against Feline Calicivirus as a Model for Norovirus Decontamination," Food Environ Virol, Dec. 2016, pp. 159-167.
Tomoroni, et al., "A Novel Laser Fiberscope for Simultaneous Imaging and Phototherapy of Peripheral Lung Cancer," Chest, vol. 156, Issue 3, Sep. 2019, 8 pages.
Tsen, KT, et al., "Inactivation of viruses by coherent excitations with a low power visible femtosecond laser," Virology Journal, Jun. 2007, BioMed Central Ltd., 5 pages.
Tsen, Shaw-Wei, et al., "Chemical-free inactivated whole influenza virus vaccine prepared by ultrashort pulsed laser treatment," Journal of Biomedical Optics, vol. 20, Issue 5, May 2015, 8 pages.
Tsen, Shaw-Wei, et al., "Inactivation of enveloped virus by laser-driven protein aggregation," Journal of Biomedical Optics, vol. 17, Issue 12, Dec. 2012, 8 pages.
Tsen, Shaw-Wei, "Pathogen Reduction in Human Plasma Using an Ultrashort Pulsed Laser," PLoS One, vol. 9, Issue 11, Nov. 2014, 8 pages.
Tsen, Shaw-Wei, et al., "Prospects for a novel ultrashort pulsed laser technology for pathogen inactivation," Journal of Biomedical Science, Jul. 2012, 11 pages.
Tsen, Shaw-Wei, et al., "Studies of inactivation mechanism of non-enveloped icosahedral virus by a visible ultrashort pulsed laser," Virology Journal, vol. 11, Issue 20, Feb. 2014, BioMed Central Ltd., 9 pages.
Vatansever, Fatma, et al., "Antimicrobial strategies centered around reactive oxygen species—bactericidal antibiotics, photodynamic therapy, and beyond," FEMS Microbiology Reviews, vol. 37, Issue 6, 2013, pp. 955-989.
Wei, Xue-Min, et al., "Relationship between nitric oxide in cervical microenvironment and different HPV types and effect on cervical cancer cells," Zhonghua Fu Chan Ke Za Zhi, vol. 46, Issue 4, Apr. 2011, pp. 260-265 (Abstract Only).
Williams, Vonetta, et al., "Human Papillomavirus Type 16 E6* Induces Oxidative Stress and DNA Damage," Journal of Virology, vol. 88, Issue 12, Jun. 2014, pp. 6751-6761.
Willoughby, Jamin, "Predicting Respiratory Toxicity Using a Human 3D Airway (EpiAirway) Model Combined with Multiple Parametric Analysis," Applied In Vitro Toxicology, vol. 1, Issue 1, 2015, pp. 55-65.
Wolf, Yuri, et al., "Origins and Evolution of the Global RNA Virome," mBio, vol. 9, Issue 6, Nov. 2018, 31 pages.
Examination Report for Australian Patent Application No. 2021239894, mailed Nov. 9, 2021, 3 pages.
First Office Action for Chinese Patent Application No. 202010561507.X, mailed Oct. 19, 2021, 54 pages.
Non-Final Office Action for U.S. Appl. No. 17/410,154, mailed Nov. 8, 2021, 16 pages.
Final Office Action for U.S. Appl. No. 17/410,154, mailed Dec. 22, 2021, 15 pages.
Non-Final Office Action for U.S. Appl. No. 16/709,550, mailed Jul. 12, 2021, 12 pages.
Non-Final Office Action for U.S. Appl. No. 16/898,385, mailed Aug. 16, 2021, 12 pages.
Notice of Allowance for U.S. Appl. No. 17/117,889, mailed Aug. 30, 2021, 9 pages.
International Search Report and Written Opinion for International Patent Application No. PCT/US2023/015757, mailed Jun. 30, 2023, 14 pages.

(56) References Cited

OTHER PUBLICATIONS

Non-Final Office Action for U.S. Appl. No. 17/148,108, mailed Jul. 19, 2023, 14 pages.
Advisory Action and Examiner-Initiated Interview Summary for U.S. Appl. No. 17/148,124, mailed May 26, 2023, 5 pages.
Non-Final Office Action for U.S. Appl. No. 17/148,133, mailed Jun. 15, 2023, 9 pages.
Final Office Action for U.S. Appl. No. 17/162,259, mailed Jul. 14, 2023, 18 pages.
Advisory Action for U.S. Appl. No. 17/162,283, mailed Jun. 23, 2023, 3 pages.
Non-Final Office Action for U.S. Appl. No. 17/173,457, mailed Jun. 9, 2023, 9 pages.
Final Office Action for U.S. Appl. No. 17/201,061, mailed Jul. 26, 2023, 17 pages.
Non-Final Office Action for U.S. Appl. No. 16/898,385, mailed Jun. 7, 2022, 13 pages.
Non-Final Office Action for U.S. Appl. No. 17/410,166, mailed May 27, 2022, 11 pages.
Notice of Acceptance for Australian Patent Application No. 2021239894, mailed Jun. 15, 2022, 3 pages.
Final Office Action for U.S. Appl. No. 17/148,108, mailed Oct. 27, 2023, 15 pages.
Final Office Action for U.S. Appl. No. 17/148,133, mailed Oct. 4, 2023, 10 pages.
Advisory Action for U.S. Appl. No. 17/162,259, mailed Sep. 21, 2023, 3 pages.
Non-Final Office Action for U.S. Appl. No. 17/162,259, mailed Oct. 26, 2023, 18 pages.
Non-Final Office Action for U.S. Appl. No. 17/162,283, mailed Sep. 1, 2023, 11 pages.
Notice of Allowance and Examiner-Initiated Interview Summary for U.S. Appl. No. 17/173,457, mailed Oct. 17, 2023, 10 pages.
Non-Final Office Action for U.S. Appl. No. 17/201,061, mailed Nov. 8, 2023, 19 pages.
Advisory Action for U.S. Appl. No. 17/201,061, mailed Sep. 27, 2023, 3 pages.
Office Action for Canadian Patent Application No. 3174573, mailed Oct. 20, 2023, 4 pages.
Notice of Allowance for Brazilian Patent Application No. BR1122020024964-1, mailed Nov. 27, 2023, 4 pages.
Non-Final Office Action for U.S. Appl. No. 17/148,090, mailed Dec. 13, 2023, 12 pages.
Non-Final Office Action for U.S. Appl. No. 17/148,124, mailed Dec. 18, 2023, 24 pages.
Advisory Action for U.S. Appl. No. 17/148,133, mailed Dec. 8, 2023, 3 pages.
Author Unknown, "Visible spectrum," Wikipedia article, en.wikipedia.org/wiki/Visible_spectrum, accessed 2024, 11 pages.
Written Decision on Registration for Korean Patent Application No. 10-2022-7036254, mailed Mar. 20, 2024, 8 pages.
Final Office Action for U.S. Appl. No. 17/148,090, mailed May 6, 2024, 9 pages.
Final Office Action for U.S. Appl. No. 17/201,061, mailed Mar. 11, 2024, 20 pages.
Advisory Action for U.S. Appl. No. 17/148,108, mailed Jan. 3, 2024, 3 pages.
Applicant-Initiated Interview Summary for U.S. Appl. No. 17/148,108, mailed Jan. 23, 2024, 2 pages.
Non-Final Office Action for U.S. Appl. No. 17/148,108, mailed Feb. 20, 2024, 10 pages.
Notice of Allowance for U.S. Appl. No. 17/148,133, mailed Jan. 24, 2024, 8 pages.
Notice of Allowance for U.S. Appl. No. 17/162,283, mailed Feb. 12, 2024, 8 pages.
Notice of Allowance for U.S. Appl. No. 17/173,457, mailed Jan. 29, 2024, 10 pages.
Examination Report for European Patent Application No. 16831333.6, mailed May 7, 2024, 7 pages.
International Search Report and Written Opinion for International Patent Application No. PCT/US2024/016811, mailed May 29, 2024, 14 pages.
Final Office Action for U.S. Appl. No. 17/148,124, mailed May 28, 2024, 23 pages.
Final Office Action for U.S. Appl. No. 17/162,259, mailed May 20, 2024, 22 pages.
Notice of Allowance for U.S. Appl. No. 17/201,061, mailed Jun. 12, 2024, 10 pages.
Office Action for Canadian Patent Application No. 3174573, mailed Aug. 5, 2024, 4 pages.
Examination Report for European Patent Application No. 21713288.5, mailed Aug. 19, 2024, 4 pages.
Advisory Action for U.S. Appl. No. 17/148,090, mailed Jul. 9, 2024, 3 pages.
Notice of Allowance for U.S. Appl. No. 17/148,108, mailed Jul. 10, 2024, 8 pages.
Advisory Action and Examiner-Initiated Interview Summary for U.S. Appl. No. 17/148,124, mailed Aug. 9, 2024, 6 pages.
Advisory Action for U.S. Appl. No. 17/162,259, mailed Jul. 25, 2024, 3 pages.

\* cited by examiner

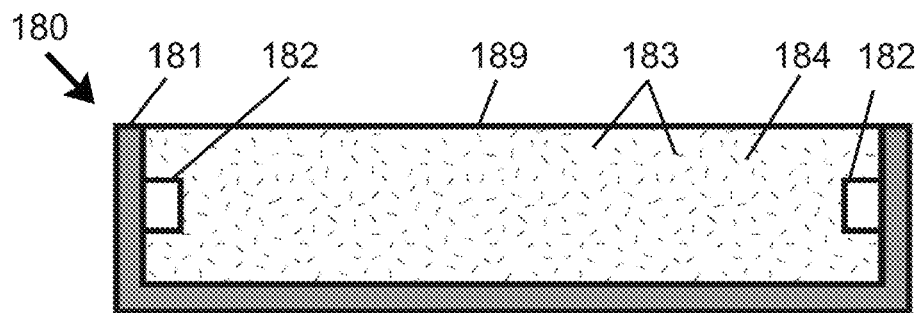
*Figure 26*
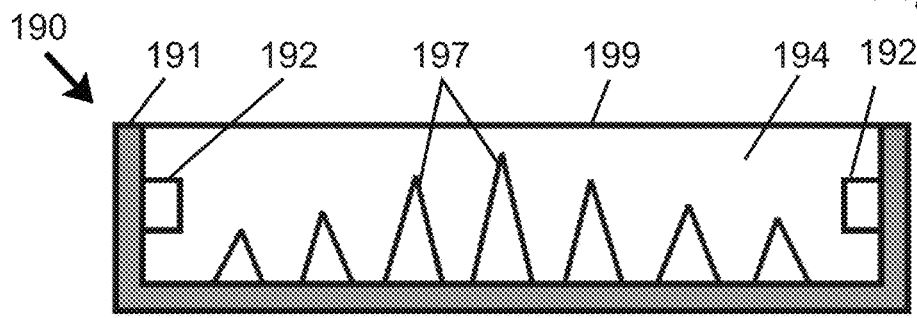
*Figure 27*
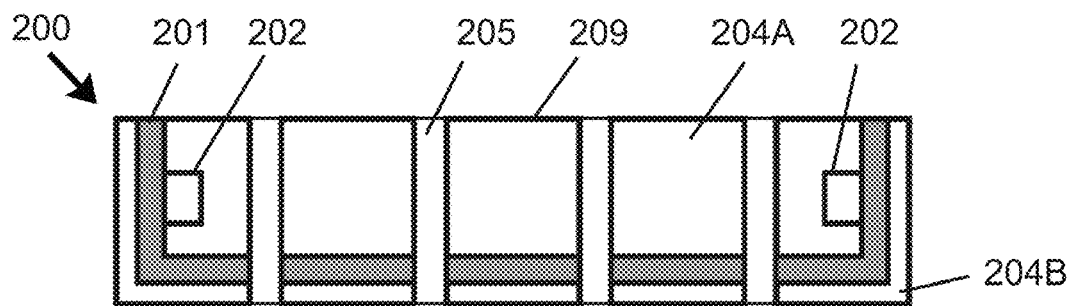
*Figure 28*
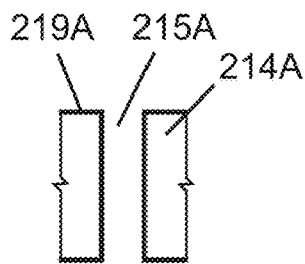 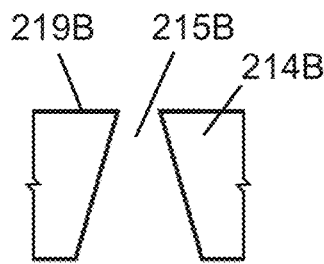 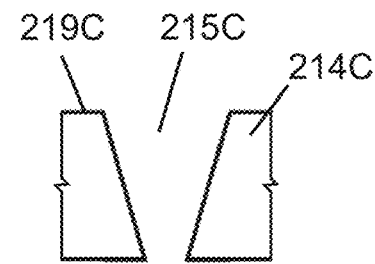
*Figure 29A*     *Figure 29B*     *Figure 29C*

Light Dose-Dependent Reduction in SARS-CoV-2 RNA at MOI 0.01

| Dose (J/cm$^2$) | 24 Hours Post-Infection ||| | 48 Hours Post-Infection ||| |
|---|---|---|---|---|---|---|---|
| | Average Cq Value | Standard Deviation of Cq | b Fold Decrease | c % Reduction | Average Cq Value | Standard Deviation of Cq | b Fold Decrease | c % Reduction |
| 0 | 18.35 | 0.90 | 1.00 | -- | 13.58 | 0.48 | 1.00 | -- |
| 7.5 | 17.99 | 0.34 | 0.78 | a 0.00 | 13.65 | 0.32 | 1.05 | 4.74 |
| 15 | 21.57 | 2.32 | 9.36 | 89.32 | 15.50 | 0.09 | 3.78 | 73.51 |
| 30 | 24.92 | 1.06 | 95.01 | 98.95 | 18.54 | 0.86 | 30.98 | 96.77 |
| 45 | 25.59 | 0.46 | 151.52 | 99.34 | 22.01 | 0.03 | 343.30 | 99.71 |
| 60 | 25.33 | 0.78 | 126.82 | 99.21 | 22.03 | 0.10 | 349.71 | 99.71 | a Values Less than 0 are Represented as 0%
b Fold Decrease Relative to 0 J/cm$^2$
c % SARS-CoV-2 Reduction Relative to 0 J/cm$^2$

*Figure 86C*

| Wavelength | MOI 0.01 | | | | MOI 0.001 | | | |
| --- | --- | --- | --- | --- | --- | --- | --- | --- |
| | CC₅₀ on Vero E6 Cells | EC₅₀ on Vero E6 Cells | SI on Vero E6 Cells | Ic₂₅ on Primary Human Trachial/ Bronchial Tissue | LTI | CC₅₀ on Vero E6 Cells | EC₅₀ on Vero E6 Cells | SI on Vero E6 Cells | Ic₂₅ on Primary Human Trachial/ Bronchial Tissue | LTI |
| 425nm | ~30.2 | ~1 | ~30 | ~157 | ~46 | ~30.2 | ~3.4 | ~9 | ~157 | ~46 |
| 450nm | >60 | ~7.2 | >8 | ~330 | ~80 | >60 | ~4.1 | >15 | ~330 | ~80 |

*Figure 95*

| SPECIES | STRAIN | PHENOTYPE | 405 nm $IC25_{405nm} = 120\ J/cm^2$ | | 425 nm $IC25_{425nm} = 160\ J/cm^2$ | |
|---|---|---|---|---|---|---|
| | | | BACTERICIDAL DOSE (J/CM²) | LTI | BACTERICIDAL DOSE (J/CM²) | LTI |
| PSEUDOMONAS AERUGINOSA | PAK | LAB STRAIN | 58 | 2.07 | 68 | 2.35 |
| PSEUDOMONAS AERUGINOSA | N0047 | MDR, CARBR, TOBRAR | 67 | 1.79 | 88 | 1.82 |
| PSEUDOMONAS AERUGINOSA | N0059 | XDR, CARBR, TOBRAR | 60 | 2.00 | 90 | 1.78 |
| PSEUDOMONAS AERUGINOSA | N0054 | MUCOID. DRUG-SUSCEPTIBLE | 53 | 2.26 | 83 | 1.93 |
| STAPHYLOCOCCUS AUREUS | N0040 | CLINICAL ISOLATE; MDR, MRSA, VANCO-S | 62 | 1.94 | >120 | <1.33 |
| STAPHYLOCOCCUS AUREUS | N0007 | MSSA; WOUND ISOLATE | >81 | <1.48 | >120 | <1.33 |
| STAPHYLOCOCCUS AUREUS | AR0215 | VISA | 60 | 2.00 | >120 | <1.33 |
| STAPHYLOCOCCUS AUREUS | AR0216 | VISA | 62 | 1.94 | >120 | <1.33 |
| HAEMOPHILUS INFLUENZAE | N0097 | RESISTANT TO CHLOR, TET, AND AMP | 18 | 6.67 | 27 | 5.93 |
| STREPTOCOCCUS PYOGENES | N0098 | ERYTHROMYCIN RESISTANT | 66 | 1.82 | 70 | 2.29 |

*Figure 104*

| STRAIN ID | SPECIES | STRAIN NAME | MUCOIDY | ANTIBIOTIC CLASSIFICATION | ANTIBIOTIC RESISTANCES | SOURCE |
|---|---|---|---|---|---|---|
| N0047 | PSEUDOMONAS AERUGINOSA | AR-BANK#0103 | NON-MUCOID | MDR | AMK-I, ATM-I, FEP-R, CAZ-R, CZA-R, CIP-R, DOR-R, GEN-R, IPM-R, LVX-R, MEM-R, TOB-R | AR ISOLATE BANK |
| N0049 | PSEUDOMONAS AERUGINOSA | PAK | NON-MUCOID | | | SCHOENFISH LAB |
| N0054 | PSEUDOMONAS AERUGINOSA | AU26773 | MUCOID | | LVX-R | BCRLR |
| N0059 | PSEUDOMONAS AERUGINOSA | AR-BANK # 0054 | NON-MUCOID | XDR | ATM-I, FEP-R, CAZ-R, CZA-R, CIP-R, DOR-I, GEN-R, IPM-R, LVX-R, MEM-R, TZP-R, TOB-R | AR ISOLATE BANK |
| N0069 | PSEUDOMONAS AERUGINOSA | AR-BANK # 0090 | NON-MUCOID | XDR | AMK-I, ATM-R, FEP-R, CAZ-R, CIP-R, C/T-R, CIP-R, DOR-R, GEN-R, IPM-R, LVX-R, MEM-R, TZP-R, TOB-R | AR ISOLATE BANK |
| N0070 | PSEUDOMONAS AERUGINOSA | AR-BANK # 0092 | NON-MUCOID | XDR | AMK-R, ATM-R, FEP-R, CAZ-R, CIP-R, DOR-R, GEN-R, IPM-R, LVX-R, MEM-R, TZP-R, TOB-R | AR ISOLATE BANK |
| N0050 | PSEUDOMONAS AERUGINOSA | AR-BANK # 0095 | NON-MUCOID | MDR | ATM-R, CIP-R, DOR-I, IPM-R, LVX-R, MEM-R, TZP-I | AR ISOLATE BANK |
| N0006 | STAPHYLOCOCCUS AUREUS | STRAIN 328; ATCC 33591 | N/A | | MRSA | SCHOENFISH LAB |
| AR-0215 | STAPHYLOCOCCUS AUREUS | | N/A | | VISA | AR ISOLATE BANK |
| AR-0216 | STAPHYLOCOCCUS AUREUS | | N/A | | VISA | AR ISOLATE BANK |
| N0098 | STREPTOCOCCUS PYOGENES | ATCC BAA-946 | N/A | | ERYTHROMYCIN-RESISTANT | ATCC |
| N0097 | HAEMOPHILUS INFLUENZAE | ATCC 33929 | N/A | | RESISTANT TO CHLORAMPHENICOL, TETRACYCLINE, AND AMPICILLIN | ATCC |

*Figure 107B*

| SPECIES | STRAIN | PHENOTYPE | BID BACTERICIDAL DOSE (J/CM2) | BID MBC DOSE (J/CM2) | BID MIC DOSE (J/CM2) |
|---|---|---|---|---|---|
| PSEUDOMONAS AERUGINOSA | N0049 | LAB STRAIN PAK | <10 | 50 | 50 |
| PSEUDOMONAS AERUGINOSA | N0047 | MDR, CARBR, TOBRAS | 30 | 20 | 20 |
| PSEUDOMONAS AERUGINOSA | N0054 | NOT MDR, CARBS, TOBRAS, MUCOID | 40 | 50 | 50 |
| PSEUDOMONAS AERUGINOSA | N0059 | XDR, CARBR, TOBRAS | 30 | 30 | 30 |
| PSEUDOMONAS AERUGINOSA | N0050 | MDR, CARBR, TOBRAS | 20 | 20 | 30 |
| PSEUDOMONAS AERUGINOSA | N0069 | XDR, CARBR, TOBRAS | 20 | 20 | 20 |
| PSEUDOMONAS AERUGINOSA | N0070 | XDR, CARBR, TOBRAS | 20 | 40 | 40 |
| PSEUDOMONAS AERUGINOSA | N0006 | 328; ATCC 33591; MRSA | 10 | >60 | >60 |
| STAPHYLOCOCCUS AUREUS | AR-0215 | VISA | 10 | >60 | >60 |
| STAPHYLOCOCCUS AUREUS | AR-0216 | VISA | 10 | >60 | >60 |

*Figure 107C*

PHOTOTHERAPEUTIC LIGHT FOR TREATMENT OF PATHOGENS

STATEMENT OF RELATED APPLICATIONS

This application claims is a continuation-in-part of U.S. patent application Ser. No. 16/898,385, filed Jun. 10, 2020, now U.S. Pat. No. 11,617,895; which is a continuation of U.S. patent application Ser. No. 16/709,550, filed on Dec. 10, 2019, now U.S. Pat. No. 11,524,173; which is a continuation of U.S. patent application Ser. No. 15/222,199, filed on Jul. 28, 2016, now U.S. Pat. No. 10,525,275; which claims the benefit of provisional patent application Ser. No. 62/197,746, filed Jul. 28, 2015, the disclosures of which is hereby incorporated herein by reference in their entireties.

This application claims the benefit of provisional patent application Ser. No. 63/123,631, filed Dec. 10, 2020, the disclosure of which is hereby incorporated herein by reference in its entirety.

This application claims the benefit of provisional patent application Ser. No. 63/084,802, filed Sep. 29, 2020, the disclosure of which is hereby incorporated herein by reference in its entirety.

This application claims the benefit of provisional patent application Ser. No. 63/074,800, filed Sep. 4, 2020, the disclosure of which is hereby incorporated herein by reference in its entirety.

This application claims the benefit of provisional patent application Ser. No. 62/987,318, filed Mar. 9, 2020, the disclosure of which is hereby incorporated herein by reference in its entirety.

TECHNICAL FIELD

The present disclosed subject matter relates generally to devices and methods for impinging light on tissue (e.g., phototherapy or light therapy) to induce one or more biological effects. Additionally, disclosed are methods and devices for delivering light as a therapeutic treatment for tissue that comes into contact with or is infected by pathogens. This disclosure additionally relates to systems and methods for phototherapeutic stimulation of nitric oxide production and/or release in tissues of mammalian subjects.

BACKGROUND

The term "phototherapy" relates to the therapeutic use of light. Various light therapies (e.g., including low level light therapy (LLLT) and photodynamic therapy (PDT)) have been publicly reported or claimed to provide various health related medical benefits—including, but not limited to: promoting hair growth; treatment of skin or tissue inflammation; promoting tissue or skin healing or rejuvenation; enhancing wound healing; pain management; reduction of wrinkles, scars, stretch marks, varicose veins, and spider veins; treating cardiovascular disease; treating erectile dysfunction; treating microbial infections; treating hyperbilirubinemia; and treating various oncological and non-oncological diseases or disorders.

Various mechanisms by which phototherapy has been suggested to provide therapeutic benefits include: increasing circulation (e.g., by increasing formation of new capillaries); stimulating the production of collagen; stimulating the release of adenosine triphosphate (ATP); enhancing porphyrin production; reducing excitability of nervous system tissues; modulating fibroblast activity; increasing phagocytosis; inducing thermal effects; stimulating tissue granulation and connective tissue projections; reducing inflammation; and stimulating acetylcholine release.

Phototherapy has also been suggested to stimulate cells to generate nitric oxide. Various biological functions attributed to nitric oxide include roles as signaling messenger, cytotoxin, antiapoptotic agent, antioxidant, and regulator of microcirculation. Nitric oxide is recognized to relax vascular smooth muscles, dilate blood vessels, inhibit aggregation of platelets, and modulate T cell-mediate immune response.

Nitric oxide is produced by multiple cell types in tissue, and is formed by the conversion of the amino acid L-arginine to L-citrulline and nitric oxide, mediated by the enzymatic action of nitric oxide synthases (NOSs). NOS is a NADPH-dependent enzyme that catalyzes the following reaction:

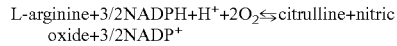

In mammals, three distinct genes encode NOS isozymes: neuronal (nNOS or NOS-I), cytokine-inducible (iNOS or NOS-II), and endothelial (eNOS or NOS-III). iNOS and nNOS are soluble and found predominantly in the cytosol, while eNOS is membrane associated. Many cells in mammals synthesize iNOS in response to inflammatory conditions.

Skin has been documented to upregulate inducible nitric oxide synthase expression and subsequent production of nitric oxide in response to irradiation stress. Nitric oxide serves a predominantly anti-oxidant role in the high levels generated in response to radiation.

Nitric oxide is a free radical capable of diffusing across membranes and into various tissues; however, it is very reactive, with a half-life of only a few seconds. Due to its unstable nature, nitric oxide rapidly reacts with other molecules to form more stable products. For example, in the blood, nitric oxide rapidly oxidizes to nitrite, and is then further oxidized with oxyhaemoglobin to produce nitrate. Nitric oxide also reacts directly with oxyhaemoglobin to produce methaemoglobin and nitrate. Nitric oxide is also endogenously stored on a variety of nitrosated biochemical structures including nitrosoglutathione (GSNO), nitrosoalbumin, nitrosohemoglobin, and a large number of nitrosocysteine residues on other critical blood/tissue proteins. The term "nitroso" is defined as a nitrosated compound (nitrosothiols (RSNO) or nitrosamines (RNNO)), via either S- or N-nitrosation. Examples of nitrosated compounds include GSNO, nitrosoalbumin, nitrosohemoglobin, and proteins with nitrosated cysteine residue. Metal nitrosyl (M-NO) complexes are another endogenous store of circulating nitric oxide, most commonly found as ferrous nitrosyl complexes in the body; however, metal nitrosyl complexes are not restricted to complexes with iron-containing metal centers, since nitrosation also occurs at heme groups and copper centers. Examples of metal nitrosyl complexes include cytochrome c oxidase (CCO-NO) (exhibiting 2 heme and 2 copper binding sites), cytochrome c (exhibiting heme center binding), and nitrosylhemoglobin (exhibiting heme center binding for hemoglobin and methemoglobin), embodying endogenous stores of nitric oxide.

FIG. 1 is a reaction sequence showing photoactivated production of nitric oxide catalyzed by iNOS, followed by binding of nitric oxide to CCO.

When nitric oxide is auto-oxidized into nitrosative intermediates, the nitric oxide is bound covalently in the body (in a "bound" state). Thus, conventional efforts to produce nitric oxide in tissue may have a limited therapeutic effect, since nitric oxide in its "gaseous" state is short-lived, and cells being stimulated to produce nitric oxide may become depleted of NADPH or L-Arginine to sustain nitric oxide production.

Viral infections pose a great challenge to human health, particularly respiratory tract infections of the Orthomyxoviridae (e.g. influenza) and Coronaviridae (e.g. SARS-CoV-2) families. Additionally, DNA viruses including the Papovaviridae family (e.g. human papillomavirus (HPV)) have extremely wide prevalence that result in low risk papillomas of the skin and high risk papillomas of mucosal epithelial tissue. Infection by the human papillomavirus (HPV) is currently the most common sexually transmitted disease (STD). While most HPV infections are asymptomatic and resolve without treatment, some infections result in warts or precancerous lesions. The presence and persistence of precancerous lesions increase the risk for a cancer developing, particularly in the cervix, vulva, vagina, penis, anus, mouth, or throat. The genotype of the HPV is significant as HPV type 16 and HPV type 18 appear to cause about 70% of cervical cancer cases. Furthermore, up to 90% of the other cancers are also linked to HPV. Fifteen HPV types are currently believed to be responsible for all cervical cancers. While HPV type 16 is most commonly associated with cervical precancerous lesions and cancerous lesions, HPV types 18, 31, 33, 35, 39, 45, 51, 52, 56, 58, 59, 66, 68, 73, and 82 are also implicated in cervical cancer. When affecting the cervix, the precancerous lesions are referred to as cervical dysplasia. It is estimated that there are around 500,000 patients per year in the United States surgically treated for cervical dysplasia. Conventional management of cervical dysplasia calls for colposcopy with endocervical sampling which allows the dysplasia to be rated as cervical intraepithelial neoplasia I, II or III (CIN I, II, or III). With CIN I and a satisfactory colposcopy, one approach is to "watch and wait" to determine whether the condition worsens over 6 months to a year as determined by colposcopy. Another approach is to perform an invasive (e.g. surgical) treatment involving the cervix. Commonly used treatment methods include medication, electro-cauterization, cryosurgery, laser vaporization, and surgery. Cryotherapy involves cooling cervical tissue to sub-zero temperature which results in freezing. While simple and relatively inexpensive, abnormal cells below the surface are untreated making the approach unsuitable for large or severe dysplasia. Loop excision, LEEP (loop electrosurgical excision procedure), is a treatment that uses a loop of wire to remove infected tissue. The wire loop is electrically energized to facilitate removal of abnormal portions of the cervix. Cramping and bleeding are common side-effects. A cone biopsy involves removal of tissue from the cervix and the endocervical canal, performed conventionally or using a laser. Bleeding and pain are common after the procedure, which is typically done under anesthesia. A hysterectomy may also be done to resolve the infection, but it is a major surgical procedure unsuitable for women who wish to become pregnant in the future. The goal of these procedures is to remove those abnormal cells from the cervix. Cervical cancer has been reported to have a global survival rate of about 52%. A non-surgical treatment that reduced or eradicated HPV viral infections could have a significant impact on women's health.

SUMMARY

Aspects of the present disclosure relate to devices and methods for impinging light on a tissue, for example within a body of a patient, where the light may include at least one characteristic that exerts or induces at least one biological effect within or on the tissue. Biological effects may include at least one of inactivating and inhibiting growth of one or more combinations of microorganisms and pathogens, including but not limited to viruses, bacteria, fungi, and other microbes, among others. Biological effects may also include one or more of upregulating a local immune response, stimulating enzymatic generation of nitric oxide to increase endogenous stores of nitric oxide, releasing nitric oxide from endogenous stores of nitric oxide, and inducing an anti-inflammatory effect. Wavelengths of light may be selected based on at least one intended biological effect for one or more of the targeted tissue and the targeted microorganisms or pathogens. In certain aspects, wavelengths of light may include visible light in any number of wavelength ranges based on the intended biological effect. Further aspects involve light impingement on tissue for multiple microorganisms and/or multiple pathogenic biological effects, either with light of a single peak wavelength or a combination of light with more than one peak wavelength. Devices and methods for light treatments are disclosed that provide light doses for inducing biological effects on various targeted pathogens and targeted tissues with increased efficacy and reduced cytotoxicity. Light doses may include various combinations of irradiances, wavelengths, and exposure times, and such light doses may be administered continuously or discontinuously with a number of pulsed exposures.

Because of the relative costs, both economically and on the health and well-being of patients, new treatments to inhibit or eradicate viral infections in tissues, particularly the mucosal epithelial surfaces like the cervix, mouth, nose, throat and anus, are greatly needed. Such treatments and devices therefore are provided for herein.

Phototherapy has attracted significant attention as a therapeutic treatment for various maladies and conditions. Devices for delivering phototherapy to inhibit or eradicate viral infections and methods of using the same are disclosed herein. Irradiances of light represented in milliwatts per square centimeter ($mW/cm^2$) have been proposed at a specific wavelength for a threshold time over a given duration to yield therapeutic dosages represented in joules per square centimeter ($J/cm^2$) which are effective for inactivating viruses or treating viral infections while maintaining the viability of epithelial tissues. These treatments can be tailored to the particular tissue being treated, as well as to the various fluids in the media, such as blood, sputum, saliva, cervical fluid, and mucous. The total dosage ($J/cm^2$) to treat an infection can be spread out over multiple administrations, with each dose applied over seconds or minutes, and with multiple doses over days or weeks, at individual doses that treat the infection while minimizing damage to the particular tissue.

Certain aspects of the disclosure relate to phototherapeutic modulation of nitric oxide in living mammalian tissue, including use of light having a first peak wavelength and a first radiant flux to release nitric oxide from endogenous stores of nitric oxide, and use of light having a second peak wavelength and a second radiant flux to stimulate enzymatic generation of nitric oxide to increase endogenous stores of nitric oxide, wherein the second peak wavelength differs from the first peak wavelength.

In a first aspect, the disclosure relates to a method of modulating nitric oxide in living mammalian tissue. The method includes impinging light having a first peak wavelength on the tissue at a first radiant flux, wherein the first peak wavelength and the first radiant flux are selected to stimulate enzymatic generation of nitric oxide to increase endogenous stores of nitric oxide. The method further includes impinging light having a second peak wavelength on the tissue at a second radiant flux, wherein the second peak wavelength and the second radiant flux are selected to release nitric oxide from the endogenous stores, wherein the second peak wavelength is greater than the first peak wavelength by at least 25 nm, by at least 50 nm, or another threshold specified herein. In certain embodiments, each of the first radiant flux and the second radiant flux is in a range of from 5 mW to 60 mW.

In certain embodiments, the enzymatic generation of nitric oxide is mediated by iNOS, nNOS, and/or eNOS in or proximate to the tissue. In certain embodiments, the endogenous stores of nitric oxide comprise nitrosoglutathione, nitrosoalbumin, nitrosohemoglobin, nitrosothiols, nitrosamines, and/or metal nitrosyl complexes in or proximate to the tissue.

In certain embodiments, the method further includes sensing a temperature condition on or proximate to (a) a therapeutic device arranged to emit at least one of the light having the first peak wavelength or the light having the second peak wavelength, or (b) the tissue; generating at least one signal indicative of the temperature condition; and controlling at least one of the following items (i) or (ii) responsive to the at least one signal: (i) impingement of light having the first peak wavelength on the tissue, or (ii) impingement of light having the second peak wavelength on the tissue.

In another aspect, the disclosure relates to a device for modulating nitric oxide in living mammalian tissue. The device includes means for impinging light having a first peak wavelength on the tissue at a first radiant flux, wherein the first peak wavelength and the first radiant flux are selected to stimulate enzymatic generation of nitric oxide to increase endogenous stores of nitric oxide. The device further includes means for impinging light having a second peak wavelength on the tissue at a second radiant flux, wherein the second peak wavelength and the second radiant flux are selected to release nitric oxide from the endogenous stores, wherein the second peak wavelength is greater than the first peak wavelength by at least 25 nm.

In certain embodiments, the device further includes means for sensing a temperature condition on or proximate to (a) the device or (b) the tissue; means for generating at least one signal indicative of the temperature condition; and means for controlling at least one of the following items (i) or (ii) responsive to the at least one signal: (i) impingement of light having the first peak wavelength on the tissue, or (ii) impingement of light having the second peak wavelength on the tissue.

In another aspect, the disclosure relates to another device for modulating nitric oxide in living mammalian tissue. The device includes at least one first light emitting device configured to impinge light having a first peak wavelength on the tissue at a first radiant flux, wherein the first peak wavelength and the first radiant flux are selected to release nitric oxide from endogenous stores of nitric oxide. The device further includes at least one second light emitting device configured to impinge light having a second peak wavelength on the tissue at a second radiant flux, wherein the second peak wavelength and the second radiant flux are selected to stimulate enzymatic generation of nitric oxide to increase endogenous stores of nitric oxide, wherein the second peak wavelength exceeds the first peak wavelength by at least 25 nm, at least 50 nm, or another threshold specified herein. In certain embodiments, the device further includes driver circuitry configured to drive the at least one first light emitting device and the at least one second light emitting device. In certain embodiments, each of the first radiant flux and the second radiant flux is in a range of from 5 mW to 60 mW.

In certain embodiments, the device further includes at least one third light emitting device configured to impinge light having a third peak wavelength on the tissue, wherein the third peak wavelength differs from each of the first peak wavelength and the second peak wavelength by at least 10 nm.

In certain embodiments, the device further includes a temperature sensor arranged to sense a temperature condition on or proximate to at least one of (a) a portion of the device or (b) the tissue, wherein at least one of initiation of operation, deviation of operation, or termination of operation of any of (i) the at least one first light emitting device or (ii) the at least one second light emitting device is responsive to an output signal of the temperature sensor.

In certain embodiments, the device further includes a flexible substrate supporting the at least one first light emitting device and the at least one second light emitting device.

In certain embodiments, the device further includes a light-transmissive (e.g., encapsulant) material layer covering the at least one first light emitting device, the at least one second light emitting device, and at least a portion of the flexible substrate.

In certain embodiments, the device further includes a plurality of holes defined in the flexible substrate and the light-transmissive material layer, wherein the plurality of holes are arranged to permit transit therethrough of at least one of air, vapor, or exudate.

In certain embodiments, the device is configured to contact, be connected to, or conform to a skin or other tissue of a patient with at least a portion of the light-transmissive material layer arranged in contact with the skin or other tissue of the patient. In other embodiments, the device is configured to be spatially separated from a targeted irradiation area, such as being arranged not to contact tissue of the patient.

In certain embodiments, the device further includes a substantially rigid substrate supporting the at least one first light emitting device and the at least one second light emitting device, wherein at least a portion of the device is configured for insertion into a body cavity of a patient.

In certain embodiments, the device further includes at least one waveguide arranged between (i) the tissue and (ii) at least one of the at least one first light emitting device or the at least one second light emitting device.

In certain embodiments, the device further includes a light scattering material, a textured light scattering surface, or a patterned light scattering surface arranged between (i) the tissue and (ii) at least one of the at least one first light emitting device or the at least one second light emitting device.

In certain embodiments, the device further includes an energy storage element arranged to supply power to the driver circuitry.

In another aspect, the disclosure relates to a device for delivering light energy to tissue of a patient. The device includes at least one first solid state light emitting device configured to impinge light having a first peak wavelength on the tissue. The device further includes at least one second solid state light emitting device configured to impinge light having a second peak wavelength on the tissue. The device additionally includes driver circuitry configured to drive the at least one first solid state light emitting device and the at least one second solid state light emitting device. The first peak wavelength and the second peak wavelength are selected from one of the following combinations (a) to (g): (a) the first peak wavelength is in a range of from 410 nm to 490 nm and the second peak wavelength is in a range of from 500 nm to 600 nm; (b) the first peak wavelength is in a range of from 620 nm to 640 nm and the second peak wavelength is in a range of from 650 nm to 670 nm; (c) the first peak wavelength is in a range of from 520 nm to 540 nm and the second peak wavelength is in a range of from 650 nm to 670 nm; (d) the first peak wavelength is in a range of from 400 nm to 420 nm and the second peak wavelength is in a range of from 620 nm to 640 nm; (e) the first peak wavelength is in a range of from 400 nm to 420 nm and the second peak wavelength is in a range of from 650 nm to 670 nm; (f) the first peak wavelength is in a range of from 400 nm to 420 nm and the second peak wavelength is in a range of from 495 nm to 515 nm; or (g) the first peak wavelength is in a range of from 400 nm to 420 nm and the second peak wavelength is in a range of from 516 nm to 545 nm. In certain embodiments, the first peak wavelength is in a range of from 400 nm to 420 nm and the second peak wavelength is in a range of from 525 nm to 535 nm.

In certain embodiments, the device further includes a temperature sensor arranged to sense a temperature condition on or proximate to at least one of (a) a portion of the device or (b) the tissue, wherein at least one of initiation of operation, deviation of operation, or termination of operation of at least one of (i) the at least one first solid state light emitting device or (ii) the at least one second solid state light emitting device is responsive to an output signal of the temperature sensor.

In another aspect, the disclosure relates to a method of modulating nitric oxide in living mammalian tissue, the method comprising: impinging light on the tissue, wherein the light impinged on the tissue comprises incoherent light emissions including a first peak wavelength in a range of from 410 nm to 440 nm and a first radiant flux, and wherein the first peak wavelength and the first radiant flux are selected to stimulate at least one of (i) enzymatic generation of nitric oxide to increase endogenous stores of nitric oxide or (ii) release of nitric oxide from endogenous stores of nitric oxide; wherein the light impinged on the tissue is substantially devoid of light emissions having a peak wavelength in a range of from 600 nm to 900 nm.

In certain embodiments, the light impinged on the tissue is devoid of emissions of any wavelength conversion material stimulated by incoherent light emissions including a first peak wavelength in a range of from 410 nm to 440 nm. In certain embodiments, the tissue is devoid of an applied or received photosensitive therapeutic compound or agent. In certain embodiments, at least 65% (or at least 80%, or at least 90%) of a fluence of light impinged on the tissue consists of the incoherent light emissions including a first peak wavelength in a range of from 410 to 440 nm. In certain embodiments, the light impinged on the tissue is substantially devoid of light emissions having a peak wavelength in a range of from 441 nm to 490 nm. In certain embodiments, the incoherent light emissions including a first peak wavelength in a range of from 410 nm to 440 nm are provided as a plurality of discrete pulses. In certain embodiments, the light impinged on the tissue further comprises incoherent light emissions including a second peak wavelength in a range of from 500 nm to 540 nm. In certain embodiments, the incoherent light emissions including a first peak wavelength in a range of from 410 nm to 440 nm are impinged on the tissue during a first time window, the incoherent light emissions including a second peak wavelength in a range of from 500 nm to 540 nm are impinged on the tissue during a second time window, and at least a portion of the second time window is non-overlapping with the first time window. In certain embodiments, the first peak wavelength and the first radiant flux are selected to release endogenous stores of nitric oxide. In certain embodiments, the second peak wavelength and the second radiant flux are selected to stimulate enzymatic generation of nitric oxide to increase endogenous stores of nitric oxide. In certain embodiments, the tissue comprises at least one of epithelial tissue, mucosal tissue, bone, connective tissue, muscle tissue, or cervical tissue. In certain embodiments, the tissue comprises dermal tissue. In certain embodiments, a method further comprises sensing a temperature condition on or proximate to (a) a therapeutic device arranged to impinge light on the tissue, or (b) the tissue; generating at least one signal indicative of the temperature condition; and controlling impingement of light on the tissue responsive to the at least one signal. In certain embodiments, the light impinged on the tissue comprises a fluence of from about 0.5 $J/cm^2$ to about 100 $J/cm^2$, or from about 5 $J/cm^2$ to about 50 $J/cm^2$.

In another aspect, the disclosure relates to a device for modulating nitric oxide in living mammalian tissue, the device comprising: an ambient light blocking element; and at least one first light emitting element positioned between the ambient light blocking element and the tissue, wherein the at least one first light emitting element is configured to impinge incoherent light on the tissue, said incoherent light having a first peak wavelength and a first radiant flux, wherein the first peak wavelength and the first radiant flux are selected to stimulate at least one of (i) enzymatic generation of nitric oxide to increase endogenous stores of nitric oxide or (ii) release of nitric oxide from endogenous stores of nitric oxide; wherein the device is substantially devoid of any light emitting element configured to impinge light on the tissue, said light having a peak wavelength in a range of from 600 nm to 900 nm.

In certain embodiments, the device is substantially devoid of any light emitting element configured to impinge light having a peak wavelength in a range of from 441 nm to 490 nm on the tissue. In certain embodiments, the device is devoid of any wavelength conversion material configured to be stimulated by the at least one first light emitting element. In certain embodiments, the device further comprises a flexible substrate supporting the at least one first light emitting element. In certain embodiments, the device is configured to contact, be connected to, or conform to the tissue with a light-transmissive material. In certain embodiments, light impinged on the tissue is substantially devoid of light emissions having a peak wavelength in a range of from 441 nm to 490 nm. In certain embodiments, the device further comprises driver circuitry configured to generate incoherent light emissions including the first peak wavelength, wherein the first peak wavelength is in a range of from 410 nm to 440 nm, and said incoherent light emissions comprise a plurality of discrete pulses.

In certain embodiments, the device further comprises at least one second light emitting element configured to impinge incoherent light on the tissue, said incoherent light having a second peak wavelength and a second radiant flux, wherein the second peak wavelength is in a range of from 500 nm to 540 nm. In certain embodiments, the device is configured to impinge incoherent light emissions including the first peak wavelength during a first time window, wherein the first peak wavelength is in a range of from 410 nm to 440 nm, and being configured to impinge incoherent light emissions including the second peak wavelength in a range of from 500 nm to 540 nm during a second time window, wherein at least a portion of the second time window is non-overlapping with the first time window. In certain embodiments, the device further comprises a probe configured for insertion into a mammalian body cavity or opening defined in a mammalian body, wherein the at least one first light emitting element is supported by the probe.

In another aspects, devices and/or methods disclosed herein may be used to modulate nitric oxide for managing or eliminating pathogens (such as bacteria, viruses, fungi, protists, or the like) in or on mammalian tissue. In additional aspects, devices and/or methods disclosed herein may be used to modulate nitric oxide for inhibiting 5$a$-reductase in mammalian tissue. In additional aspects, devices and/or methods disclosed herein may be used to modulate nitric oxide to promote collagen synthesis. In additional aspects, devices and/or methods disclosed herein may be used to increase NO to levels suitable to induce cell death. In further aspects, devices and/or methods disclosed herein may be used for generation of, or promoting reaction with, reactive oxygen species and free radicals. In additional aspects, devices and/or methods disclosed herein may be used to increase vasodilation and decrease inflammation.

In illustrative embodiments, provided is a method for treating a viral-infected tissue, the method comprises irradiating the tissue with a light from a light source with a particular dose ($J/cm^2$), and repeating the irradiating step for N iterations to constitute a treatment duration, wherein N is an integer greater than 1. In one embodiment, the method comprises delivering a light dosage of at least about 10 $J/cm^2$ per day. In another embodiment, the method comprises delivering a light dosage of between about 10 to about 100 $J/cm^2$ per day. In certain examples, N is between 2 and 21 and the irradiating step could occur once, twice, or thrice a day. In some embodiments, N is 10 or greater. As an example, the period of time could be for 1 to about 10 minutes. In other embodiments, repeating occurs at least daily for at least 3 days. In still other embodiments, the period of time is at greater than 10 minutes, irradiating occurs at least twice daily for at least 3 days.

In preferred embodiments, the light source, such as laser light, LED light, OLED light, and the like, any of which can be pulsed, is visible light ranging from 400 to 700 nm that provides minimal damage to epithelial tissue. In one illustrative embodiment, the light source includes an LED with a spectral maximum between about 420 nm and about 430 nm. In another embodiment, the light source or the light therefrom is devoid of emissions of any wavelength conversion material stimulated by the incoherent light emissions including a first peak wavelength in a range of from 410 nm to 440 nm. In another embodiment, the tissue is devoid of an applied or received photosensitive therapeutic compound or agent. In another embodiment, at least 65% of a fluence of light irradiating the tissue consists of the incoherent light emissions including a first peak wavelength in a range of from 410 to 440 nm. In another embodiment, the light source or the light therefrom is substantially devoid of light emissions having a peak wavelength in a range of from 441 nm to 490 nm.

Embodiments of antiviral phototherapy detailed in this disclosure can be effective against both DNA and RNA virus infections. According to some embodiments, provided herein are methods of treating and/or preventing a viral infection. A method of treating and/or preventing a viral infection may comprise administering light to the skin of a subject, thereby treating and/or preventing the viral infection in the subject. In some embodiments, a method may suppress and/or inhibit viral replication of a virus and/or enhance the local immune response of a subject. In some embodiments, a method of treating and/or preventing a virus-related gastrointestinal condition may comprise administering light via colorectal administration via a probe inserted into the body cavity of a subject, thereby treating and/or preventing the virus-related colorectal or intestinal condition in the subject. Viruses in the GI tract include rotavirus, picornavirus, and coronavirus. In other embodiments, a method of treating and/or preventing a virus-related central nervous system (CNS) infection may comprise administering light transcranially, through the nose of a patient, or upon implantation of a light source into the tissue of a subject, thereby treating and/or preventing the virus-related CNS condition in the subject. In specific embodiments, intranasal administration to the nasal mucosa can be used as a method of treating and/or preventing a virus-related infection. According to other embodiments, a method of treating and/or preventing a virus-related bloodstream infection may comprise transdermal administration of light to superficial vasculature, administering light to blood passed through an extra-corporeal loop, shining light on a blood product derived from the patient for use on other patients, and other methods for illumination of biological fluids of a subject, thereby treating and/or preventing the virus-related blood stream infection in the subject. In other embodiments, the light is applied external to the body to the joints including those in the feet and hands, as well as the ankles, elbows, knees, and shoulders as a method of treating and/or preventing a joint arthritis related to side effects caused by autoimmune reactions to viruses.

Further embodiments of the present disclosure describe an intravaginal light delivery device configured for delivering illumination to treatment areas in and around a cervix, the device comprising a cylindrical shaft removably inserted within a flexible light cover having a light transmission portion, wherein, the cylindrical shaft comprises a light source and control hardware therefore being oriented to transmit light in an axial direction from the cylindrical shaft, and the flexible light cover is a hollow cylinder having an inside diameter matched to an outer diameter of the cylindrical shaft so that sliding the flexible light cover over the cylindrical shaft nests the cylindrical shaft within so that the light source is positioned to transmit light through a light transmission portion.

In one embodiment, the light source comprises an LED with a spectral maximum between about 420 nm and about 430 nm. In another embodiment, the light source is devoid of emissions of any wavelength conversion material stimulated by the incoherent light emissions including a first peak wavelength in a range of from 410 nm to 440 nm. In one embodiment, the light source provides at least 65% of a fluence of light having a first peak wavelength in a range of from 410 to 440 nm. In another embodiment, the light source is substantially devoid of light emissions having a peak wavelength in a range of from 441 nm to 490 nm. In yet another embodiment, the light source delivers a radiant flux of 5 mW to 60 mW. In other embodiments, the light source has at least one of the following features: a light output of between 1 and 15 $J\ cm^{-2}\ min^{-1}$, a first peak wavelength between about 410 and 440 nm with a full width half maximum (FWHM) of less than about 20 nm, is substantially devoid of ultraviolet radiation emissions, is substantially devoid of light emissions having a peak wavelength in a range of from 441 to 490 nm, or is capable of delivering about 100 $J\ cm^{-2}$ in 10 minutes, 30 minutes, 1 hour, or 4 hours. In illustrative embodiments, the intravaginal light delivery device further includes a battery or power supply capable of delivering about 100 J cm$^{-2}$ in 10 minutes, 30 minutes, 1 hour, or 4 hours.

In illustrative embodiments, the intravaginal light delivery device includes a flexible light cover with a treatment cup disposed about the light transmission portion. In another embodiment, the flexible light cover further comprises a cervical probe configured to spread cervical surfaces such that the cervical probe extends within the cervix, the cervical probe being configured to transmit light. In another embodiment, the flexible light cover includes a reversibly extendible cup. In another embodiment, the treatment cup is asymmetric. As such, the treatment cup may be non-axially oriented to provide light delivery at an angle of greater than about 5 degrees from an axis defined by the center of the cylindrical shaft.

In another aspect, a method comprises: providing a light source configured to emit light comprising a first light characteristic; and irradiating mammalian tissue within a body with the light to induce a biological effect, wherein the biological effect comprises altering a concentration of one or more pathogens within the body and altering growth of the one or more pathogens within the body. In certain embodiments, the first light characteristic comprises at least one of a first peak wavelength and a radiant flux. In certain embodiments, the first light characteristic is the first peak wavelength and the first peak wavelength is in a range from 400 nanometers (nm) to 900 nm, or in a range from 400 nm to 450 nm, or in a range from 410 nm to 440 nm. In certain embodiments, less than 5% of the light is in a wavelength range that is less than 400 nm. In certain embodiments, a full width half maximum of the first peak wavelength is less than or equal to 100 nm, or less than or equal to 40 nm. In certain embodiments, the first light characteristic is the radiant flux and the radiant flux is in a range from 5 milliwatts (mW) to 5000 mW. In certain embodiments, the radiant flux is configured to provide an irradiance to the tissue in a range from 5 mW per square centimeter (mW/cm$^2$) to 200 mW/cm$^2$.

In certain embodiments, the biological effect comprises inactivating the one or more pathogens that are in a cell-free environment in the body and inhibiting replication of the one or more pathogens that are in a cell-associated environment in the body. In certain embodiments, the biological effect further comprises upregulating a local immune response within the body. In certain embodiments, the biological effect comprises stimulating at least one of enzymatic generation of nitric oxide to increase endogenous stores of nitric oxide and releasing nitric oxide from endogenous stores of nitric oxide.

In certain embodiments, impinging light to the tissue within the body comprises administering a dose of light in a range from 0.5 joules per square centimeter (J/cm$^2$) to 100 J/cm$^2$, or in a range from 2 J/cm$^2$ to 50 J/cm$^2$. In certain embodiments, administering the dose of light comprises providing light with an irradiance to the tissue that is in a range from 5 mW/cm$^2$ to 200 mW/cm$^2$ over a time period in a range from 10 seconds to 1 hour. In certain embodiments, the irradiance is delivered in a continuous manner. In certain embodiments, the irradiance is delivered in a plurality of discrete pulses. In certain embodiments, the plurality of discrete pulses comprises a plurality of equal pulses that is delivered during the time period. In certain embodiments, the plurality of discrete pulses comprises a plurality of dissimilar pulses that is delivered during the time period In certain embodiments, the dose of light is repeatably administered to provide a cumulative dose in a range from 1 J/cm$^2$ to 1000 J/cm$^2$ over a cumulative time period. In certain embodiments, the dose of light is in a range from 0.5 J/cm$^2$ to 50 J/cm$^2$ and the dose of light is repeatably administered at least two times over the cumulative time period. In certain embodiments, administering the dose of light comprises providing light with an irradiance in a range from 0.1 mW/cm$^2$ to 10 watts per square centimeter (W/cm$^2$) over a time period in a range from 10 seconds to 1 hour, wherein the irradiance is delivered in a plurality of discrete pulses.

In certain embodiments, impinging light to the tissue within the body comprises administering a dose of light with a light therapeutic index of greater than or equal to 2, the light therapeutic index being defined as a dose concentration that reduces tissue viability by 25% divided by a dose concentration that reduces cellular percentage of the pathogens by 50%. In certain embodiments, light therapeutic index is in a range from 2 to 250.

In certain embodiments, the one or more pathogens comprise at least one of a virus, a bacteria, and a fungus. In certain embodiments, the one or more pathogens comprise coronaviridae. In certain embodiments, the one or more pathogens comprise orthomyxoviridae. In certain embodiments, one or more pathogens comprise at least two types of viruses. In certain embodiments, the one or more pathogens comprise coronaviridae and orthomyxoviridae.

In certain embodiments, the light is provided by at least one of a light-emitting diode, an organic light-emitting diode, and a laser.

In certain embodiments, the tissue comprises mucosal epithelial tissue. In certain embodiments, the light is provided at a tissue depth of less than or equal to 2.5 mm.

In certain embodiments, the first light characteristic is a first peak wavelength and the first peak wavelength is in a range from 400 nm to 900 nm and the light further comprises a second peak wavelength that is in a range from 400 nm to 900 nm, wherein the second peak wavelength differs from the first peak wavelength by at least 10 nm. In certain embodiments, a full width half maximum of the second peak wavelength is less or equal to 100 nm. In certain embodiments, impinging light to the tissue within the body comprises administering first dose of light and a second dose of light for a single type of microorganism.

In another aspect, a method comprises: providing light comprising a first peak wavelength and a second peak wavelength; and irradiating mammalian tissue with the light; wherein the first peak wavelength differs from the second wavelength by at least 5 nm, the first peak wavelength is configured to induce a first biological effect, and the second peak wavelength is configured to induce a second biological effect that is different than the first biological effect. In certain embodiments, the first biological effect and the second biological effect comprise different ones of inactivating pathogens that are in a cell-free environment, inhibiting replication of pathogens that are in a cell-associated environment, upregulating a local immune response, stimulating enzymatic generation of nitric oxide to increase endogenous stores of nitric oxide, releasing nitric oxide from endogenous stores of nitric oxide, and inducing an anti-inflammatory effect. In certain embodiments, the first peak wavelength is in a range from 400 nm to 900 nm and the second peak wavelength is in a range from 400 nm to 900 nm. In certain embodiments, the first peak wavelength is in a range from 400 nm to 490 nm and the second peak wavelength is in a range from 490 nm to 900 nm. In certain embodiments, the first peak wavelength is in a range from 400 nm to 490 nm and the second peak wavelength is in a range from 320 nm to 400 nm. In certain embodiments, the first peak wavelength is a range of from 410 nm to 440 nm. In certain embodiments, the light further comprises a third peak wavelength that is configured to induce a third biological effect that is different than the first biological effect and the second biological effect, wherein: the first peak wavelength is in a range from 400 nm to 490 nm; the second peak wavelength is in a range from 490 nm to 900 nm; and the third peak wavelength is in a range from 200 nm to 400 nm.

In certain embodiments, impinging light to the tissue comprises administering the first peak wavelength in a first time window and the second peak wavelength in a second time window. In certain embodiments, the first time window is the same as the second time window. In certain embodiments, the first time window is different than the second time window. In certain embodiments, the first time window overlaps with the second time window. In certain embodiments, the first time window is non-overlapping with the second time window.

In another aspect, a method comprises: providing a first dose of light to mammalian tissue that is configured to induce a first biological effect for a first pathogen; and providing a second dose of light to the mammalian tissue that is configured to induce a second biological effect for at least one of the first pathogen and a second pathogen, wherein the first pathogen is different than the second pathogen. In certain embodiments, the first biological effect comprises at least one of inactivating the first pathogen in a cell-free environment, inhibiting replication of the first pathogen in a cell-associated environment, upregulating a local immune response in the mammalian tissue, stimulating enzymatic generation of nitric oxide to increase endogenous stores of nitric oxide in the mammalian tissue, releasing nitric oxide from endogenous stores of nitric oxide in the mammalian tissue, and inducing an anti-inflammatory effect in the mammalian tissue. In certain embodiments, the second biological effect comprises at least one of inactivating the second pathogen in a cell-free environment, inhibiting replication of the second pathogen in a cell-associated environment, upregulating a local immune response in the mammalian tissue, stimulating enzymatic generation of nitric oxide to increase endogenous stores of nitric oxide in the mammalian tissue, releasing nitric oxide from endogenous stores of nitric oxide in the mammalian tissue, and inducing an anti-inflammatory effect in the mammalian tissue. In certain embodiments, the first pathogen comprises at least one of a virus, a bacteria, and a fungus and the second pathogen comprises a different one of a virus, a bacteria, and a fungus.

In certain embodiments, the first dose of light is administered with a first light therapeutic index of greater than or equal to 2, the first light therapeutic index being defined as a dose concentration of the first dose that reduces viability of the mammalian tissue by 25% divided by a dose concentration of the first dose that reduces cellular percentage of the first pathogen by 50%; and the second dose of light is administered with a second light therapeutic index of greater than or equal to 2, the second light therapeutic index being defined as a dose concentration of the second dose that reduces viability of the mammalian tissue by 25% divided by a dose concentration of the second dose that reduces cellular percentage of the second pathogen by 50%. In certain embodiments, the first light therapeutic index and the second light therapeutic index are both in a range from 2 to 250.

In certain embodiments, the first dose of light comprises a first peak wavelength in a range from 400 nm to 490 nm, and the second dose of light comprises a second peak wavelength in a range from 490 nm to 900 nm. In certain embodiments, the first dose of light comprises a first peak wavelength in a range from 400 nm to 490 nm, and the second dose of light comprises a second peak wavelength in a range from 320 nm to 400 nm. In certain embodiments, each of the first dose of light and the second dose of light are in a range from 0.5 $J/cm^2$ to 100 $J/cm^2$. In certain embodiments, the first dose of light and the second dose of light are repeatably administered to provide a cumulative dose in a range from 1 $J/cm^2$ to 1000 $J/cm^2$. In certain embodiments, the first dose of light comprises a first peak wavelength in a range from 410 nm to 440 nm.

In another aspect, an illumination device comprises: at least one light source arranged to impinge light on mammalian tissue within a body, the light comprising a first light characteristic and configured to induce a biological effect; and driver circuitry configured to drive the at least one light source; wherein the biological effect comprises altering a concentration of one or more pathogens within the body and altering growth of the one or more pathogens within the body. In certain embodiments, the illumination device further comprises an optic that is arranged to pass the light from the at least one light source for irradiating the mammalian tissue within the body. In certain embodiments, the optic is further arranged in optical communication with a camera for viewing the mammalian tissue within the body. In certain embodiments, the optic resides on an illumination head of the illumination device and the illumination head is angled from a lengthwise direction of the illumination device. In certain embodiments, the illumination head is removably attached to the illumination device. In certain embodiments, the illumination device further comprises a light guide that is arranged between the optic and the at least on light source. In certain embodiments, the illumination device further comprises a protective covering that comprises a same material as the optic. In certain embodiments, the illumination device is configured to be user controlled.

In certain embodiments, the illumination device is configured to be at least partially inserted within a body cavity, wherein the mammalian tissue is included within the body cavity. In certain embodiments, the at least one light source is arranged outside of the body cavity when the illumination device is partially inserted within the body cavity. In certain embodiments, the at least one light source is arranged within the body cavity when the illumination device is partially inserted within the body cavity. In certain embodiments, the illumination device is configured to be fully inserted within a body cavity, wherein the mammalian tissue is included within the body cavity. In certain embodiments, the illumination device further comprises a cable that is configured to retrieve the illumination device from the body cavity.

In certain embodiments, the illumination device further comprises a microcontroller that is configured to control the driver circuitry. In certain embodiments, the microcontroller is further configured to receive an input from at least one sensor for controlling the at least one light source. In certain embodiments, the at least one sensor comprises one or more of a temperature sensor and a proximity sensor.

In certain embodiments, the biological effect further comprises upregulating a local immune response within the body. In certain embodiments, the biological effect comprises stimulating at least one of enzymatic generation of nitric oxide to increase endogenous stores of nitric oxide and releasing nitric oxide from endogenous stores of nitric oxide. In certain embodiments, the biological effect comprises inactivating the one or more pathogens that are in a cell-free environment within the body. In certain embodiments, the biological effect comprises inhibiting replication of the one or more pathogens that are in a cell-associated environment within the body.

In certain embodiments, impinging the light on the mammalian tissue within the body comprises administering a dose of light in a range from 0.5 J/cm$^2$ to 100 J/cm$^2$. In certain embodiments, the first light characteristic comprises at least one of a first peak wavelength and a radiant flux. In certain embodiments, the first light characteristic is the first peak wavelength and the first peak wavelength is in a range from nm to 900 nm. In certain embodiments, the first peak wavelength is in a range from 410 nm to 440 nm. In certain embodiments, the light further comprises a second peak wavelength in a range from 400 nm to 900 nm, and the second peak wavelength is different than the first peak wavelength.

In another aspect, a method comprises: providing light comprising a first peak wavelength in a range from 400 nm to 900 nm; and administering a dose of the light to mammalian tissue within a body to induce a biological effect, the dose of light comprising providing an irradiance to the mammalian tissue over a time period of at most 1 hour, the irradiance being delivered in a plurality of discrete pulses; wherein the biological effect comprises altering a concentration of one or more pathogens within the body and altering growth of the one or more pathogens within the body. In certain embodiments, the irradiance is a range from 0.1 mW/cm$^2$ to 10 W/cm$^2$. In certain embodiments, the dose of light is a range from 0.5 (J/cm$^2$ to 100 J/cm$^2$. In certain embodiments, the dose of light is in a range from 2 J/cm$^2$ to 50 J/cm$^2$. In certain embodiments, the plurality of discrete pulses comprises a plurality of equal pulses that is delivered during the time period. In certain embodiments, the plurality of discrete pulses comprises a plurality of dissimilar pulses that is delivered during the time period. In certain embodiments, the irradiance progressively increases during the plurality of dissimilar pulses. In certain embodiments, the irradiance progressively decreases during the plurality of dissimilar pulses. In certain embodiments, the dose of light is repeatably administered to provide a cumulative dose in a range from one J/cm$^2$ to 1000 J/cm$^2$ over a cumulative time period. In certain embodiments, the dose of light is provided with a light therapeutic index of greater than or equal to 2, the light therapeutic index being defined as a dose concentration that reduces tissue viability by 25% divided by a dose concentration that reduces cellular percentage of the one or more pathogens by 50%.

In another aspect, any of the foregoing aspects, and/or various separate aspects and features as described herein, may be combined for additional advantage. Any of the various features and elements as disclosed herein may be combined with one or more other disclosed features and elements unless indicated to the contrary herein.

Those skilled in the art will appreciate the scope of the present disclosure and realize additional aspects thereof after reading the following detailed description of the preferred embodiments in association with the accompanying drawing figures.

BRIEF DESCRIPTION OF DRAWINGS

The accompanying drawing figures incorporated in and forming a part of this specification illustrate several aspects of the disclosure, and together with the description serve to explain the principles of the disclosure.

FIG. 26 is a side cross-sectional schematic view of a portion of a device for delivering light energy to living mammalian tissue, wherein the device is edge lit along multiple edges with multiple light emitting sources supported by a flexible PCB having a reflective surface, other non-light-transmitting surfaces of the device are further bounded by the flexible PCB, the flexible PCB and light emitting sources are covered with an encapsulant material, and a wavelength conversion material is distributed in the encapsulant material.

FIG. 27 is a side cross-sectional schematic view of a portion of a device for delivering light energy to living mammalian tissue, wherein the device is edge lit along multiple edges with multiple light emitting sources supported by a flexible PCB having a reflective surface, other non-light-transmitting surfaces of the device are further bounded by the flexible PCB with raised light extraction features being supported by the flexible PCB, and encapsulant material is provided over the flexible PCB, the light emitting sources, and the light extraction features.

FIG. 28 is a side cross-sectional schematic view of a portion of a device for delivering light energy to living mammalian tissue, wherein the device is edge lit along multiple edges with multiple light emitting sources supported by a flexible PCB having a reflective surface, other non-light-transmitting surfaces of the device are further bounded by the flexible PCB, an encapsulant material is arranged above and below the PCB and over the light emitting sources, and holes or perforations are defined through both the substrate and the encapsulant material.

FIG. 29A is a cross-sectional view of a first exemplary hole definable through a device for delivering light energy to living mammalian tissue, the hole having a diameter that is substantially constant with depth.

FIG. 29B is a cross-sectional view of a second exemplary hole definable through a device for delivering light energy to living mammalian tissue, the hole having a diameter that increases with increasing depth.

FIG. 29C is a cross-sectional view of a third exemplary hole definable through a device for delivering light energy to living mammalian tissue, the hole having a diameter that decreases with increasing depth.

FIG. 86C is a table showing an evaluation of SARS-CoV-2 RNA with reverse transcription polymerase chain reaction (rRT-PCR) for samples collected for the $TCID_{50}$ assays of FIGS. 86A-86B.

FIG. 91A is a chart showing raw luminescence values (RLU) for different seedings of Vero E6 cell densities and various doses of light ($J/cm^2$).

FIG. 91B is a chart showing percent viability for the different seedings of Vero E6 cell densities and various doses of light of FIG. 91A.

FIG. 91C is a chart comparing RLU versus total cell number to show that CellTiterGlo One Solution (CTG) is an effective reagent for measuring cell densities of above $10^6$ Vero E6 cells.

FIG. 92A is a chart of $TCID_{50}$/ml versus dose at 24 hours and 48 hours post infection for Calu-3 cells infected with SARS-CoV-2.

FIG. 92B is a chart showing the percent reduction in SARS-Cov-2 compared with percent cytotoxicity for the Calu-3 cells of FIG. 92A.

FIG. 93A is a chart illustrating percent reduction in SARS-CoV-2 replication versus percent cell cytotoxicity for Vero E6 cells infected with a MOI of 0.01 after various doses of light at 425 nm.

FIG. 93B is a chart illustrating percent reduction in SARS-CoV-2 replication versus percent cell cytotoxicity for Vero E6 cells infected with a MOI of 0.001 after various doses of light at 425 nm.

FIG. 93C is a chart representing percent viability at various doses for primary human tracheal/bronchial tissue from a single donor after various doses of light at 425 nm.

FIG. 94A is a chart illustrating percent reduction in SARS-CoV-2 replication versus percent cell cytotoxicity for Vero E6 cells infected with a MOI of 0.01 after various doses of light at 450 nm.

FIG. 94B is a chart illustrating percent reduction in SARS-CoV-2 replication versus percent cell cytotoxicity for Vero E6 cells infected with a MOI of 0.001 after various doses of light at 450 nm.

FIG. 94C is a chart representing percent viability at various doses for primary human tracheal/bronchial tissue from a single donor after various doses of light at 450 nm.

FIG. 95 is a table summarizing the results illustrated in FIGS. 93A-93C and 94A-94C.

Figure 96A:
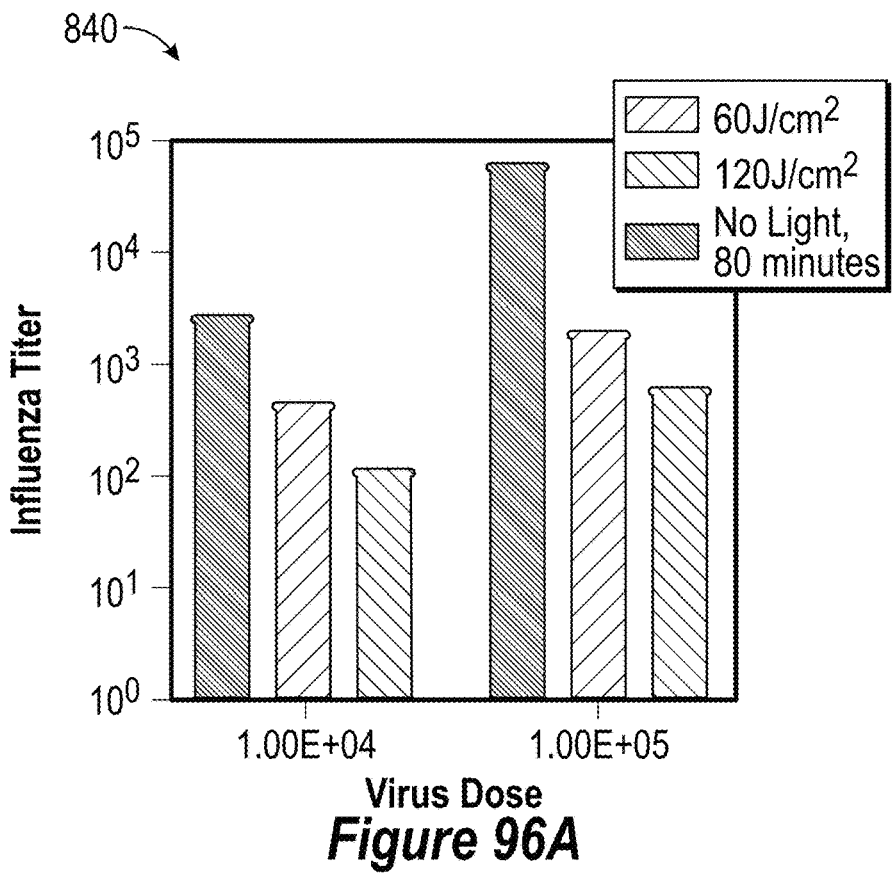

FIG. 96A is a chart showing the titer of wild-type (WT) influenza A virus based on remaining viral loads for different initial viral doses after treatment with different doses of 425 nm light.

Figure 96B:
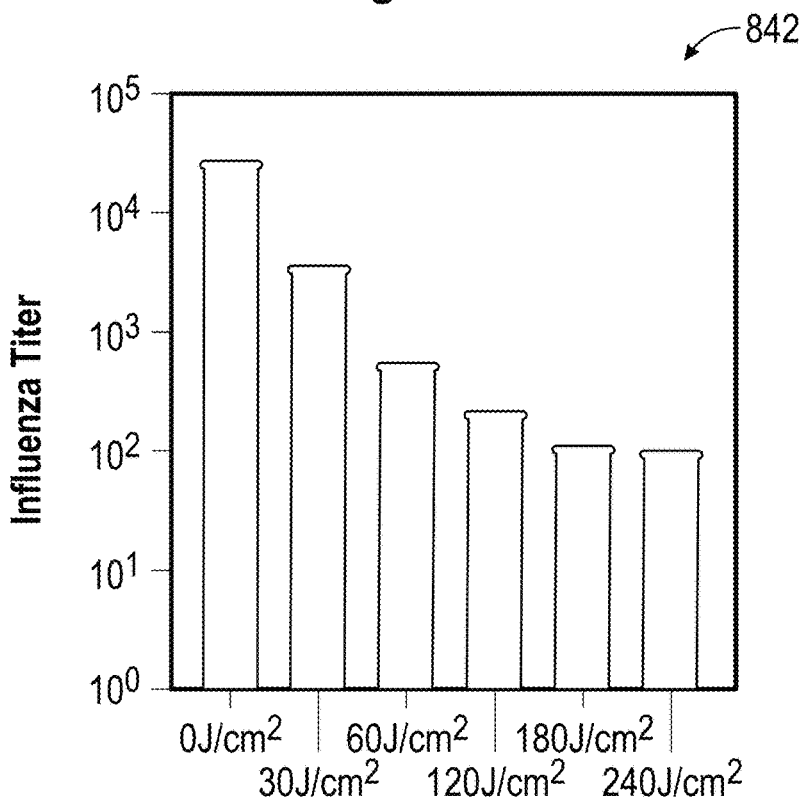

FIG. 96B is a chart showing the titer of Tamiflu-resistant influenza A virus based on remaining viral load for a single initial viral dose after treatment of different doses of 425 nm light.

Figure 97A:
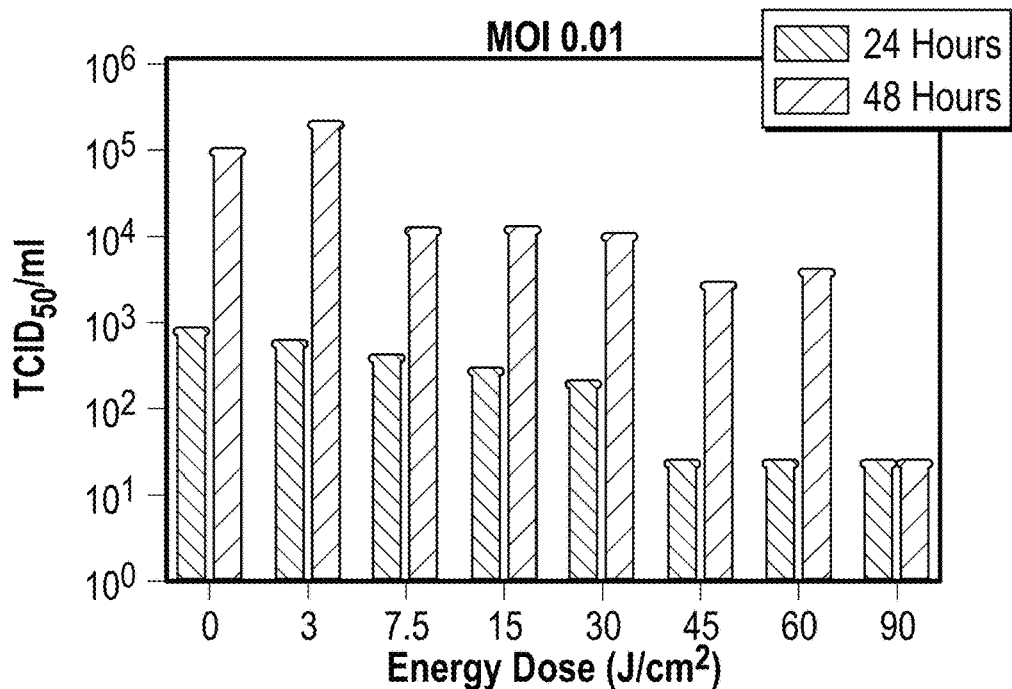

FIG. 97A is a chart showing the $TCID_{50}$/ml versus energy dose for WT influenza A treated with light at 425 nm at various doses with a MOI for the WT influenza A of 0.01.

Figure 97B:
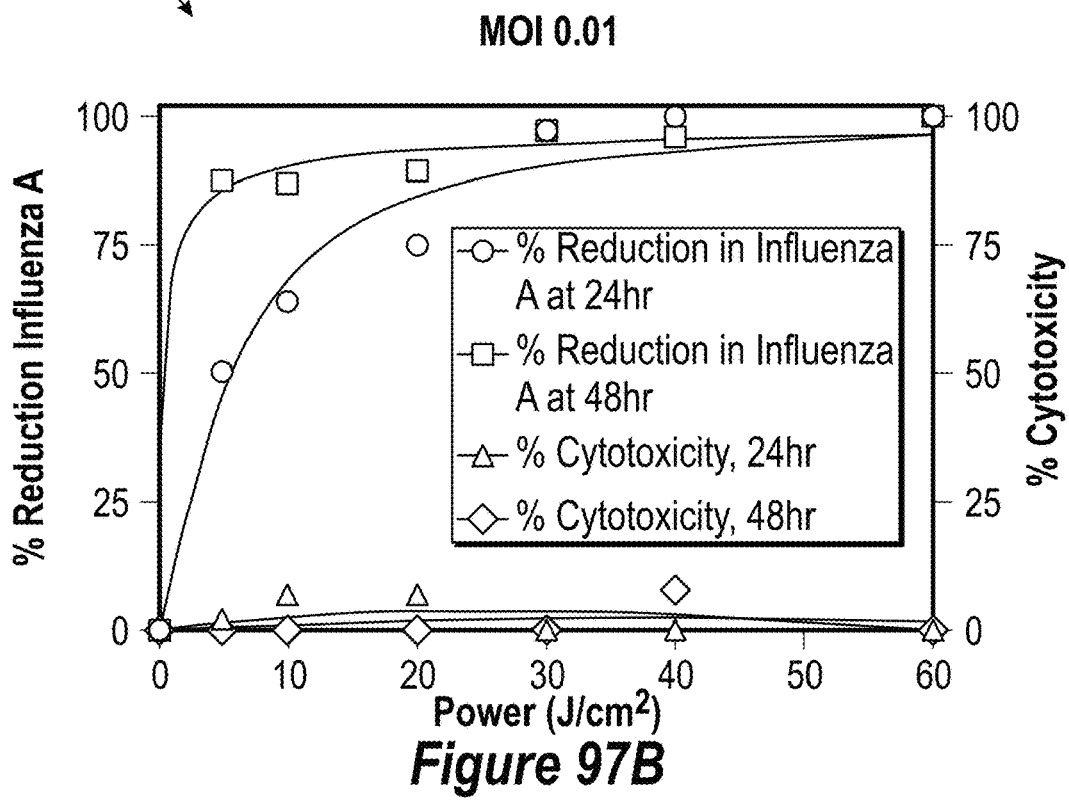

FIG. 97B is a plot showing the percent reduction in viral loads of WT influenza A and percent cytotoxicity against the treated cells when influenza A-infected Madin-Darby Canine Kidney (MDCK) cells were exposed to 425 nm light at various doses and a MOI for the WT influenza A was provided at 0.01.

Figure 97C:
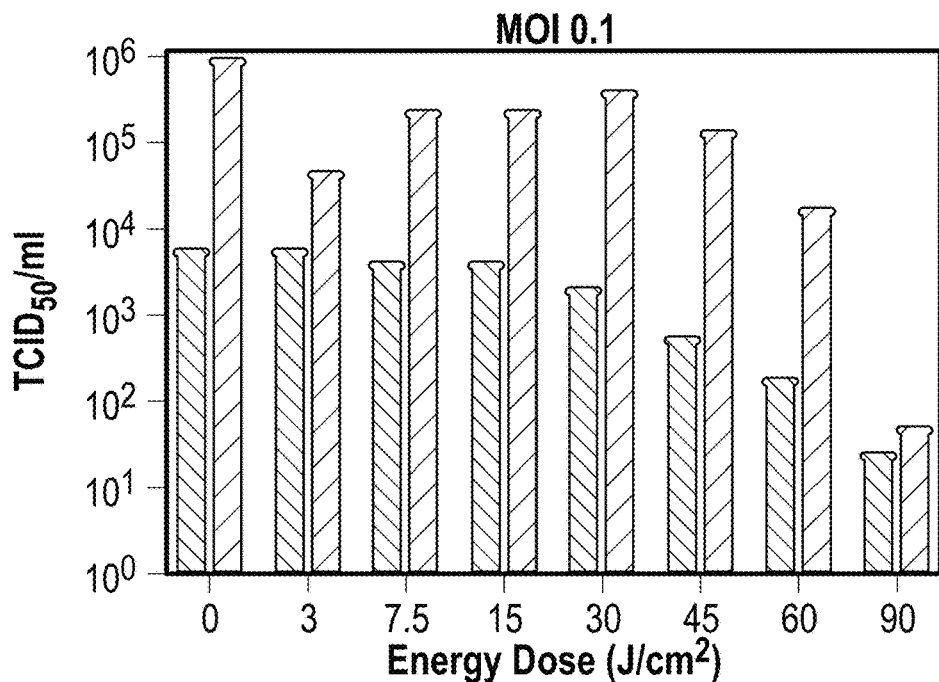

FIG. 97C illustrates the $TCID_{50}$ of cells infected with WT influenza A and treated with 425 nm light at various doses with a MOI for the WT influenza A of 0.1.

Figure 97D:
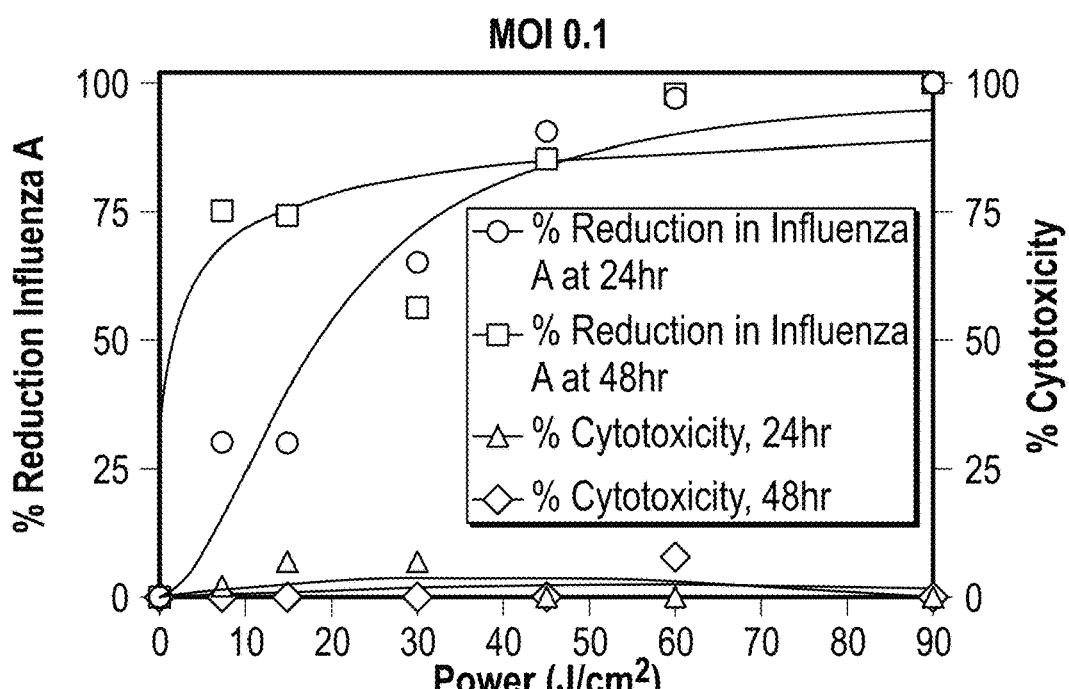

FIG. 97D illustrates the percent reduction in viral loads of WT influenza A and percent cytotoxicity against the treated cells when influenza A-infected Madin-Darby Canine Kidney (MDCK) cells were exposed to 425 nm light at various doses and a MOI for the WT-influenza A was provided at 0.1.

Figure 98A:
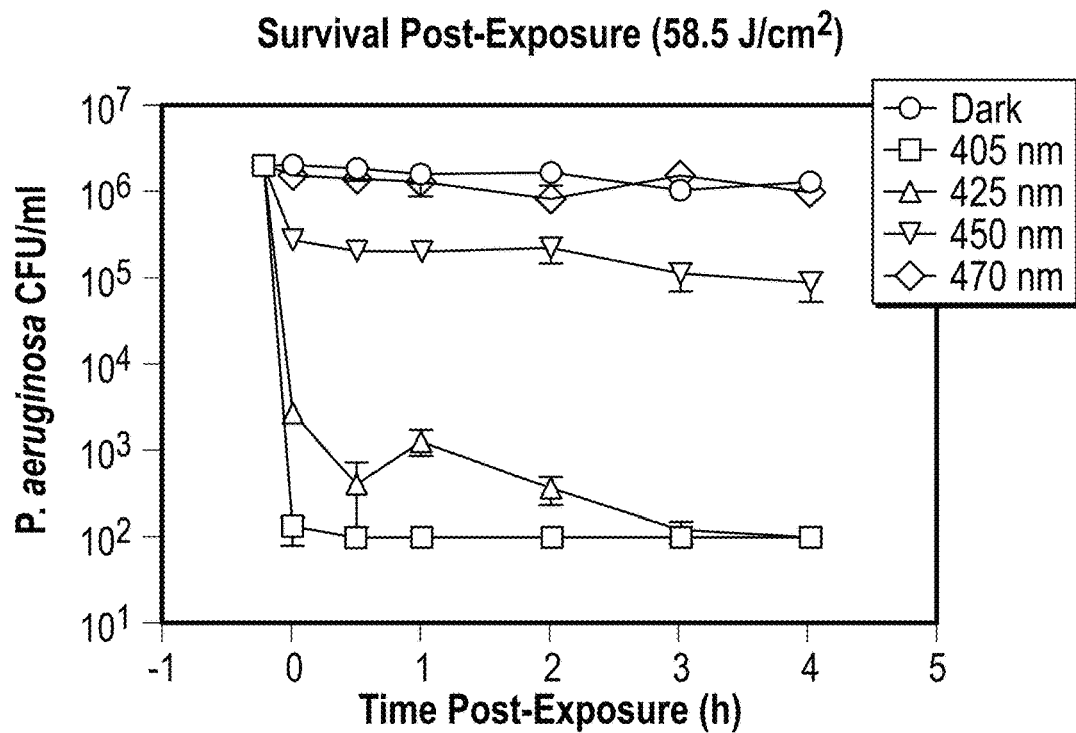

FIG. 98A is a chart showing the effectiveness of light at 405, 425, 450, and 470 nm and administered with a dose of 58.5 J/cm$^2$, in terms of hours post-exposure, at killing *P. aeruginosa*.

Figure 98B:
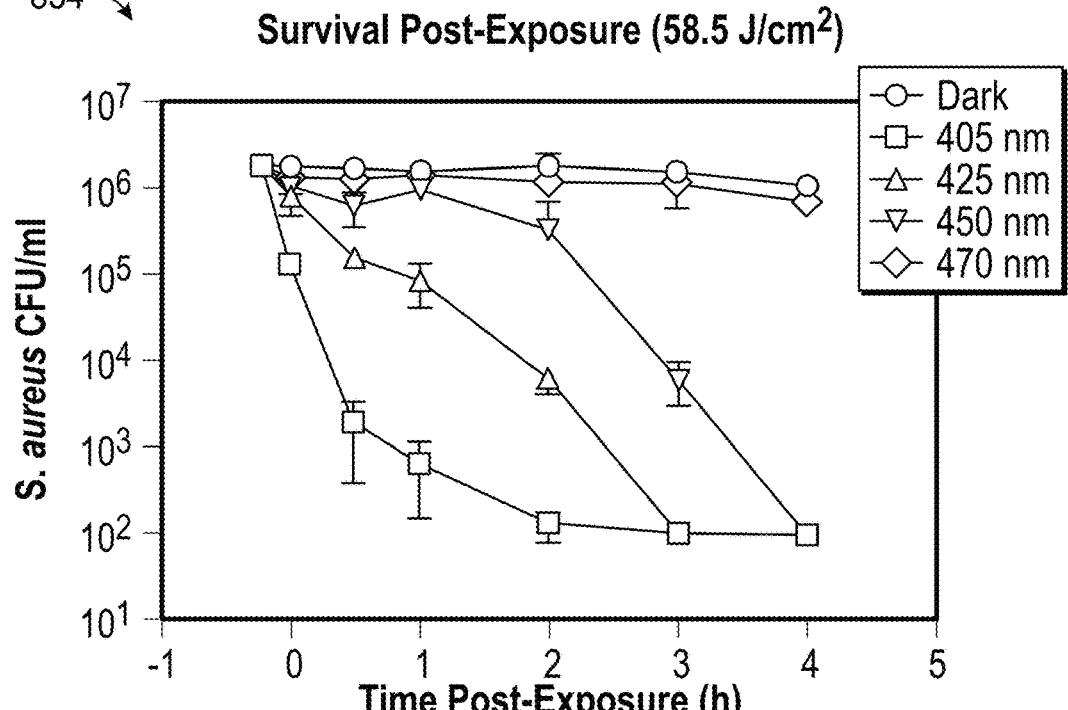

FIG. 98B is a chart showing the effectiveness of light at 405, 425, 450, and 470 nm, and administered with a dose of 58.5 J/cm$^2$, in terms of hours post-exposure, at killing *S. aureus*.

Figure 99A:
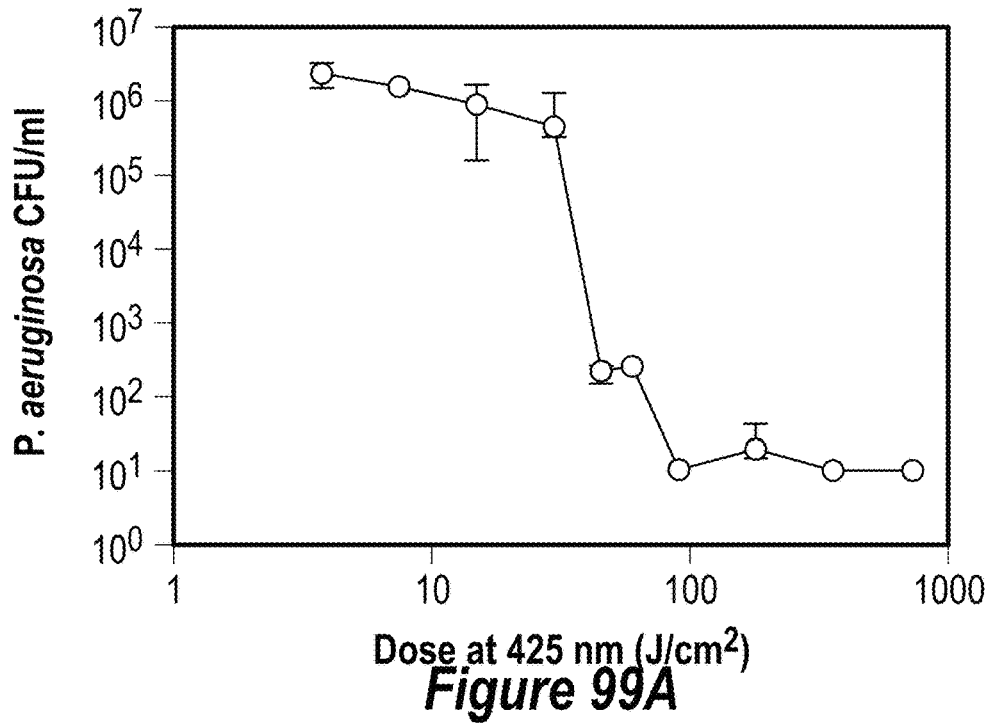

FIG. 99A is a chart showing the effectiveness of light at 425 nm and administered with doses ranging from 1 to 1000 J/cm$^2$ at killing *P. aeruginosa*.

Figure 99B:
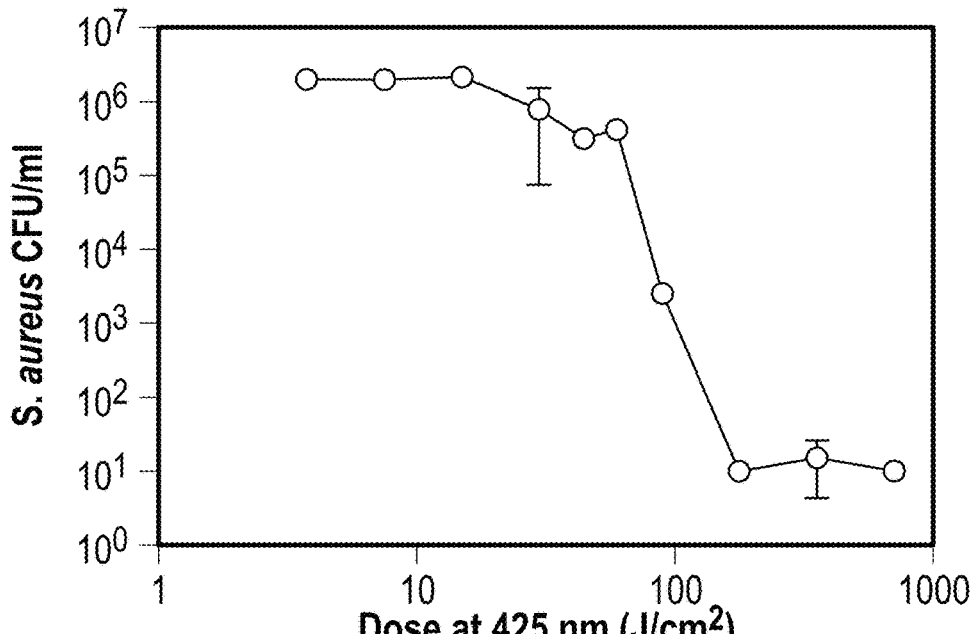

FIG. 99B is a chart showing the effectiveness of light at 425 nm and administered with doses ranging from 1 to 1000 J/cm$^2$ at killing *S. aureus*.

Figure 100A:
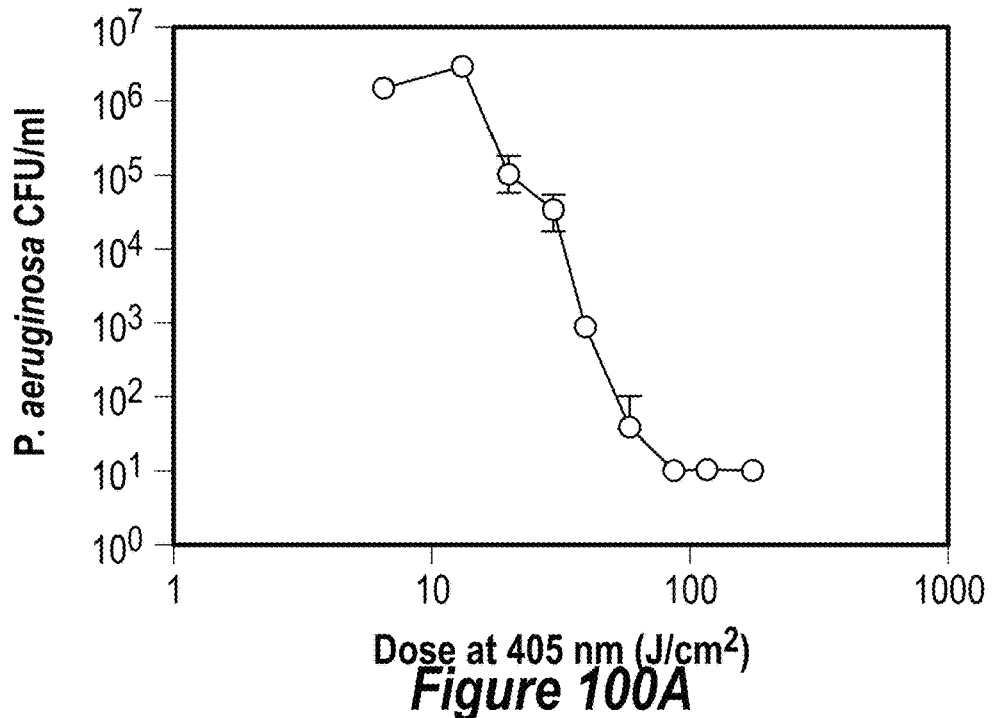

FIG. 100A is a chart showing the effectiveness of light at 405 nm and administered with doses ranging from 1 to 1000 J/cm$^2$ at killing *P. aeruginosa*.

Figure 100B:
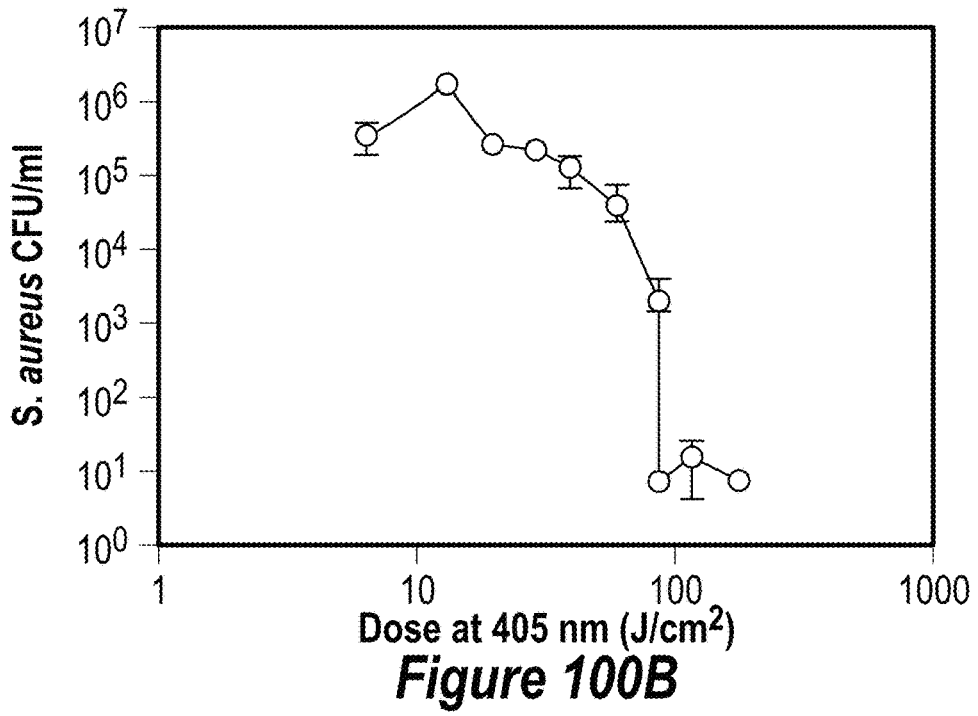

FIG. 100B is a chart showing the effectiveness of light at 405 nm and administered with doses ranging from 1 to 1000 J/cm$^2$ at killing *S. aureus*.

Figure 101:
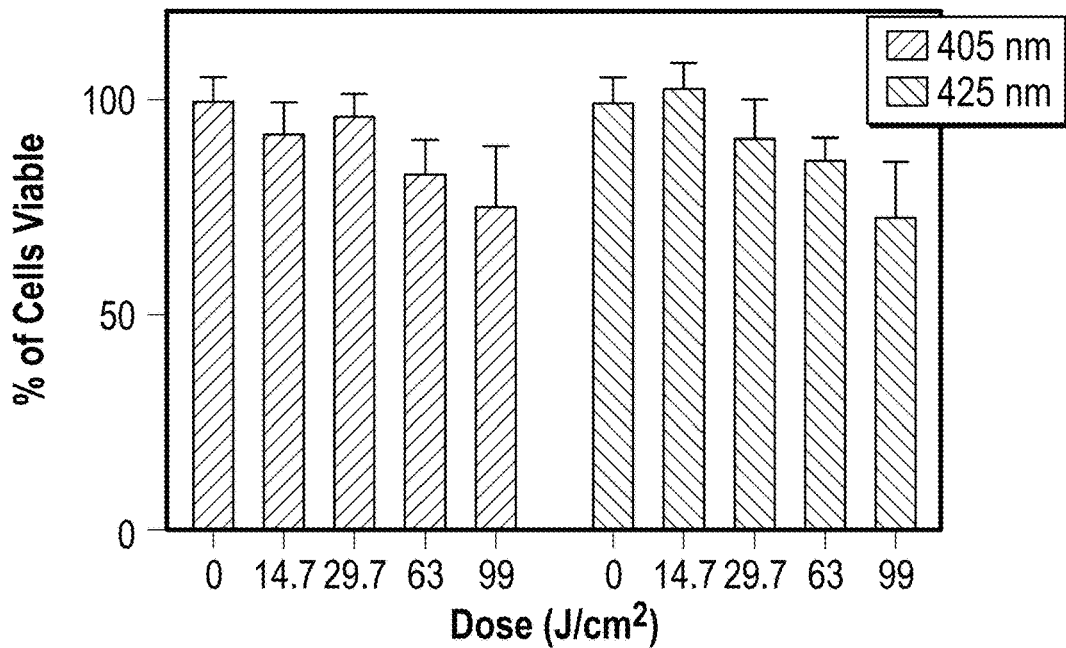

FIG. 101 is a chart showing the toxicity of 405 nm and 425 nm light in primary human aortic endothelial cells (HAEC).

Figure 102A:
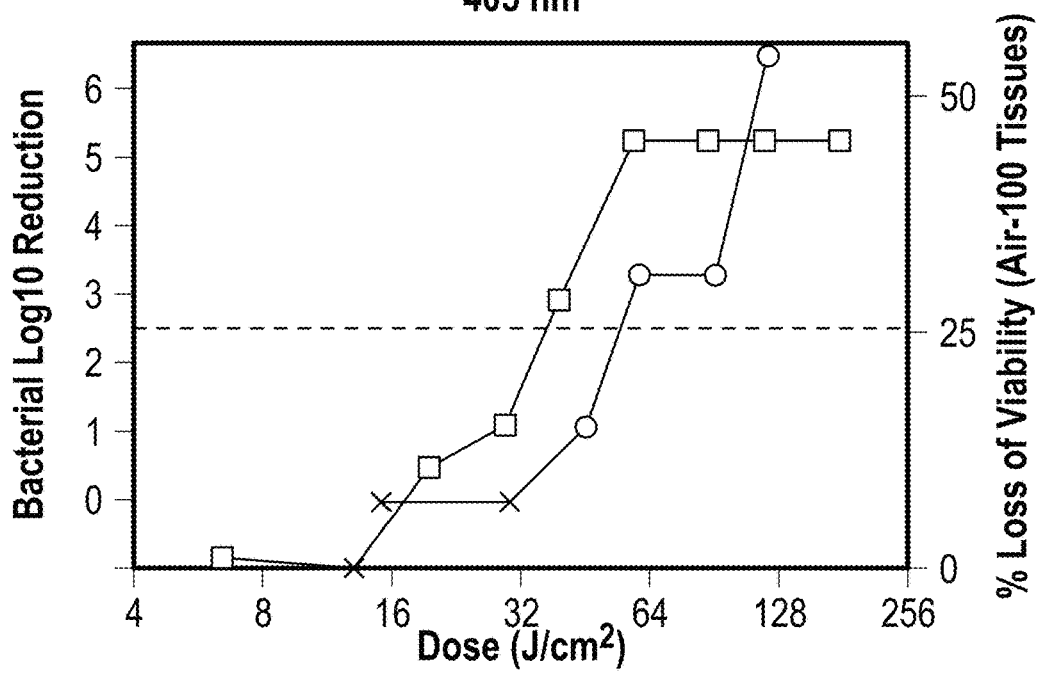

FIG. 102A is a chart showing the bacterial $\log_{10}$ reduction and the % loss of viability of infected AIR-100 tissues following exposure of the tissue to doses of light ranging from 4 to 512 J/cm$^2$ at 405 nm.

Figure 102B:
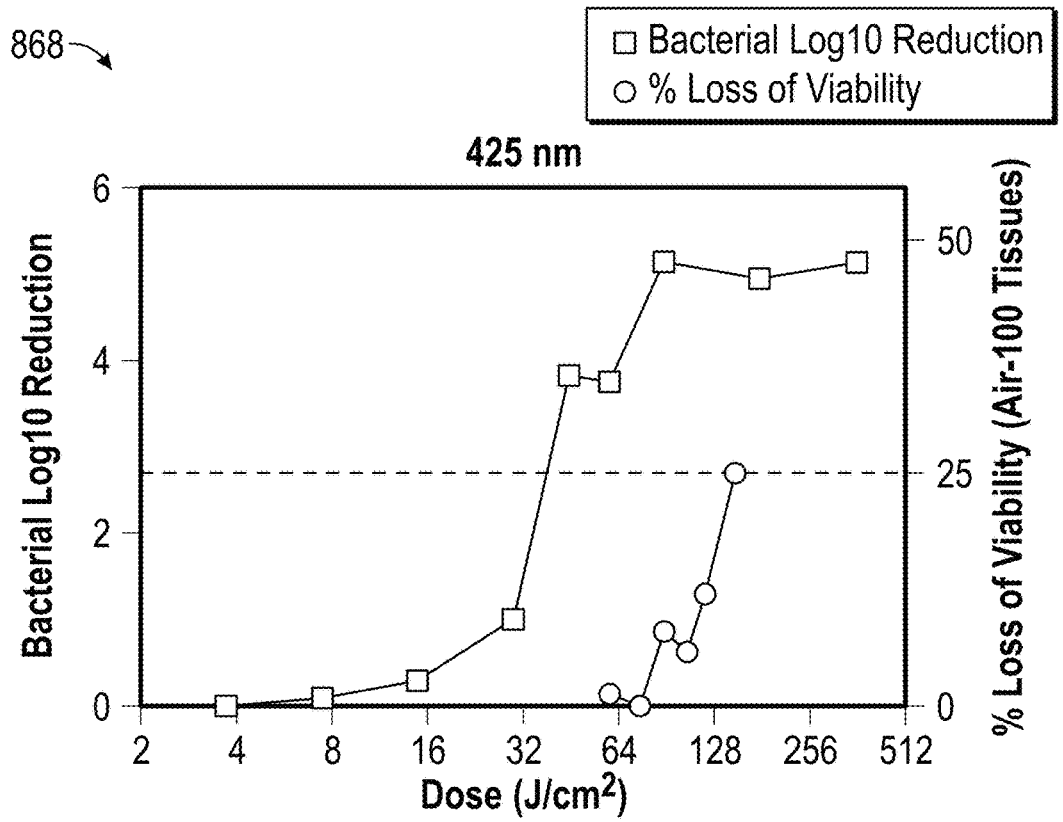

FIG. 102B is a chart showing the bacterial $\log_{10}$ reduction and the % loss of viability of infected AIR-100 tissues following exposure of the tissue to doses of light ranging from 4 to 512 J/cm$^2$ at 425 nm.

Figure 102C:
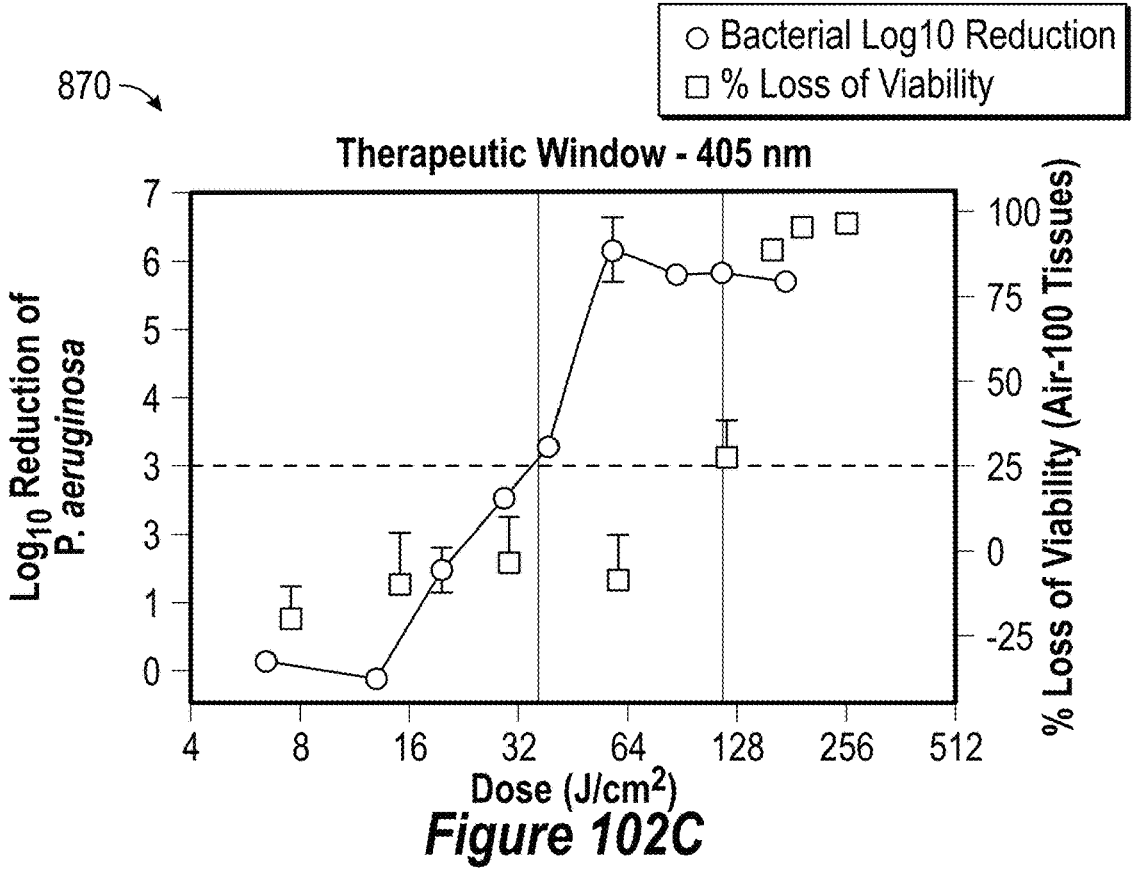

FIG. 102C is a chart showing the bacterial $\log_{10}$ reduction and the % loss of viability of infected AIR-100 tissues with gram negative bacteria (e.g., *P. aeruginosa*) following exposure of the tissue to doses of light ranging from 4 to 512 J/cm$^2$ at 405 nm.

Figure 102D:
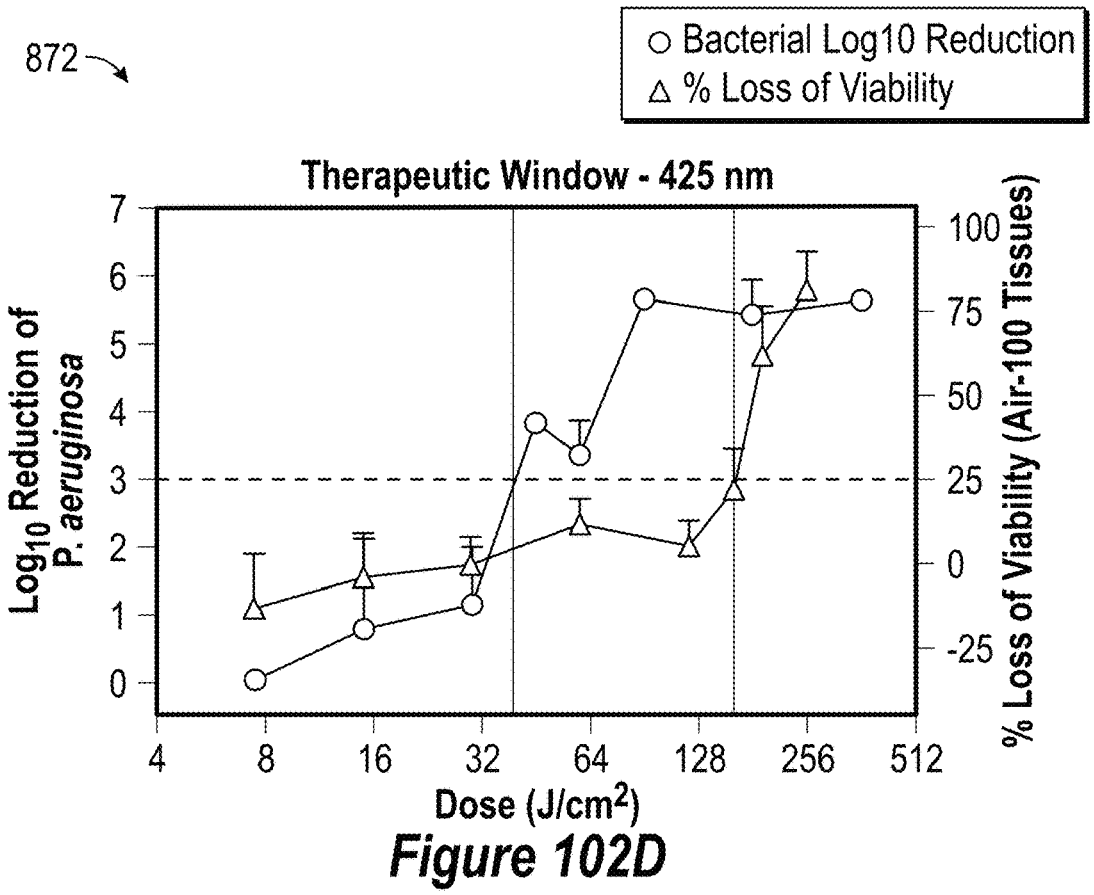

FIG. 102D is a chart showing the bacterial $\log_{10}$ reduction and the % loss of viability of infected AIR-100 tissues with gram negative bacteria (e.g., *P. aeruginosa*) following exposure of the tissue to doses of light ranging from 4 to 512 J/cm$^2$ at 425 nm.

Figure 102E:
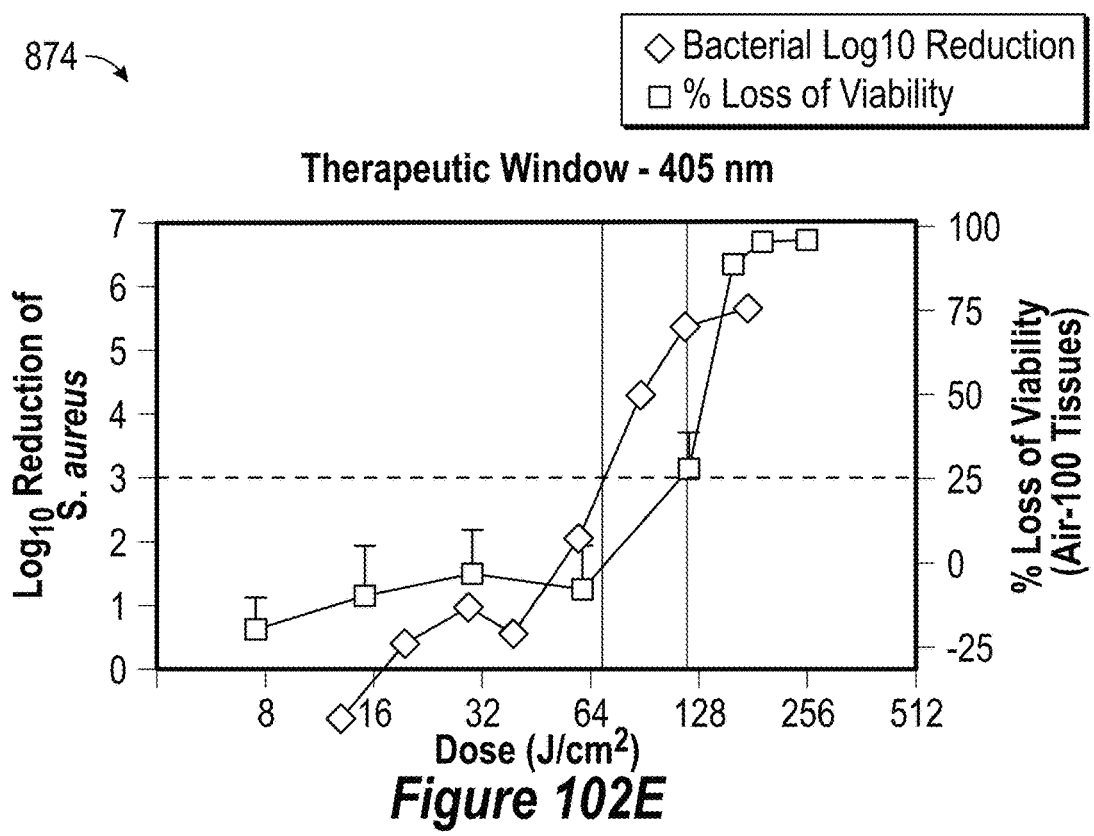

FIG. 102E is a chart showing the bacterial $\log_{10}$ reduction and the % loss of viability of infected AIR-100 tissues with gram positive bacteria (e.g., *S. aureus*) following exposure of the tissue to doses of light ranging from 4 to 512 J/cm$^2$ at 405 nm.

Figure 102F:
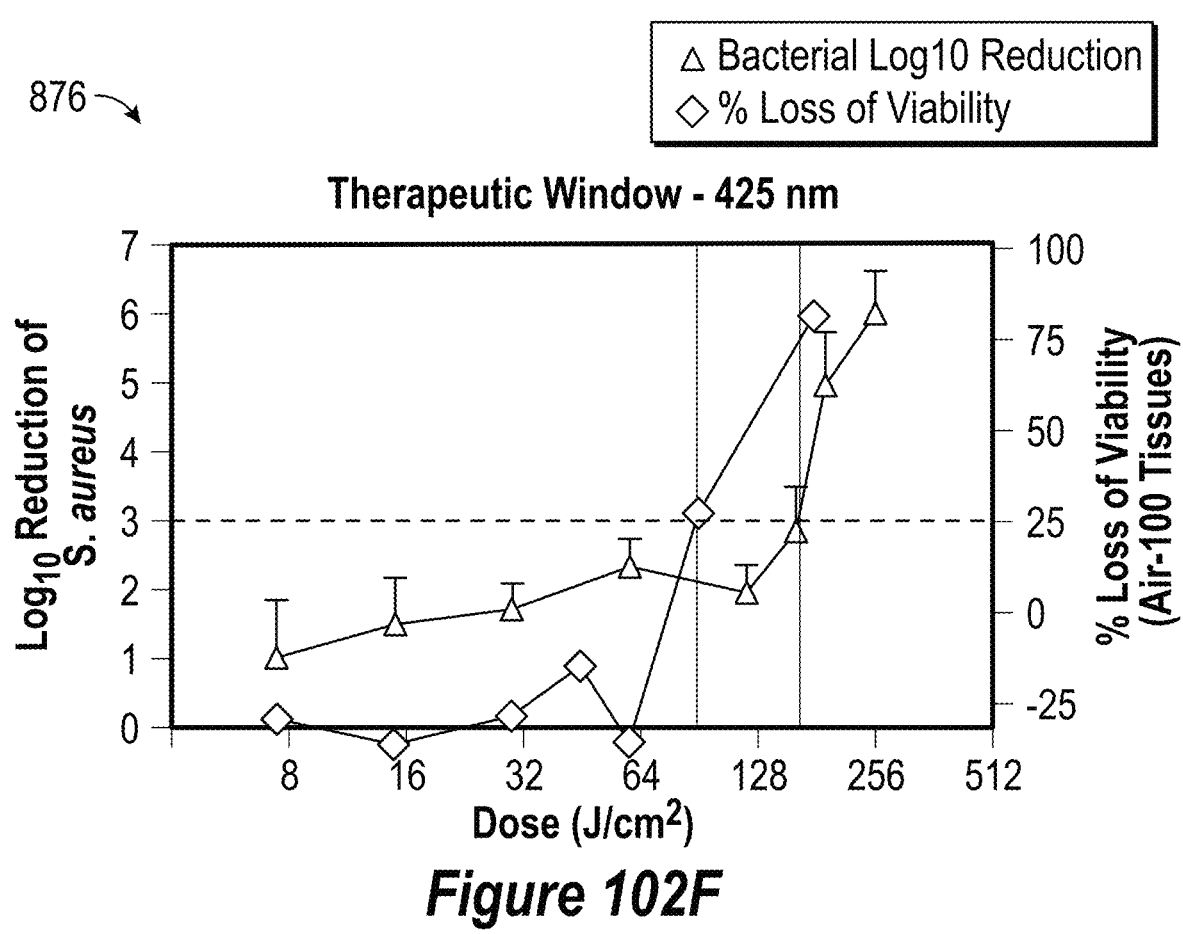
Figure 103A:
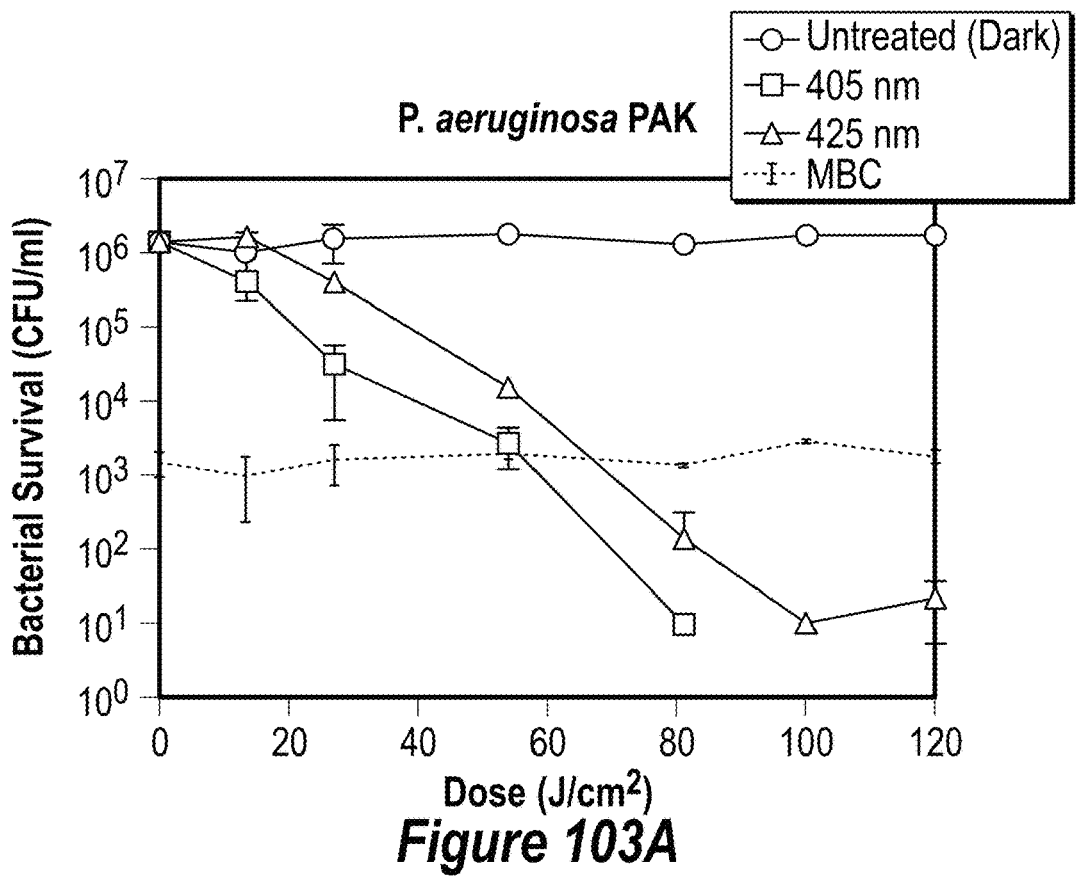
Figure 103B:
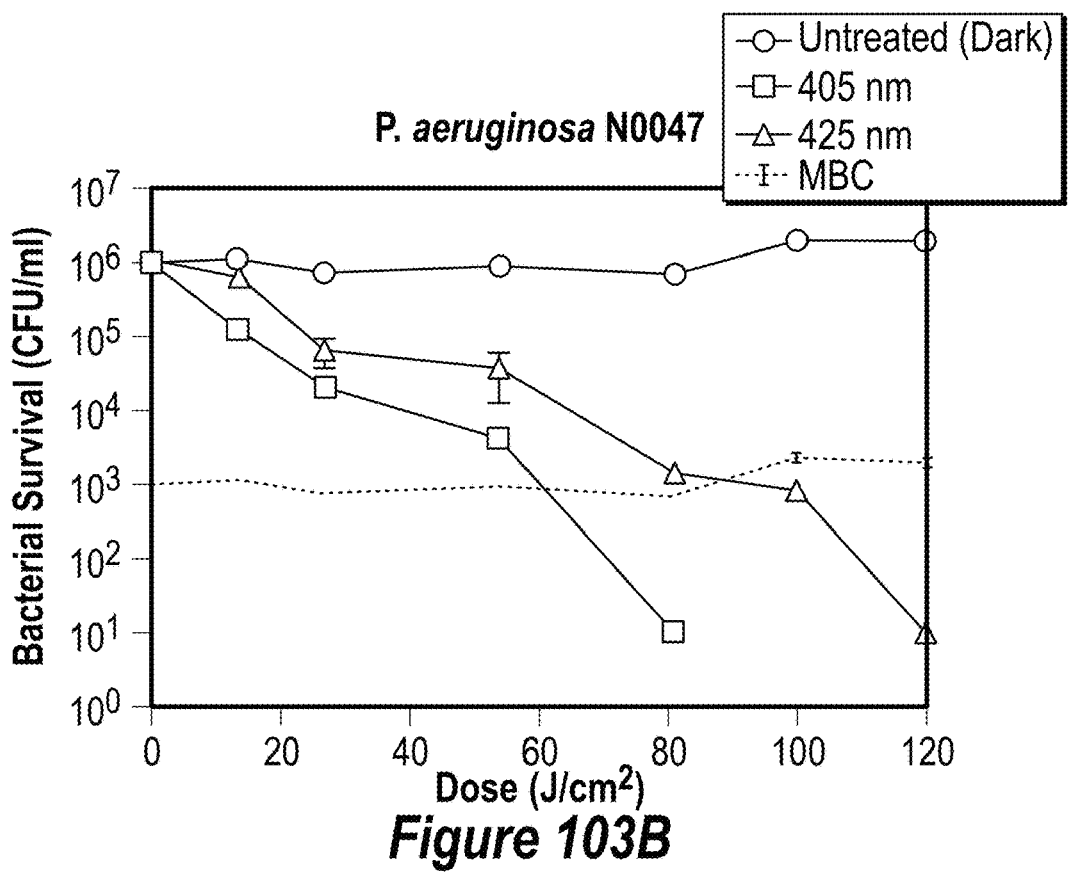
Figure 103C:
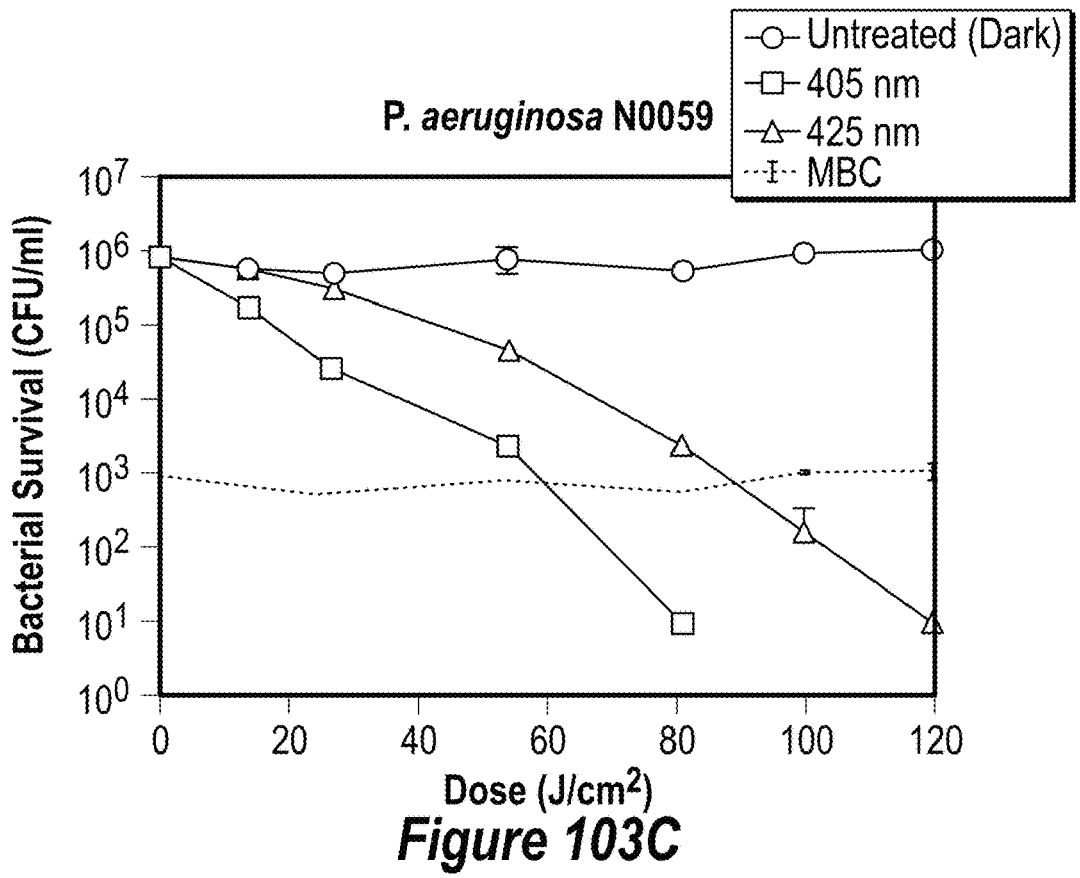
Figure 103D:
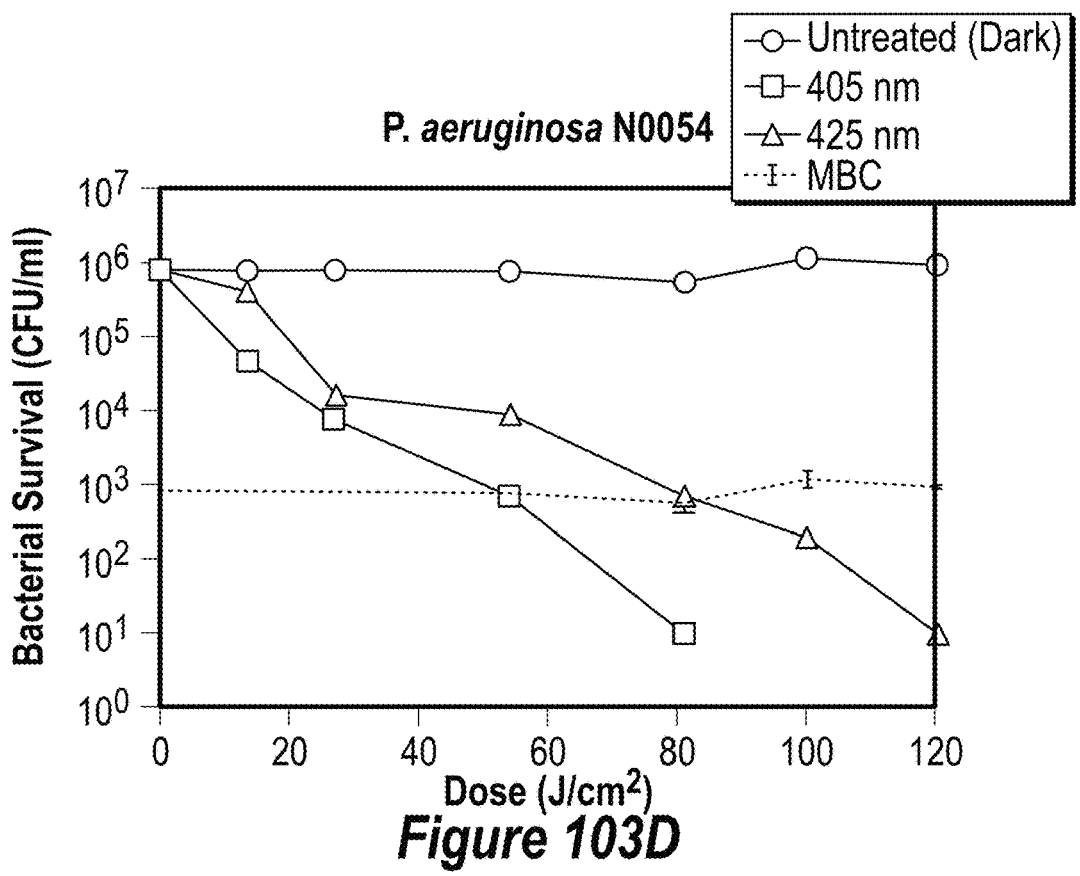
Figure 103E:
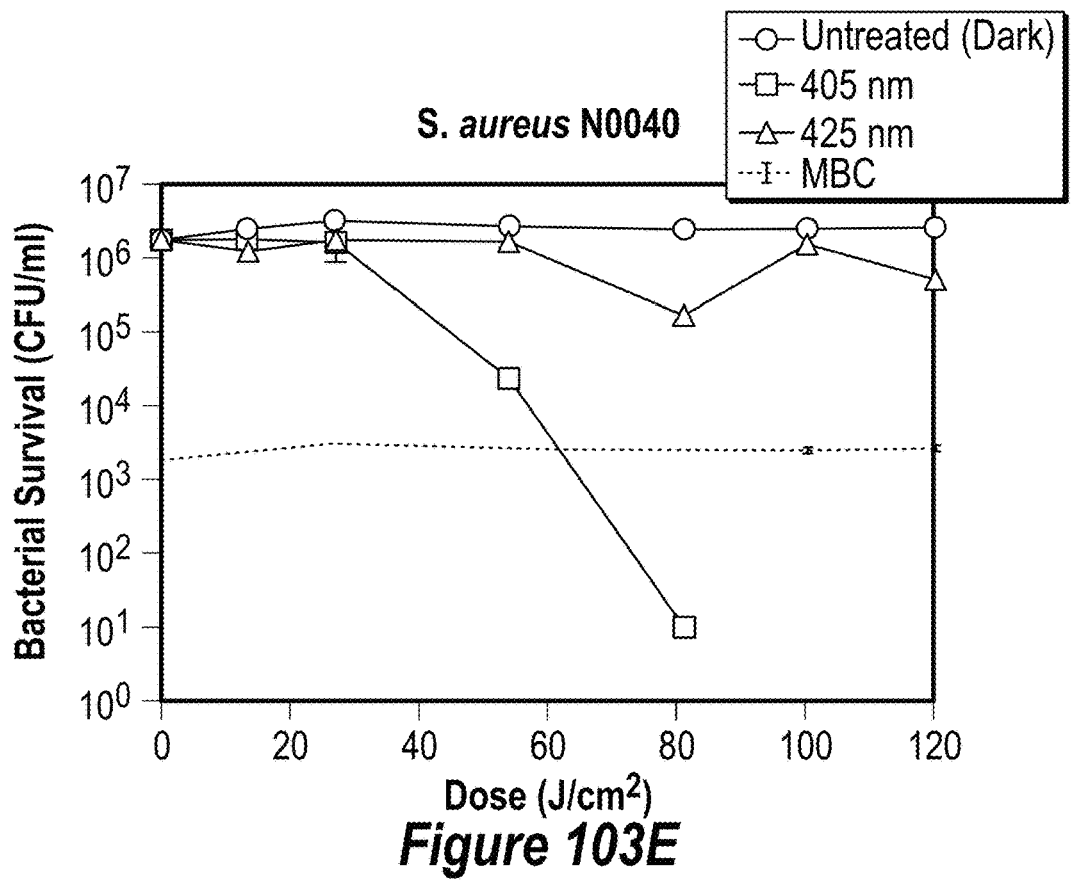
Figure 103F:
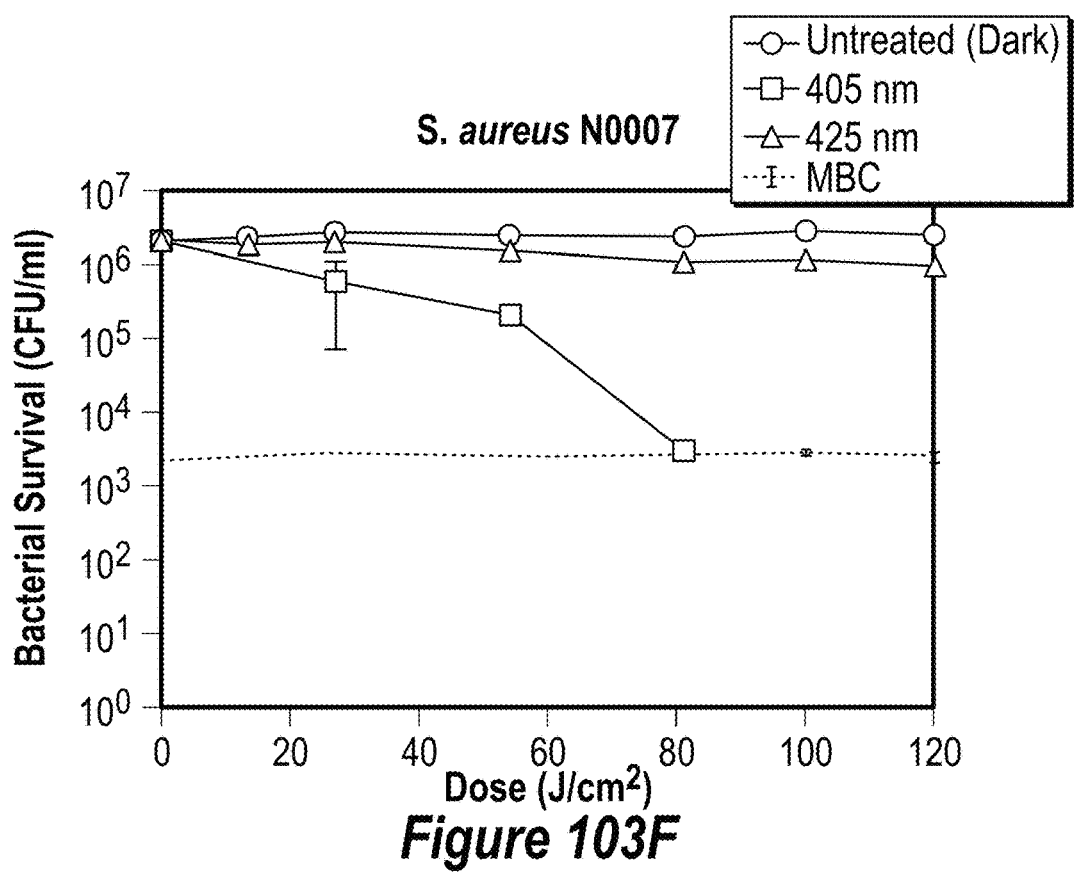
Figure 103G:
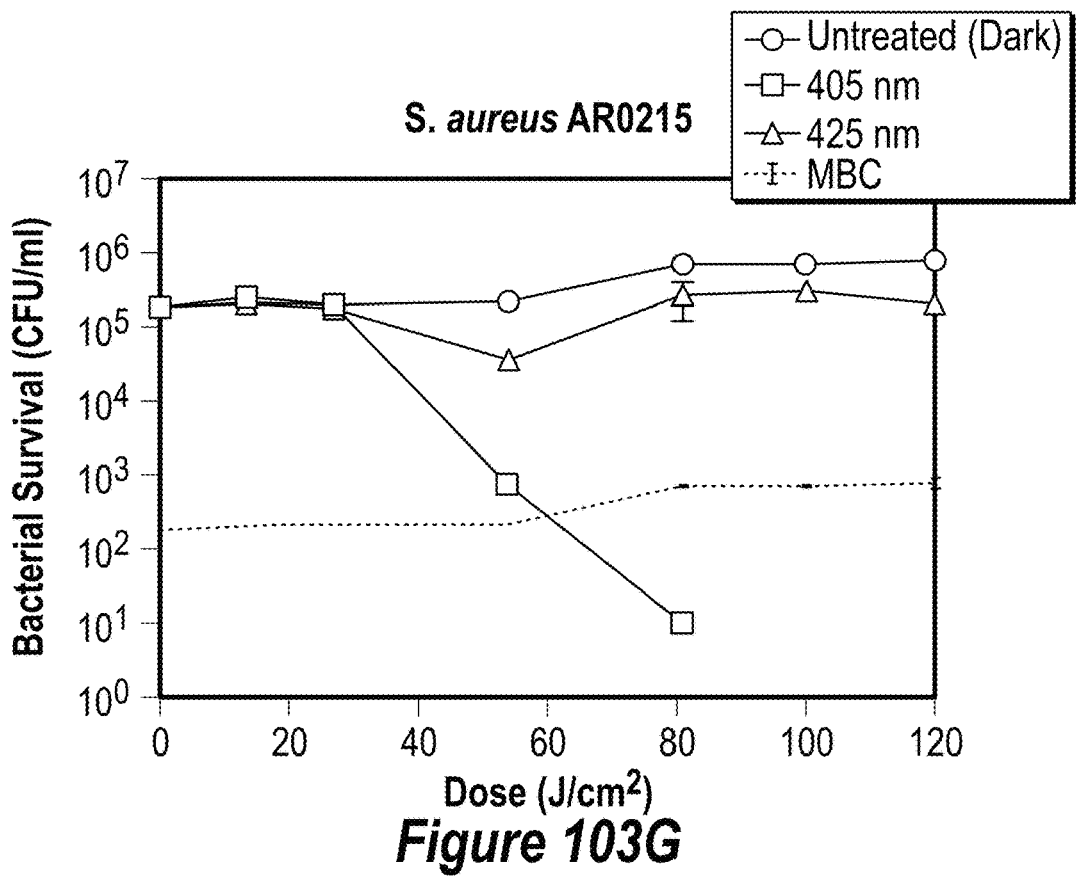
Figure 103H:
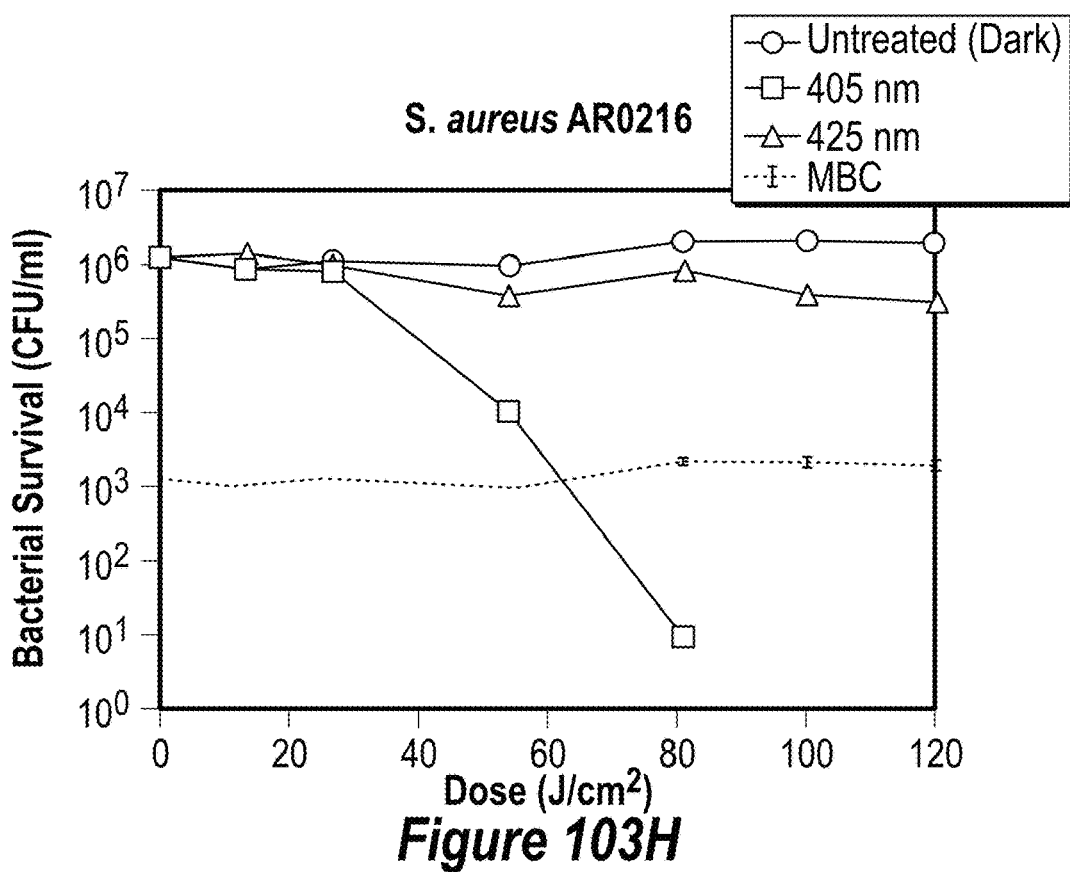
Figure 103I:
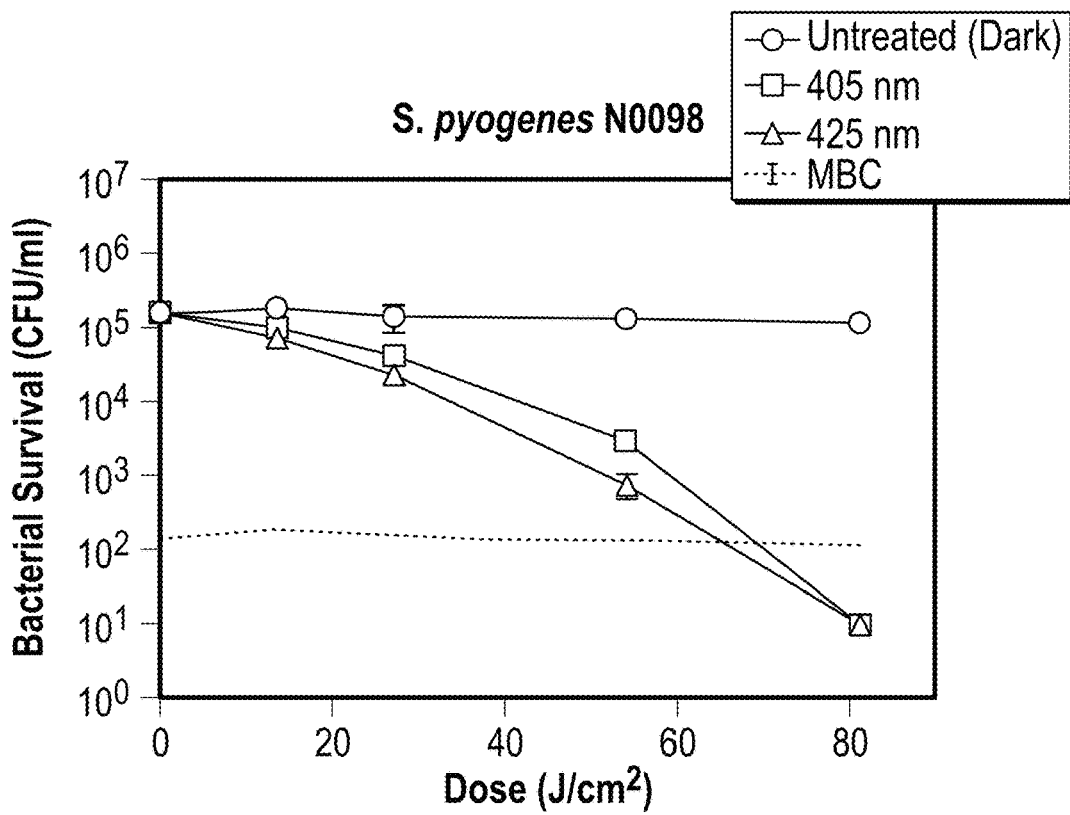
Figure 103J:
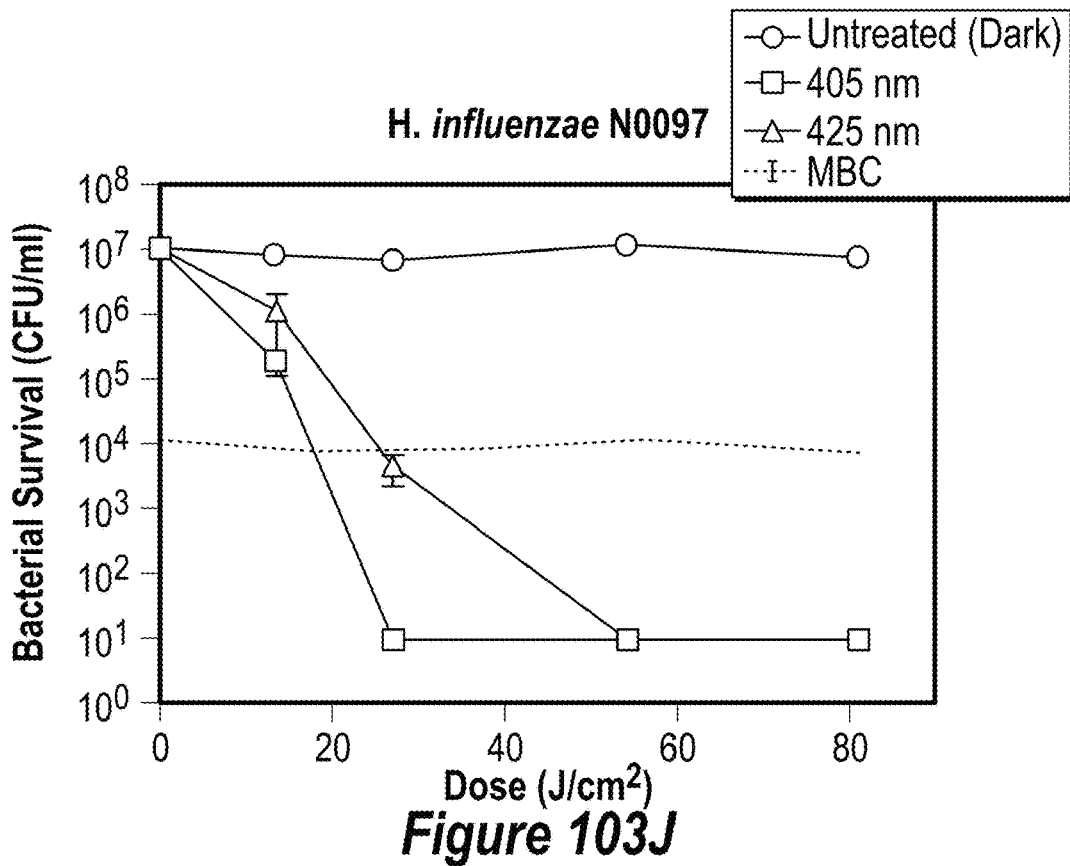

FIG. 102F is a chart showing the bacterial $\log_{10}$ reduction and the % loss of viability of infected AIR-100 tissues with gram positive bacteria (e.g., *S. aureus*) following exposure of the tissue to doses of light ranging from 4 to 512 J/cm$^2$ at 425 nm.

FIGS. 103A-103J are a series of charts showing the effect of light at 405 nm and 425 nm, at differing dosage levels, in terms of bacterial survival vs. dose (J/cm$^2$) for both *P. aeruginosa* and *S. aureus* bacteria.

Figure 79A:
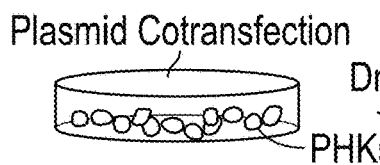
FIGS. 79A-79F is an illustration of an experimental design for treatment of human papillomavirus (HPV)-infected tissues where an HPV-infected organotypic epithelial raft culture model was used to prepare HPV-infected tissue for performing anti-viral experiments.

FIG. 104 is a table summarizing the light therapeutic index (LTI) calculations and corresponding bactericidal doses for the bacterial experiments illustrated in FIGS. 79A-80.

Figure 105:
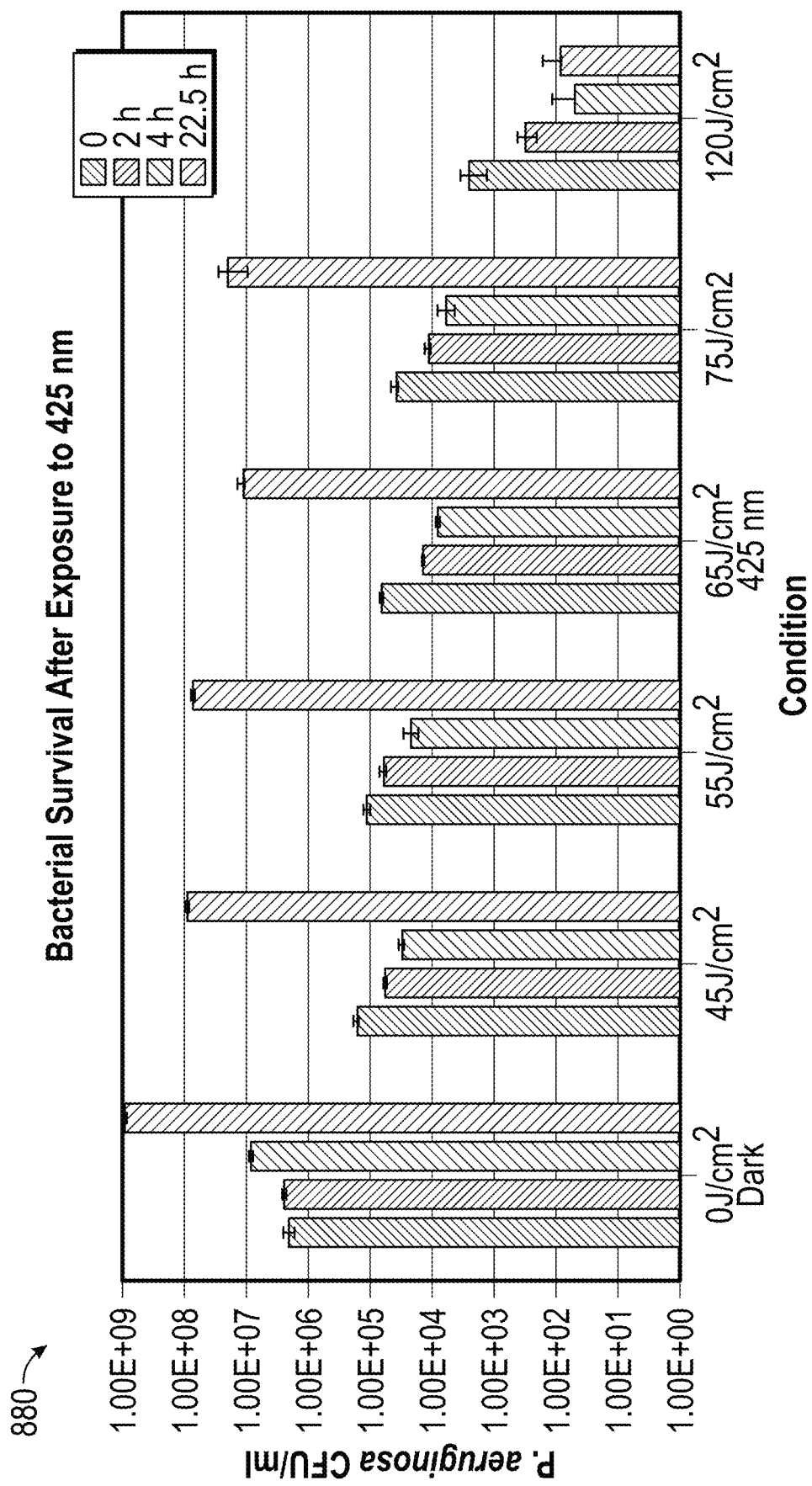

FIG. 105 is a chart showing the effect of 425 nm light at various doses at killing *P. aeruginosa* over a period of time from 0 hours, 2 hours, 4 hours, and 22.5 hours.

Figure 106:
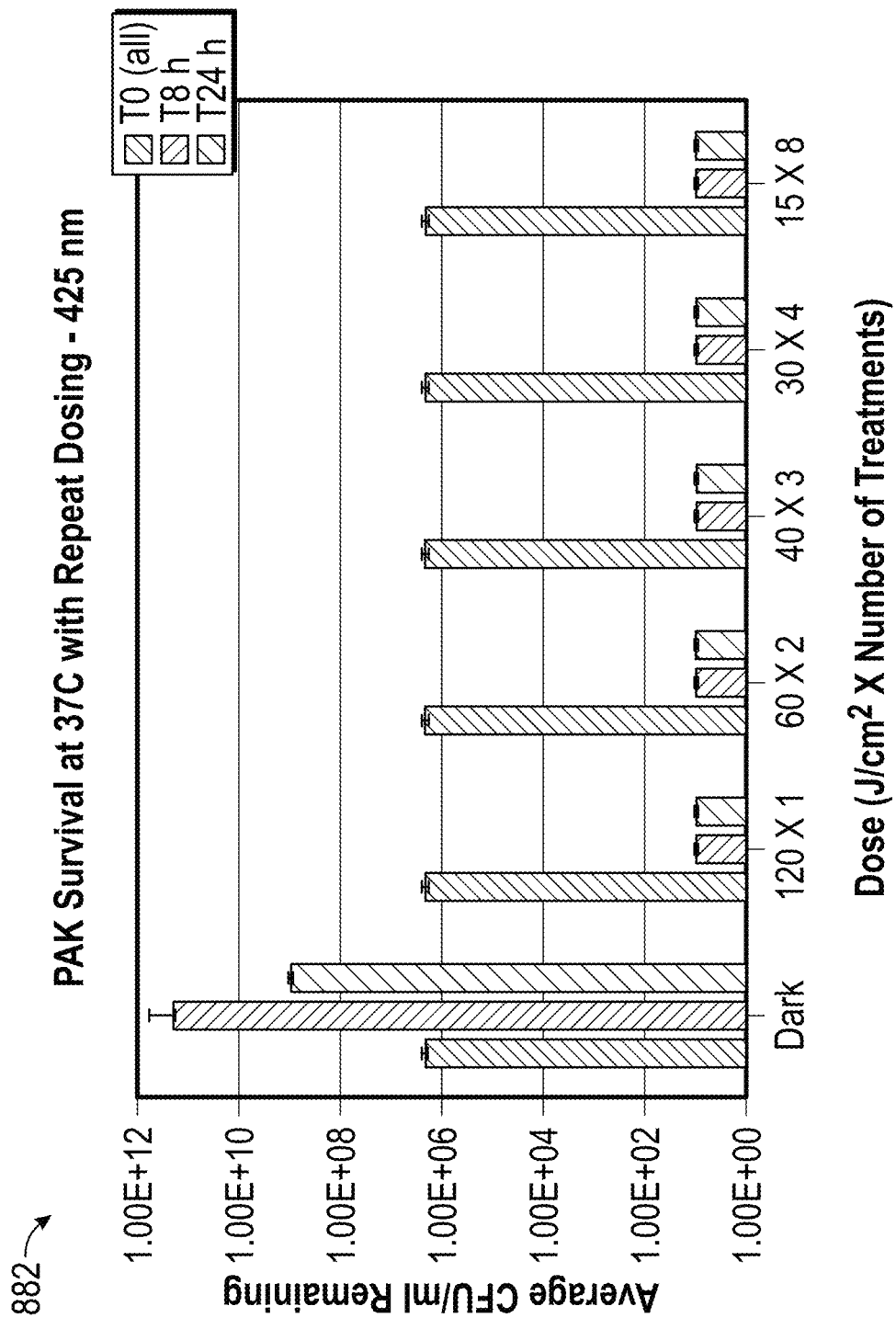

FIG. 106 is a chart showing that whether all of the light (J/cm$^2$) is administered in one dose or in a series of smaller doses, the antimicrobial effect (average CFU/ml) vs. dose (J/cm$^2$×number of treatments) is largely the same, at 8 hours and 48 hours post-administration.

Figure 107A:
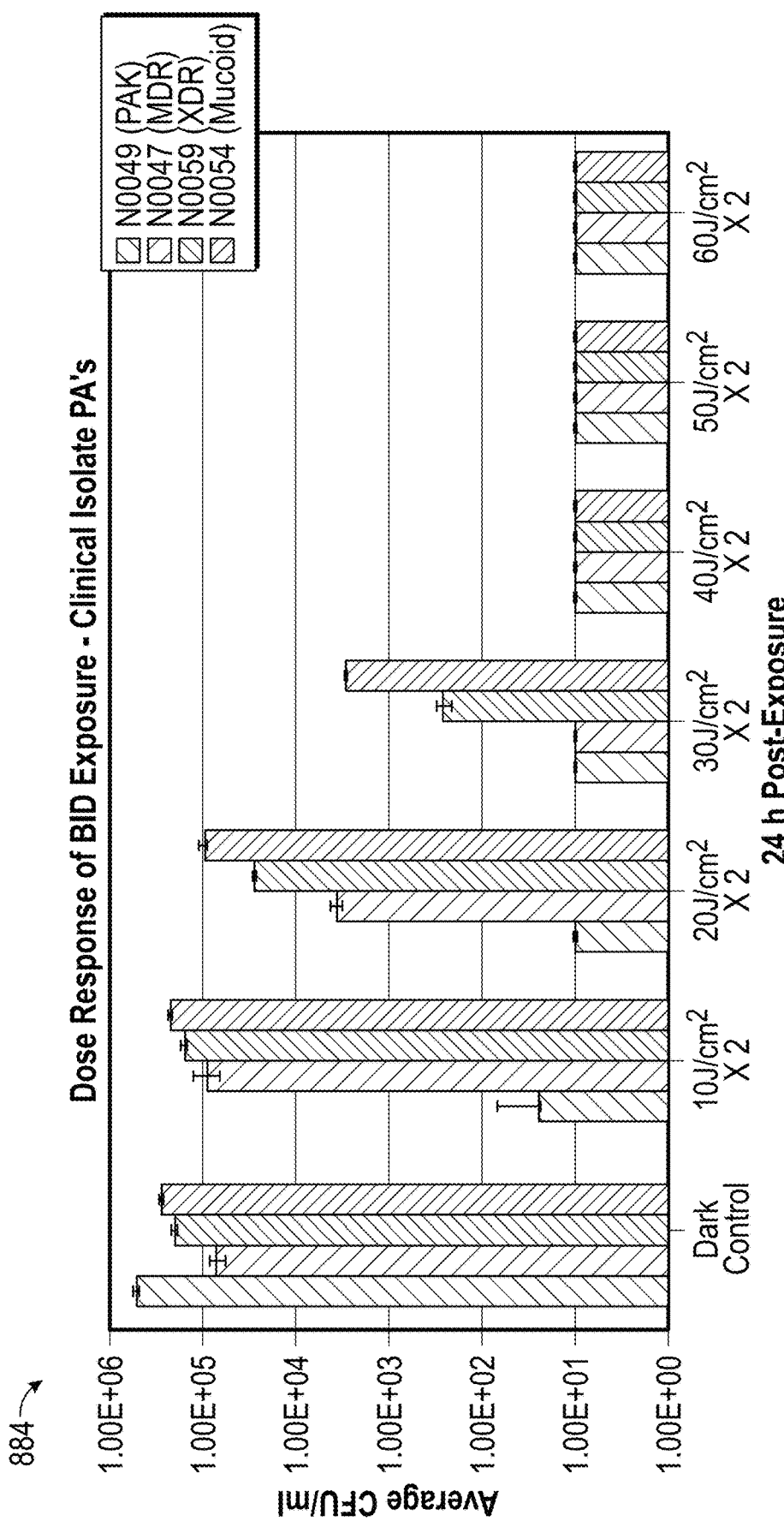

FIG. 107A is a chart showing the treatment of a variety of drug-resistant bacteria (Average CFU/ml) vs. dose (J/cm$^2$) at 24 hours post-exposure.

FIG. 107B is a table summarizing the tested bacteria species and strains.

FIG. 107C is a table that summarizes the efficacy of twice daily dosing of 425 nm light against difficult-to-treat clinical lung pathogens.

DETAILED DESCRIPTION

The embodiments set forth below represent the necessary information to enable those skilled in the art to practice the embodiments and illustrate the best mode of practicing the embodiments. Upon reading the following description in light of the accompanying drawing figures, those skilled in the art will understand the concepts of the disclosure and will recognize applications of these concepts not particularly addressed herein. It should be understood that these concepts and applications fall within the scope of the disclosure and the accompanying claims.

It should be understood that, although the terms first, second, etc. may be used herein to describe various elements, these elements should not be limited by these terms. These terms are only used to distinguish one element from another. For example, a first element could be termed a second element, and, similarly, a second element could be termed a first element, without departing from the scope of the present disclosure. As used herein, the term "and/or" includes any and all combinations of one or more of the associated listed items.

It should be understood that when an element such as a layer, region, or substrate is referred to as being "on" or extending "onto" another element, it can be directly on or extend directly onto the other element or intervening elements may also be present. In contrast, when an element is referred to as being "directly on" or extending "directly onto" another element, there are no intervening elements present. Likewise, it will be understood that when an element such as a layer, region, or substrate is referred to as being "over" or extending "over" another element, it can be directly over or extend directly over the other element or intervening elements may also be present. In contrast, when an element is referred to as being "directly over" or extending "directly over" another element, there are no intervening elements present. It should also be understood that when an element is referred to as being "connected" or "coupled" to another element, it can be directly connected or coupled to the other element or intervening elements may be present. In contrast, when an element is referred to as being "directly connected" or "directly coupled" to another element, there are no intervening elements present.

It should be understood that, although the terms "upper," "lower," "bottom," "intermediate," "middle," "top," and the like may be used herein to describe various elements, these elements should not be limited by these terms. These terms are only used to distinguish one element from another. For example, a first element could be termed an "upper" element and, similarly, a second element could be termed an "upper" element depending on the relative orientations of these elements, without departing from the scope of the present disclosure.

The terminology used herein is for the purpose of describing particular embodiments only and is not intended to be limiting of the disclosure. As used herein, the singular forms "a," "an," and "the" are intended to include the plural forms as well, unless the context clearly indicates otherwise. It will be further understood that the terms "comprises," "comprising," "includes," and/or "including" when used herein specify the presence of stated features, integers, steps, operations, elements, and/or components, but do not preclude the presence or addition of one or more other features, integers, steps, operations, elements, components, and/or groups thereof.

Unless otherwise defined, all terms (including technical and scientific terms) used herein have the same meaning as commonly understood by one of ordinary skill in the art to which this disclosure belongs. It will be further understood that terms used herein should be interpreted as having meanings that are consistent with their meanings in the context of this specification and the relevant art and will not be interpreted in an idealized or overly formal sense unless expressly so defined herein.

Embodiments are described herein with reference to schematic illustrations of embodiments of the disclosure. As such, the actual dimensions of the layers and elements can be different, and variations from the shapes of the illustrations as a result, for example, of manufacturing techniques and/or tolerances, are expected. For example, a region illustrated or described as square or rectangular can have rounded or curved features, and regions shown as straight lines may have some irregularity. Thus, the regions illustrated in the figures are schematic and their shapes are not intended to illustrate the precise shape of a region of a device and are not intended to limit the scope of the disclosure. Additionally, sizes of structures or regions may be exaggerated relative to other structures or regions for illustrative purposes and, thus, are provided to illustrate the general structures of the present subject matter and may or may not be drawn to scale. Common elements between figures may be shown herein with common element numbers and may not be subsequently re-described.

Aspects of the present disclosure relate to devices and methods for impinging light on a tissue, for example within a body of a patient, where the light may include at least one characteristic that exerts or induces at least one biological effect within or on the tissue. Biological effects may include at least one of inactivating and inhibiting growth of one or more combinations of microorganisms and pathogens, including but not limited to viruses, bacteria, fungi, and other microbes, among others. Biological effects may also include one or more of upregulating a local immune response, stimulating enzymatic generation of nitric oxide to increase endogenous stores of nitric oxide, releasing nitric oxide from endogenous stores of nitric oxide, and inducing an anti-inflammatory effect. Wavelengths of light may be selected based on at least one intended biological effect for one or more of the targeted tissue and the targeted microorganisms or pathogens. In certain aspects, wavelengths of light may include visible light in any number of wavelength ranges based on the intended biological effect. Further aspects involve light impingement on tissue for multiple microorganisms and/or multiple pathogenic biological effects, either with light of a single peak wavelength or a combination of light with more than one peak wavelength. Devices and methods for light treatments are disclosed that provide light doses for inducing biological effects on various targeted pathogens and targeted tissues with increased efficacy and reduced cytotoxicity. Light doses may include various combinations of irradiances, wavelengths, and exposure times, and such light doses may be administered continuously or discontinuously with a number of pulsed exposures.

Certain aspects of the disclosure relate to phototherapeutic modulation of nitric oxide in living mammalian tissue, including use of light having a first peak wavelength and a first radiant flux to release nitric oxide from endogenous stores of nitric oxide, and use of light having a second peak wavelength and a second radiant flux to increase endogenous stores of nitric oxide (e.g., to increase expression of nitric oxide synthase enzymes), wherein the second peak wavelength differs from the first peak wavelength. The photoinitiated release of endogenous stores of nitric oxide effectively regenerates "gaseous" (or unbound) nitric oxide that was autoxidized into nitrosative intermediates and bound covalently in the body in a "bound" state. By stimulating release of nitric oxide from endogenous stores, nitric oxide may be maintained in a gaseous state for an extended duration and/or a spatial zone of nitric oxide release may be expanded.

Certain aspects of the disclosure relate to phototherapeutic modulation of nitric oxide in living mammalian tissue, including use of light having a first peak wavelength and a first radiant flux to stimulate enzymatic generation of nitric oxide to increase endogenous stores of nitric oxide (e.g., to increase expression of nitric oxide synthase enzymes), and release nitric oxide from the endogenous stores. The photoinitiated release of endogenous stores of nitric oxide effectively regenerates "gaseous" (or unbound) nitric oxide that was autooxidized into nitrosative intermediates and bound covalently in the body in a "bound" state. By stimulating release of nitric oxide from endogenous stores, nitric oxide may be maintained in a gaseous state for an extended duration and/or a spatial zone of nitric oxide release may be expanded.

Figure 1:
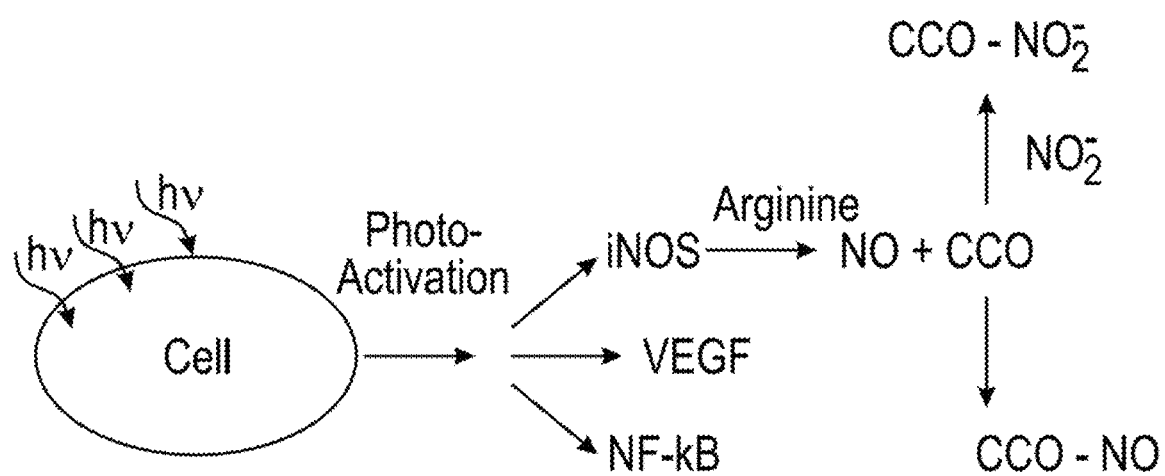
FIG. 1 is a reaction sequence showing photoactivated production of nitric oxide (NO) catalyzed by iNOS, followed by binding of NO to CCO.
Figure 2A:
FIG. 2A is a reaction sequence showing photomodulated release of NO from nitrosothiols (RSNO).
Figure 2B:
FIG. 2B is a reaction sequence showing photomodulated release of NO from metal nitrosyls (M-NO).
Figure 2C:
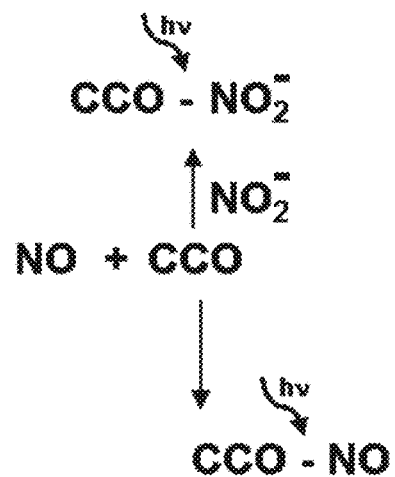
FIG. 2C is a reaction sequence showing loading of cytochrome c oxidase (CCO) with NO (yielding CCO-NO and CCO-NO$_2^-$) followed by photomodulated release of nitric oxide from the CCO-NO and CCO-NO$_2^-$.

As noted previously, nitric oxide is endogenously stored on a variety of nitrosated biochemical structures. Upon receiving the required excitation energy, both nitroso and nitrosyl compounds undergo hemolytic cleavage of S—N, N—N, or M-N bonds to yield free radical nitric oxide. Nitrosothiols and nitrosamines are photoactive and can be phototriggered to release nitric oxide by wavelength specific excitation. FIG. 2A is a reaction sequence showing photomodulated release of NO from nitrosothiols (RSNO). Similar results may be obtained with metal nitrosyls and NO-loaded chromophores (such as, but not limited to, CCO-NO). FIG. 2B is a reaction sequence showing photomodulated release of NO from metal nitrosyls (M-NO). FIG. 2C is a reaction sequence showing loading of cytochrome c oxidase (CCO) with NO (yielding CCO-NO and CCO-NO$_2^-$), followed by photomodulated release of nitric oxide from the CCO-NO and CCO-NO$_2^-$. In each case, providing light energy of a specified peak wavelength and radiant flux to tissue may stimulate release of endogenous stores of NO to permit NO to be maintained in a gaseous state in living tissue for a longer duration than would be encountered in the absence of the provision of such light energy.

Figure 3:
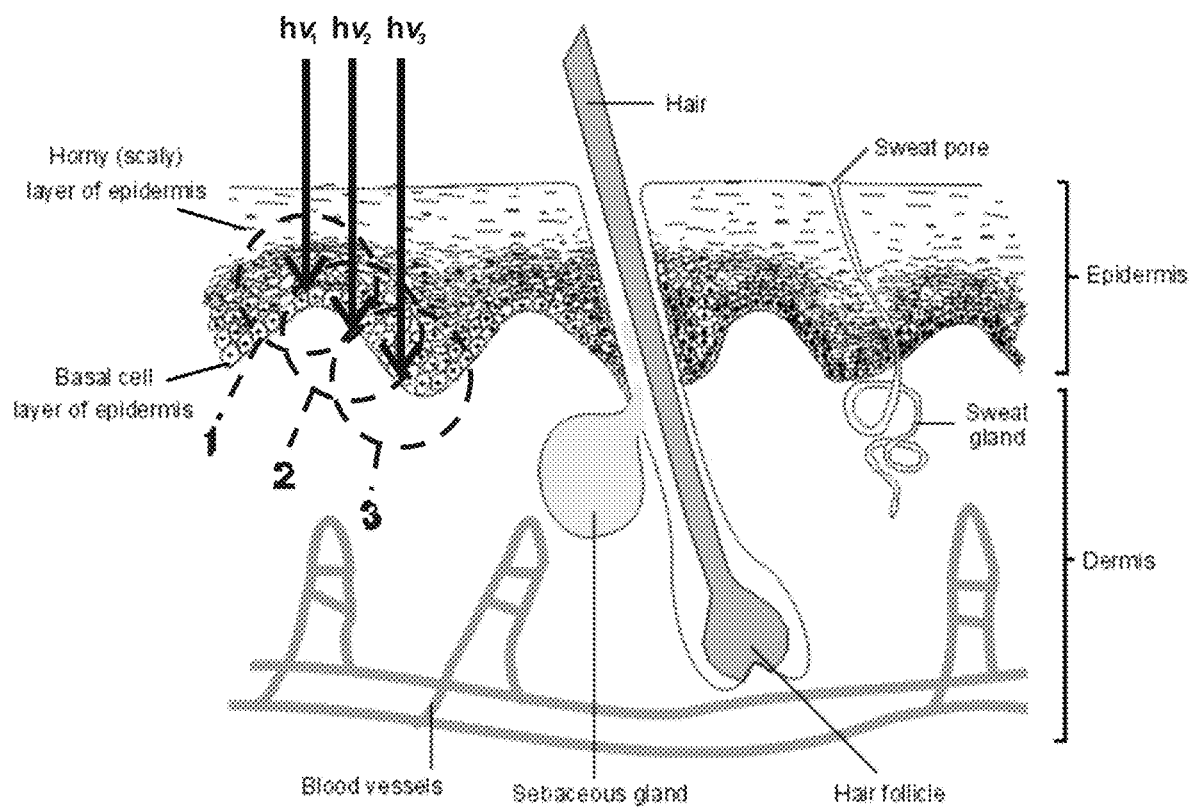
FIG. 3 is a cross-sectional view of epidermis and dermis layers of human skin with schematic illustration of overlapping zones in which NO is released from endogenous stores of NO by photomodulation.

FIG. 3 is a cross-sectional view of epidermis and dermis layers of human skin with schematic illustration of overlapping zones 1-3 in which endogenous stores of NO are generated and/or NO is released from endogenous stores by photomodulation. (The zones 1-3 are not necessarily illustrated to scale.) It has been reported that NO may diffuse in mammalian tissue by a distance of up to about 500 microns. In certain embodiments, photons of a first energy $h\upsilon_1$ may be supplied to the tissue to stimulate enzymatic generation of NO to increase endogenous stores of NO in a first diffusion zone 1. Photons of a second energy $h\upsilon_2$ may be supplied to the tissue in a region within or overlapping the first diffusion zone 1 to trigger release of NO from endogenous stores, thereby creating a second diffusion zone 2. Alternatively, or additionally, photons of a second energy $h\upsilon_2$ may be supplied to stimulate enzymatic generation of NO to increase endogenous stores of NO in the second diffusion zone 2. Photons of a third energy $h\upsilon_3$ may be supplied to the tissue in a region within or overlapping the second diffusion zone 2 to trigger release of endogenous stores, thereby creating a third diffusion zone 3. Alternatively, or additionally, photons of a third energy $h\upsilon_3$ may be supplied to stimulate enzymatic generation of NO to increase endogenous stores of NO in the third diffusion zone 3. In certain embodiments, the first, second, and third diffusion zones 1-3 may have different average depths relative to an outer epidermal surface. In certain embodiments, the first photon energy $h\upsilon_1$, the second photon energy $h\upsilon_2$, and the third photon energy $h\upsilon_3$ may be supplied at different peak wavelengths, wherein different peak wavelengths may penetrate mammalian tissue to different depths—since longer wavelengths typically provide greater penetration depth. In certain embodiments, sequential or simultaneous impingement of increasing wavelengths of light may serve to "push" a nitric oxide diffusion zone deeper within mammalian tissue than might otherwise be obtained by using a single (e.g., long) wavelength of light.

Light having a first peak wavelength and a first radiant flux to release nitric oxide from endogenous stores of nitric oxide may be referred to herein as "endogenous store releasing light" or "ES releasing light;" and light having a second peak wavelength and a second radiant flux to stimulate enzymatic generation of nitric oxide to increase endogenous stores of nitric oxide may be referred to herein as "endogenous store increasing light" or "ES increasing light."

In certain embodiments, the second peak wavelength (of the ES increasing light) is greater than the first peak wavelength (of the ES releasing light) by at least 25 nm, at least 40 nm, at least 50 nm, at least 60 nm, at least 75 nm, at least 85 nm, at least 100 nm, or another threshold specified herein.

In certain embodiments, each of the ES increasing light and the ES releasing light has a radiant flux in a range of at least 5 mW, or at least 10 mW, or at least 15 mW, or at least 20 mW, or at least 30 mW, or at least 40 mW, or at least 50 mW, or in a range of from 5 mW to 60 mW, or in a range of from 5 mW to 30 mW, or in a range of from 5 mW to 20 mW, or in a range of from 5 mW to 10 mW, or in a range of from 10 mW to 60 mW, or in a range of from 20 mW to 60 mW, or in a range of from 30 mW to 60 mW, or in a range of from 40 mW to 60 mW, or in another range specified herein.

In certain embodiments, the ES increasing light has a greater radiant flux than the ES releasing light. In certain embodiments, the ES releasing light has a greater radiant flux than the ES increasing light.

In certain embodiments, one or both of the ES increasing light and the ES releasing light has a radiant flux profile that is substantially constant during a treatment window. In certain embodiments, at least one of the ES increasing light and the ES releasing light has a radiant flux profile that increases with time during a treatment window. In certain embodiments, at least one of the ES increasing light and the ES releasing light has a radiant flux profile that decreases with time during a treatment window. In certain embodiments, one of the ES increasing light or the ES releasing light has a radiant flux profile that decreases with time during a treatment window, while the other of the ES increasing light or the ES releasing light has a radiant flux profile that increases with time during a treatment window.

In certain embodiments, ES releasing light is applied to tissue during a first time window, ES increasing light is applied to the tissue during a second time window, and the second time window overlaps with the first time window. In other embodiments, ES releasing light is applied to tissue during a first time window, ES increasing light is applied to the tissue during a second time window, and the second time is non-overlapping or is only partially overlapping with the first time window. In certain embodiments, the second time window is initiated more than one minute, more than 5 minutes, more than 10 minutes, more than 30 minutes, or more than one hour after conclusion of the first time window. In certain embodiments, ES releasing light is applied to tissue during a first time window, ES increasing light is applied to the tissue during a second time window, and the first time window and the second time window are substantially the same. In other embodiments, the second time window is longer than the first time window.

In certain embodiments, one or both of ES increasing light and ES releasing light may be provided by a steady state source providing a radiant flux that is substantially constant over a prolonged period without being pulsed.

In certain embodiments, one or both of ES increasing light and ES releasing light may include more than one discrete pulse (e.g., a plurality of pulses) of light. In certain embodiments, more than one discrete pulse of ES releasing light is impinged on tissue during a first time window, and/or more than one discrete pulse of ES increasing light is impinged on tissue during a second time window. In certain embodiments, the first time window and the second time window may be coextensive, may be overlapping but not coextensive, or may be non-overlapping.

In certain embodiments, at least one of radiant flux and pulse duration of ES releasing light may be reduced from a maximum value to a non-zero reduced value during a portion of a first time window. In certain embodiments, at least one of radiant flux and pulse duration of ES releasing light may be increased from a non-zero value to a higher value during a portion of a first time window. In certain embodiments, at least one of radiant flux and pulse duration of ES increasing light may be reduced from a maximum value to a non-zero reduced value during a portion of a second time window. In certain embodiments, at least one of radiant flux and pulse duration of ES increasing light may be increased from a non-zero value to a higher value during a portion of a second time window.

In certain embodiments, each of ES increasing light and ES releasing light consists of non-coherent light. In certain embodiments, each of ES increasing light and ES releasing light consists of coherent light. In certain embodiments, one of the ES increasing light or the ES releasing light consists of non-coherent light, and the other of the ES increasing light or the ES releasing light consists of coherent light.

In certain embodiments, the ES releasing light is provided by at least one first light emitting device and the ES increasing light is provided by at least one second light emitting device. In certain embodiments, the ES releasing light is provided by a first array of light emitting devices and the ES increasing light is provided by a second array of light emitting devices.

In certain embodiments, at least one of the ES increasing light or the ES releasing light is provided by at least one solid state light emitting device. Examples of solid state light emitting devices include (but are not limited to) light emitting diodes, lasers, thin film electroluminescent devices, powdered electroluminescent devices, field induced polymer electroluminescent devices, and polymer light-emitting electrochemical cells. In certain embodiments, the ES releasing light is provided by at least one first solid state light emitting device and the ES increasing light is provided by at least one second solid state light emitting device. In certain embodiments, ES increasing light and ES releasing light may be generated by different emitters contained in a single solid state emitter package, wherein close spacing between adjacent emitters may provide integral color mixing. In certain embodiments, the ES releasing light may be provided by a first array of solid state light emitting devices and the ES increasing light may be provided by a second array of solid state light emitting devices. In certain embodiments, an array of solid state emitter packages each including at least one first emitter and at least one second emitter may be provided, wherein the array of solid state emitter packages embodies a first array of solid state emitters arranged to generate ES releasing light and embodies a second array of solid state emitters arranged to generate ES increasing light. In certain embodiments, an array of solid state emitter packages may embody packages further including third, fourth, and/or fifth solid state emitters, such that a single array of solid state emitter packages may embody three, four, or five arrays of solid state emitters, wherein each array is arranged to generate emissions with a different peak wavelength.

In certain embodiments, at least one of the ES increasing light or the ES releasing light is provided by at least one light emitting device devoid of a wavelength conversion material. In other embodiments, at least one of the ES increasing light or the ES releasing light is provided by at least one light emitting device arranged to stimulate a wavelength conversion material, such as a phosphor material, a fluorescent dye material, a quantum dot material, and a fluorophore material.

In certain embodiments, the ES increasing light and the ES releasing light consist of substantially monochromatic light. In certain embodiments, the ES releasing light includes a first spectral output having a first full width at half maximum value of less than 25 nm (or less than 20 nm, or less than 15 nm, or in a range of from 5 nm to 25 nm, or in a range of from 10 nm to 25 nm, or in a range of from 15 nm to 25 nm), and/or the ES increasing light includes a second spectral output having a second full width at half maximum value of less than 25 nm (or less than 20 nm, or less than 15 nm, or in a range of from 5 nm to 25 nm, or in a range of from 10 nm to 25 nm, or in a range of from 15 nm to 25 nm). In certain embodiments, less than 5% of the first spectral output is in a wavelength range of less than 400 nm, and less than 1% of the second spectral output is in a wavelength range of less than 400 nm.

In certain embodiments, the ES releasing light is produced by one or more first light emitters having a single first peak wavelength, and the ES increasing light is produced by one or more second light emitters having a single second peak wavelength. In other embodiments, the ES increasing light may be produced by at least two light emitters having different peak wavelengths (e.g., differing by at least 5 nm, at least 10 nm, at least 15 nm, at least 20 nm, or at least 25 nm), and/or the ES releasing light may be produced by at least two light emitters having different peak wavelengths (e.g., differing by at least 5 nm, at least 10 nm, at least 15 nm, at least 20 nm, or at least 25 nm).

Ultraviolet light (e.g., UV-A light having a peak wavelength in a range of from 350 nm to 395 nm, and UV-B light having a peak wavelength in a range of from 320 nm to 350 nm) may be effective as ES increasing or ES releasing light; however, overexposure to ultraviolet light may lead to detrimental health effects including premature skin aging and potentially elevated risk for certain types of cancer. In certain embodiments, UV light (e.g., having peak wavelengths in a range of from 320 nm to 399 nm) may be used as ES increasing or ES releasing light; however, in other embodiments, UV light may be avoided.

In certain embodiments, ES increasing light and ES releasing light are substantially free of UV light. In certain embodiments, less than 5% of the ES increasing light is in a wavelength range of less than 400 nm, and less than 1% of the ES releasing light output is in a wavelength range of less than 400 nm. In certain embodiments, ES increasing light includes a peak wavelength in a range of from 400 nm to 490 nm, or from 400 nm to 450 nm, or from 400 nm to 435 nm, or from 400 nm to 420 nm, or from 410 nm to 440 nm, or from 420 nm to 440 nm.

In certain embodiments, ES increasing light may include a wavelength range and flux that may alter the presence, concentration, or growth of pathogens (e.g., bacteria, viruses, fungi, protists, and/or other microbes) in or on living mammalian tissue receiving the light. UV light and near-UV light (e.g., having peak wavelengths from 400 nm to 435 nm, or more preferably from 400 nm to 420 nm) in particular may affect microbial growth. Effects on microbial growth may depend on the wavelength range and dose. In certain embodiments, ES increasing or ES releasing light may include near-UV light having a peak wavelength in a range of from 400 nm to 420 nm to provide a bacteriostatic effect (e.g., with pulsed light having a radiant flux of <9 mW), provide a bactericidal effect (e.g., with substantially steady state light having a radiant flux in a range of from 9 mW to 17 mW), or provide an antimicrobial effect (e.g., with substantially steady state light having a radiant flux in a range of greater than 17 mW, such as in a range of from 18 mW to 60 mW). In certain embodiments, ES increasing or ES releasing light in a near-UV range (e.g., from 400 nm to 420 nm) may also affect microbial growth (whether in a bacteriostatic range, bactericidal range, or an antimicrobial range) for uses such as wound healing, reduction of acne blemishes, or treatment of atopic dermatitis. Such function(s) may be in addition to the function of the ES increasing light to increase endogenous stores of nitric oxide in living tissue.

In certain embodiments, ES increasing light may include a peak wavelength in a range of from 500 nm to 900 nm, or in a range of from 490 nm to 570 nm, or in a range of from 510 nm to 550 nm, or in a range of from 520 nm to 540 nm, or in a range of from 525 nm to 535 nm, or in a range of from 528 nm to 532 nm, or in a range of about 530 nm.

Applicant has found that the ability to generate and release nitric oxide is dependent on the wavelength and fluence of light used. To investigate whether certain wavelengths of light may be more effective than others at releasing endogenous stores of NO (i.e., to serve as ES releasing light), Applicant performed various experiments. One series of experiments included generating nitric oxide-loaded hemoglobin (Hb-NO), irradiating the Hb-NO with different wavelengths of light produced by substantially monochromatic LEDs, and comparing absorbance spectra for Hb, for the Hb-NO prior to the LED irradiation, and for the Hb-NO after the LED irradiation. The Hb-NO was generated by mixing 10 μM Hb with 1 μM Prolino (a NO source). The mixture was then stirred and incubated one hour, and then was allowed to rest for 5 minutes. Irradiation with LED light was performed under vacuum to facilitate removal of NO liberated from the Hb-NO.

Figure 4A:
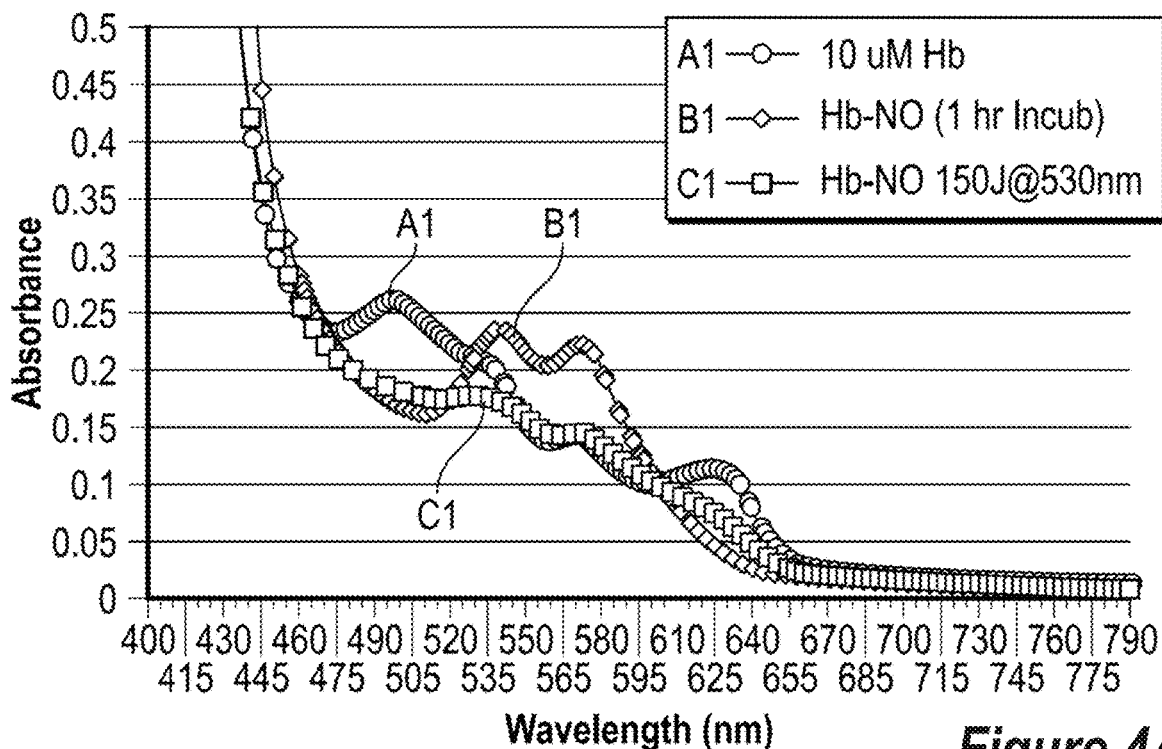
FIG. 4A includes superimposed plots of absorbance versus wavelength for hemoglobin (Hb), nitric oxide-loaded hemoglobin (Hb-NO) prior to irradiation, and Hb-NO following absorption of 150 J of light emissions of a green LED having a peak wavelength of 530 nm.

FIG. 4A includes superimposed plots of absorbance versus wavelength for hemoglobin (Hb) (line "A1"), for nitric oxide-loaded hemoglobin (Hb-NO) prior to irradiation (line "B1"), and for Hb-NO following absorption of 150 J of light emissions of a green LED having a peak wavelength of 530 nm (line "C1"). A comparison of line A1 and line B1 shows the presence of two peaks at about 540 nm and about 577 nm, representing the presence of NO in the Hb-NO. A comparison of line C1 and line B1 shows that the two peaks at about 540 nm and about 577 nm present in the Hb-NO were eliminated, thereby evidencing release of NO from the Hb-NO attributable to irradiation of Hb-NO with 530 nm peak wavelength green light.

Figure 4B:
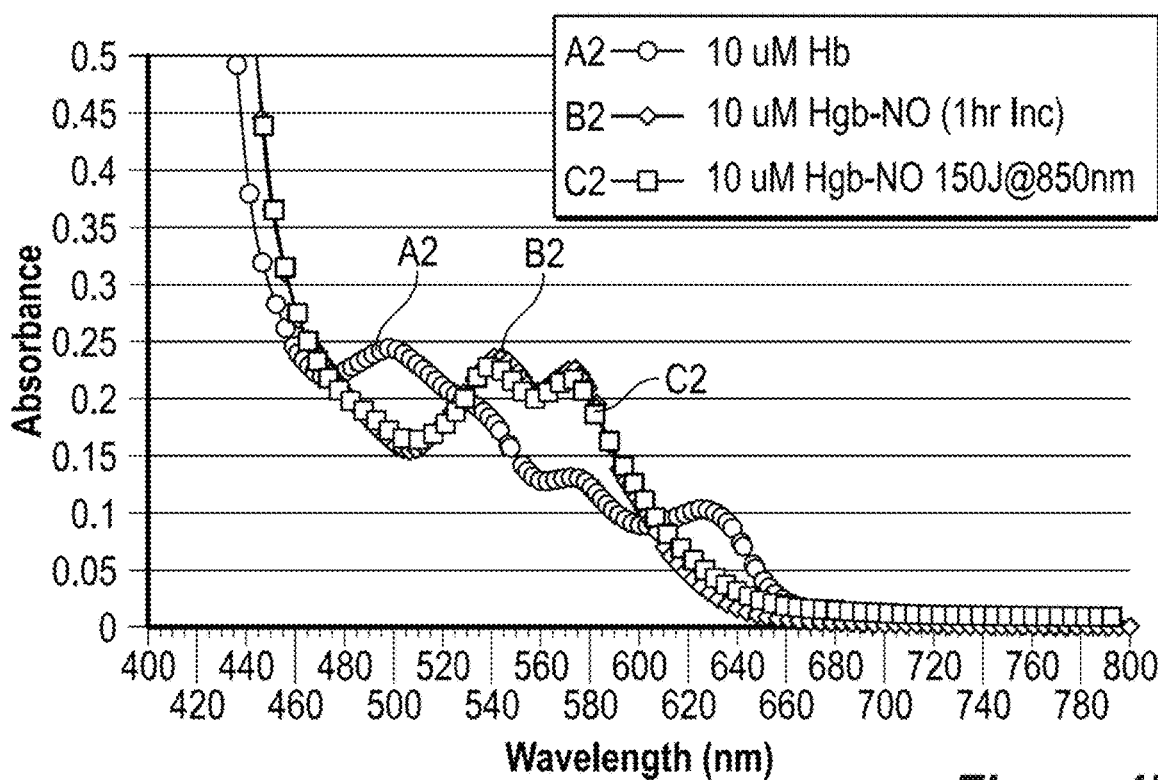
FIG. 4B includes superimposed plots of absorbance versus wavelength for Hb, Hb-NO prior to irradiation, and Hb-NO following absorption of 150 J of light emissions of an IR LED source having a peak wavelength of 850 nm.

FIG. 4B includes superimposed plots of absorbance versus wavelength for Hb (line "A2"), for Hb-NO prior to irradiation (line "B2"), and for Hb-NO following absorption of 150 J of light emissions of an IR LED source having a peak wavelength of 850 nm (line "C2"). A comparison of line A2 and line B2 shows the presence of two peaks at about 540 nm and about 577 nm, representing the presence of NO in the Hb-NO. A comparison of lines C1 and B1, however, reveals that such lines substantially coincide with one another. This evidences that impingement of 850 nm peak wavelength light on Hb-NO was ineffective in releasing NO.

Figure 5:
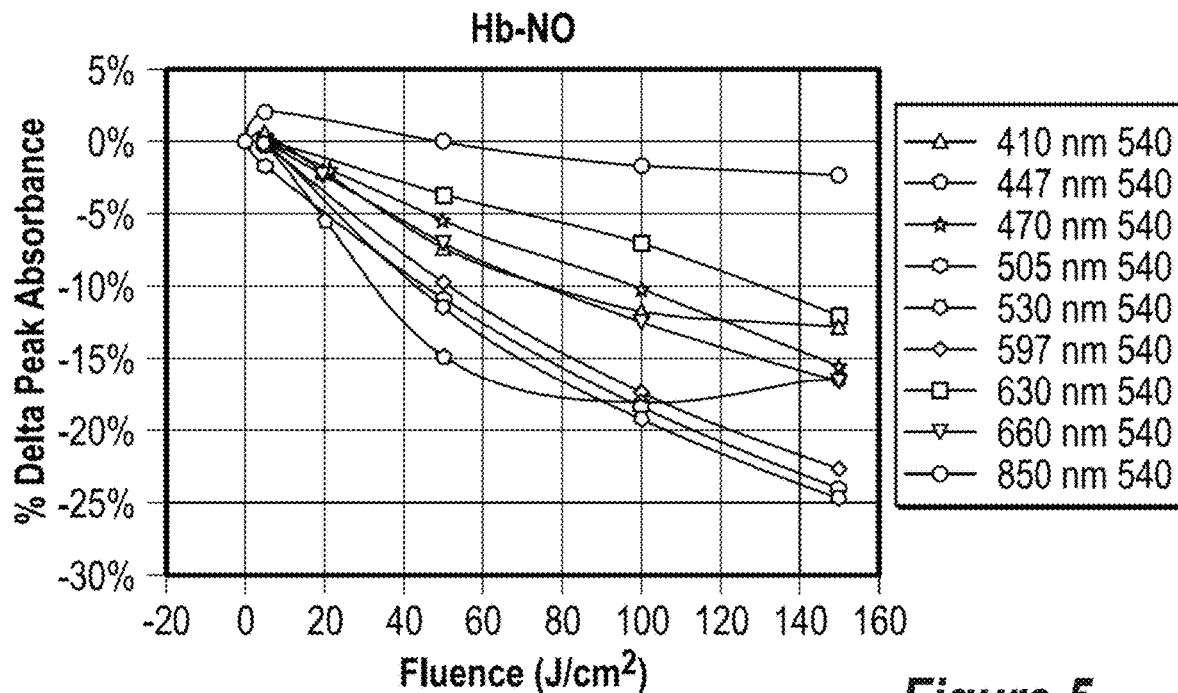
FIG. 5 is a plot of percentage change in peak absorbance for the 540 nm peak of Hb-NO versus fluence (Joules per square centimeter) for nine different wavelengths of light (from 410 nm to 850 nm).

Nine LED light sources providing nine different peak wavelengths (i.e., 410 nm, 447 nm, 470 nm, 505 nm, 530 nm, 597 nm, 630 nm, 660 nm, and 850 nm) were tested to determine their relative effectiveness in releasing NO from Hb-NO. FIG. 5 is a plot of percentage change in peak absorbance for the 540 nm peak of Hb-NO versus fluence (Joules per square centimeter) for the nine different wavelengths of light from 410 nm to 850 nm. As shown in FIG. 5, the wavelengths identified to be most effective in releasing NO from Hb-NO were determined to be the following, from best to worst: 530 nm, 505 nm, 597 nm, 447 nm, 660 nm, 470 nm, 410 nm, 630 nm, and 850 nm.

Figure 6:
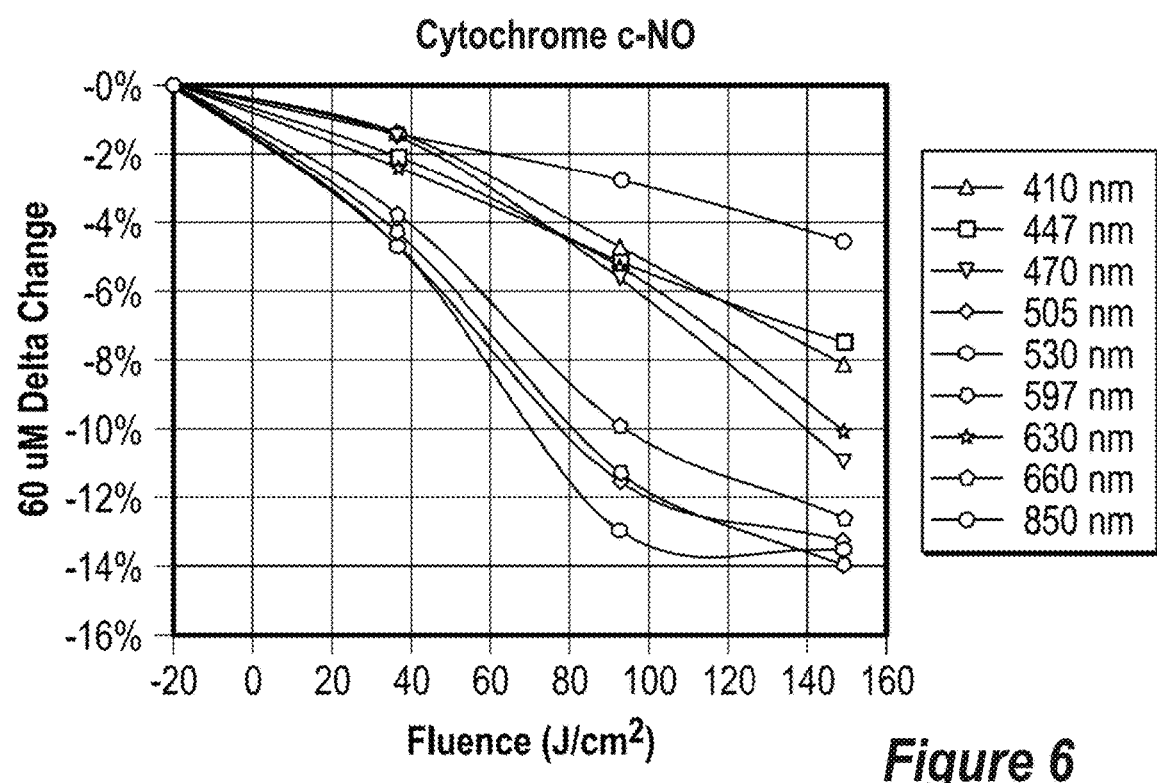
FIG. 6 is a plot of percentage change in peak absorbance for Cytochrome c-NO versus fluence (Joules per square centimeter) for nine different wavelengths of light (from 410 nm to 850 nm).

Another series of experiments included generating nitric oxide-loaded cytochrome c (Cytochrome c-NO), irradiating the Cytochrome c-NO with different wavelengths of light produced by substantially monochromatic LEDs, and comparing absorbance spectra for Cytochrome c, for the Cytochrome c-NO prior to the LED irradiation, and for the Cytochrome c-NO after the LED irradiation. 60 μM Cytochrome c was used according to a procedure otherwise similar to that described above in connection with Hb. FIG. 6 is a plot of percentage change in peak absorbance for Cytochrome c-NO versus fluence (Joules per square centimeter) for nine different wavelengths of light (from 410 nm to 850 nm). As shown in FIG. 6, the wavelengths identified to be most effective in releasing NO from Cytochrome c-NO were determined to be the following, from best to worst: 530 nm, 597 nm, 505 nm, 660 nm, 470 nm, 630 nm, 410 nm, 447 nm, and 850 nm. Notably, 530 nm was determined to be the most effective peak wavelength of light for releasing NO from both Hb-NO and Cytochrome c-NO.

Figure 7:
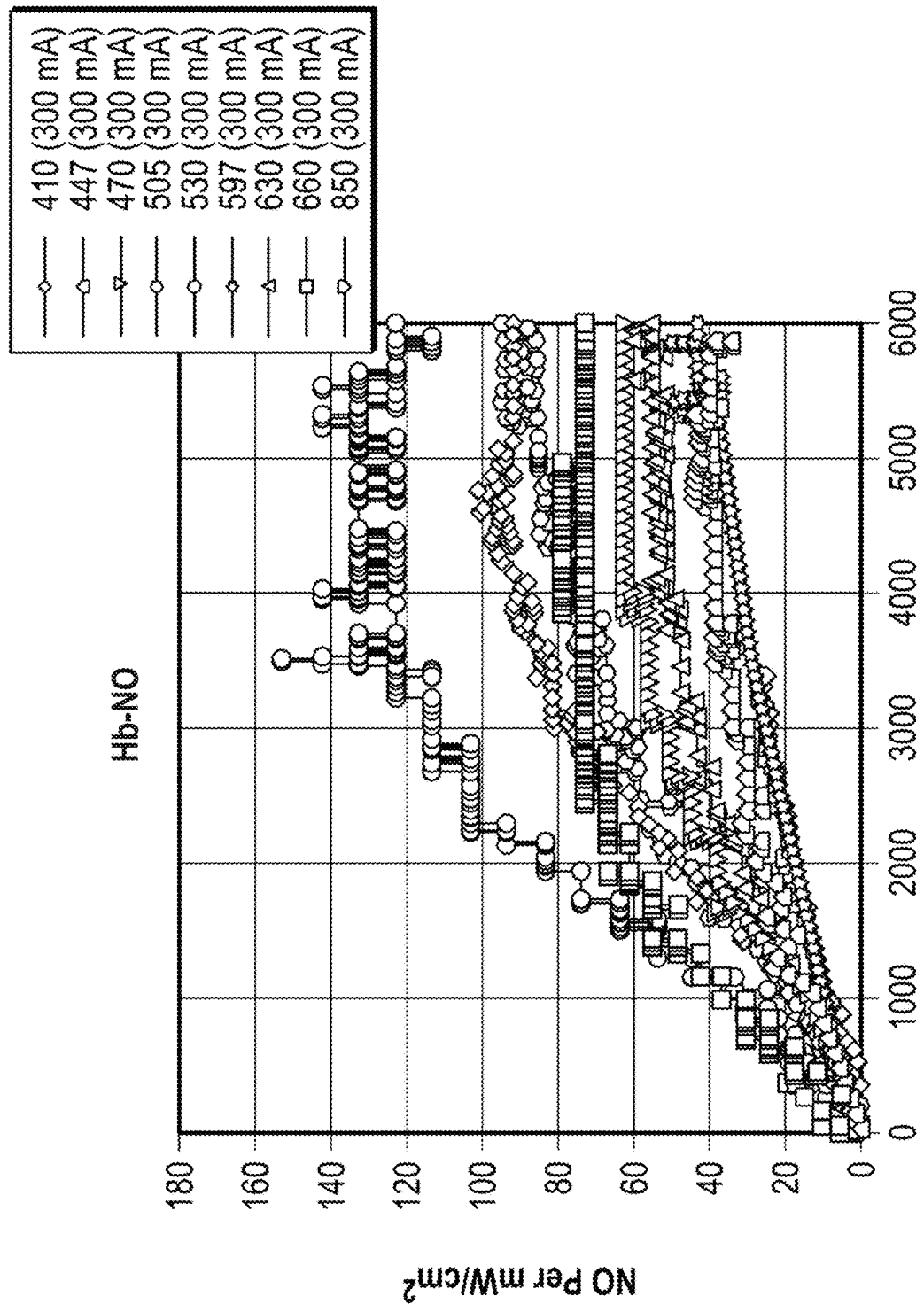
FIG. 7 is a plot of released NO (ppb) per milliwatt per square centimeter versus time for the photomodulated release of NO from Hb-NO for nine different wavelengths of light (from 410 nm to 850 nm).

The results shown in FIG. 5 for Hb-NO were not normalized to radiant flux, and it is recognized that different LEDs have different efficiencies. To address this issue, the results for Hb-NO were normalized to a 300 mA value. FIG. 7 is a plot of released NO per milliwatt per square centimeter versus time for the photomodulated release of NO from Hb-NO for nine different wavelengths of light (from 410 nm to 850 nm). As shown in FIG. 7, 530 nm was determined to be the single most efficient single peak wavelength (per milliwatt of power) for releasing NO from Hb-NO.

To determine whether various combinations of two peak wavelengths might be more or less effective than single peak wavelengths in releasing NO from Hb-NO, additional experiments were performed using Hb-NO. Hb-NO was generated by mixing 10 μM Hb with 1 μM Prolino (a NO source), then the mixture was stirred and incubated one hour, and the mixture was allowed to rest for 5 minutes. Irradiation with two peak wavelengths of LED light was performed under vacuum to facilitate removal of NO liberated from the Hb-NO. Results for three different combinations of two peak wavelengths are shown in FIGS. 8A to 8C, together with results obtained for individual constituents of the combinations.

Figure 8A:
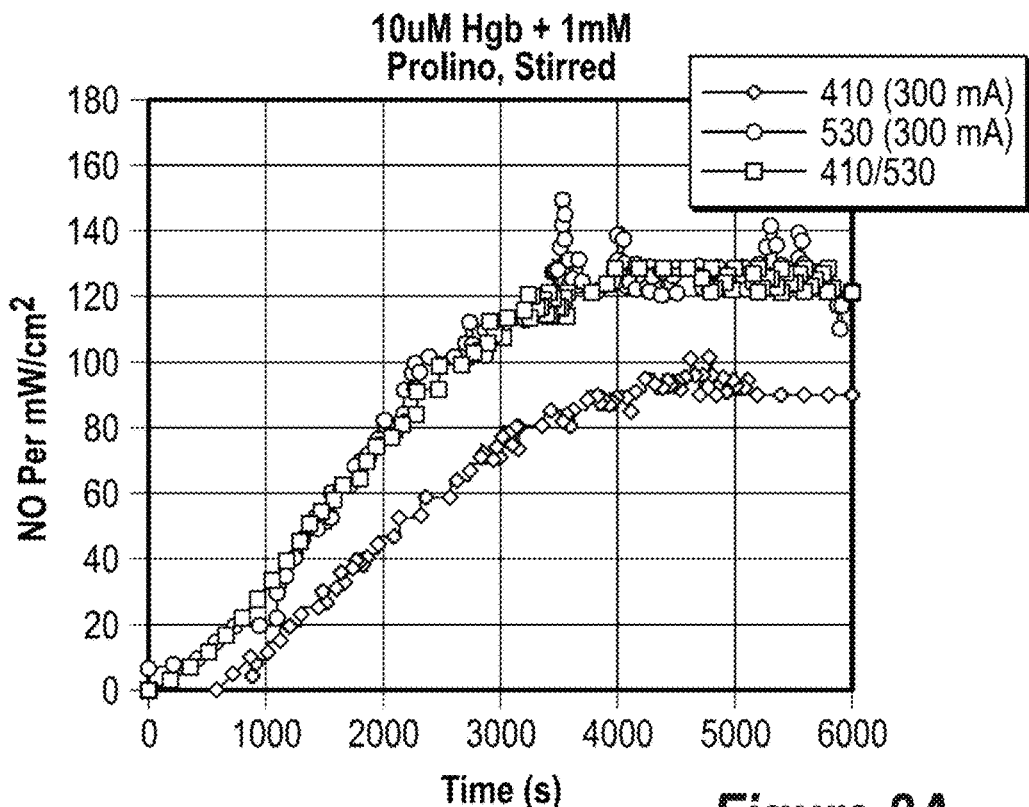
FIG. 8A includes superimposed plots of released NO (ppb) per milliwatt per square centimeter versus time for irradiation of Hb-NO with (i) a 410 nm peak wavelength blue LED device, (ii) a 530 nm peak wavelength green LED device, and (iii) the 410 nm peak wavelength blue LED device in combination with the 530 nm peak wavelength green LED device.

FIG. 8A includes superimposed plots of released NO per milliwatt per square centimeter versus time for irradiation of Hb-NO with (i) a 410 nm peak wavelength blue LED device, (ii) a 530 nm peak wavelength green LED device, and (iii) the 410 nm peak wavelength blue LED device in combination with the 530 nm peak wavelength green LED device. As expected from the prior experiments, the 410 nm light was significantly less effective than the 530 nm light at releasing NO from Hb-NO. Surprisingly, however, the combination of equal parts of 410 nm light and 530 nm light appeared to be equally as effective as 530 nm light alone. Such a combination may be beneficial since a 410 nm blue LED is significantly more efficient than a 530 nm green LED, such that a combination of equal parts of 410 nm LED emissions and 530 nm LED emissions may use 26% less electric power than emissions of a 530 nm LED alone, when operated to provide the same radiant flux.

Figure 8B:
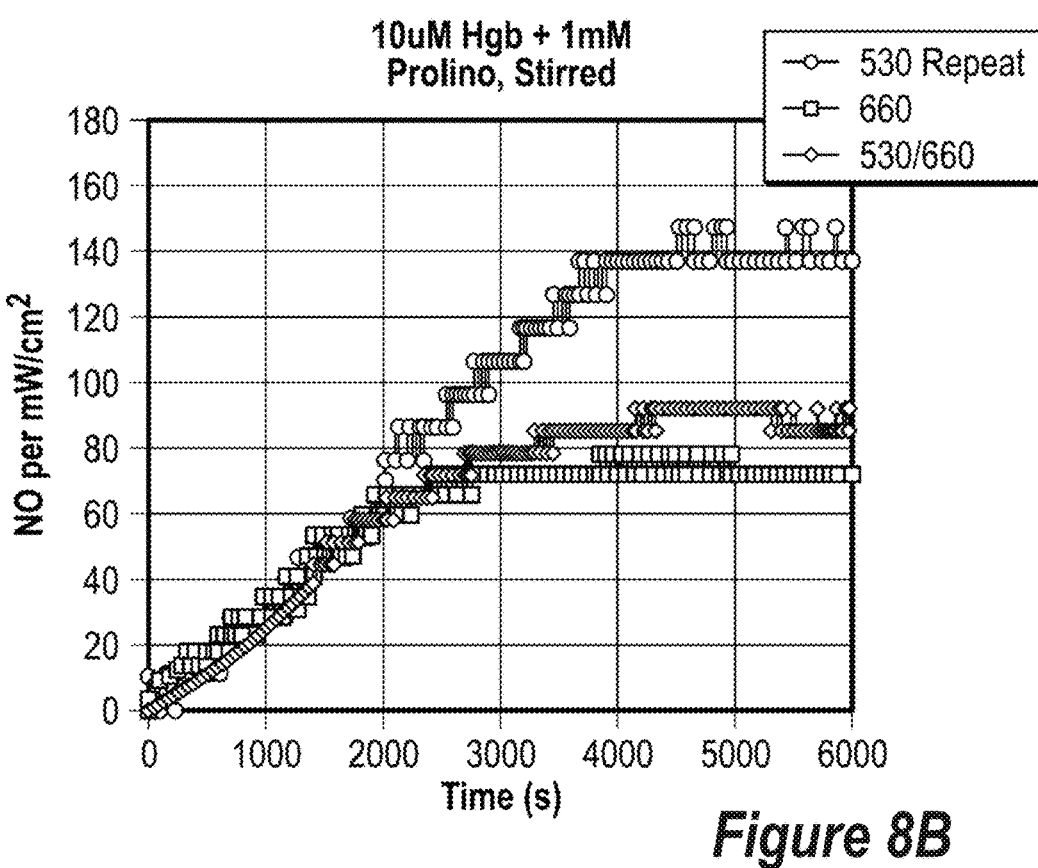
FIG. 8B includes superimposed plots of released NO (ppb) per milliwatt per square centimeter versus time for irradiation of Hb-NO with (i) a 530 nm peak wavelength green LED device, (ii) a 660 nm peak wavelength red LED device, and (iii) the 530 nm peak wavelength green LED device in combination with the 660 nm peak wavelength red LED device.
Figure 8C:
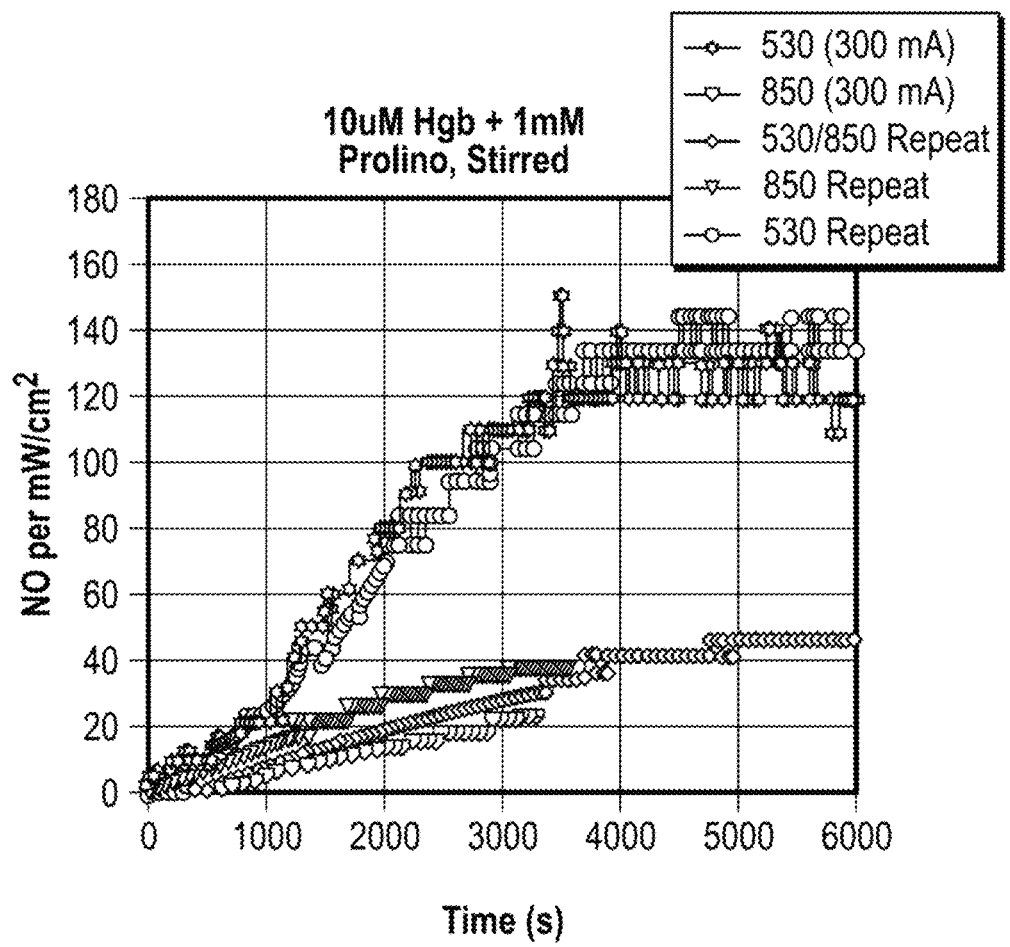
FIG. 8C includes superimposed plots of released NO (ppb) per milliwatt per square centimeter versus time for irradiation of Hb-NO with (i) a 530 nm peak wavelength green LED device (including one repeat run), (ii) a 850 nm peak wavelength infrared LED device (including one repeat run), and (iii) the 530 nm peak wavelength green LED device in combination with the 850 nm peak wavelength infrared LED device.

FIG. 8B includes superimposed plots of released NO per milliwatt per square centimeter versus time for irradiation of Hb-NO with (i) a 530 nm peak wavelength green LED device, (ii) a 660 nm peak wavelength red LED device, and (iii) the 530 nm peak wavelength green LED device in combination with the 660 nm peak wavelength red LED device. As expected from the prior experiments, the 660 nm red light was significantly less effective than the 530 nm green light at releasing NO from Hb-NO. The combination of equal parts of 530 nm green light and 660 nm red light was only slightly better than 660 nm red light alone at releasing NO from Hb-NO.

Notably, as shown in FIG. 8B, the release of NO from Hb-NO appears to be the same for 530 nm green light, 660 nm red light, and a combination of 530 nm green and 660 nm light for the time window of from 0 seconds to about 2000 seconds, but the effectiveness of the different sources diverges thereafter. Without intending to be bound by any particular theory or explanation of this phenomenon, it is suggested that NO binds to Hb-NO at multiple sites, and that removal of a second or subsequent NO molecule from Hb-NO may require more energy than removal of a first NO molecule, perhaps due to a change in shape of the Hb-NO after removal of a first NO molecule.

FIG. 8C includes superimposed plots of released NO per milliwatt per square centimeter versus time for irradiation of Hb-NO with (i) a 530 nm peak wavelength green LED device (including one repeat run), (ii) a 850 nm peak wavelength infrared LED device (including one repeat run), and (iii) the 530 nm peak wavelength green LED device in combination with the 850 nm peak wavelength infrared LED device. As expected from the prior experiments, the 850 nm infrared light was ineffective at releasing NO from Hb-NO. The combination of equal parts of 530 nm green light and 850 nm infrared light was also ineffective at releasing NO from Hb-NO. This shows that the addition of 530 nm green light was unable to enhance the effectiveness of 850 nm infrared light in releasing NO from Hb-NO.

In certain embodiments, ES releasing light that includes light having a first peak wavelength is impinged on living tissue, ES increasing light that includes light having a second peak wavelength is impinged on the living tissue, and furthermore a light having a third peak wavelength may be impinged on the living tissue. In certain embodiments, the light having a third peak wavelength may be provided at substantially the same time as (or during a time window overlapping at least one time window of) one or both of the ES increasing light and the ES releasing light. In certain embodiments, the light having a third peak wavelength differs from each of the first peak wavelength and the second peak wavelength by at least 10 nm. In certain embodiments, the light having a third peak wavelength exceeds the second peak wavelength by at least 20 nm. In certain embodiments, the light having a third peak wavelength is provided with a radiant flux in a range of from 5 mW to 60 mW. In certain embodiments, the third peak wavelength is in a range of from 600 nm to 900 nm, or in a range of from 600 nm to 700 nm. In certain embodiments, the third peak wavelength is in a range of from 320 nm to 399 nm.

In certain embodiments, light having a third peak wavelength in a range of from 620 nm to 670 nm (e.g., including specific wavelengths of about 630 nm and about 660 nm) may be useful to provide anti-inflammatory effects and/or to promote vasodilation. Anti-inflammatory effects may be useful to promote wound healing, to reduce acne blemishes, to promote facial aesthetics, and/or to treat atopic dermatitis and other topical dermatological disorders. Vasodilation may also be beneficial to treat androgenic alopecia or other topical dermatological disorders.

In certain embodiments, light having a third peak wavelength may be useful to promote thermal and/or infrared heating of living mammalian tissue, such as may be useful in certain contexts including wound healing.

In certain embodiments utilizing modulated light therapy to control NO generation and release, human immune response may be altered and/or controlled. Such responses may include, but are not limited to: ATP production; DNA and RNA synthesis; gene transcription; extracellular matrix (e.g., collagen and elastin) secretion; protein expression (including but not limited to NOS enzymes); cell signaling pathways (including cytokine expression (e.g., interleukins), growth factors (e.g., vascular endothelial growth factor, insulin growth factor, insulin-like growth factors, fibroblast growth factors, and tumor necrosis factors); Wnt signaling pathways; and NF-kB pathways); cellular viability; cellular apoptosis; cellular proliferation and migration; reactive oxygen species generation; cellular response to reactive oxygen species (e.g., expression of superoxide dismutase); and inhibition of the enzyme 5α-reductase (to decrease DHT production and thereby reduce or reverse hair loss).

Methods and devices disclosed herein for photomodulation of nitric oxide in living mammalian tissue are contemplated for use with a wide variety of tissues. In certain embodiments, the tissue comprises epithelial tissue. In certain embodiments, the tissue comprises mucosal tissue. In certain embodiments, the tissue is within a body cavity of a patient. In certain embodiments, the tissue comprises cervical tissue.

In certain embodiments, the impinging of light having a first peak wavelength and the impinging of light having a second peak wavelength is performed with a single therapeutic device.

In certain embodiments, a device for photomodulation of nitric oxide in living mammalian tissue as disclosed herein may include a flexible substrate supporting one or more light emitting elements and arranged to conform to at least a portion of a human body. In certain embodiments, a flexible substrate may include a flexible printed circuit board (PCB), such as may include at least one polyimide-containing layer and at least one layer of copper or another electrically conductive material. In other embodiments, a device for photomodulation of nitric oxide as disclosed herein may include a rigid substrate supporting one or more light emitting elements. In certain embodiments, one or more surfaces of a device for photomodulation of nitric oxide may include a light-transmissive encapsulant material arranged to cover any light emitter(s) and at least a portion of an associated substrate (e.g., flexible PCB). A preferred encapsulant material is silicone, which may be applied by any suitable means such as molding, dipping, spraying, dispensing, or the like. In certain embodiments, one or more functional materials may be added to or coated on an encapsulant material. In certain embodiments, at least one surface, or substantially all surfaces (e.g., front and back surfaces) of a flexible PCB may be covered with encapsulant material.

In certain embodiments, a substrate as described herein may be arranged to support one or more light emitting elements. In certain embodiments, one or more light emitting elements may include multi-emitting light emitting devices such as multi-LED packages. In certain embodiments, one or more light emitting elements may be arranged for direct illumination, wherein at least a portion of emissions generated by the one or more light emitting elements is arranged to be transmitted directly through a light-transmissive external surface of a device without need for an intervening waveguide or reflector. In certain embodiments, one or more light emitting elements may be arranged for indirect illumination (e.g., side illumination), wherein emissions generated by the one or more light emitting elements are arranged to be transmitted to a light-transmissive external surface via a waveguide and/or a reflector, without a light emitting element being in direct line-of-sight arrangement relative to a light-transmissive external surface. In certain embodiments, a hybrid configuration may be employed, including one or more light emitting elements arranged for direct illumination, and further including one or more light emitting elements arranged for indirect illumination. In certain embodiments, one or more reflective materials (e.g., reflective flexible PCB or other reflective films) may be provided along selected surfaces of a device to reduce internal absorption of light and to direct light emissions toward an intended light-transmissive surface. In certain embodiments, a flexible light emitting device may include a substantially uniform thickness. In other embodiments, a flexible light emitting device may include a thickness that varies with position, such as a thickness that tapers in one direction or multiple directions. In certain embodiments, presence of a tapered thickness may help a flexible light emitting device to more easily be wrapped against or to conform to areas of a mammalian (e.g., human) body.

In certain embodiments, one or multiple holes or perforations may be defined in a substrate and any associated encapsulant material. In certain embodiments, holes may be arranged to permit transit of air, such as may be useful for thermal management. In certain embodiments, holes may be arranged to permit transit of wound exudate. In certain embodiments, one or more holes may be arranged to permit sensing of at least one condition through the hole(s). Holes may be defined by any suitable means such as laser perforation, die pressing, slitting, punching, blade cutting, and roller perforation. In certain embodiments, holes may have uniform or non-uniform size, placement, and/or distribution relative to a substrate and encapsulant material.

In certain embodiments, a device for photomodulation of nitric oxide in living mammalian tissue as disclosed herein may include one or more light-affecting elements such as one or more light extraction features, wavelength conversion materials, light diffusion or scattering materials, and/or light diffusion or scattering features. In certain embodiments, one or more light affecting elements may be arranged in a layer between a light emitting element and a light transmissive surface of a device. In certain embodiments, an encapsulant material (e.g., encapsulant material layer) may be arranged between at least one light emitting element and one or more light affecting elements. In certain embodiments, one or more light affecting elements may be formed or dispersed within an encapsulant material.

In certain embodiments, impingement of light on living tissue and/or operation of a device as disclosed herein may be responsive to one or more signals generated by one or more sensors or other elements. Various types of sensors are contemplated, including temperature sensors, photosensors, image sensors, proximity sensors, pressure sensors, chemical sensors, biosensors, accelerometers, moisture sensors, oximeters, current sensors, voltage sensors, and the like. Other elements that may affect impingement of light and/or operation of a device as disclosed herein include a timer, a cycle counter, a manually operated control element, a wireless transmitter and/or receiver (as may be embodied in a transceiver), a laptop or tablet computer, a mobile phone, or another portable electronic or digital device external to a lighting device. Wired and/or wireless communication between a device as disclosed herein and one or more signal generating or signal receiving elements may be provided.

In certain embodiments, impingement of light on living tissue and/or operation of a device as disclosed herein may be responsive to one or more temperature signals. For example, a temperature condition may be sensed on or proximate to (a) a device arranged to emit ES increasing light and/or ES releasing light or (b) the tissue; at least one signal indicative of the temperature condition may be generated; and operation of a lighting device may be controlled responsive to the at least one signal. Such control may include initiation of operation, deviation (or alteration) of operation, or termination of operation of light emitting elements, such as elements arranged to emit ES increasing light and/or ES releasing light. In certain embodiments, thermal foldback protection may be provided at a threshold temperature (e.g., >42° Celsius) to prevent a user from experiencing burns or discomfort. In certain embodiments, thermal foldback protection may trigger a light emitting device to terminate operation, reduce current, or change an operating state in response to receipt of a signal indicating an excess temperature condition.

In certain embodiments, a device for modulating nitric oxide in living mammalian tissue as disclosed herein may be used for wound care, and may include one or more sensors. In certain embodiments, one or more light emitters and photodiodes may be provided to illuminate a wound site with one or more selected wavelengths (e.g., green light) to detect blood flow in or proximate to the wound site to provide photoplethysmography data. One sensor or multiple sensors may be provided. A device may alternatively or additionally include sensors arranged to detect blood pressure, bandage or dressing covering pressure, heart rate, temperature, presence or concentration of chemical or biological species (e.g., in wound exudate), or other conditions.

In certain embodiments, a device for modulating nitric oxide in living mammalian tissue as disclosed herein may include a memory element to store information indicative of one or more sensor signals. Such information may be used for diagnosis, assessing patient compliance, assessing patient status, assessing patient improvement, and assessing function of the device. In certain embodiments, information indicative of one or more sensor signals may be transmitted via wired or wireless means (e.g., via Bluetooth, WiFi, Zigbee, or another suitable protocol) to a mobile phone, a computer, a data logging device, or another suitable device that may optionally be connected to a local network, a wide-area network, a telephonic network, or other communication network. In certain embodiments, a data port (e.g., micro USB or other type) may be provided to permit extraction or interrogation of information contained in a memory.

Details of illustrative devices that may be used for modulating nitric oxide in living mammalian tissue are described hereinafter.

Figure 9:
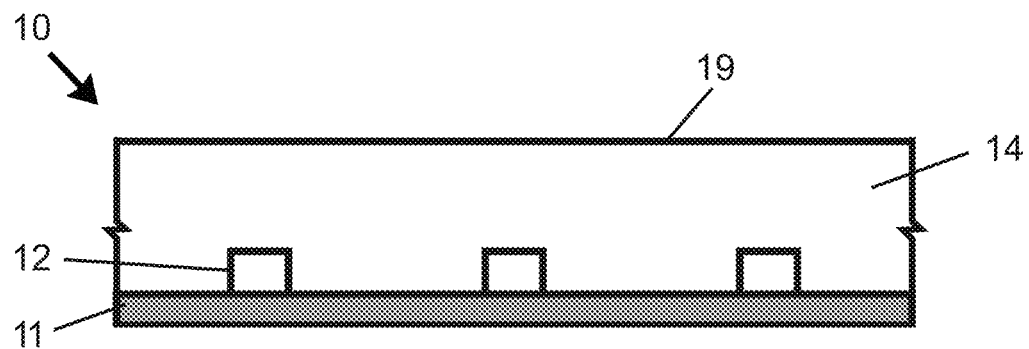
FIG. 9 is a side cross-sectional schematic view of a portion of a device for delivering light energy to living mammalian tissue, the device including multiple direct view light emitting sources supported by a substrate and covered with an encapsulant material layer.

FIG. 9 is a side cross-sectional schematic view of a portion of a device 10 for delivering light energy to living mammalian tissue, the device 10 including multiple direct view light emitting sources 12 supported by a substrate 11 and covered with an encapsulant material 14, which may be embodied in a sheet or layer. The substrate 11 preferably includes a flexible PCB, which may include a reflective surface to reflect light toward a light-transmissive outer surface 19 of the device 10. As shown in FIG. 9, the encapsulant material 14 covers the light emitting sources 12 and an upper surface of the substrate 11; however, it is to be appreciated that in certain embodiments the encapsulant material 14 may cover both upper and lower surfaces of the substrate 11. In certain embodiments, different light emitting sources 12 may generate light having different peak wavelengths. In certain embodiments, one or more light emitting sources 12 may include a multi-emitter package arranged to generate one or multiple peak wavelengths of light. In certain embodiments, one or more light emitting sources 12 may be arranged to produce one or both of ES increasing light and ES releasing light.

Figure 10:
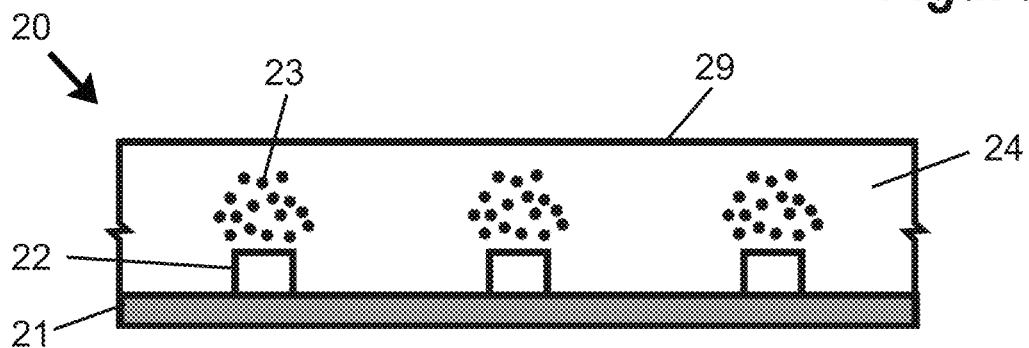
FIG. 10 is a side cross-sectional schematic view of a portion of a device for delivering light energy to living mammalian tissue, the device including multiple direct view light emitting sources supported by a substrate and covered with an encapsulant material layer, wherein at least one functional material (e.g., wavelength conversion and/or scattering material) is disposed within the encapsulant material layer.

FIG. 10 is a side cross-sectional schematic view of a portion of a device 20 for delivering light energy to living mammalian tissue, the device 20 including multiple direct view light emitting sources 22 supported by a substrate 21 and covered with an encapsulant material 24, which may be embodied in a sheet or layer. The substrate 21 preferably includes a flexible PCB, which may include a reflective surface to reflect light toward a light-transmissive outer surface 29 of the device 20. At least one functional material (e.g., wavelength conversion material and/or scattering material) 23 is disposed within the encapsulant material 24. In certain embodiments, the at least one functional material 23 includes one or more wavelength conversion materials, such as at least one of a phosphor material, a fluorescent dye material, a quantum dot material, and a fluorophore material. In certain embodiments, wavelength materials of different peak wavelengths may be applied over different light emitting sources 22. In certain embodiments, the at least one functional material 23 is applied by dispensing or printing. In certain embodiments, one or more light emitting sources 22 may include a multi-emitter package arranged to generate one or multiple peak wavelengths of light. In certain embodiments, one or more light emitting sources 22 may be arranged to produce one or both of ES increasing light and ES releasing light.

Figure 11:
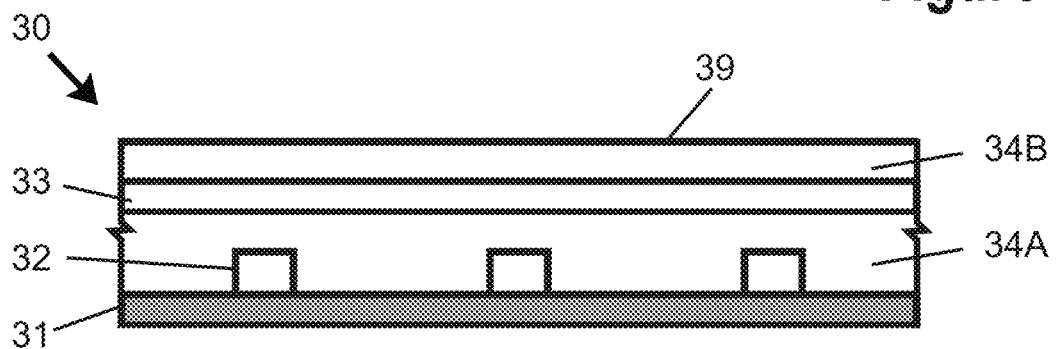
FIG. 11 is a side cross-sectional schematic view of a portion of a device for delivering light energy to living mammalian tissue, the device including multiple direct view light emitting sources supported by a substrate and covered with two encapsulant material layers, with at least one functional material (e.g., wavelength conversion and/or scattering material) layer disposed between the encapsulant material layers.

FIG. 11 is a side cross-sectional schematic view of a portion of a device 30 for delivering light energy to living mammalian tissue, the device 30 including multiple direct view light emitting sources 32 supported by a substrate 31 and covered with two encapsulant material layers 34A, 34B, with at least one functional material (e.g., wavelength conversion and/or scattering material) sheet or layer 33 disposed between the encapsulant material layers 34A, 34B. The substrate 31 preferably includes a flexible PCB, which may include a reflective surface to reflect light toward a light-transmissive outer surface 39 of the device 30. In certain embodiments, the at least one functional material sheet or layer 33 includes one or more wavelength conversion materials, such as at least one of a phosphor material, a fluorescent dye material, a quantum dot material, or a fluorophore material. In certain embodiments, one or more light emitting sources 32 may include a multi-emitter package arranged to generate one or multiple peak wavelengths of light. In certain embodiments, one or more light emitting sources 32 may be arranged to produce one or both of ES increasing light and ES releasing light.

Figure 12:
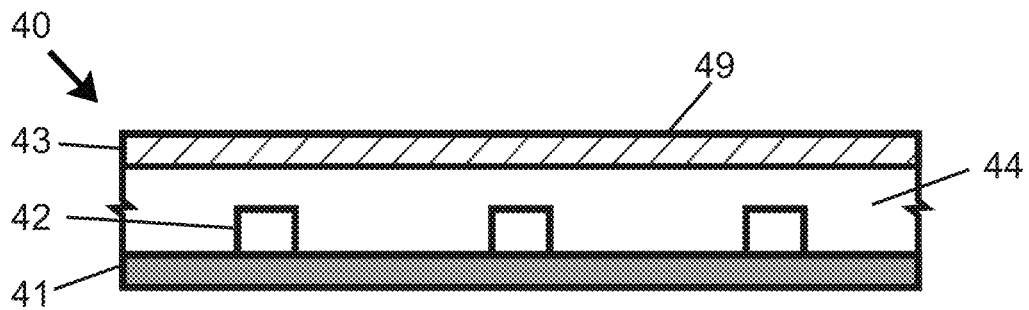
FIG. 12 is a side cross-sectional schematic view of a portion of a device for delivering light energy to living mammalian tissue, the device including multiple direct view light emitting sources supported by a substrate and covered by an encapsulant layer, wherein the encapsulant layer is covered with a diffusion or scattering material layer.

FIG. 12 is a side cross-sectional schematic view of a portion of a device 40 for delivering light energy to living mammalian tissue, the device 40 including multiple direct view light emitting sources 42 supported by a substrate 41 and covered by an encapsulant material 44, which may be embodied in a sheet or layer. The substrate 41 preferably includes a flexible PCB, which may include a reflective surface to reflect light toward a light-transmissive outer surface 49 of the device 40. The encapsulant material 44 is covered with a diffusion or scattering material layer 43. In certain embodiments, the diffusion or scattering material layer 43 may include acrylic, PET-G, silicone, or a polymeric sheet. In certain embodiments, the diffusion or scattering material layer 43 may include scattering particles such as zinc oxide, silicon dioxide, titanium dioxide, or the like. In certain embodiments, one or more light emitting sources 42 may include a multi-emitter package arranged to generate one or multiple peak wavelengths of light. In certain embodiments, one or more light emitting sources 42 may be arranged to produce one or both of ES increasing light and ES releasing light.

Figure 13:
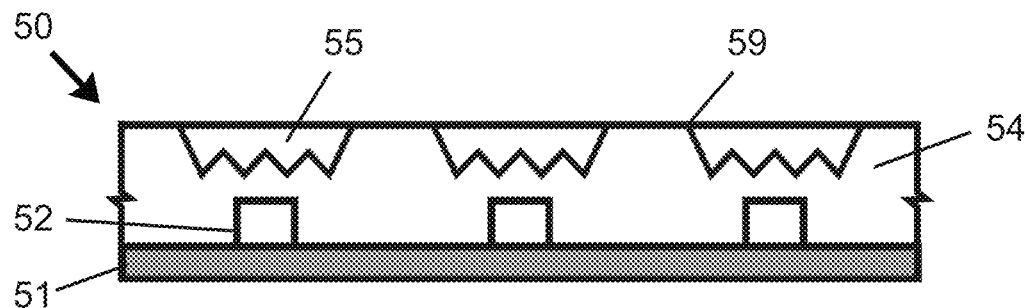
FIG. 13 is a side cross-sectional schematic view of a portion of a device for delivering light energy to living mammalian tissue, the device including multiple direct view light emitting sources supported by a substrate, multiple molded features overlying the light emitting sources, and an encapsulant or light coupling material arranged between the light emitting sources and the molded features.

FIG. 13 is a side cross-sectional schematic view of a portion of a device 50 for delivering light energy to living mammalian tissue, the device 50 including multiple direct view light emitting sources 52 supported by a substrate 51. The substrate 51 preferably includes a flexible PCB, which may include a reflective surface to reflect light toward a light-transmissive outer surface 59 of the device 50. Multiple molded features 55 (e.g., molded from silicone) overlie the light emitting sources 52. An encapsulant or light coupling material 54 is arranged between the light emitting sources 52 and the molded features 55. In certain embodiments, light coupling material 54 may include a light coupling gel with an index of refraction that differs from an index of refraction of the molded features 55. The molded features 55 may be arranged along the light transmissive outer surface 59 of the device 50. In certain embodiments, one or more light emitting sources 52 may include a multi-emitter package arranged to generate one or multiple peak wavelengths of light. In certain embodiments, one or more light emitting sources 52 may be arranged to produce one or both of ES increasing light and ES releasing light.

Figure 14:
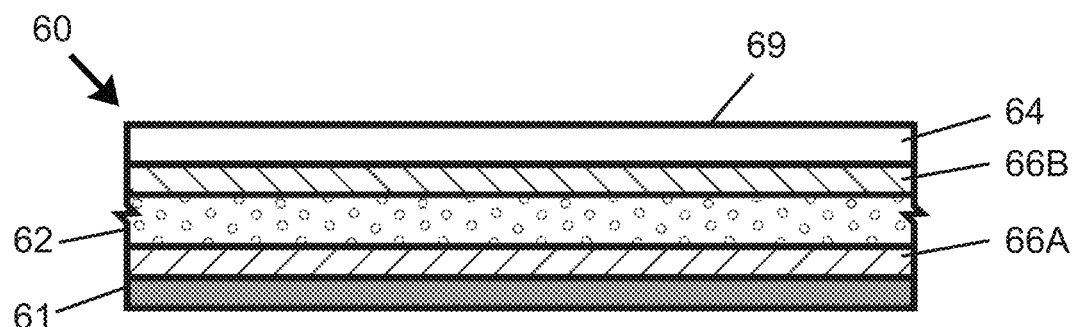
FIG. 14 is a side cross-sectional schematic view of a portion of a device for delivering light energy to living mammalian tissue, the device including a flexible substrate, one or more organic light emitting diode layers arranged between an anode and cathode, and an encapsulant layer arranged over the cathode.

FIG. 14 is a side cross-sectional schematic view of a portion of a device 60 for delivering light energy to living mammalian tissue, the device 60 including a flexible substrate 61, a passive-matrix organic light emitting diode (OLED) structure (embodied in an anode layer 66A, a cathode layer 66B, and an OLED stack 62 between the anode and cathode layers 66A, 66B. In certain embodiments, the OLED stack 62 may be configured to generate multiple wavelengths of light. The substrate 61 preferably includes a flexible PCB, which may include a reflective surface to reflect light toward a light-transmissive outer surface 69 of the device 60. An encapsulant layer 64 is arranged over the cathode layer 66B and preferably defines the light-transmissive outer surface 69 of the device 60. In certain embodiments, one or more light emitting wavelengths produced by the OLED stack 62 may include ES increasing light and/or ES releasing light.

Figure 15:
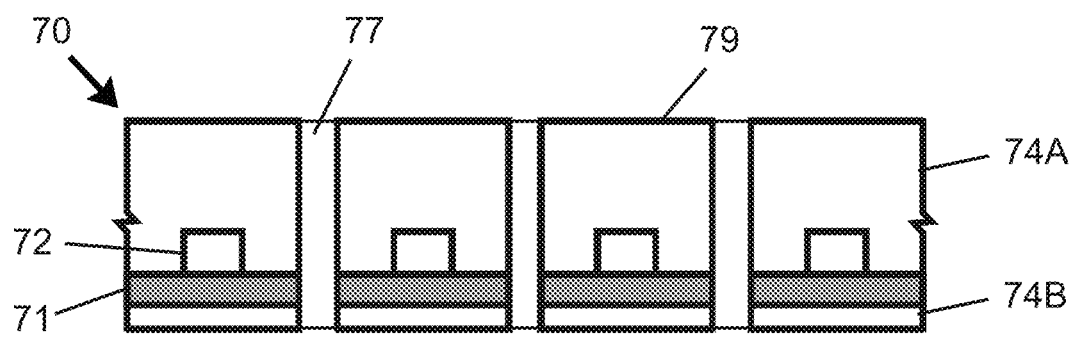
FIG. 15 is a side cross-sectional schematic view of a portion of a device for delivering light energy to living mammalian tissue, the device including a flexible substrate, multiple direct view light emitting sources supported by the substrate, encapsulant material layers arranged above and below the substrate and over the light emitting sources, and holes or perforations defined through both the substrate and the encapsulant material layers.

FIG. 15 is a side cross-sectional schematic view of a portion of a device 70 for delivering light energy to living mammalian tissue, the device 70 including a flexible substrate 71, multiple direct view light emitting sources 72 supported by the substrate 71, and encapsulant material layers 74A, 74B arranged above and below the substrate 71, respectively. The substrate 71 preferably includes a flexible PCB, which may include a reflective surface to reflect light toward a light-transmissive outer surface 79 of the device 70. The light emitting device 70 further includes holes or perforations 77 defined through both the substrate 71 and the encapsulant material layers 74A, 74B. In certain embodiments, one or more light emitting sources 72 may be arranged to produce one or both of ES increasing light and ES releasing light.

Figure 16:
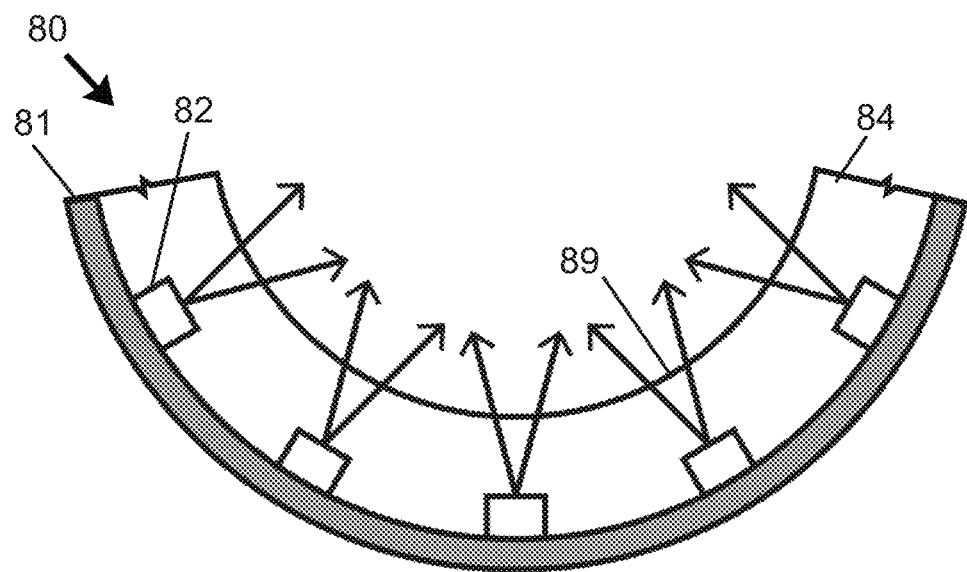
FIG. 16 is a side cross-sectional schematic view of a portion of a device for delivering light energy to living mammalian tissue, wherein the device includes multiple direct view light emitting sources supported by a substrate and covered by an encapsulant layer, and the device is arranged in a concave configuration.

FIG. 16 is a side cross-sectional schematic view of a portion of a device 80 for delivering light energy to living mammalian tissue, wherein the device 80 includes multiple direct view light emitting sources 82 supported by a flexible substrate 81 and covered by an encapsulant layer 84. The substrate 81 preferably includes a flexible PCB, which may include a reflective surface to reflect light toward a light-transmissive outer surface 89 of the device 80. The device 80 is preferably flexible to permit it to be bent or shaped into a variety of shapes to conform to a portion of a mammalian body. As illustrated, the device 80 is arranged in a concave configuration with the multiple light emitting sources 82 arranged to direct emissions toward a center of curvature of the device 80. In certain embodiments, one or more light emitting sources 82 may be arranged to produce one or both of ES increasing light and ES releasing light.

Figure 17:
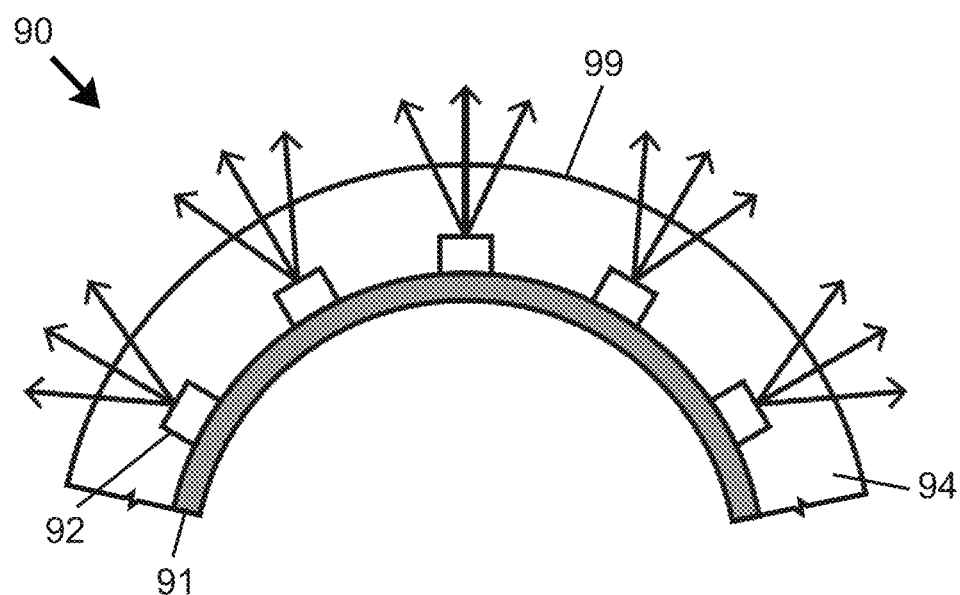
FIG. 17 is a side cross-sectional schematic view of a portion of a device for delivering light energy to living mammalian tissue, wherein the device includes multiple direct view light emitting sources supported by a substrate and covered by an encapsulant layer, and the device is arranged in a convex configuration.

FIG. 17 is a side cross-sectional schematic view of a portion of a device 90 for delivering light energy to living mammalian tissue, wherein the device 90 includes multiple direct view light emitting sources 92 supported by a flexible substrate 91 and covered by an encapsulant layer 94. The substrate 91 preferably includes a flexible PCB, which may include a reflective surface to reflect light toward a light-transmissive outer surface 99 of the device 90. The device 90 is preferably flexible to permit it to be bent or shaped into a variety of shapes to conform to a portion of a mammalian body. As illustrated, the device 90 is arranged in a convex configuration with the multiple light emitting elements 92 arranged to direct emissions away from a center of curvature of the device 90. In certain embodiments, one or more light emitting sources 92 may be arranged to produce one or both of ES increasing light and ES releasing light.

Figure 18:
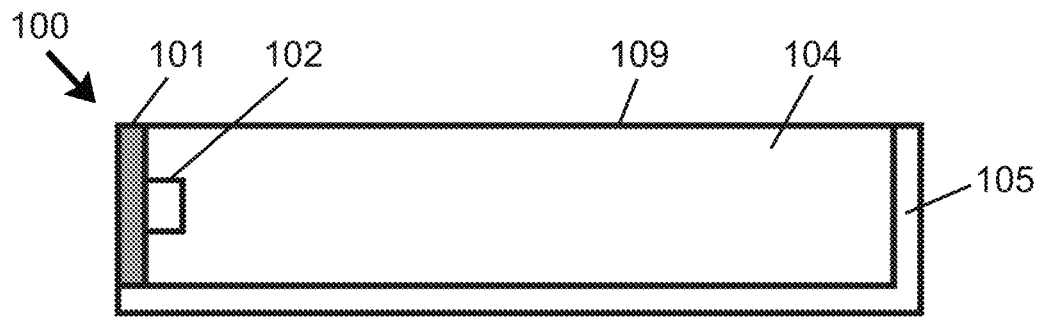
FIG. 18 is a side cross-sectional schematic view of a portion of a device for delivering light energy to living mammalian tissue, wherein the device is edge lit with one or more light emitting sources supported by a flexible printed circuit board (PCB), other non-light-transmitting surfaces of the device are bounded by a flexible reflective substrate, and the flexible PCB and light emitting source(s) are covered with an encapsulant material.

FIG. 18 is a side cross-sectional schematic view of a portion of a device 100 for delivering light energy to living mammalian tissue, wherein the device 100 is edge lit with one or more light emitting sources 102 supported by a flexible printed circuit board (PCB) 101 that preferably includes a reflective surface. Other non-light-transmissive surfaces of the device 100 are bounded by a flexible reflective substrate 105 arranged to reflect light toward a light-transmissive outer surface 109 of the device 100. The flexible PCB 101, the light emitting source(s) 102, and the flexible reflective substrate 105 are covered with an encapsulant material 104, which may include silicone. As illustrated, the device 100 may include a substantially constant thickness. In certain embodiments, one or more light emitting sources 102 may be arranged to produce one or both of ES increasing light and ES releasing light.

Figure 19:
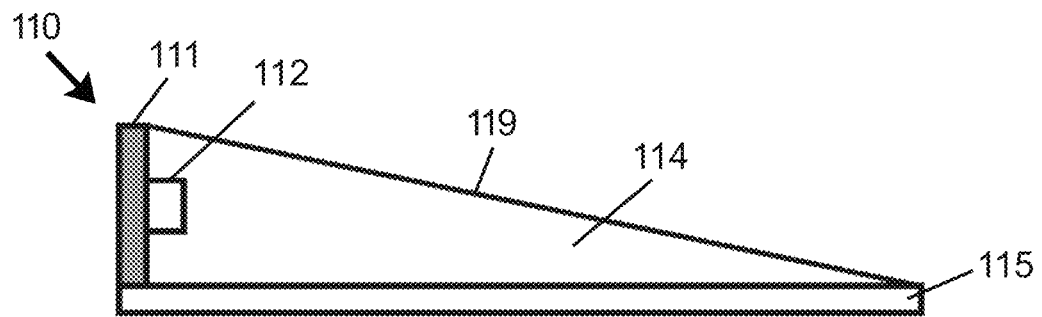
FIG. 19 is a side cross-sectional schematic view of a portion of a device for delivering light energy to living mammalian tissue, wherein the device is edge lit with one or more light emitting sources supported by a flexible printed circuit board (PCB), another non-light-transmitting surface of the device is bounded by a flexible reflective substrate, the flexible PCB and light emitting source(s) are covered with an encapsulant material, and the device is tapered in thickness.

FIG. 19 is a side cross-sectional schematic view of a portion of a device 110 for delivering light energy to living mammalian tissue, wherein the device 110 is edge lit with one or more light emitting sources 112 supported by a flexible PCB 111 that preferably includes a reflective surface. A non-light-transmitting face of the device 110 is bounded by a flexible reflective substrate 115 arranged to reflect light toward a light-transmissive outer surface 119 of the device 110. The flexible PCB 111, the light emitting source(s) 112, and the flexible reflective substrate 115 are covered with an encapsulant material 114, which may include silicone. As illustrated, the device 110 may include a thickness that is tapered with distance away from the light emitting sources 112. Such tapered thickness may enable the device 110 to more easily be wrapped against or to conform to areas of a mammalian (e.g., human) body. In certain embodiments, one or more light emitting sources 112 may be arranged to produce one or both of ES increasing light and ES releasing light.

Figure 20:
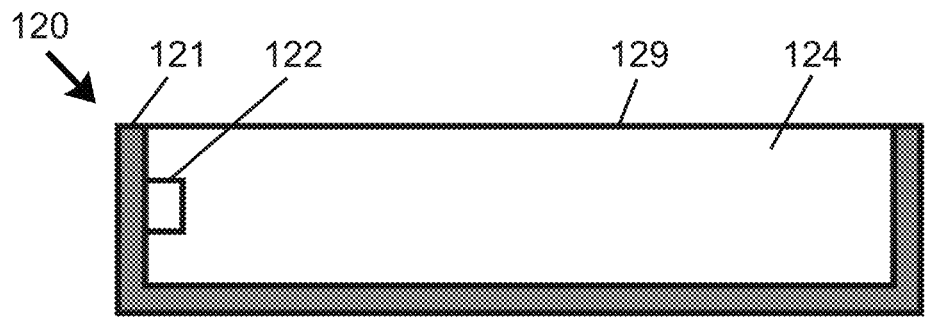
FIG. 20 is a side cross-sectional schematic view of a portion of a device for delivering light energy to living mammalian tissue, wherein the device is edge lit with one or more light emitting sources supported by a flexible PCB having a reflective surface, non-light-transmitting surfaces of the device are further bounded by the flexible PCB, and the flexible PCB and light emitting source(s) are covered with an encapsulant material.

FIG. 20 is a side cross-sectional schematic view of a portion of a device 120 for delivering light energy to living mammalian tissue, wherein the device 120 is edge lit with one or more light emitting sources 122 supported by a flexible PCB 121 that bounds multiple edges and a face of the device 120. The flexible PCB 121 preferably includes a reflective surface arranged to reflect light toward a light-transmissive outer surface 129 of the device 120. The flexible PCB 121 and the light emitting source(s) 122 are covered with an encapsulant material 124, which may include silicone. In certain embodiments, one or more light emitting sources 122 may be arranged to produce one or both of ES increasing light and ES releasing light.

Figure 21:
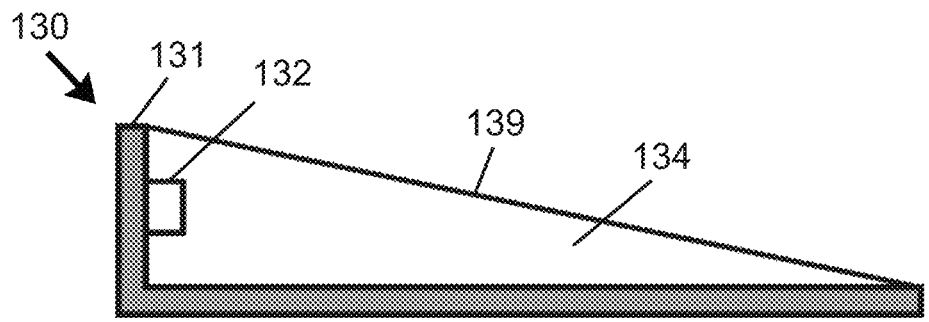
FIG. 21 is a side cross-sectional schematic view of a portion of a device for delivering light energy to living mammalian tissue, wherein the device is edge lit with one or more light emitting sources supported by a flexible PCB having a reflective surface, another non-light-transmitting surface of the device is further bounded by the flexible PCB, the flexible PCB and light emitting source(s) are covered with an encapsulant material, and the device is tapered in thickness.

FIG. 21 is a side cross-sectional schematic view of a portion of a device 130 for delivering light energy to living mammalian tissue, wherein the device 130 is edge lit with one or more light emitting sources 132 supported by a flexible PCB 131 that bounds one edge and one face of the device 130. The flexible PCB 131 preferably includes a reflective surface arranged to reflect light toward a light-transmissive outer surface 139 of the device 130. The flexible PCB 131 and the light emitting source(s) 132 are covered with an encapsulant material 134, which may include silicone. As illustrated, the device 130 may include a thickness that is tapered with distance away from the light emitting sources 132. In certain embodiments, one or more light emitting sources 132 may be arranged to produce one or both of ES increasing light and ES releasing light.

Figure 22:
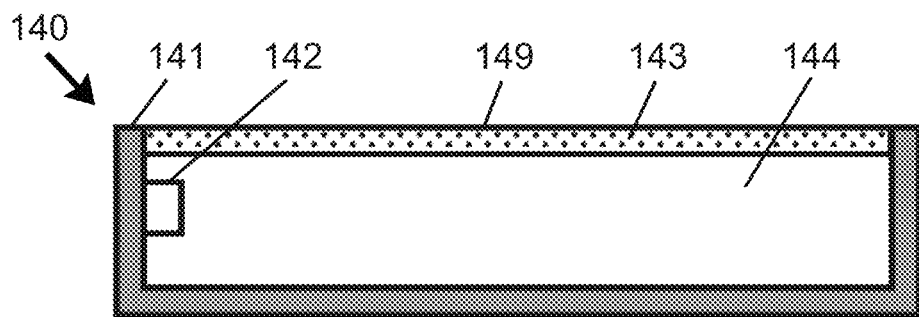
FIG. 22 is a side cross-sectional schematic view of a portion of a device for delivering light energy to living mammalian tissue, wherein the device is edge lit with one or more light emitting sources supported by a flexible PCB having a reflective surface, other non-light-transmitting surfaces of the device are further bounded by the flexible PCB, the flexible PCB and light emitting source(s) are covered with an encapsulant material, and a light-transmitting face of the device includes a diffusing and/or scattering layer.

FIG. 22 is a side cross-sectional schematic view of a portion of a device 140 for delivering light energy to living mammalian tissue, wherein the device 140 is edge lit with one or more light emitting sources 142 supported by a flexible PCB 141 that bounds multiple edges and a face of the device 140. In certain embodiments, one or more light emitting sources 142 may include a multi-emitter package arranged to generate one or multiple peak wavelengths of light. The flexible PCB 141 preferably includes a reflective surface arranged to reflect light toward a light-transmissive outer surface 149 of the device 140. The flexible PCB 141 and the light emitting source(s) 142 are covered with an encapsulant material 144, which may include silicone. Between the light-transmissive outer surface 149 and the encapsulant material 144, the device 140 further includes a diffusing and/or scattering layer 143. In certain embodiments, the diffusing and/or scattering layer 143 may include a sheet of material; in other embodiments, the diffusing and/or scattering layer 143 may include particles applied in or on the encapsulant material 144. In certain embodiments, one or more light emitting sources 142 may be arranged to produce one or both of ES increasing light and ES releasing light.

Figure 23:
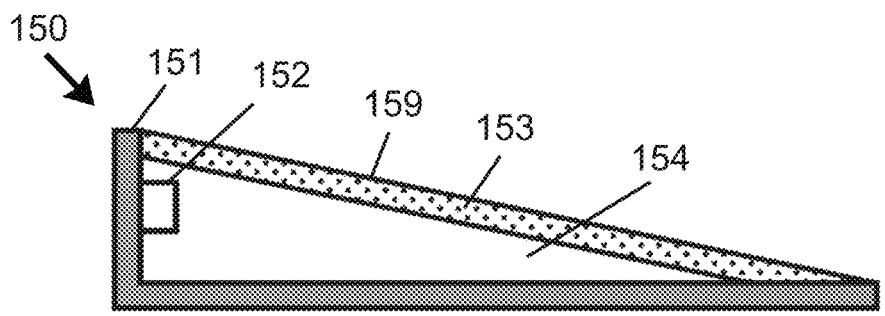
FIG. 23 is a side cross-sectional schematic view of a portion of a device for delivering light energy to living mammalian tissue, wherein the device is edge lit with one or more light emitting sources supported by a flexible PCB having a reflective surface, another non-light-transmitting surface of the device is further bounded by the flexible PCB, the flexible PCB and light emitting source(s) are covered with an encapsulant material, a light transmitting face of the device is tapered in thickness, and the light-transmitting face includes a diffusing and/or scattering layer.

FIG. 23 is a side cross-sectional schematic view of a portion of a device 150 for delivering light energy to living mammalian tissue, wherein the device 150 is edge lit with one or more light emitting sources 152 supported by a flexible PCB 151 that bounds one edge and one face of the device 150. In certain embodiments, one or more light emitting sources 152 may include a multi-emitter package arranged to generate one or multiple peak wavelengths of light. The flexible PCB 151 preferably includes a reflective surface arranged to reflect light toward a light-transmissive outer surface 159 of the device 150. The flexible PCB 151 and the light emitting source(s) 152 are covered with an encapsulant material 154, which may include silicone. Between the light-transmissive outer surface 159 and the encapsulant material 154, the device 150 further includes a diffusing and/or scattering layer 153. In certain embodiments, the diffusing and/or scattering layer 153 may include a sheet of material; in other embodiments, the diffusing and/or scattering layer 153 may include particles applied in or on the encapsulant material 154. As illustrated, the device 150 may include a thickness that is tapered with distance away from the light emitting sources 152. In certain embodiments, one or more light emitting sources 152 may be arranged to produce one or both of ES increasing light and ES releasing light.

Figure 24:
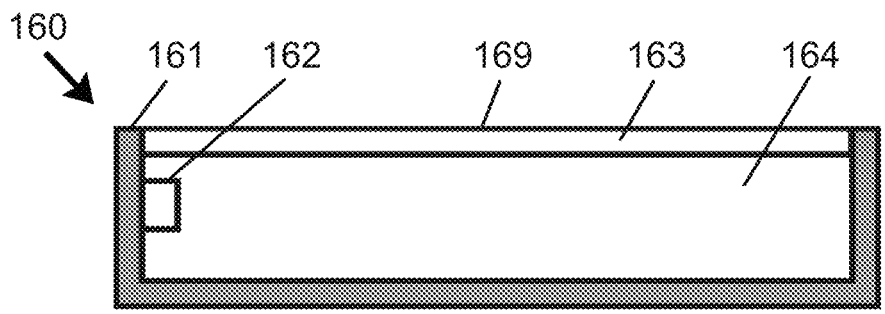
FIG. 24 is a side cross-sectional schematic view of a portion of a device for delivering light energy to living mammalian tissue, wherein the device is edge lit with one or more light emitting sources supported by a flexible PCB having a reflective surface, other non-light-transmitting surfaces of the device are further bounded by the flexible PCB, the flexible PCB and light emitting source(s) are covered with an encapsulant material, and a light-transmitting face of the device includes a wavelength conversion material layer.

FIG. 24 is a side cross-sectional schematic view of a portion of a device 160 for delivering light energy to living mammalian tissue, wherein the device 160 is edge lit with one or more light emitting sources 162 supported by a flexible PCB 161 that bounds multiple edges and a face of the device 160. In certain embodiments, one or more light emitting sources 162 may include a multi-emitter package arranged to generate one or multiple peak wavelengths of light. The flexible PCB 161 preferably includes a reflective surface arranged to reflect light toward a light-transmissive outer surface 169 of the device 160. The flexible PCB 161 and the light emitting source(s) 162 are covered with an encapsulant material 164, which may include silicone. Between the light-transmissive outer surface 169 and the encapsulant material 164, the device 160 further includes a wavelength conversion material 163. In certain embodiments, the wavelength conversion material 163 may include a sheet or layer of material; in other embodiments, the wavelength conversion material 163 may include particles applied in or on the encapsulant material 164. In certain embodiments, one or more light emitting sources 162 may be arranged to produce one or both of ES increasing light and ES releasing light.

Figure 25:
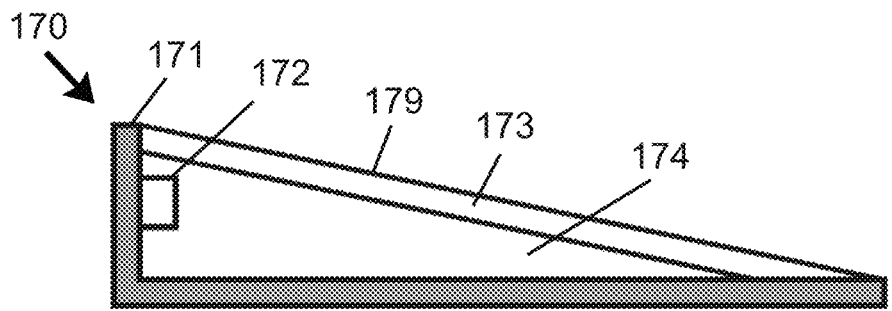
FIG. 25 is a side cross-sectional schematic view of a portion of a device for delivering light energy to living mammalian tissue, wherein the device is edge lit with one or more light emitting sources supported by a flexible PCB having a reflective surface, another non-light-transmitting surface of the device is further bounded by the flexible PCB, the flexible PCB and light emitting source(s) are covered with an encapsulant material, a light transmitting face of the device is tapered in thickness, and the light-transmitting face includes a wavelength conversion material layer.

FIG. 25 is a side cross-sectional schematic view of a portion of a device 170 for delivering light energy to living mammalian tissue, wherein the device 170 is edge lit with one or more light emitting sources 172 supported by a flexible PCB 171 that bounds one edge and one face of the device 170. In certain embodiments, one or more light emitting sources 172 may include a multi-emitter package arranged to generate one or multiple peak wavelengths of light. The flexible PCB 171 preferably includes a reflective surface arranged to reflect light toward a light-transmissive outer surface 179 of the device 170. The flexible PCB 171 and the light emitting source(s) 172 are covered with an encapsulant material 174, which may include silicone. Between the light-transmissive outer surface 179 and the encapsulant material 174, the device 170 further includes a wavelength conversion material 173. In certain embodiments, the wavelength conversion material 173 may include a sheet or layer of material; in other embodiments, the wavelength conversion material 173 may include particles applied in or on the encapsulant material 174. As illustrated, the device 170 may include a thickness that is tapered with distance away from the light emitting sources 172. In certain embodiments, one or more light emitting sources 172 may be arranged to produce one or both of ES increasing light and ES releasing light.

FIG. 26 is a side cross-sectional schematic view of a portion of a device 180 for delivering light energy to living mammalian tissue, wherein the device 180 is edge lit along multiple edges with multiple light emitting sources 182 supported by a flexible PCB 181 having a reflective surface arranged to reflect light toward a light-transmissive outer surface 189 of the device 180. The flexible PCB 181 and light emitting sources 182 are covered with an encapsulant material 184, and a wavelength conversion material 183 is distributed in the encapsulant material 184. In certain embodiments, one or more light emitting sources 182 may include a multi-emitter package arranged to generate one or multiple peak wavelengths of light. In certain embodiments, one or more light emitting sources 182 may be arranged to produce one or both of ES increasing light and ES releasing light.

FIG. 27 is a side cross-sectional schematic view of a portion of a device 190 for delivering light energy to living mammalian tissue, wherein the device 190 is edge lit along multiple edges with multiple light emitting sources 192 supported by a flexible PCB 191 having a reflective surface arranged to reflect light toward a light-transmissive outer surface 199 of the device 190. The device 190 further includes raised light extraction features 197 supported by the flexible PCB 191, with such features 197 serving to reflect laterally-transmitted light toward the outer surface 199. An encapsulant material 194 is provided over the flexible PCB 191, the light emitting sources 192, and the light extraction features 197. In certain embodiments, one or more light emitting sources 192 may include a multi-emitter package arranged to generate one or multiple peak wavelengths of light. In certain embodiments, one or more light emitting sources 192 may be arranged to produce one or both of ES increasing light and ES releasing light.

In certain embodiments, the light extraction features 197 may be dispensed, molded, layered, or painted on the flexible PCB 191. In certain embodiments, different light extraction features 197 may include different indices of refraction. In certain embodiments, different light extraction features 197 may include different sizes and/or shapes. In certain embodiments, light extraction features 197 may be uniformly or non-uniformly distributed over the flexible PCB 191. In certain embodiments, light extraction features 197 may include tapered surfaces. In certain embodiments, different light extraction features 197 may include one or more connected portions or surfaces. In certain embodiments, different light extraction features 197 may be discrete or spatially separated relative to one another. In certain embodiments, light extraction features 197 may be arranged in lines, rows, zig-zag shapes, or other patterns. In certain embodiments, one or more wavelength conversion materials may be arranged on or proximate to one or more light extraction features 197.

FIG. 28 is a side cross-sectional schematic view of a portion of a device 200 for delivering light energy to living mammalian tissue, wherein the device 200 is edge lit along multiple edges with multiple light emitting sources 202 supported by a flexible PCB 201 having a reflective surface arranged to reflect light toward a light-transmissive outer surface 209 of the device 200. In certain embodiments, one or more light emitting sources 202 may be arranged to produce one or both of ES increasing light and ES releasing light. Encapsulant material layers 204A, 204B are arranged above and below the flexible PCB 201 and over the light emitting sources 202. Holes or perforations 205 are defined through the flexible PCB 201 and the encapsulant material layers 204A, 204B. The holes or perforations 205 preferably allow passage of at least one of air and exudate through the device 200.

Holes or perforations defined through a device (e.g., through a PCB and encapsulant layers) as described herein may include holes of various shapes and configurations. Holes may be round, oval, rectangular, square, polygonal, or any other suitable axial shape. Cross-sectional shapes of holes or perforations may be constant or non-constant. Cross-sectional shapes that may be employed according to certain embodiments are shown in FIGS. 29A-29C. FIG.

29A is a cross-sectional view of a first exemplary hole 215A definable through an encapsulant layer 214A of a device for delivering light energy to living mammalian tissue, the hole 215A having a diameter that is substantially constant with depth and extending to an outer light transmissive surface 219A. FIG. 29B is a cross-sectional view of a second exemplary hole 215B definable through an encapsulant layer 214B of a device for delivering light energy to living mammalian tissue, the hole 215B having a diameter that increases with increasing depth and extending to an outer light transmissive surface 219B. FIG. 29C is a cross-sectional view of a third exemplary hole 215C definable through an encapsulant layer 214C of a device for delivering light energy to living mammalian tissue, the hole 215C having a diameter that decreases with increasing depth and extending to an outer light transmissive surface 219C.

In certain embodiments, perforations or holes may encompass at least 2%, at least 5%, at least 7%, at least 10%, at least 15%, at least 20%, or at least 25% of a facial area of a device for delivering light energy to living mammalian tissue as disclosed herein. In certain embodiments, one or more of the preceding ranges may be bounded by an upper limit of no greater than 10%, no greater than 15%, no greater than 20%, or no greater than 30%. In certain embodiments, perforations or holes may be provided with substantially uniform size and distribution, with substantially uniform distribution but non-uniform size, with non-uniform size and non-uniform distribution, or any other desired combination of size and distribution patterns.

Figure 30:
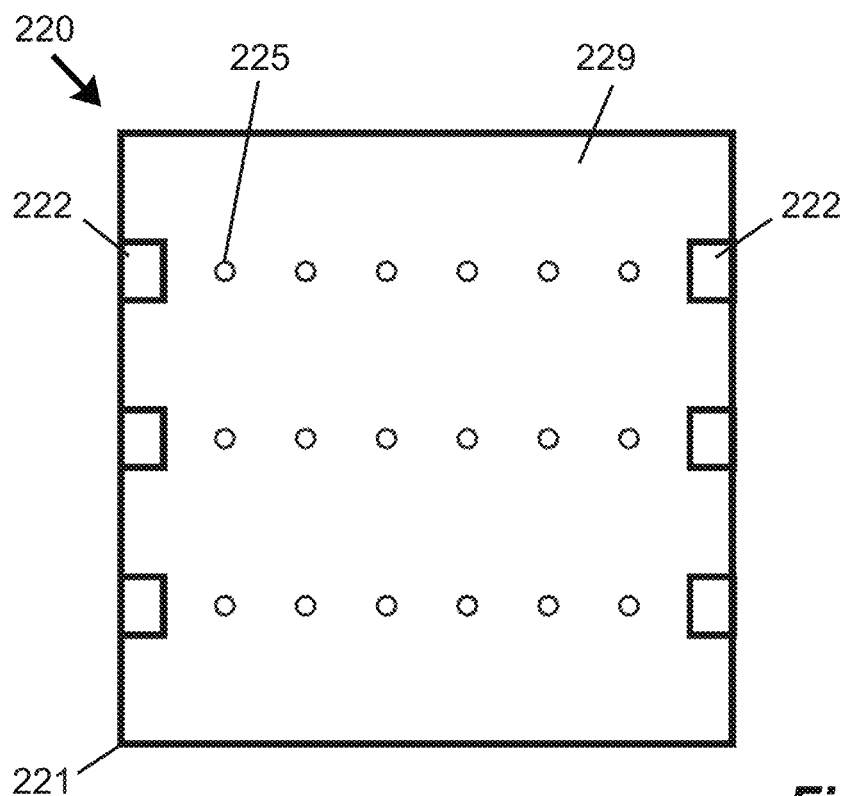
FIG. 30 is a top schematic view of at least a portion of a device for delivering light energy to living mammalian tissue, wherein the device is edge lit along multiple edges with multiple light emitting sources supported by a flexible PCB, and multiple holes or perforations of substantially uniform size and substantially uniform distribution are defined through the flexible PCB.

FIG. 30 is a top schematic view of at least a portion of a device 220 for delivering light energy to living mammalian tissue, wherein the device 220 is edge lit along multiple edges with multiple light emitting sources 222 supported by a flexible PCB 221. The flexible PCB 221 is preferably encapsulated on one or both sides with an encapsulant material. Multiple holes or perforations 225 of substantially uniform size and substantially uniform distribution are defined through the flexible PCB 221 and any associated encapsulant material layers. The flexible PCB 221 preferably includes a reflective material arranged to reflect light toward a light transmissive outer surface 229 of the device 220. In certain embodiments, one or more light emitting sources 222 may be arranged to produce one or both of ES increasing light and ES releasing light.

Figure 31:
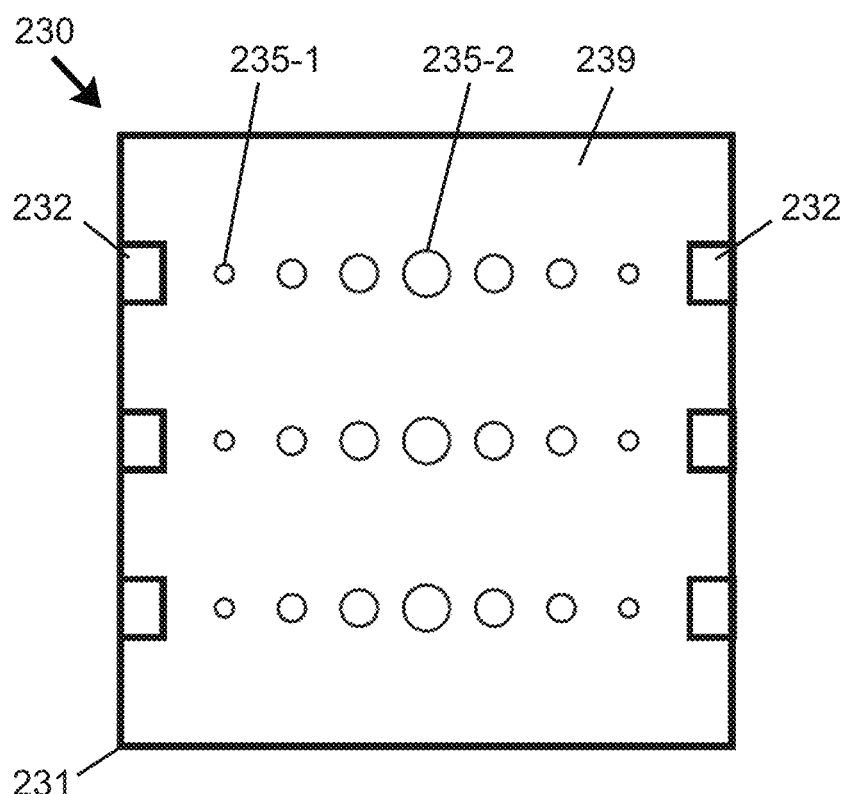
FIG. 31 is a top schematic view of at least a portion of a device for delivering light energy to living mammalian tissue, wherein the device is edge lit along multiple edges with multiple light emitting sources supported by a flexible PCB, and multiple holes or perforations of different sizes but with a substantially uniform distribution are defined through the flexible PCB.

FIG. 31 is a top schematic view of at least a portion of a device 230 for delivering light energy to living mammalian tissue, wherein the device 230 is edge lit along multiple edges with multiple light emitting sources 232 supported by a flexible PCB 231. The flexible PCB 231 is preferably encapsulated on one or both sides with an encapsulant material. Multiple holes or perforations 235-1, 235-2 of differing sizes, but substantially uniform distribution, are defined through the flexible PCB 231 and any associated encapsulant material layers. The flexible PCB 231 preferably includes a reflective material arranged to reflect light toward a light transmissive outer surface 239 of the device 230. In certain embodiments, one or more light emitting sources 232 may be arranged to produce one or both of ES increasing light and ES releasing light.

Figure 32:
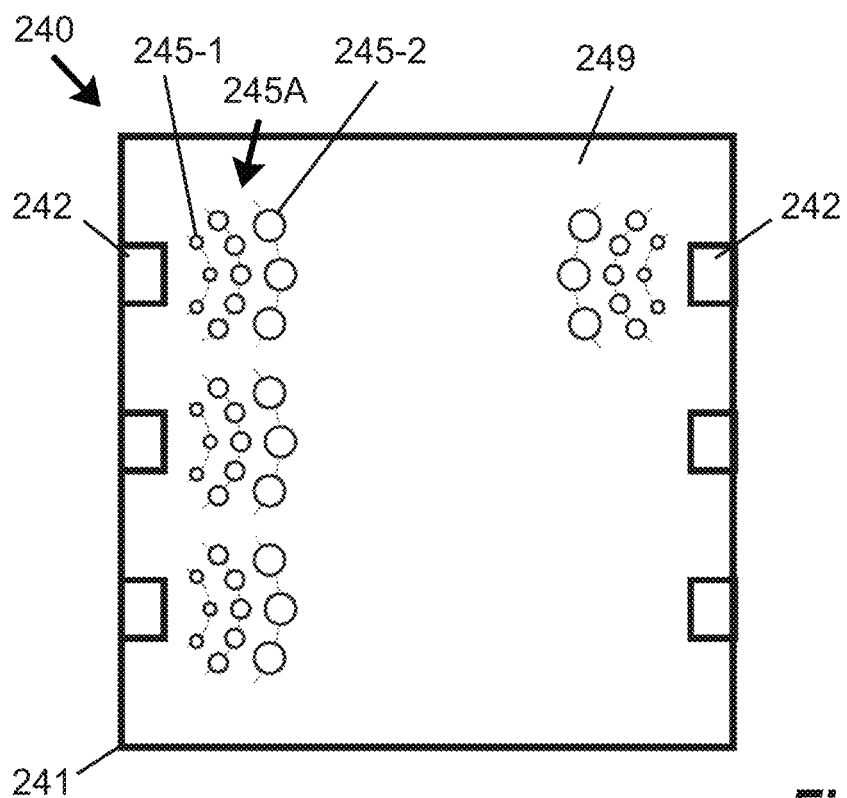
FIG. 32 is a top schematic view of at least a portion of a device for delivering light energy to living mammalian tissue, wherein the device is edge lit along multiple edges with multiple light emitting sources supported by a flexible PCB, and multiple holes or perforations of different sizes are provided in clusters and defined through the flexible PCB proximate to selected light emitting sources.

FIG. 32 is a top schematic view of at least a portion of a device 240 for delivering light energy to living mammalian tissue, wherein the device 240 is edge lit along multiple edges with multiple light emitting sources 242 supported by a flexible PCB 241. The flexible PCB 241 is preferably encapsulated on one or both sides with an encapsulant material. The flexible PCB 241 preferably includes a reflective material arranged to reflect light toward a light transmissive outer surface 249 of the device 240. Multiple holes or perforations 245-1, 245-2 of different sizes are provided in one or more clusters 245A (e.g., proximate to one or more light emitting sources 242) and defined through the flexible PCB 241 and any associated encapsulant material layers. In certain embodiments, one or more light emitting sources 242 may be arranged to produce one or both of ES increasing light and ES releasing light.

Figure 33:
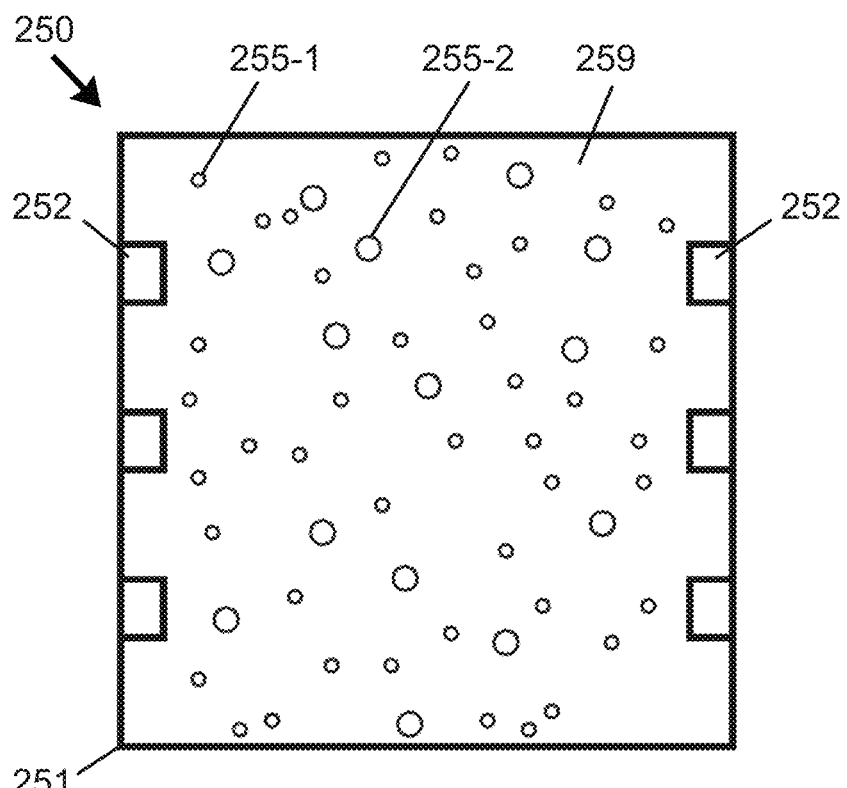
FIG. 33 is a top schematic view of at least a portion of a device for delivering light energy to living mammalian tissue, wherein the device is edge lit along multiple edges with multiple light emitting sources supported by a flexible PCB, and multiple holes or perforations of different sizes and with a non-uniform (e.g., random) distribution are defined through the flexible PCB.

FIG. 33 is a top schematic view of at least a portion of a device 250 for delivering light energy to living mammalian tissue, wherein the device 250 is edge lit along multiple edges with multiple light emitting sources 252 supported by a flexible PCB 251. The flexible PCB 251 is preferably encapsulated on one or both sides with an encapsulant material. The flexible PCB 251 preferably includes a reflective material arranged to reflect light toward a light transmissive outer surface 259 of the device 250. Multiple holes or perforations 255-1, 255-2 of different sizes and with a non-uniform (e.g., random) distribution are defined through the flexible PCB 251 and any associated encapsulant material layers. In certain embodiments, one or more light emitting sources 252 may be arranged to produce one or both of ES increasing light and ES releasing light.

Figure 34A:
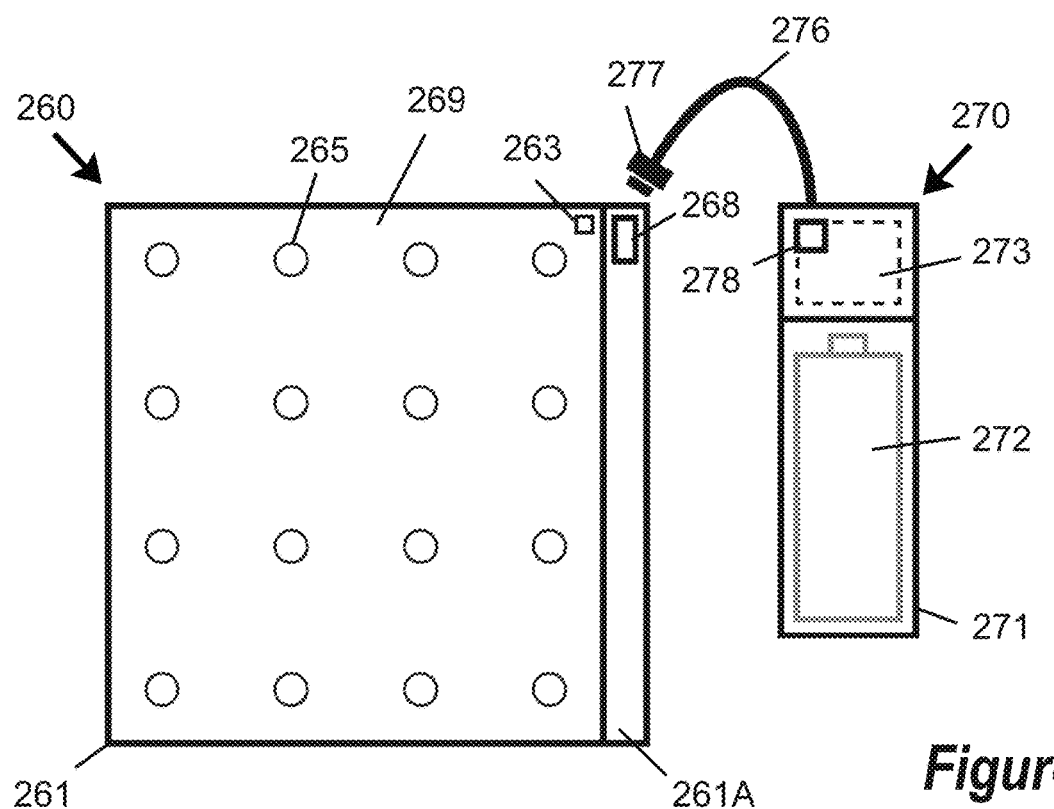
FIG. 34A is a top schematic view of at least a portion of a light emitting device for delivering light energy to living mammalian tissue and at least a portion of a battery/control module, wherein an elongated electrical cord is associated with the battery/control module for connecting the battery/control module to the light emitting device.

FIG. 34A is a top schematic view of at least a portion of a light emitting device 260 for delivering light energy to living mammalian tissue and at least a portion of a battery/control module 270, wherein an elongated electrical cable 276 is associated with the battery/control module 270 for connecting the battery/control module 270 to the light emitting device 260. The light emitting device 260 is edge lit along one edge with a light emitting region 261A supported by a flexible PCB 261. The flexible PCB 261 is preferably encapsulated on one or both sides with an encapsulant material. The flexible PCB 261 preferably includes a reflective material arranged to reflect light toward a light transmissive outer surface 269 of the device 260. Multiple holes or perforations 265 are defined through the flexible PCB 261 and any associated encapsulant material layers. One or more sensors 263 (e.g., temperature sensors or any other types of sensors disclosed herein) are arranged in or on the flexible PCB 261. A socket 268 associated with the light emitting device 260 is arranged to receive a plug 277 to which the electrical cable 276 from the battery/control module 270 is attached. The battery/control module 270 includes a body 271, a battery 272, and a control board 273, which may include an emitter driver circuit and/or any suitable control, sensing, interface, data storage, and/or communication components as disclosed herein. The battery/control module 270 may further include a port or other interface 278 to enable communication with an external device (e.g., laptop or tablet computer, a mobile phone, or another portable digital device) via wired or wireless means.

Figure 34B:
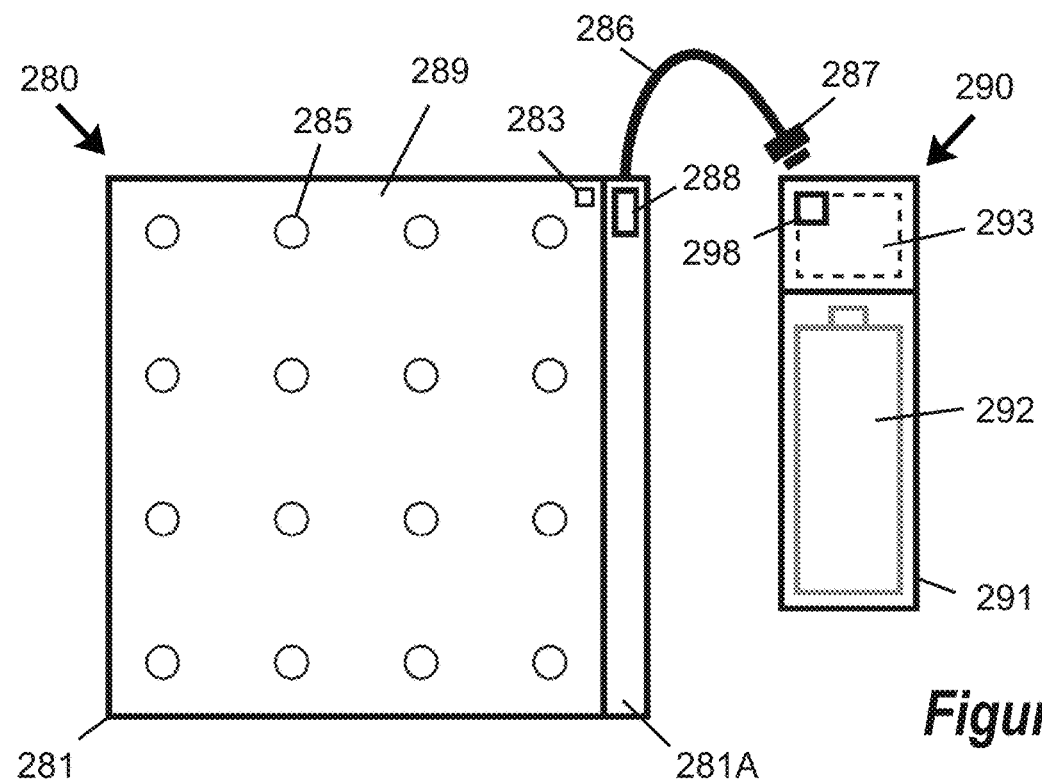
FIG. 34B is a top schematic view of at least a portion of a light emitting device for delivering light energy to living mammalian tissue and at least a portion of a battery/control module, wherein an elongated electrical cord is associated with the light emitting device for connecting the light emitting device to the battery/control module.

FIG. 34B is a top schematic view of at least a portion of a light emitting device 280 for delivering light energy to living mammalian tissue and at least a portion of a battery/control module 290, wherein an elongated electrical cable 286 is associated with the light emitting device 280 for connecting the light emitting device 280 to the battery/control module 290. The light emitting device 280 is edge lit along one edge with a light emitting region 281A supported by a flexible PCB 281. The flexible PCB 281 is preferably encapsulated on one or both sides with an encapsulant material. The flexible PCB 281 preferably includes a reflective material arranged to reflect light toward a light transmissive outer surface 289 of the device 280. Multiple holes or perforations 285 are defined through the flexible PCB 281 and any associated encapsulant material layers. One or more sensors 283 (e.g., temperature sensors or any other types of sensors disclosed herein) are arranged in or on the flexible PCB 281. A socket 298 associated with the battery/control module 290 is arranged to receive a plug 287 to which the electrical cable 286 from the light emitting device 280 is attached. The battery/control module 290 includes a body 291, a battery 292, and a control board 293, which may include an emitter driver circuit and/or any suitable control, sensing, interface, data storage, and/or communication components as disclosed herein. The light emitting device 280 may further include a port or other interface 288 to enable communication with an external device (e.g., laptop or tablet computer, a mobile phone, or another portable digital device) via wired or wireless means.

Figure 35:
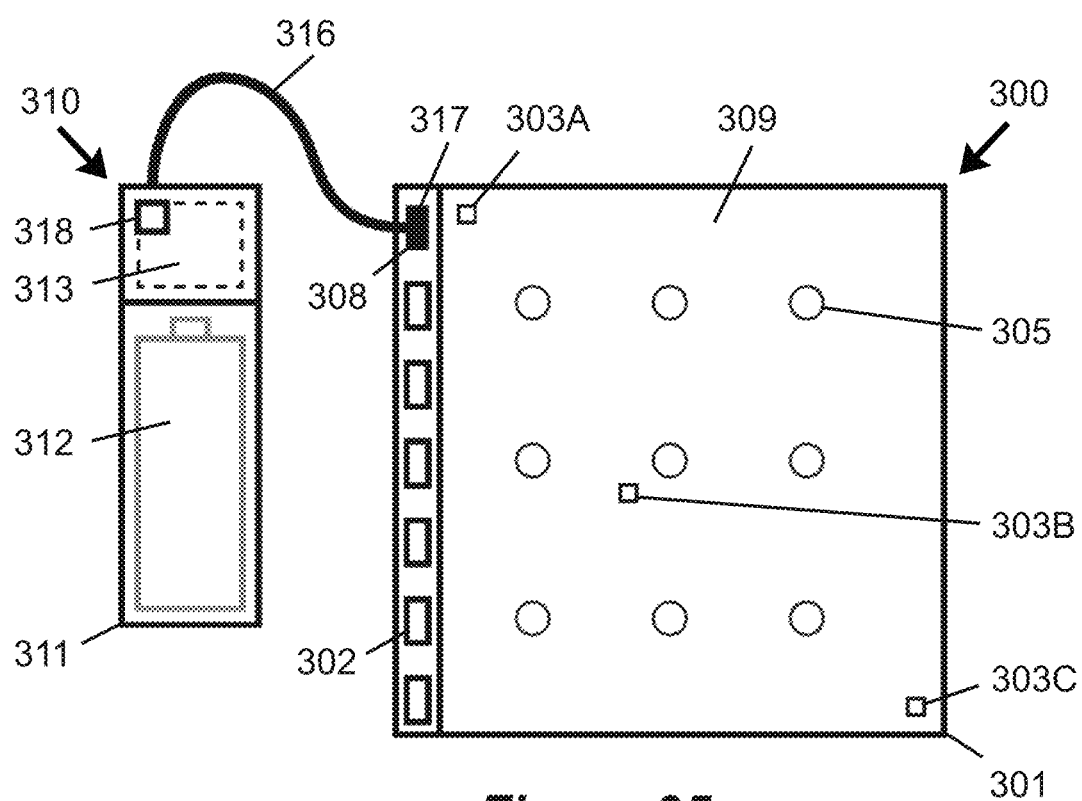
FIG. 35 is a top schematic view of at least a portion of a light emitting device for delivering light energy to living mammalian tissue and being connected via an electrical cord to a battery/control module, wherein the light emitting device includes multiple light emitters, multiple holes or perforations, and multiple sensors.

FIG. 35 is a top schematic view of at least a portion of a light emitting device 300 for delivering light energy to living mammalian tissue and being connected via an electrical cord 316 to a battery/control module 310, wherein the light emitting device 300 includes multiple light emitters 302 supported by a flexible PCB 301, multiple holes or perforations 305, and multiple sensors 303A-303C. The flexible PCB 301 is preferably encapsulated on one or both sides with an encapsulant material. The flexible PCB 301 preferably includes a reflective material arranged to reflect light toward a light transmissive outer surface 309 of the device 300. Multiple holes or perforations 305 are defined through the flexible PCB 301 and any associated encapsulant material layers. Multiple sensors 303A-303C are arranged in or on the flexible PCB 301. In certain embodiments, the sensors 303A-303C may differ in type from one another. In certain embodiments, the sensors 303A-303C may include one or more light emitters and photodiodes to illuminate a wound site with one or more selected wavelengths (e.g., green light) to detect blood flow in or proximate to a wound site to provide photoplethysmography data. The sensors 303A-303C may alternatively or additionally be arranged to detect blood pressure, bandage or dressing covering pressure, heart rate, temperature, presence or concentration of chemical or biological species (e.g., in wound exudate), or other conditions. A socket 308 associated with the light emitting device 300 is arranged to receive a plug 317 to which the electrical cord 316 from the battery/control module 310 is attached. The battery/control module 310 includes a body 311, a battery 312, and a control board 313, which may include an emitter driver circuit and/or any suitable control, sensing, interface, data storage, and/or communication components as disclosed herein. The battery/control module 310 may further include a port or other interface 318 to enable communication with an external device (e.g., laptop or tablet computer, a mobile phone, or another portable digital device) via wired or wireless means.

Figure 36A:
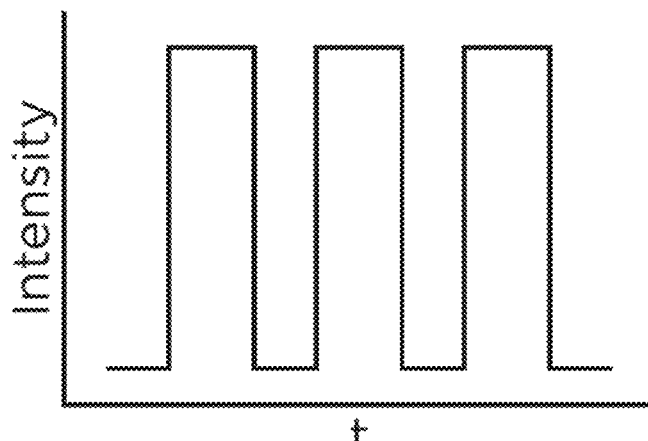
FIG. 36A is a plot of intensity versus time (t) embodying a first exemplary illumination cycle that may be used with at least one emitter of a light emitting device for delivering light energy to living mammalian tissue as disclosed herein.
Figure 36B:
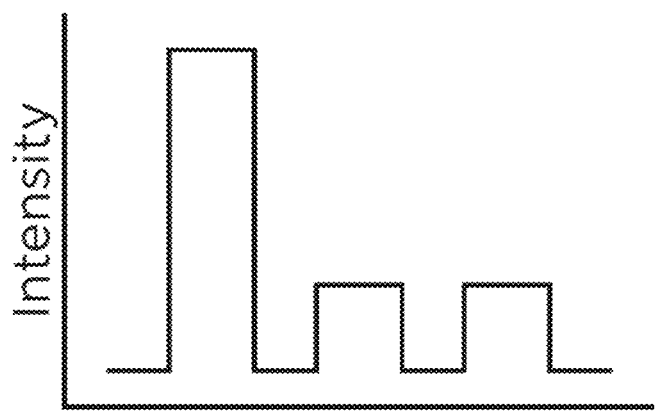
FIG. 36B is a plot of intensity versus time (t) embodying a second exemplary illumination cycle that may be used with at least one emitter of a light emitting device for delivering light energy to living mammalian tissue as disclosed herein.
Figure 36C:
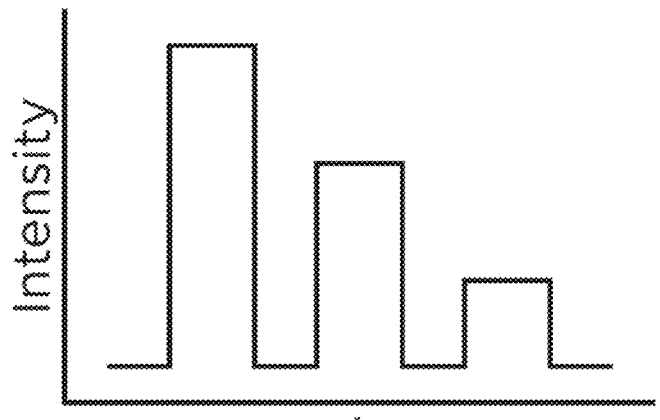
FIG. 36C is a plot of intensity versus time (t) embodying a third exemplary illumination cycle that may be used with at least one emitter of a light emitting device for delivering light energy to living mammalian tissue as disclosed herein.

FIGS. 36A-36C illustrate different pulse profiles that may be used with devices and methods according to the present disclosure. FIG. 36A is a plot of intensity versus time embodying a first exemplary illumination cycle that may be used with at least one emitter of a light emitting device for delivering light energy to living mammalian tissue as disclosed herein. As shown in FIG. 36A, a series of discrete pulses of substantially equal intensity may be provided during at least one time window or a portion thereof. FIG. 36B is a plot of intensity versus time embodying a second exemplary illumination cycle that may be used with at least one emitter of a light emitting device disclosed herein. As shown in FIG. 36B, intensity may be reduced from a maximum (or high) value to a reduced but non-zero value during at least one time window. FIG. 36C is a plot of intensity versus time embodying a third exemplary illumination cycle that may be used with at least one emitter of a light emitting device disclosed herein. As shown in FIG. 36C, intensity may be steadily reduced from a maximum (or high) value to sequentially reduced values over time. Other pulse profiles may be used according to certain embodiments.

Figure 37:
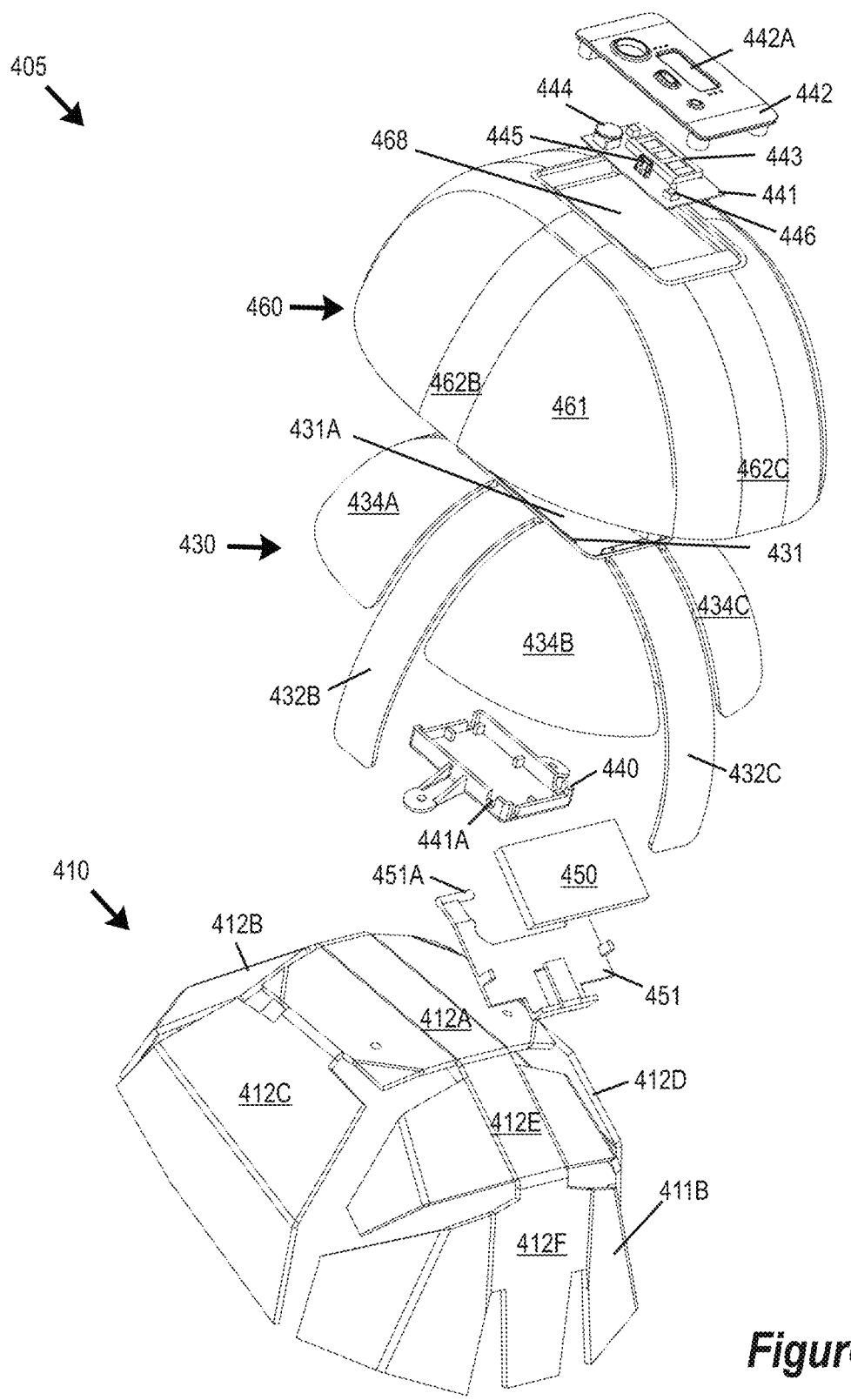
FIG. 37 is an exploded view of a light emitting device embodied in a wearable cap for delivering light energy to a scalp of a patient, the device including at least one light emitter supported by a flexible PCB arranged in a concave configuration, a concave support member shaped to receive the flexible PCB and support a battery and control module, and a fabric covering arranged to cover the support member and flexible substrate.

FIG. 37 is an exploded view of a light emitting device 405 embodied in a wearable cap for delivering light energy to a scalp of a patient. The device 405 includes multiple light emitters and standoffs supported by a flexible PCB 410 including multiple interconnected panels 412A-412F arranged in a concave configuration. A concave shaping member 430 (including a central frame 431, ribs 432A-432D, and curved panels 434A-434D) is configured to receive the flexible PCB 410. The ribs 432A-432D and curved panels 434A-434D project generally outwardly and downwardly from the central frame 431. Gaps are provided between portions of adjacent ribs 432A-432D and curved panels 434A-434D to accommodate outward expansion and inward contraction, and to enable transfer of heat and/or fluid (e.g., evaporation of sweat). A fabric covering member 460 is configured to cover the concave shaping member 430 and the flexible PCB 410 contained therein. A battery 450 and a battery holder 451 are arranged between the flexible PCB 410 and the concave shaping member 430. An electronics housing 440 is arranged to be received within an opening 431A defined in the central frame 431 of the concave shaping member 430. Pivotal coupling elements 441A, 451A are arranged to pivotally couple the battery holder 451 to the electronics housing 440. An electronics board 441 is insertable into the electronics housing 440, which is enclosed with a cover 442. Arranged on the electronics board 441 are a cycle counter 443, a control button 444, a charging/data port 445, and a status lamp 446. The various elements associated with the electronics housing 440 and the electronics board 441 may be referred to generally as a "control module." Windows 442A defined in the cover 442 provide access to the cycle counter 443, the control button 444, the charging/data port 445, and the status lamp 446. The fabric covering element 460 includes a fabric body 461 and multiple internal pockets 462A-462D arranged to receive portions of the ribs 432A-432D. An opening 468 at the top of the fabric covering element 460 is arranged to receive the cover 442.

Figure 38:
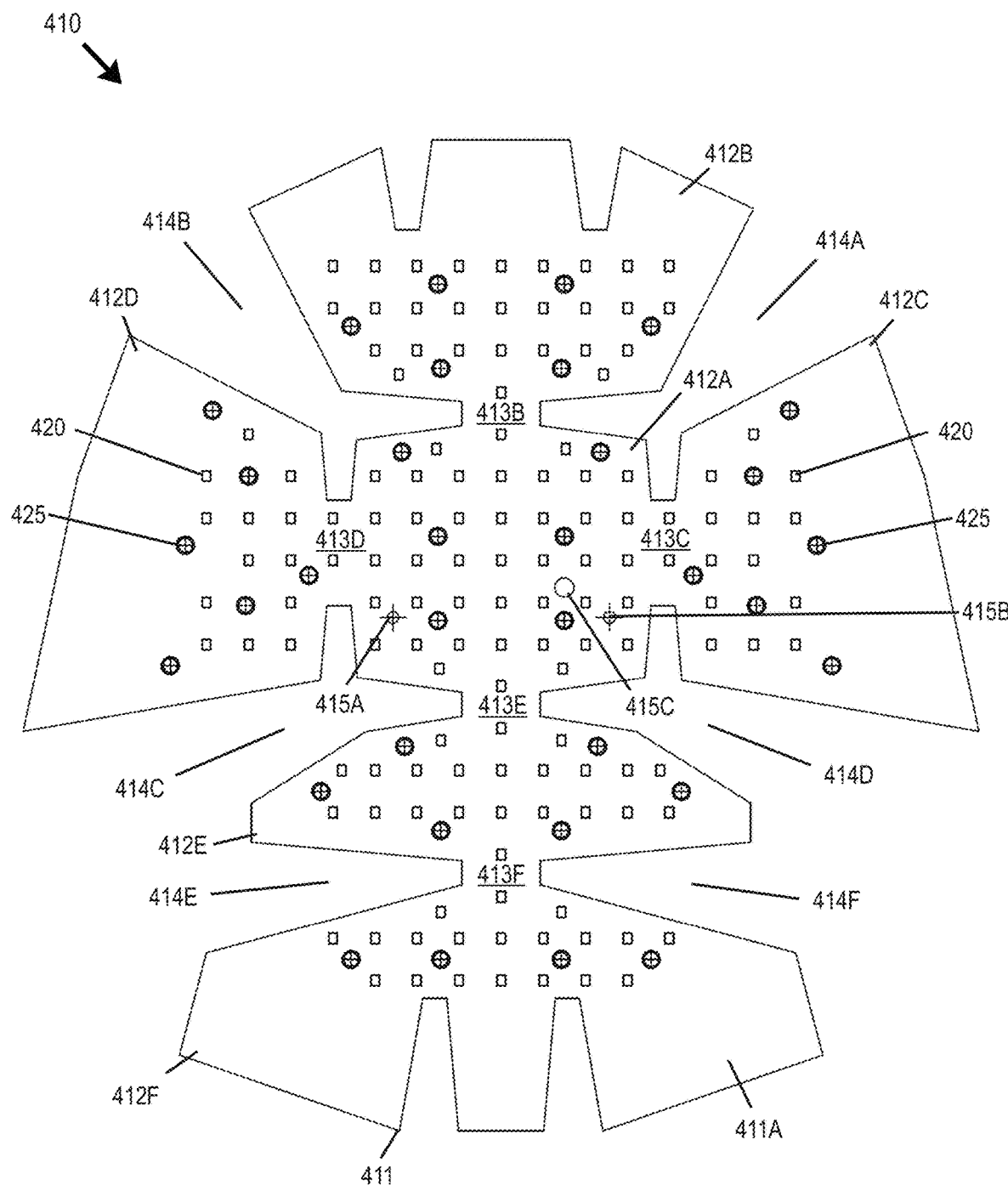
FIG. 38 is a bottom plan view of the flexible PCB of FIG. 37 prior to being shaped into a concave configuration.

FIG. 38 is a bottom plan view of the flexible PCB 410 including light emitters 420 and standoffs 425 arranged thereon. The PCB 410 includes a polyimide substrate 411, an inner surface 411A, and an outer surface 411B (shown in FIG. 37). In one embodiment, the light emitters 420 include a total of 280 light emitting diodes arranged as 56 strings of 5 LEDs, with a string voltage of 11V, a current limit of 5 mA, and a power consumption of 3.08 watts. FIG. 38 illustrates 36 standoffs 425 extending from the inner surface 411A of the flexible PCB 410. The flexible PCB 410 includes six interconnected panels 412A-412F, with the panels 412A-412F being connected to one another via narrowed tab regions 413B-413F. Gaps 414A-414F are provided between the various panels 412A-412F, with such gaps 414A-414F (which are extended proximate to the narrowed tab regions 413B-413F) being useful to permit transport of heat and/or fluid (e.g., evaporation of sweat) between the panels 412A-412F. As shown in FIG. 38, holes 415A, 415B are defined through the substrate 411 to receive fasteners (not shown) for joining the flexible PCB 410 to corresponding holes (not shown) defined in the electronics housing 440. A further opening 415C may be provided for sensor communication between a proximity sensor (e.g., photosensor) and the interior of the flexible PCB 410 when the flexible PCB 410 is shaped into a concave configuration.

Figure 39:
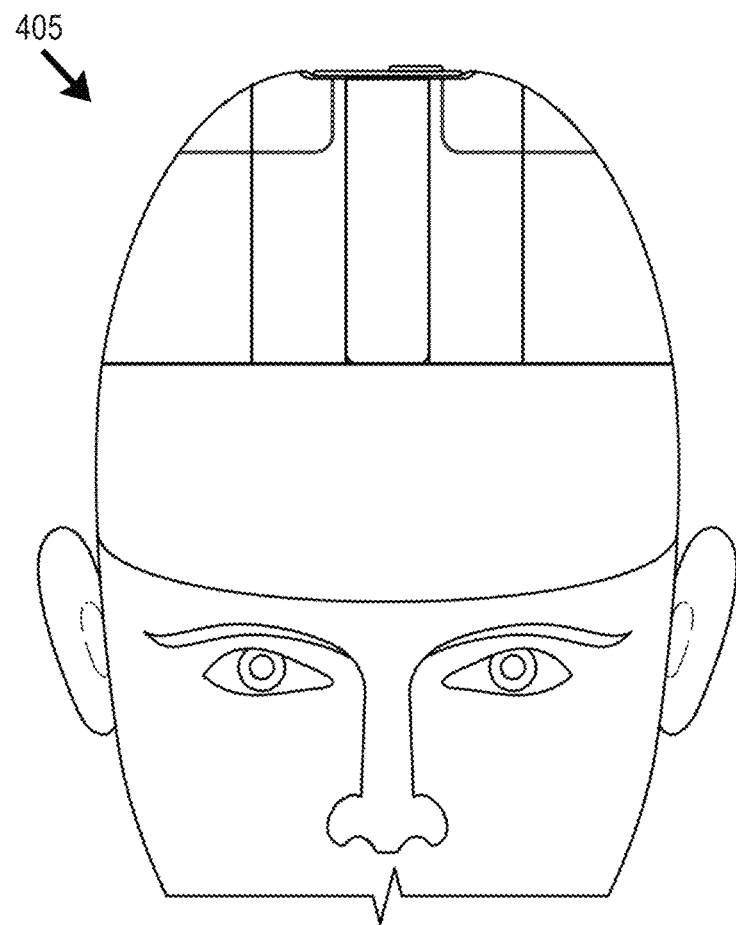
FIG. 39 is a front elevation view of the light emitting device of FIG. 37 affixed to a modeled human head.

FIG. 39 is a front elevation view of the assembled light emitting device 405 embodied in the wearable cap of FIG. 37 superimposed over a modeled human head. As shown in FIG. 39, the device 405 is embodied in a cap with a lower edge between a user's forehead and hairline, and above a user's ears.

Figure 40:
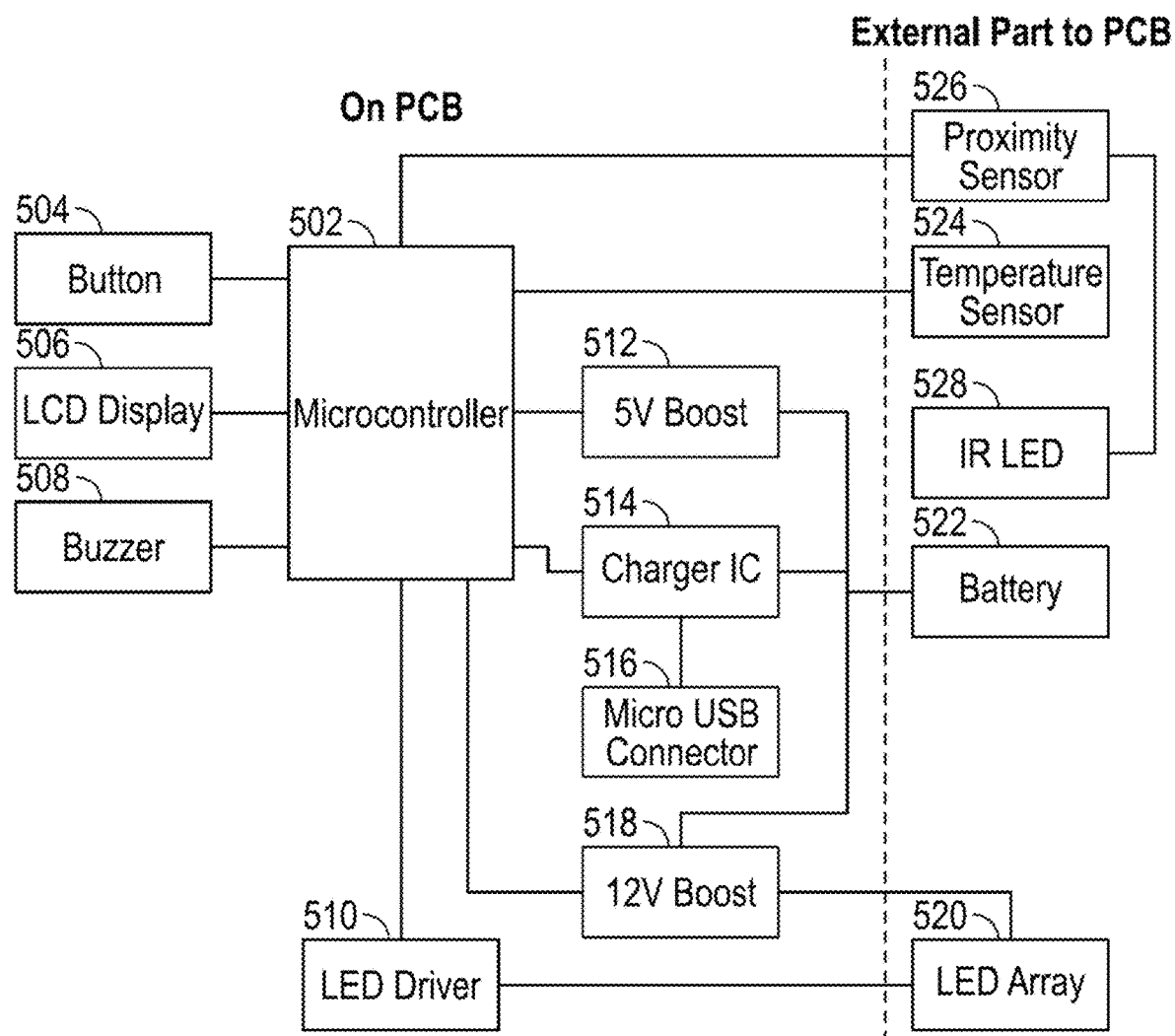
FIG. 40 is a schematic diagram showing interconnections between components of a light emitting device or delivering light energy to tissue of a patient according to one embodiment.

FIG. 40 is a schematic diagram showing interconnections between components of a light emitting device for delivering light energy to tissue of a patient according to one embodiment. A microcontroller 502 is arranged to receive power from a battery 522 (nominally 3.7V) via a 5V voltage boost circuit 512. The microcontroller may be arranged to control a charging integrated circuit 514 arranged between a microUSB connector 516 and the battery 522, wherein the microUSB connector 516 may be used to receive current for charging the battery 522. In certain embodiments, the microUSB connector 516 may also be used for communicating data and/or instructions to or from the microcontroller 502 and/or an associated memory. The microcontroller 502 is also arranged to control a 12V boost circuit 518 for increasing voltage to one or more LED arrays 520. The microcontroller 502 further controls one or more LED driver circuits 510 arranged to drive the LED array(s) 520. The microcontroller 502 is also arranged to receive inputs from a user input button 504, a temperature sensor 524, and a proximity sensor 526 (which includes an infrared LED 528). The microcontroller 502 is further arranged to provide output signals to a LCD display 506 and a buzzer 508. Certain components are located off-board relative to a controller PCB, as indicated by the vertical dashed line in FIG. 40. In operation of the light emitting device, a user may depress the button 504 to start operation. If the proximity sensor 526 detects that the device has been placed in suitable proximity to desired tissue, then the microcontroller 502 may trigger the LED driver circuit(s) 510 to energize the LED array(s) 520. Temperature during operation is monitored with the temperature sensor 524. If an excess temperature condition is detected, then the microcontroller 502 may take appropriate action to reduce current supplied by the LED driver circuit(s) 510 to the LED array(s) 520. Operation may continue until a timer (e.g., internal to the microcontroller 502) causes operation to terminate automatically. One or more indicator LEDs (not shown) may provide a visible signal indicative of charging status of the battery 522. Audible signals for commencement and termination of operation may be provided by the buzzer 508 or a suitable speaker. Information relating to usage cycles, usage time, or any other suitable parameter may be displayed by the LCD display 506.

Figure 41:
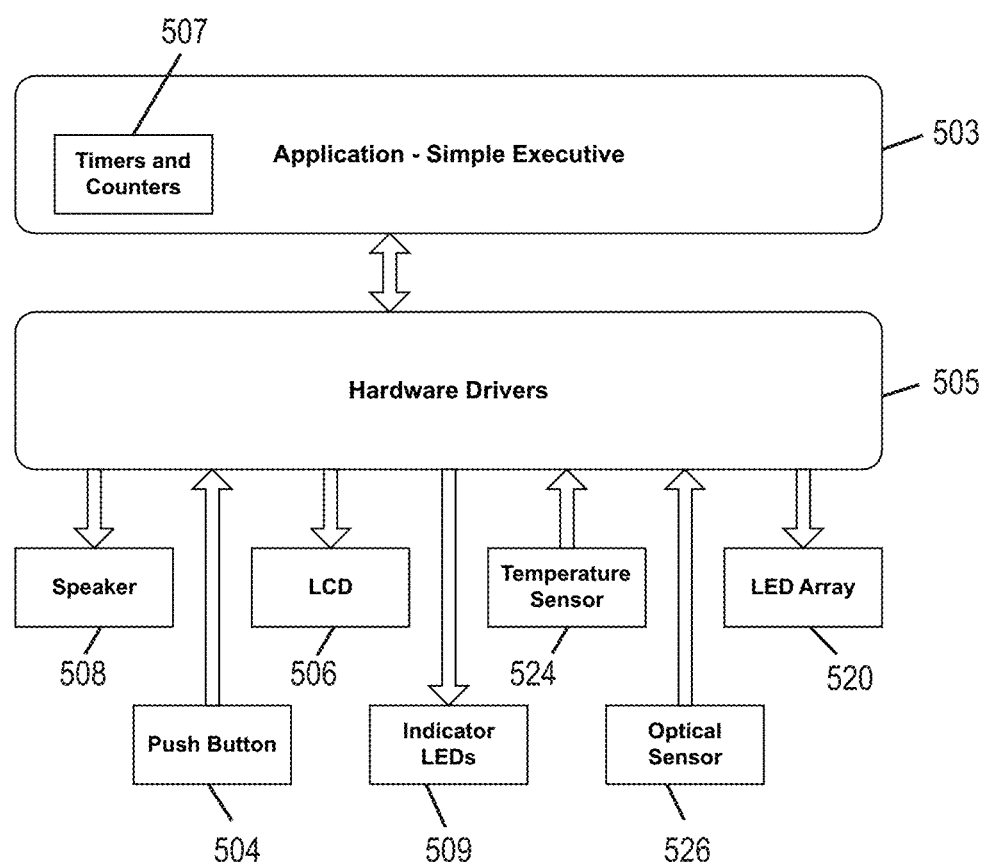
FIG. 41 is a schematic diagram depicting an interface between hardware drivers, functional components, and a software application suitable for operating a light emitting device according to FIG. 40.

FIG. 41 is a schematic diagram depicting an interface between hardware drivers, functional components, and a software application suitable for operating a light emitting device according to FIG. 40. Application executive functions 503, including timers and counters 507, may be performed with one or more integrated circuits (such as the microcontroller 502 illustrated in FIG. 40). Hardware drivers 505 may be used to interface with various input and output elements, such as the LED array(s) 520, the speaker or buzzer 508, the LCD display 506, the temperature sensor 524, the push button 504, the indicator LEDs 509, and the optical sensor (proximity sensor) 526.

Figure 42:
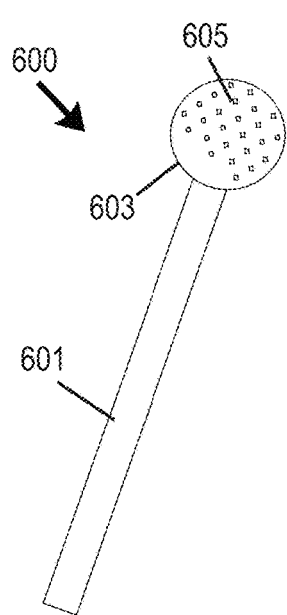
FIG. 42 is a schematic elevation view of at least a portion of a light emitting device for delivering light energy to tissue in an internal cavity of a patient according to one embodiment.

FIG. 42 is a schematic elevation view of at least a portion of a light emitting device 600 for delivering light energy to tissue in an internal cavity (e.g., body cavity) of a patient according to one embodiment. In certain embodiments, a body cavity may comprise a vaginal cavity, an oral cavity, or an esophageal cavity. If used in an oral or esophageal cavity, one or more unobstructed channels or tubes (not shown) may be provided in, on, or through the device 600 to avoid interruption with patient breathing. The device 600 includes a body 601 that may be rigid, semi-rigid, or articulated. A treatment head 603 has arranged therein or thereon one or more light emitters 605, which are preferably encapsulated in silicone or another suitable light transmissive material. In certain embodiments, the one or more light emitters 605 may be arranged to produce ES increasing light and ES releasing light for impingement on tissue located within an internal cavity of a patient to trigger release of NO. In certain embodiments, the light emitters may be external to the body 601, and light emissions of the light emitters may be extracted at features that are arranged on the end of the body 601 (e.g., in or along treatment head 603), and light may exit the treatment head 603 at apertures or positions corresponding to element number 605.

Figure 43A:
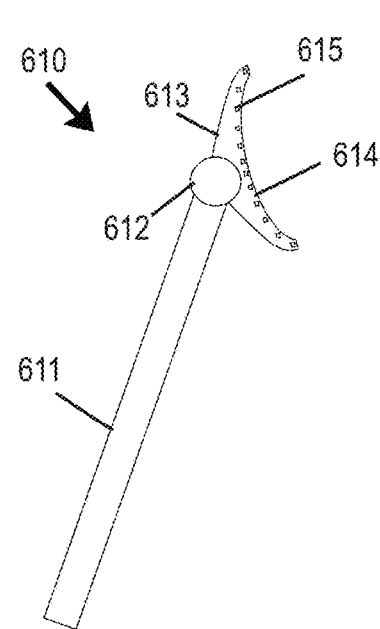
FIG. 43A is a schematic elevation view of at least a portion of a light emitting device including a concave light emitting surface for delivering light energy to cervical tissue of a patient according to one embodiment.

FIG. 43A is a schematic elevation view of at least a portion of a light emitting device 610 including a concave light emitting surface 614 including one or more light emitters 615 for delivering light energy to cervical tissue of a patient according to one embodiment. The device 610 includes a body 611 that may be rigid, semi-rigid, or articulated. A joint 612 may be arranged between the body 611 and a treatment head 613. The treatment head 613 has arranged therein or thereon the one or more light emitters 615, which are preferably encapsulated in silicone or another suitable light transmissive material. In certain embodiments, the one or more light emitters 615 may be configured to generate emissions suitable for neutralizing pathogens such as human papilloma virus (HPV) present on cervical tissue. In certain embodiments, the one or more light emitters 615 may be arranged to produce ES increasing light and ES releasing light for impingement on tissue located within an internal cavity of a patient to trigger release of NO.

Figure 43B:
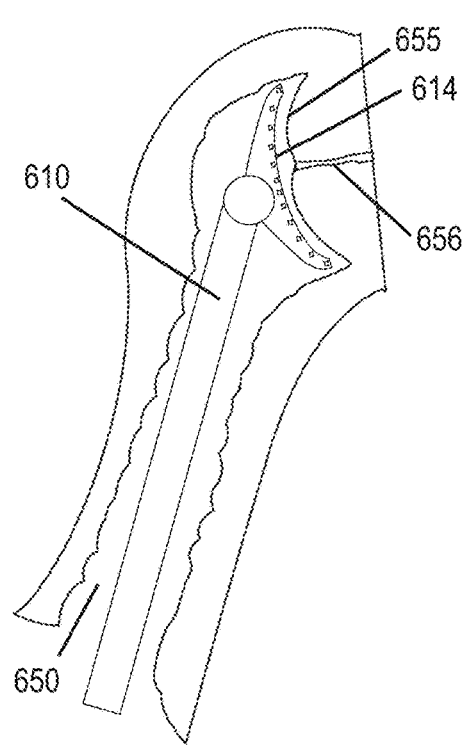
FIG. 43B illustrates the device of FIG. 43A inserted into a vaginal cavity to deliver light energy to cervical tissue of a patient.

FIG. 43B illustrates the device 610 of FIG. 43A inserted into a vaginal cavity 650 to deliver light energy to cervical tissue 655 of a patient proximate to a cervical opening 656. The concave light emitting surface 614 may be configured to approximately match a convex profile of the cervical tissue 655.

Figure 44A:
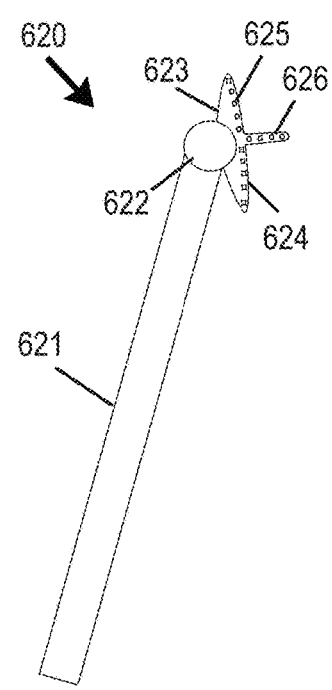
FIG. 44A is a schematic elevation view of at least a portion of a light emitting device including a probe-defining light emitting surface for delivering light energy to cervical tissue of a patient according to another embodiment.

FIG. 44A is a schematic elevation view of at least a portion of a light emitting device 620 including a light emitting surface 624 with a protruding probe portion 626 for delivering light energy to cervical tissue of a patient according to another embodiment. The probe portion 626 includes light emitters and is arranged to deliver light energy into a cervical opening. The device 620 includes a body 621 that may be rigid, semi-rigid, or articulated. A joint 622 may be arranged between the body 621 and a treatment head 623. The treatment head 623 has arranged therein or thereon one or more light emitters 625, which are preferably encapsulated in silicone or another suitable light transmissive material. The treatment head 623 may include the light emitting surface 624, which may optionally be convex to cast a wider output beam. In certain embodiments, the one or more light emitters 625 may be configured to generate emissions suitable for neutralizing pathogens such as human papilloma virus (HPV) present on cervical tissue. In certain embodiments, the one or more light emitters 625 may be arranged to produce ES increasing light and ES releasing light for impingement on tissue located within an internal cavity of a patient to trigger release of NO.

Figure 44B:
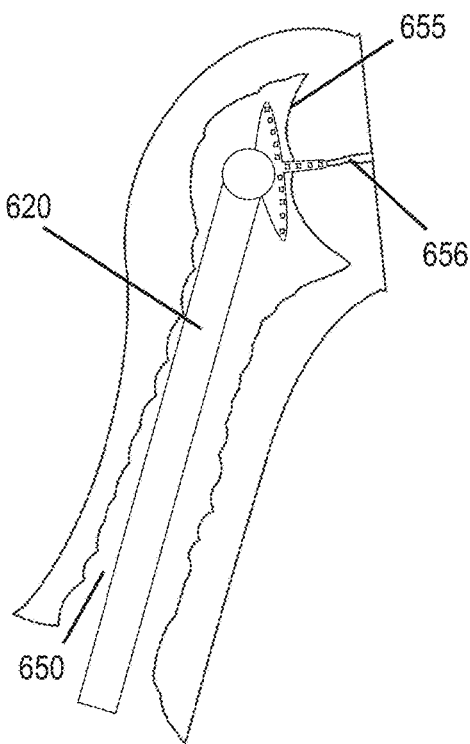
FIG. 44B illustrates the device of FIG. 44A inserted into a vaginal cavity, with a probe portion of the light-emitting surface inserted into a cervical opening, to deliver light energy to cervical tissue of a patient.

FIG. 44B illustrates the device 620 of FIG. 44A inserted into a vaginal cavity 650 to deliver light energy to cervical tissue 655 of a patient proximate and within to a cervical opening 656. The primary light emitting surface 624 may be arranged to impinge light on cervical tissue bounding the vaginal cavity 650, whereas the probe portion 626 may be inserted into the cervical opening 656 to deliver additional light energy therein to increase the amount of cervical tissue subject to receipt of light energy for addressing one or more conditions including pathogen (e.g., HPV) neutralization.

To investigate whether NO may be photomodulated in at least certain types of cells for extended periods (e.g., hours) and to evaluate potential toxicity of photomodulation, Applicant performed various experiments on two types of cells—namely, keratinocytes and fibroblasts.

Figure 45:
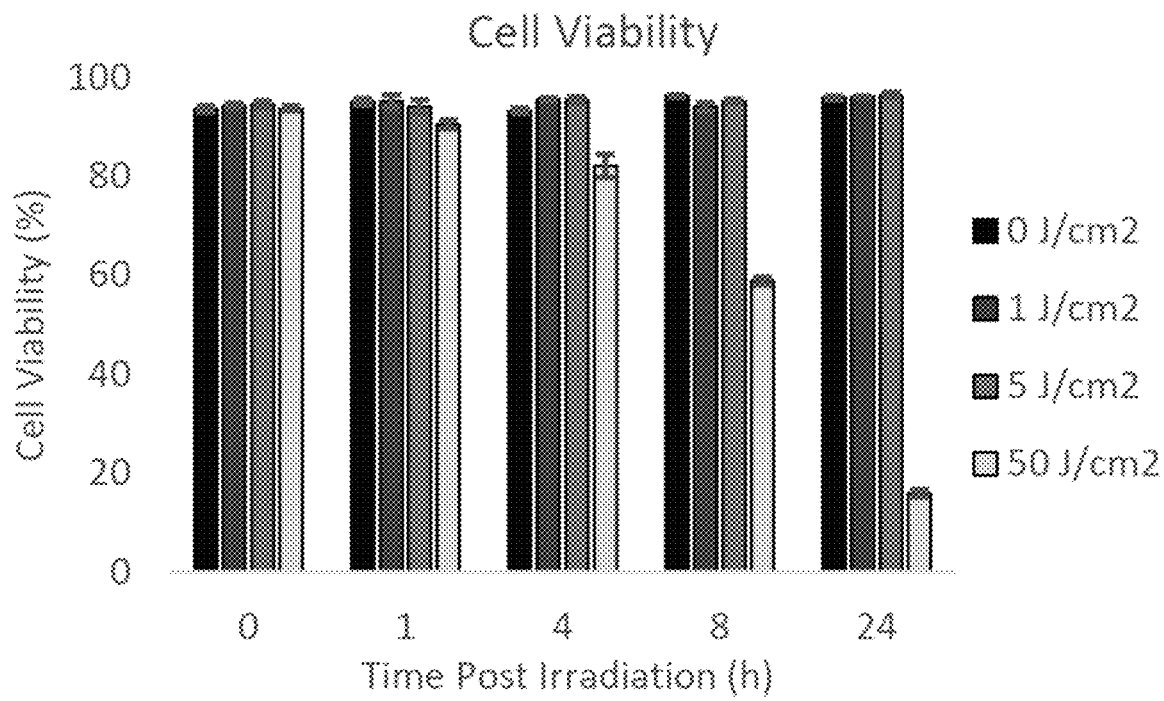
FIG. 45 is a bar chart identifying percentage of viable cells as a function of time post 420 nm irradiation (from 0 to 24 hours) for four different fluence values ranging from 0 J/cm$^2$ to 50 J/cm$^2$ for NO generation in keratinocytes resulting from photobiomodulation.

Referring to FIGS. 45-48, isolated keratinocytes were exposed to 420 nm light to achieve doses of 0, 1, 5, and 50 J/cm$^2$. Fluence of light was found to determine efficacy of NO modulation as well as cytotoxicity. As shown in FIG. 45, cell viability over periods from 0 to 24 hours from light exposure was unaffected by doses of 0, 1, and 5 J/cm$^2$, but light exposure at 50 J/cm$^2$ resulted in a substantial drop in cell viability, declining to a value below 20% within 24 hours after irradiation.

Figure 46:
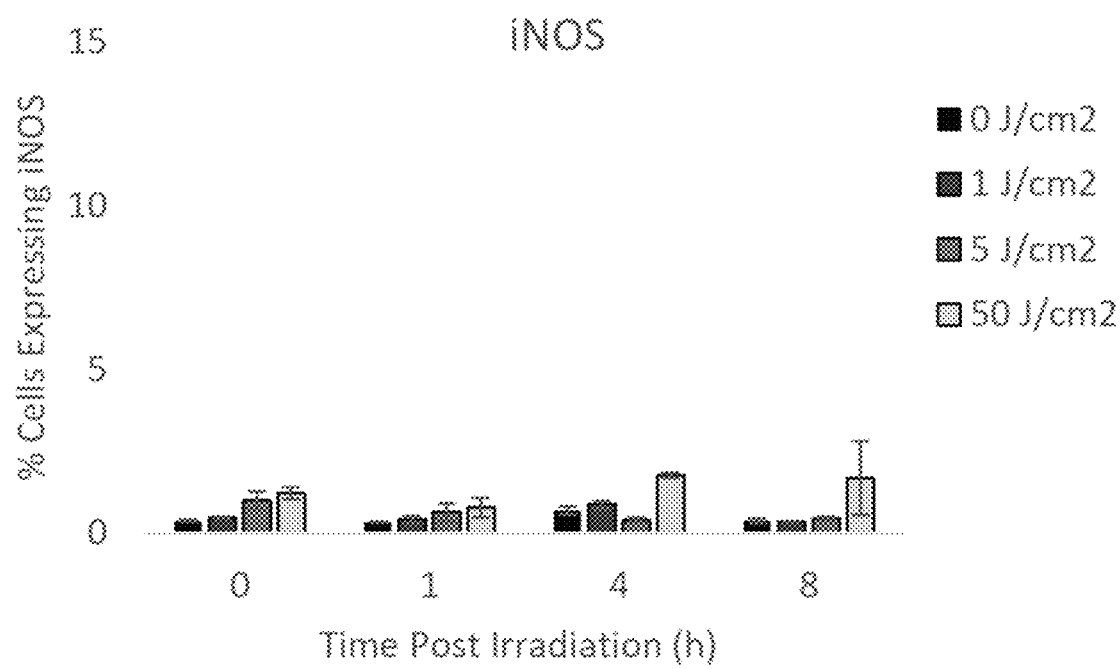
FIG. 46 is a bar chart identifying percentage of cells expressing iNOS as a function of time post 420 nm irradiation (from 0 to 8 hours) for four different fluence values ranging from 0 J/cm$^2$ to 50 J/cm$^2$ for NO generation in keratinocytes resulting from photobiomodulation.
Figure 47:
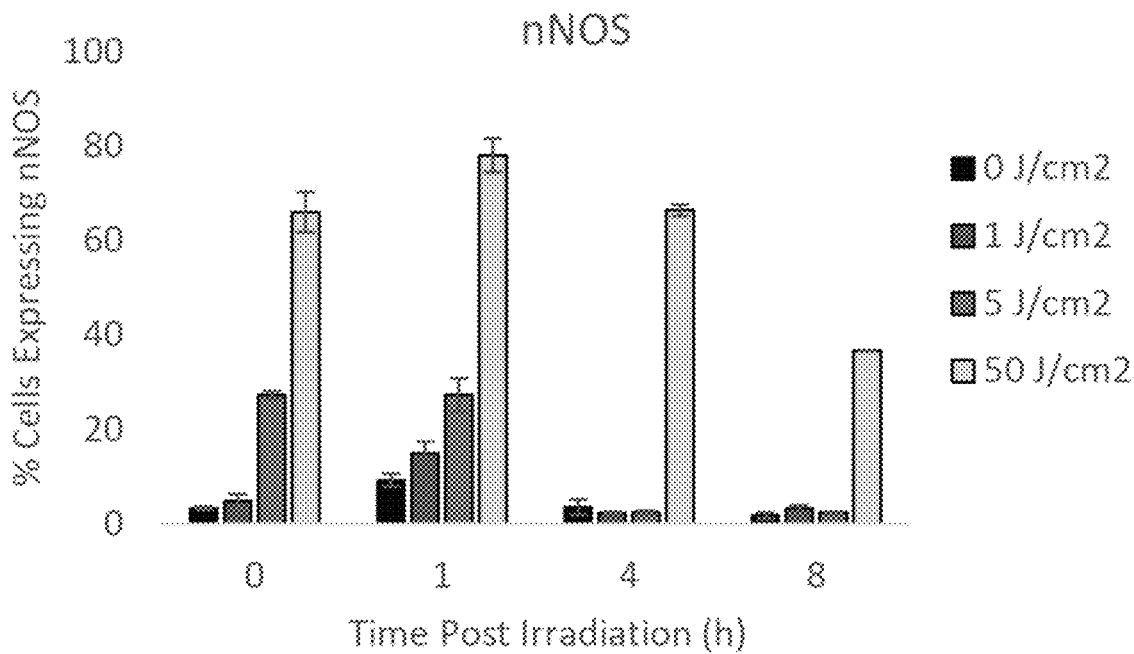
FIG. 47 is a bar chart identifying percentage of cells expressing nNOS as a function of time post 420 nm irradiation (from 0 to 8 hours) for four different fluence values ranging from 0 J/cm$^2$ to 50 J/cm$^2$ for NO generation in keratinocytes resulting from photobiomodulation.

Referring to FIGS. 46 and 47, the amount of NOS enzymes (namely, iNOS in FIG. 46, and nNOS in FIG. 47) expressed in the keratinocyte cells was quantified at intervals of 0 hours (immediately), 1 hour, 4 hours, and 8 hours after irradiation ended. The number of cells exhibiting iNOS and nNOS increased with increasing irradiation. In FIG. 46, the percentage of cells expressing iNOS generally remained the same or decreased 1 hour after light exposure; the percentage of cells expressing iNOS increased for doses of 1 and 50 J/cm$^2$ at a time 4 hours after light exposure, and the percentage of cells expressing iNOS remained elevated only for the dose of 50 J/cm$^2$ at a time 24 hours after light exposure. In FIG. 47, the percentage of cells expressing nNOS generally increased for all doses of 0, 1, 5, and 50 J/cm$^2$ at a time 1 hour after light exposure, the percentage of cells expressing nNOS remained elevated only for the dose of 50 J/cm$^2$ at time periods of 4 hours and 8 hours after light exposure. FIGS. 46 and 47 show the capability of generated nitric oxide synthases with photomodulation.

Figure 48:
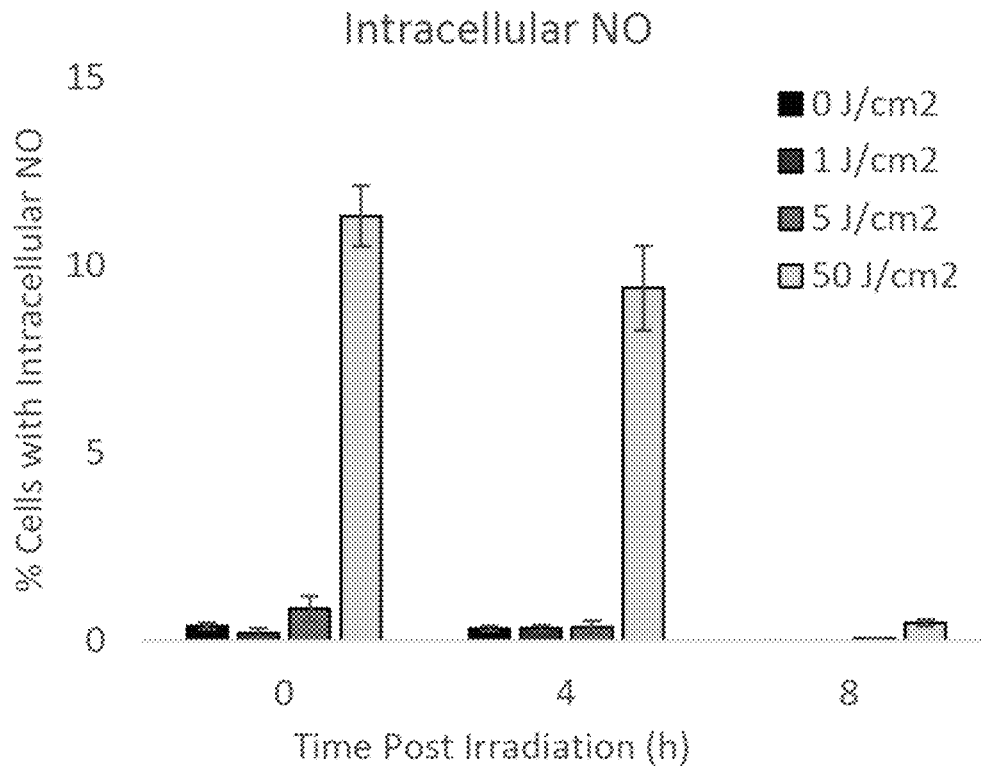
FIG. 48 is a bar chart identifying percentage of cells with intracellular NO as a function of time post 420 nm irradiation (from 0 to 8 hours) for four different fluence values ranging from 0 J/cm$^2$ to 50 J/cm$^2$ for NO generation in keratinocytes resulting from photobiomodulation.

Referring to FIG. 48, intracellular NO was measured with 4-Amino-5-Methylamino-2',7'-Difluorofluorescein Diacetate (DAF-FM Diacetate). The number of cells exhibiting intracellular NO increased with increasing irradiation. Intracellular NO was measured immediately after light exposure as well as 4 and 8 hours after exposure. FIG. 48 shows that NO is released for greater than 4 hours after irradiation, thereby suggesting enzymatic NO generation.

Figure 49:
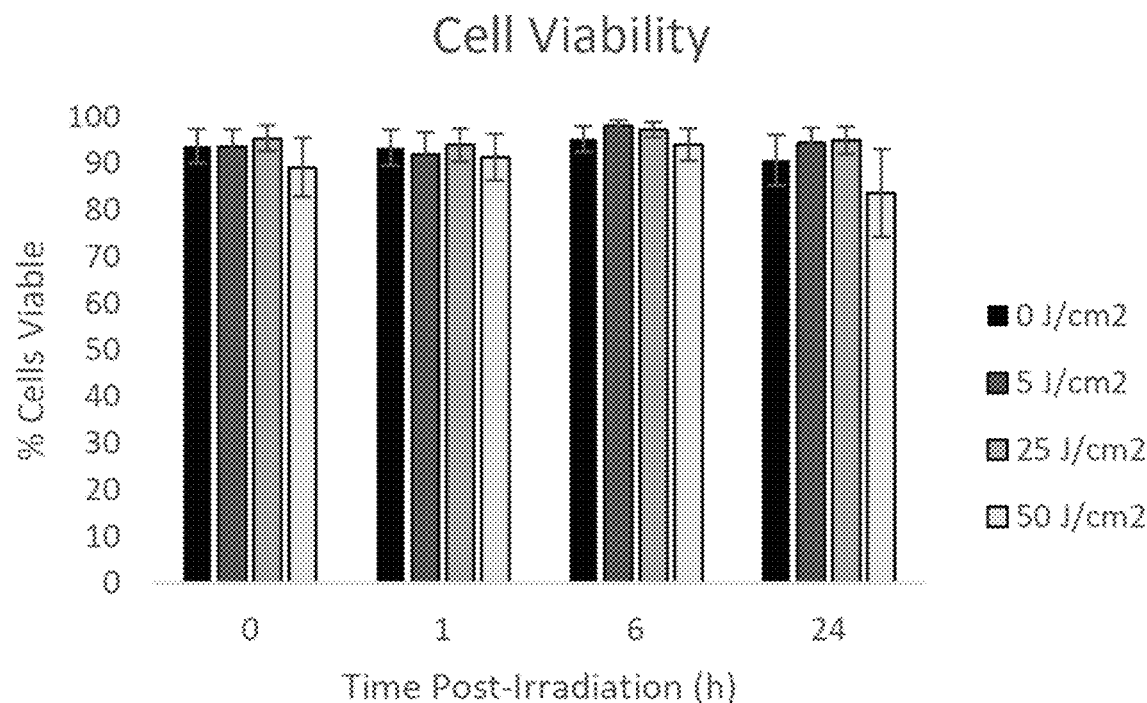
FIG. 49 is a bar chart identifying percentage of viable cells as a function of time post 420 nm irradiation (from 0 to 24 hours) for four different fluence values ranging from 0 J/cm$^2$ to 50 J/cm$^2$ for NO generation in fibroblasts resulting from photobiomodulation.

Turning to FIGS. 49-52, isolated fibroblasts were exposed to 420 nm light to achieve doses of 0, 5, 25, and 50 J/cm$^2$. Fluence of light was found to determine efficacy of NO modulation as well as cytotoxicity. As shown in FIG. 49, cell viability over periods from 0 to 24 hours from light exposure was substantially unaffected by doses of 0, 5, 25, and 50 J/cm$^2$.

Figure 50:
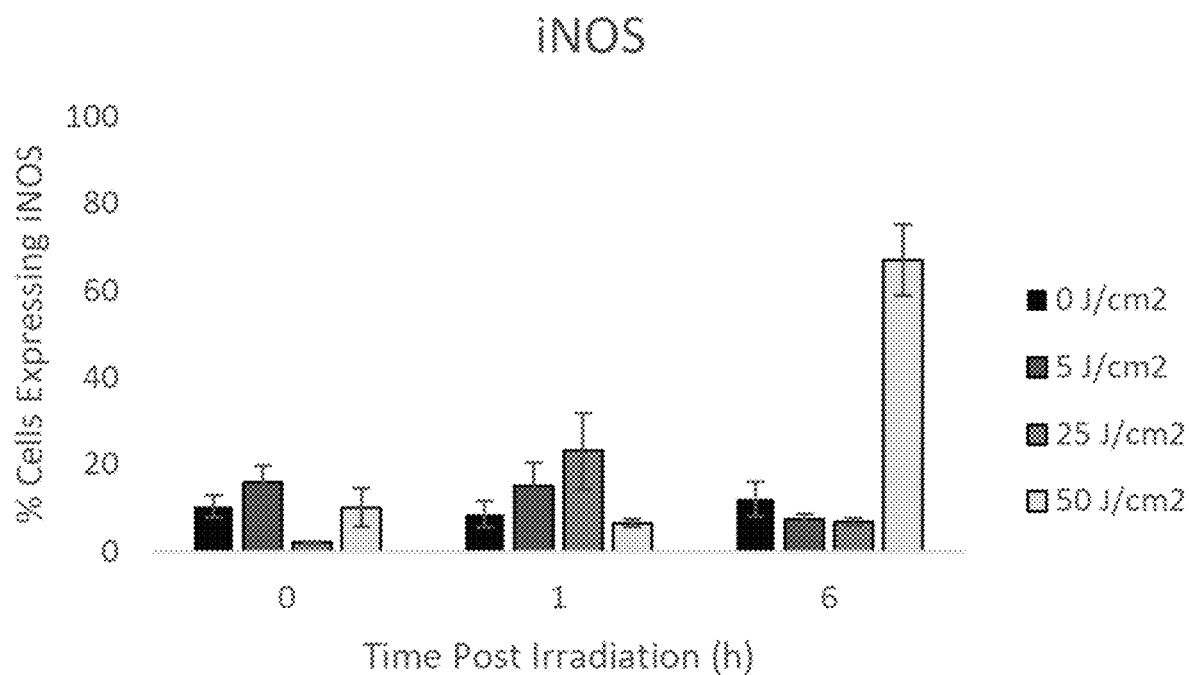
FIG. 50 is a bar chart identifying percentage of cells expressing iNOS as a function of time post 420 nm irradiation (from 0 to 6 hours) for four different fluence values ranging from 0 J/cm$^2$ to 50 J/cm$^2$ for NO generation in fibroblasts resulting from photobiomodulation.
Figure 51:
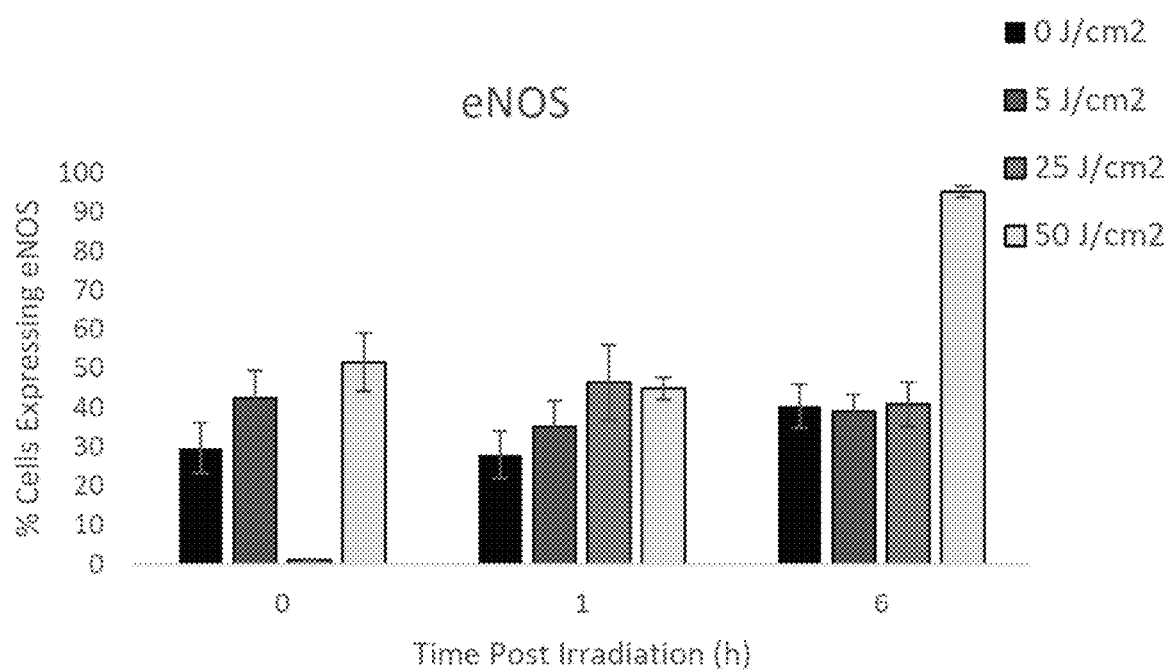
FIG. 51 is a bar chart identifying percentage of cells expressing eNOS as a function of time post 420 nm irradiation (from 0 to 6 hours) for four different fluence values ranging from 0 J/cm$^2$ to 50 J/cm$^2$ for NO generation in fibroblasts resulting from photobiomodulation.

Referring to FIGS. 50 and 51, the amount of NOS enzymes (namely, iNOS in FIG. 50, and eNOS in FIG. 51) expressed in the fibroblast cells was quantified at intervals of 0 hours (immediately), 1 hour, and 6 hours after irradiation ended. In both figures, the number of cells exhibiting iNOS or eNOS generally increased with increasing irradiation. In FIG. 50, the percentage of cells expressing iNOS was particularly elevated for the dose of 50 J/cm$^2$ at a time period of 6 hours after irradiation, thereby suggesting enzymatic NO generation. Referring to FIG. 51, the percentage of cells expressing eNOS remained generally elevated at a time period of 6 hours after irradiation, but the dose of 50 J/cm$^2$ was particularly elevated at this time period.

Figure 52:
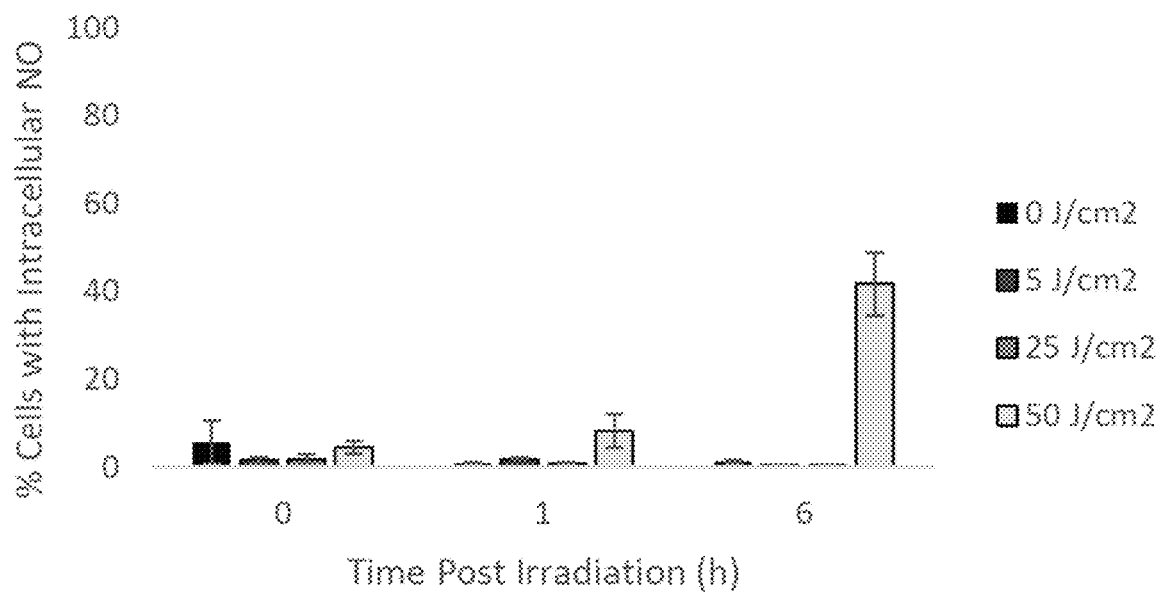
FIG. 52 is a bar chart identifying percentage of cells with intracellular NO as a function of time post 420 nm irradiation (from 0 to 6 hours) for four different fluence values ranging from 0 J/cm$^2$ to 50 J/cm$^2$ for NO generation in fibroblasts resulting from photobiomodulation.

Referring to FIG. 52, intracellular NO was measured with 4-Amino-5-Methylamino-2',7'-Difluorofluorescein Diacetate (DAF-FM Diacetate). The number of cells exhibiting intracellular NO increased with increasing irradiation. Intracellular NO was measured immediately after light exposure as well as 1 and 6 hours after exposure. FIG. 52 shows that NO is released for greater than 4 hours after irradiation, thereby suggesting enzymatic NO generation. The percentage of cells with intracellular NO remained elevated at 1 hour and 6 hours after irradiation for the dose of 50 J/cm$^2$, but was particularly elevated at 6 hours for 50 J/cm$^2$.

Taken in combination, FIGS. 49-52 demonstrate the capability of generating nitric oxide synthases and NO using 420 nm light for 6 hours post irradiation without associated toxicity.

Efficacy of the liberation of nitric oxide from protein complexes (by breaking nitroso or nitrosyl bonds) depends on the wavelength of light used. Different types of bonds (e.g., RSNO, RNNO, and metal-NO) may require different light wavelength and light irradiation values to effectuate release of nitric oxide. To investigate whether certain light wavelengths and light irradiation values may be more effective than others at releasing different endogenous stores of NO (i.e., to serve as ES releasing light), Applicant performed various experiments with hemoglobin-NO, S-nitrosoglutathione (GSNO), albumin-NO, cytochrome c-NO, cytochrome c-oxidase-NO, and mitochondria-NO. Details of these experiments are described hereinafter in connection with FIGS. 53 to 64.

Figure 53:
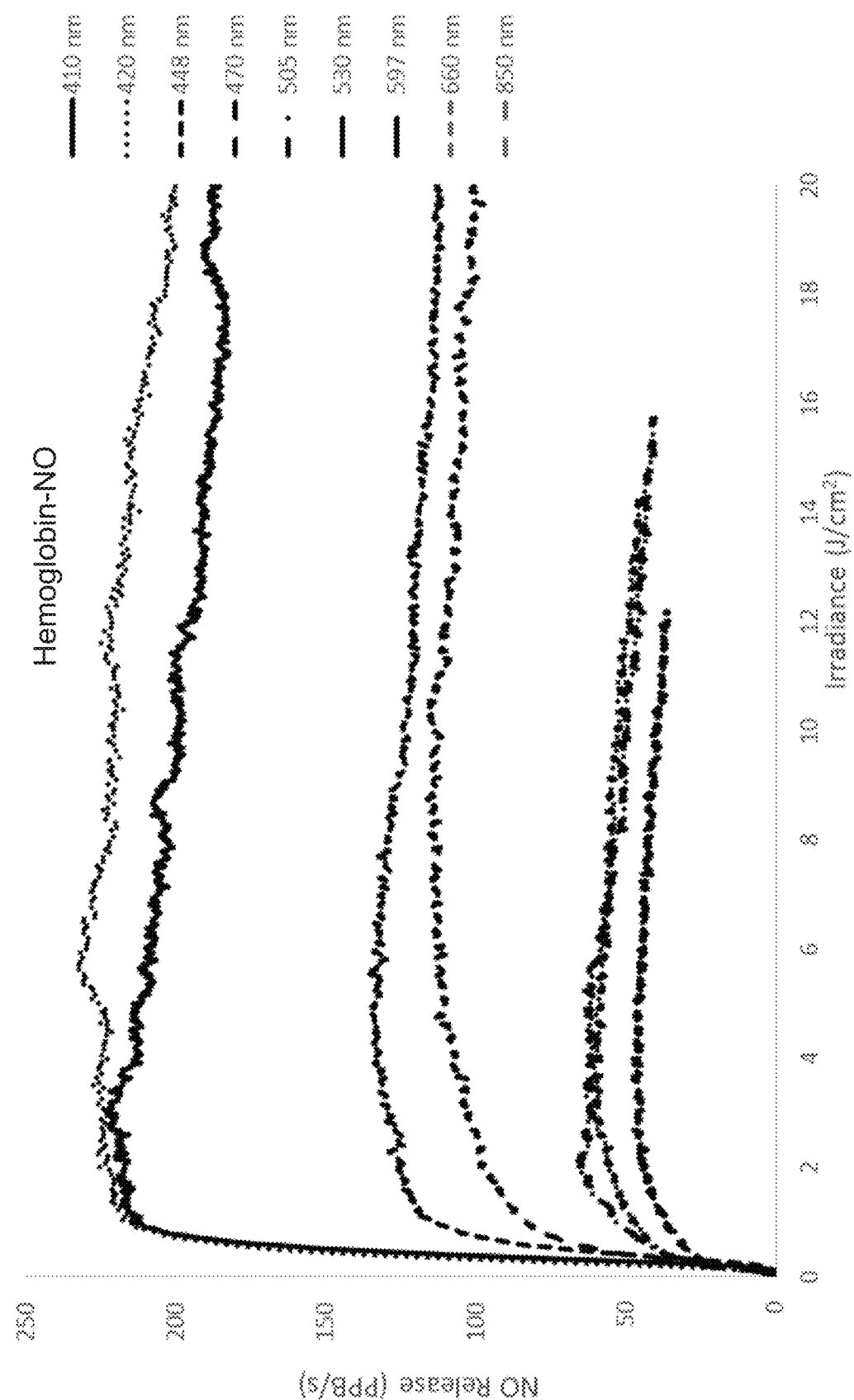
FIG. 53 is a plot of NO release rate (PPB/s) versus irradiance (J/cm$^2$) from hemoglobin-NO for nine (9) different wavelengths of incoherent light ranging from 410 to 850 nm.
Figure 54:
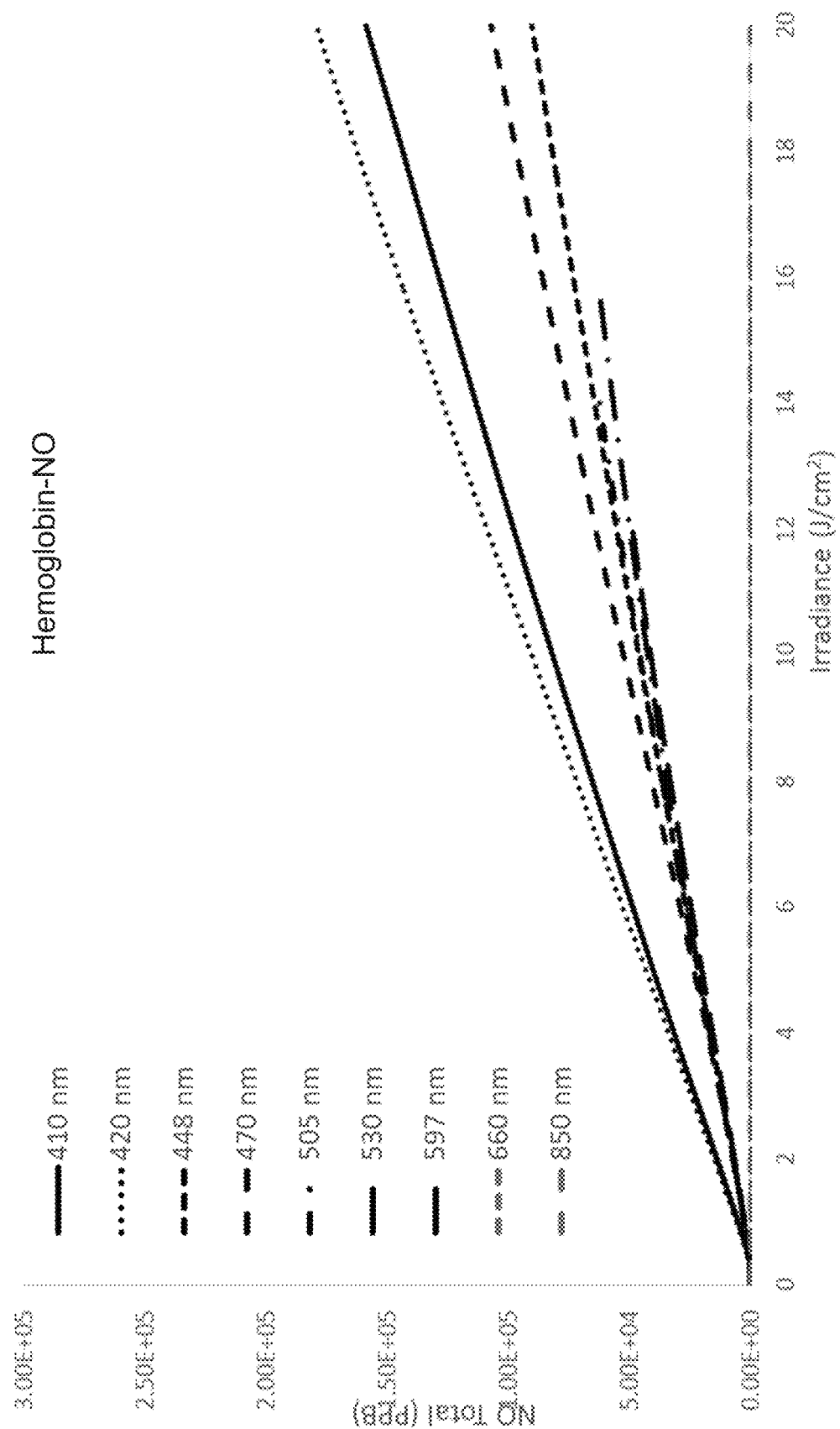
FIG. 54 is a plot of total NO release (PPB) versus irradiance (J/cm$^2$) from hemoglobin-NO for nine (9) different wavelengths of incoherent light ranging from 410 to 850 nm.

FIG. 53 is a plot of NO release rate (PPB/s) versus irradiance (J/cm$^2$) from hemoglobin-NO for nine (9) different wavelengths of incoherent light ranging from 410 nm to 850 nm. Nitric oxide was added to hemoglobin by reacting proline-NONOate with hemoglobin in PBS (pH 6.5) under anaerobic conditions and in the dark. After 45 minutes of reaction, the NO release was measured as a function of irradiation using a chemiluminescence detector. As shown, all wavelengths resulted in release of NO (at a roughly constant rate for all irradiance values greater than about 2 J/cm$^2$), but the release rate was highest for 420 nm light, second highest for 410 nm light, and lowest for longer wavelengths (e.g., 850 nm light). Referring to FIG. 54, total NO released from hemoglobin was quantified by integrating the data on NO release rate of FIG. 53. A linear relationship is observed for each wavelength, with higher irradiance values resulting in higher total NO release. The highest amount of total NO release was achieved with 420 nm light, the second highest amount was achieved with 410 nm light, and the lowest amount of total NO release was achieved with 597 nm light. Notably, FIG. 54 omits data for 660 nm light and 850 nm light.

Figure 55:
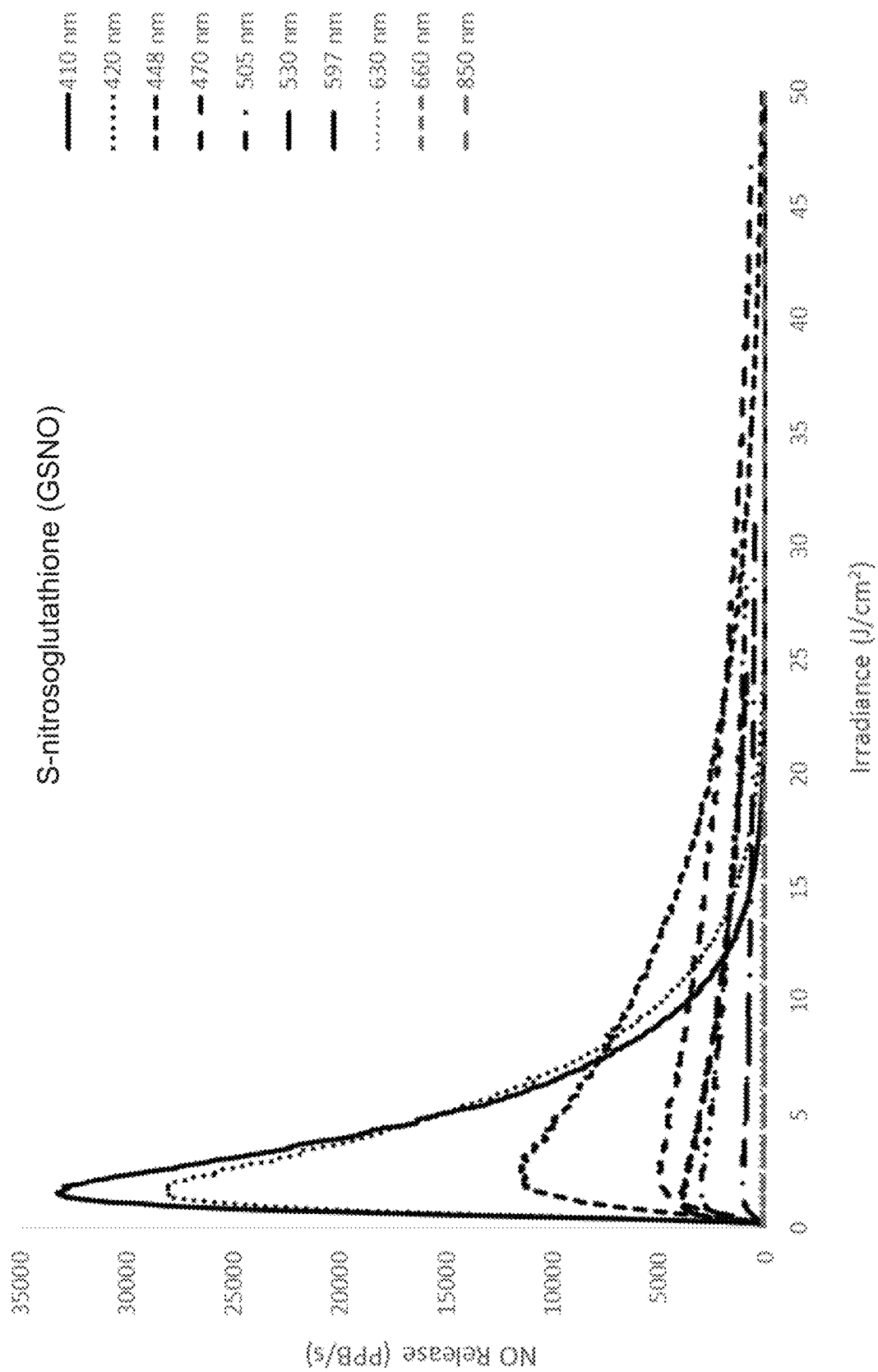
FIG. 55 is a plot of NO release rate (PPB/s) versus irradiance (J/cm$^2$) from S-nitrosoglutathione (GSNO) for ten (10) different wavelengths of incoherent light ranging from 410 nm to 850 nm.
Figure 56:
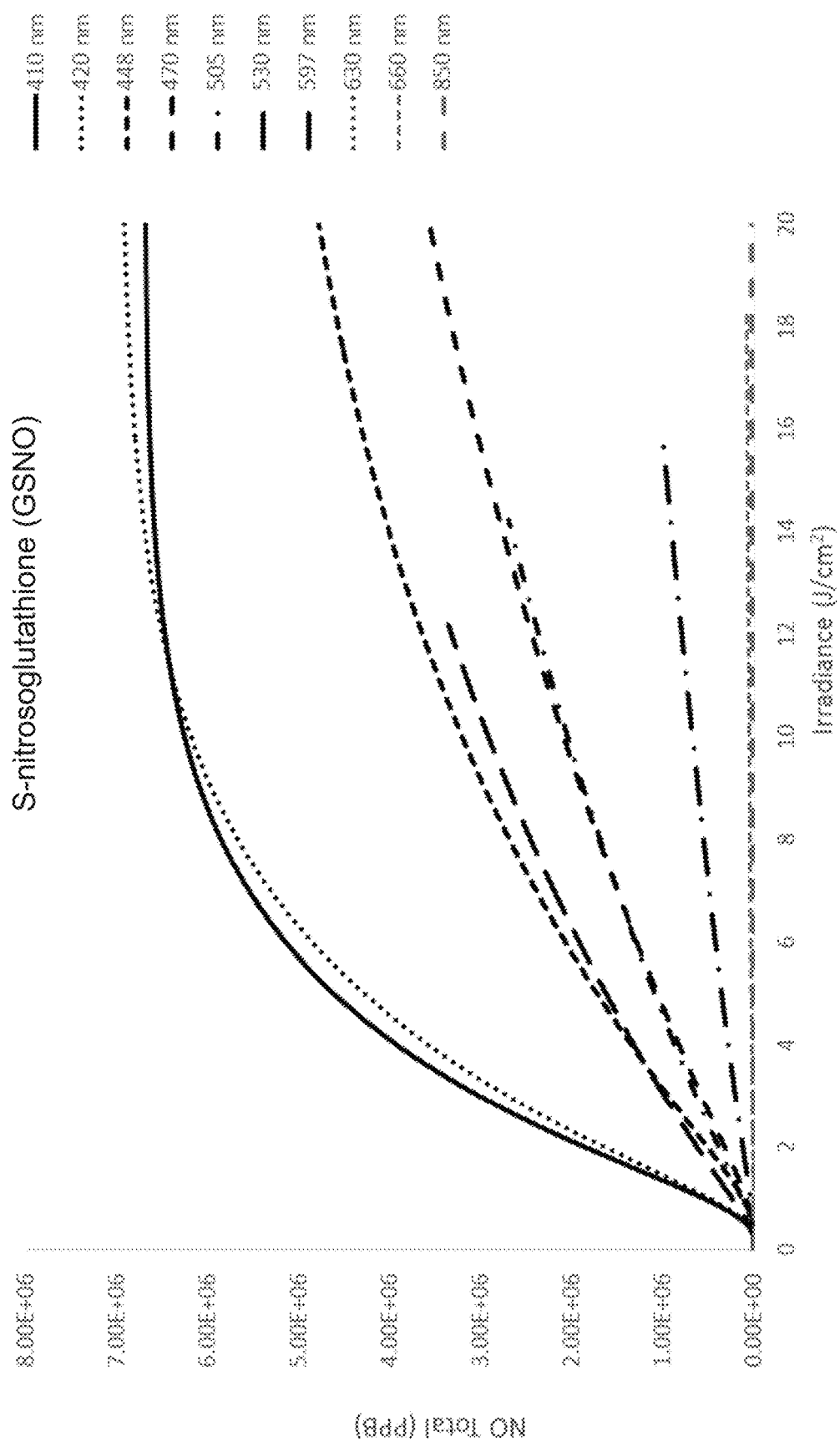
FIG. 56 is a plot of total NO release (PPB) versus irradiance (J/cm$^2$) from S-nitrosoglutathione (GSNO) for ten (10) different wavelengths of incoherent light ranging from 410 nm to 850 nm.

FIG. 55 is a plot of NO release rate (PPB/s) versus irradiance (J/cm2) from S-nitrosoglutathione (GSNO) for ten (10) different wavelengths of incoherent light ranging from 410 nm to 850 nm. The NO-release from S-nitrosoglutathione was measured in PBS (pH 6.5), at room temperature as a function of irradiation via chemiluminescent detection. As shown, all wavelengths resulted in some release of NO, but the release rate was highest for the shortest wavelength (410 nm) light and lowest for the longest wavelength (850 nm) light. Referring to FIG. 56, total NO released from hemoglobin was quantified by integrating the data on NO release rate of FIG. 55. The highest amounts of total NO release were achieved with 410 nm and 420 nm light, and the lowest amount of total NO release was achieved with 850 nm light.

Figure 57:
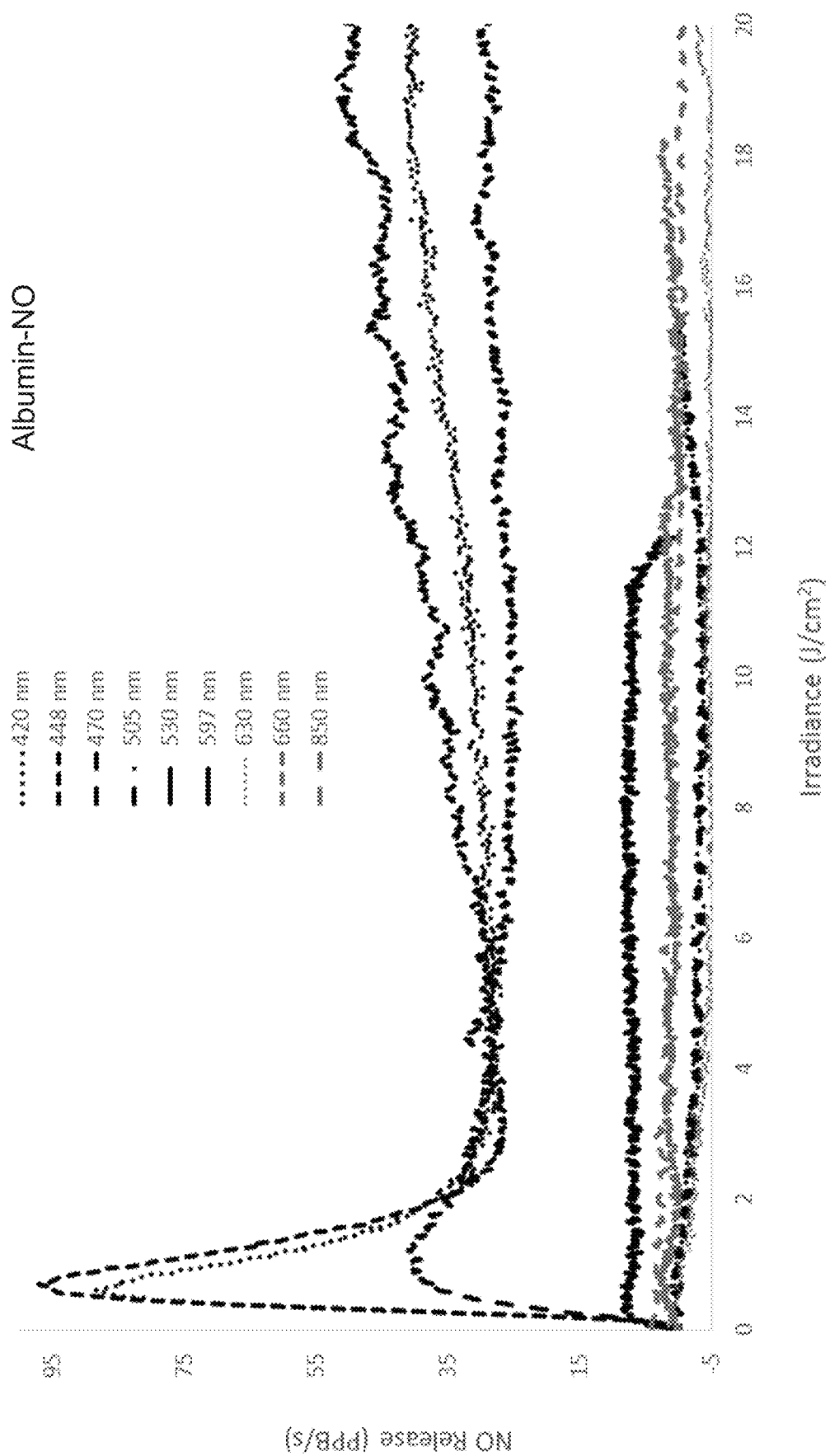
FIG. 57 is a plot of NO release rate (PPB/s) versus irradiance (J/cm$^2$) from albumin-NO for nine (9) different wavelengths of incoherent light ranging from 420 nm to 850 nm.
Figure 58:
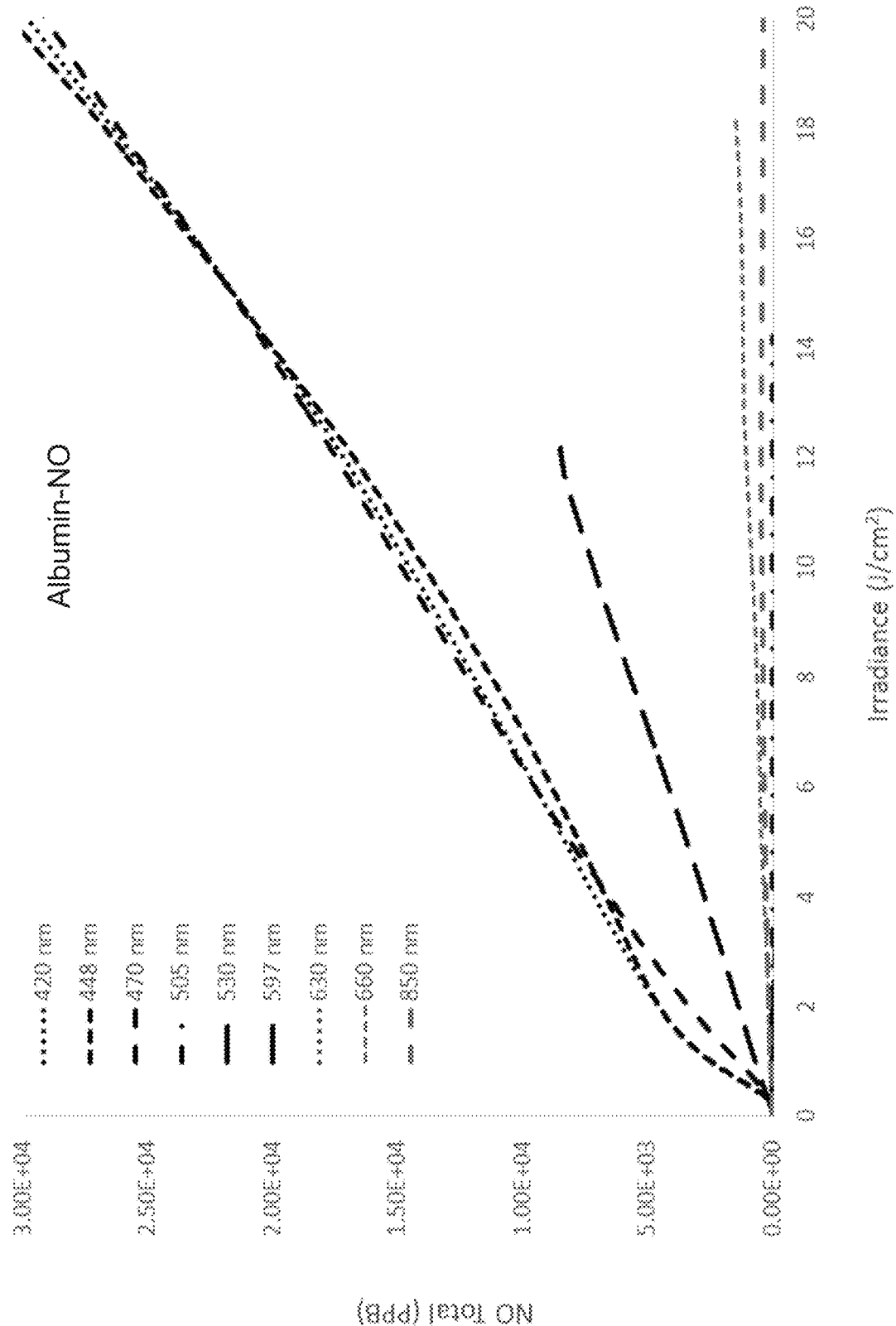
FIG. 58 is a plot of total NO release (PPB) versus irradiance (J/cm$^2$) from albumin-NO for nine (9) different wavelengths of incoherent light ranging from 420 nm to 850 nm.

FIG. 57 is a plot of NO release rate (PPB/s) versus irradiance ($J/cm^2$) from albumin-NO for nine (9) different wavelengths of incoherent light ranging from 420 nm to 850 nm. Nitric oxide was added to bovine serum albumin by reacting with proline-NONOate in PBS (pH 6.5) under anaerobic conditions and in the dark. After 45 minutes of reaction, the NO release was measured as a function of irradiation using a chemiluminescence detector. As shown, the highest NO release rate was achieved for the wavelength of 448 nm, and the second and third highest NO release rates were achieved for wavelengths of 420 nm and 470 nm, respectively, with each of the foregoing three wavelengths causing an initial spike or increase in NO release rate followed by a lower release rate. Referring to FIG. 58, total NO released from albumin-NO was quantified by integrating the data on NO release rate of FIG. 57. Similar amounts of total NO release were achieved for 420 nm light, 448 nm light, and 470 nm light. An intermediate amount of total NO release was achieved for 505 nm light. Relatively little total NO release was achieved for light of other wavelengths.

Figure 59:
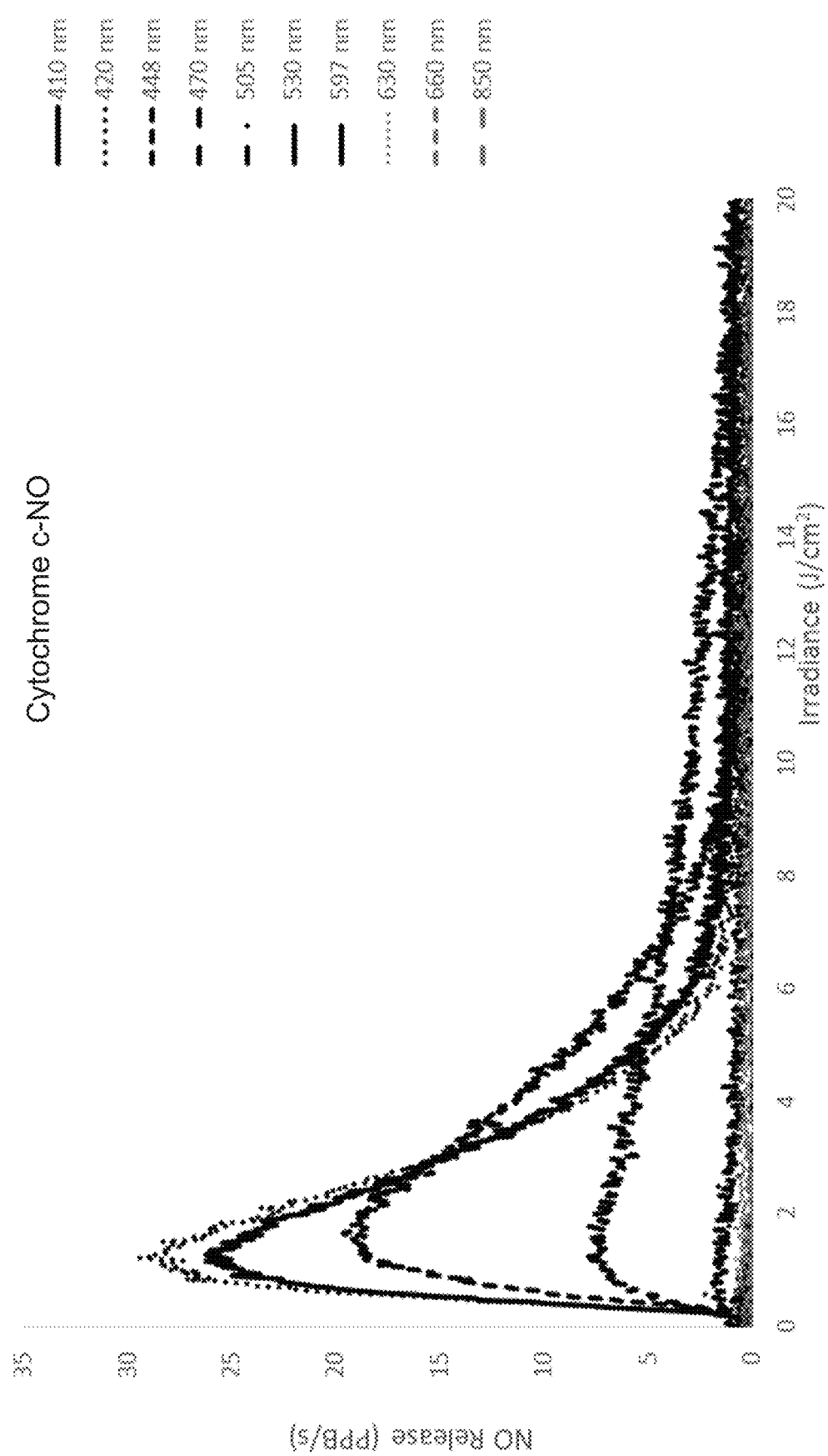
FIG. 59 is a plot of NO release rate (PPB/s) versus irradiance (J/cm$^2$) from cytochrome c-NO for ten (10) different wavelengths of incoherent light ranging from 410 nm to 850 nm.
Figure 60:
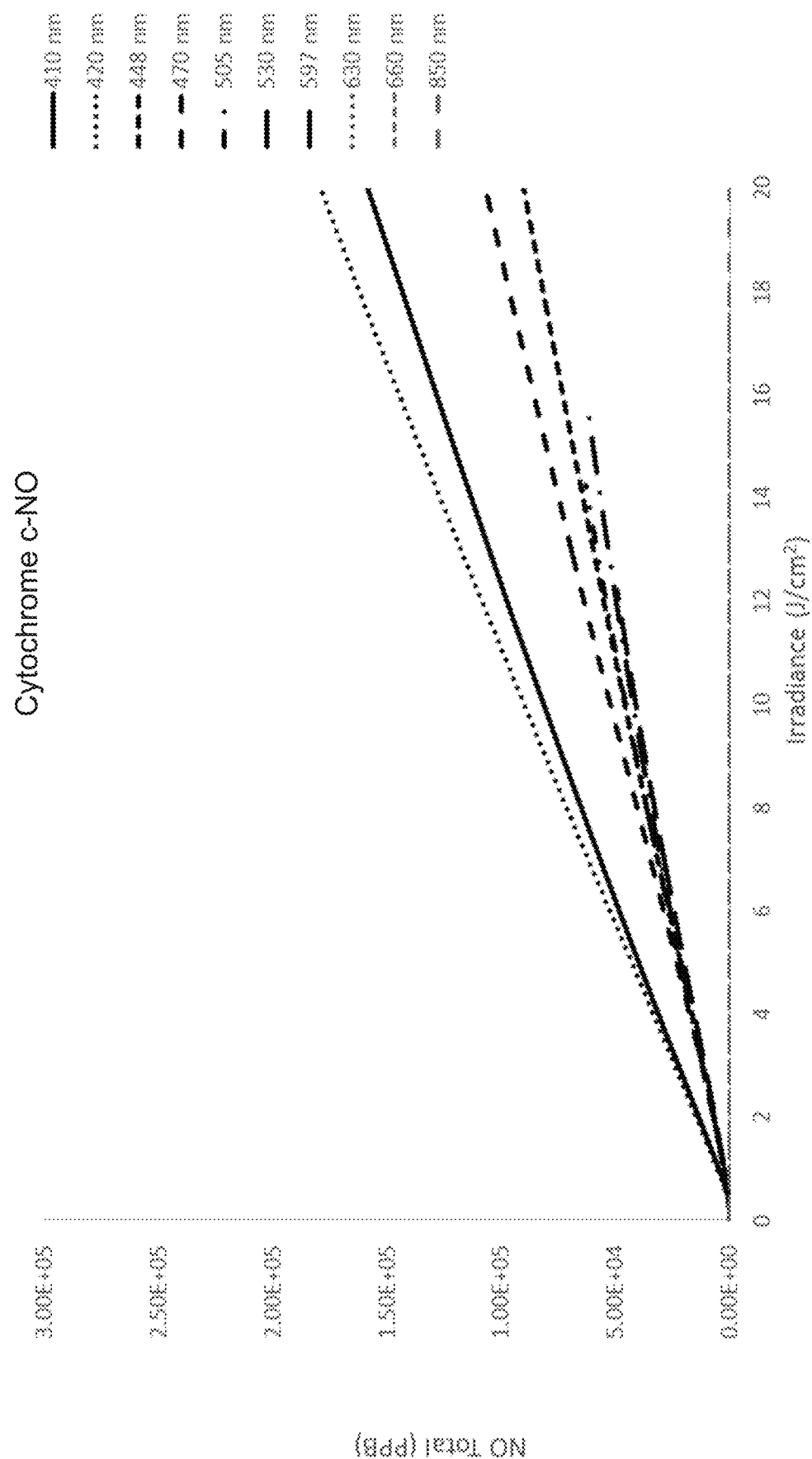
FIG. 60 is a plot of total NO release (PPB) versus irradiance (J/cm$^2$) from cytochrome c-NO for ten (10) different wavelengths of incoherent light ranging from 410 nm to 850 nm.

FIG. 59 is a plot of NO release rate (PPB/s) versus irradiance ($J/cm^2$) from cytochrome c-NO for ten (10) different wavelengths of incoherent light ranging from 410 nm to 850 nm. Nitric oxide was added to cytochrome c by reacting proline-NONOate in PBS (pH 6.5) under anaerobic conditions and in the dark. After 45 minutes of reaction, the NO release was measured as a function of irradiation using a chemiluminescence detector. As shown, the highest four NO release rates were achieved for 420 nm light, 410 nm light, 448 nm light, and 470 nm light, respectively, with each exhibiting a peak release rate near an irradiance value of about 2 $J/cm^2$, while all wavelengths exhibiting a reduced or negligible NO release rate as irradiance values approached 20 $J/cm^2$. Referring to FIG. 60, total NO released from cytochrome c-NO was quantified by integrating the data on NO release rate of FIG. 59. As shown, the highest four amounts of total NO release were achieved for 420 nm light, 410 nm light, 448 nm light, and 470 nm light, respectively.

Figure 61:
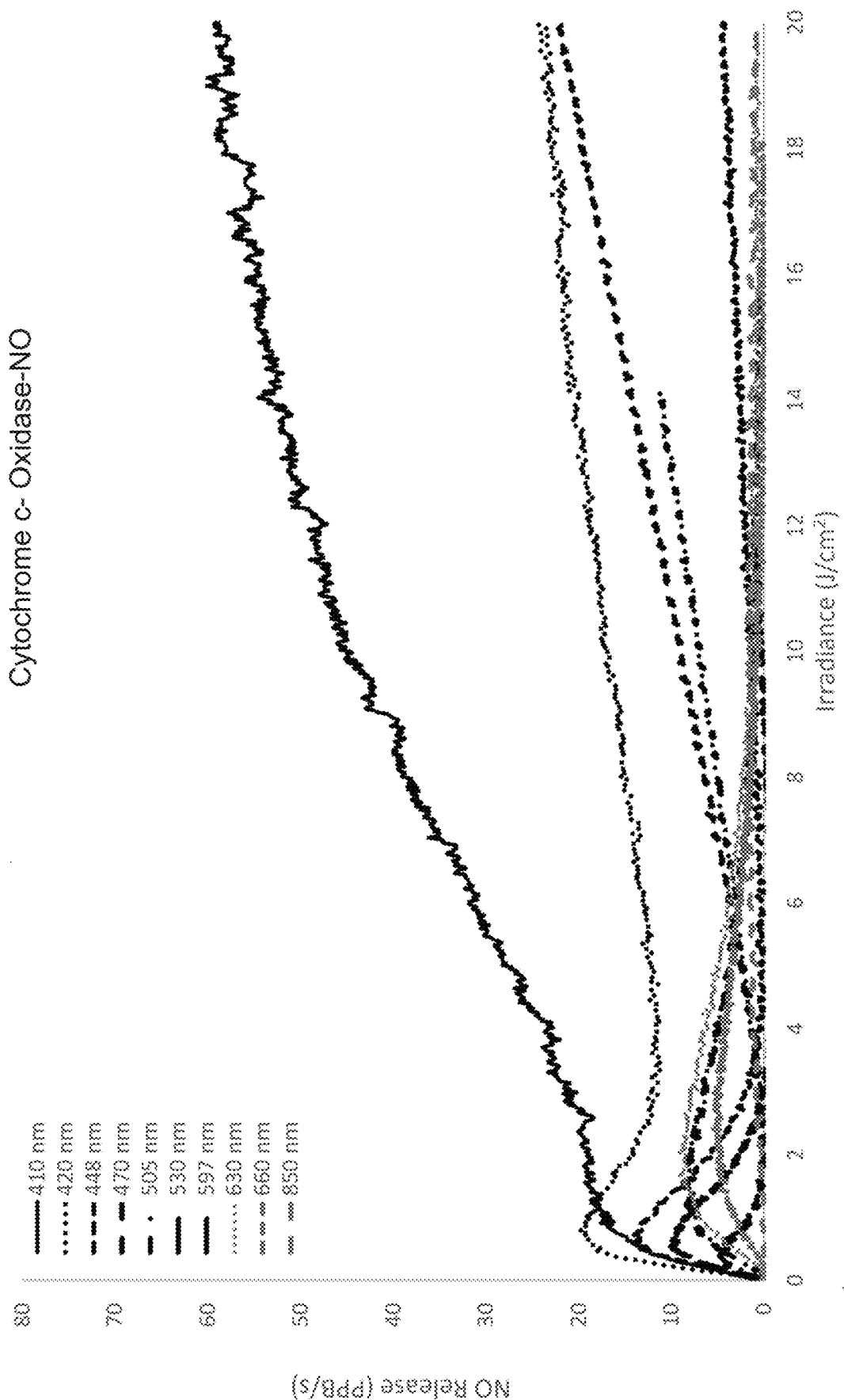
FIG. 61 is a plot of NO release rate (PPB/s) versus irradiance (J/cm$^2$) from cytochrome c-oxidase-NO for ten (10) different wavelengths of incoherent light ranging from 410 nm to 850 nm.
Figure 62:
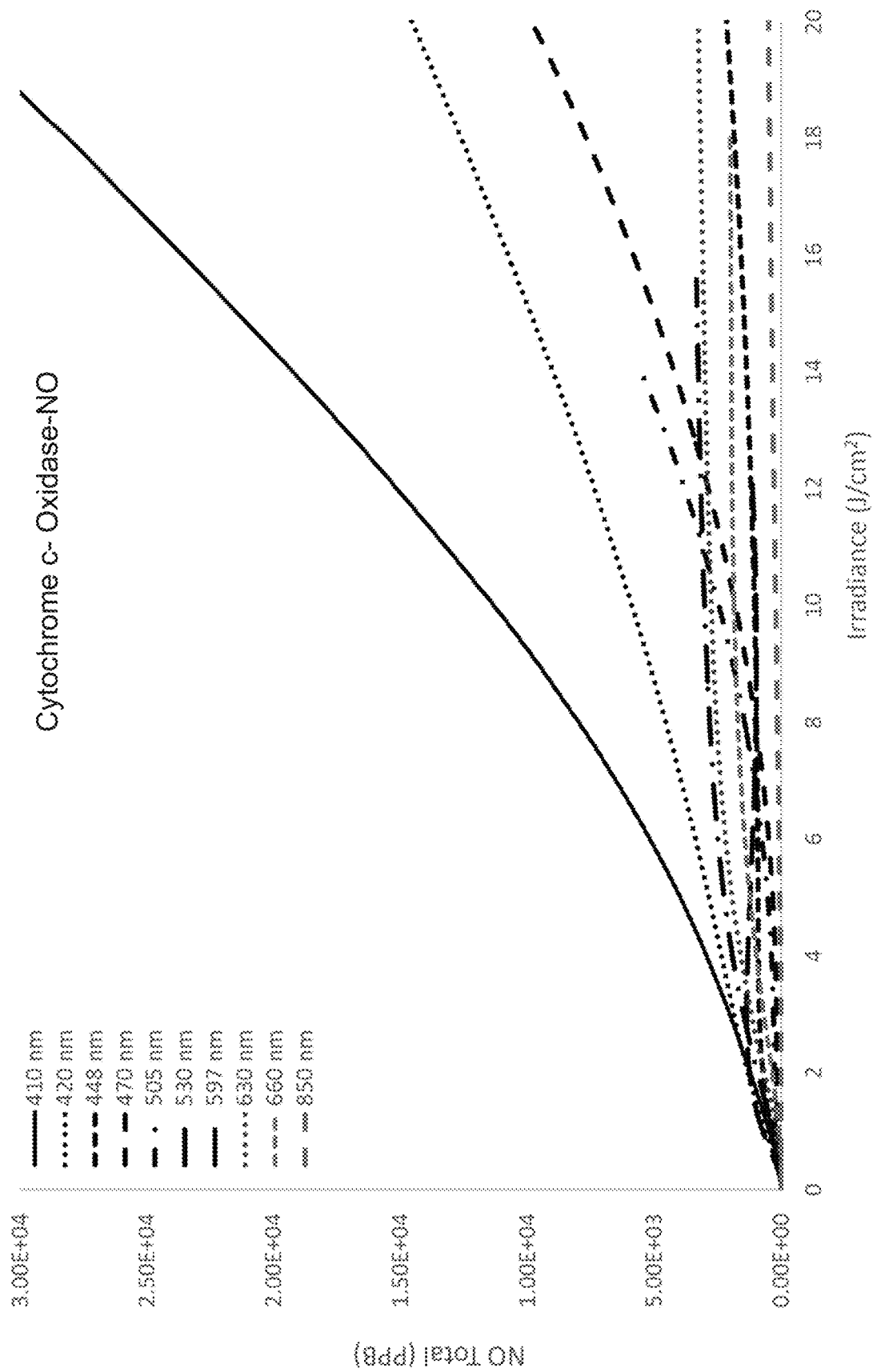
FIG. 62 is a plot of total NO release (PPB) versus irradiance (J/cm$^2$) from cytochrome c-oxidase-NO for ten (10) different wavelengths of incoherent light ranging from 410 nm to 850 nm.

FIG. 61 is a plot of NO release rate (PPB/s) versus irradiance ($J/cm^2$) from cytochrome c-oxidase NO for ten (10) different wavelengths of incoherent light ranging from 410 nm to 850 nm. Nitric oxide was added to cytochrome c oxidase by reacting with proline-NONOate in PBS (pH 6.5) under anaerobic conditions and in the dark. After 45 minutes of reaction, the NO release was measured as a function of irradiation using a chemiluminescence detector. As shown, the highest four NO release rates were achieved for 410 nm light, 420 nm light, 448 nm light, and 470 nm light, respectively. For 410 nm light, NO release rate generally increased with increasing irradiance, whereas for other wavelengths, at least a local peak of NO release rate was achieved for irradiance values of around 1 to 2 $J/cm^2$, followed by an increase in NO release rate with increasing irradiance for 420 nm light, 448 nm light, and 470 nm light, but higher wavelengths of light resulted in decreased NO release rate with increasing irradiance. Referring to FIG. 62, total NO released from cytochrome c-oxidase-NO was quantified by integrating the data on NO release rate of FIG. 61. The highest three amounts of total NO release were achieved for 410 nm light, 420 nm light, and 448 nm light, respectively, with greater slopes for shorter wavelengths.

Figure 63:
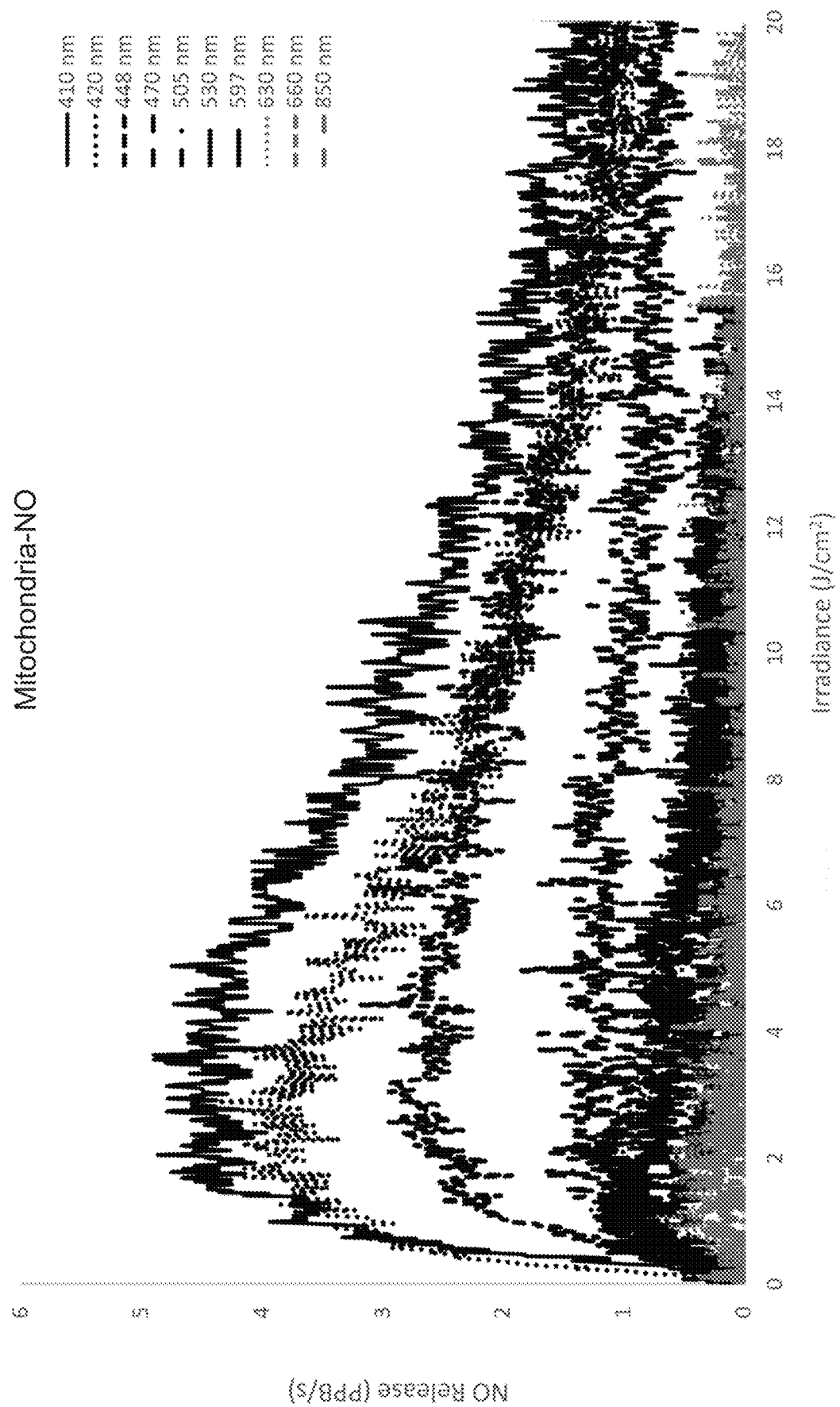
FIG. 63 is a plot of NO release rate (PPB/s) versus irradiance (J/cm$^2$) from mitochondria-NO for ten (10) different wavelengths of incoherent light ranging from 410 nm to 850 nm.
Figure 64:
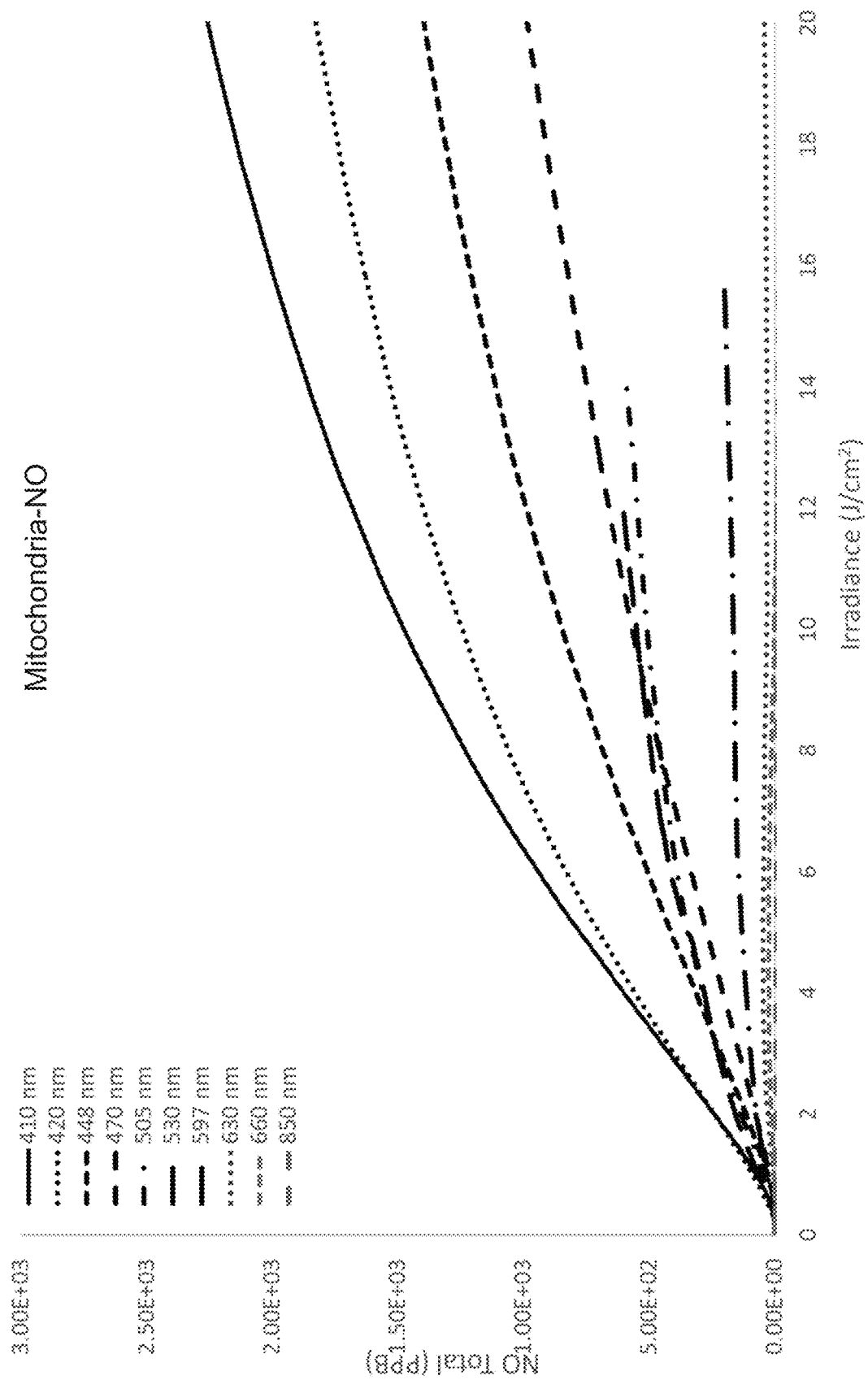
FIG. 64 is a plot of total NO release (PPB) versus irradiance (J/cm$^2$) from mitochondria-NO for ten (10) different wavelengths of incoherent light ranging from 410 nm to 850 nm.

FIG. 63 is a plot of NO release rate (PPB/s) versus irradiance ($J/cm^2$) from mitochondria-NO for ten (10) different wavelengths of incoherent light ranging from 410 nm to 850 nm. Nitric oxide was added to mitochondria isolated from bovine heart by reacting it with S-nitrosoglutatione in PBS (pH 6.5) under anaerobic conditions and in the dark. After 45 minutes of reaction, the NO release was measured as a function of irradiation using a chemiluminescence detector. As shown, the highest four NO release rates were achieved for 410 nm light, 420 nm light, 448 nm light, and 470 nm light, respectively. For each wavelength, a peak of NO release rate was achieved for irradiance values in a range of from about 2 to 4 $J/cm^2$, followed by a decrease in NO release rate with increasing irradiance. Referring to FIG. 64, total NO released from mitochondria-NO was quantified by integrating the data on NO release rate of FIG. 63. The highest four amounts of total NO release were achieved for 410 nm light, 420 nm light, 448 nm light, and 470 nm light, respectively.

The preceding FIGS. 53 to 64 show that different types of bonds (e.g., RSNO, RNNO, and metal-NO) may require different light wavelengths and/or light irradiation values to effectuate release of nitric oxide. Based on the data represented in FIGS. 53 to 64, an important wavelength of interest is 420 nm, since this wavelength represents perhaps the closest safe wavelength to the ultraviolet range (since substantially all incoherent emissions having a peak wavelength of 420 nm, including portions tailing above and below this peak value, remain well above the 400 nm UV threshold), exhibits a demonstrated high (or highest) NO release from a wide range of proteins (Hemoglobin-NO, S-Nitrosglutathione (GSNO), Albumin-NO, Cytochrome c-NO, Cytochrome c oxidase-NO, and Mitochondria-NO), and appears to lead to enzymatic generation of NO. A secondary wavelength of interest is 530 nm, since it appears to be more effective than longer wavelength red at triggering NO release from GSNO. These conclusions contradict various findings in the art (e.g., by Karu, T, Handbook of Laser Wavelengths, Chapter 48, "Low-Power Laser Therapy", pp. 48-1 to 48-25 (2003); by Ball, K., et al., "Low intensity light stimulates nitrite-dependent nitric oxidant synthesis but not oxygen consumption by cytochrome c oxidase: implications for phototherapy," Journal of Photochemistry and Photobiology B: Biology 102 (2011) 182-191; and by Hamblin, M., "The Role of Nitric Oxide in Low Level Light Therapy," Proc. of SPIE Vol. 6846, 684602, (2008)) that red light including wavelengths in a range of from 605 nm to 820 nm may be particularly suitable for releasing NO from heme groups of CCO, for release of NO from CCO generally, and for increased ATP synthesis.

Based on the findings that short wavelength blue light is effective for enhancing endogenous stores of nitric oxide and/or triggering nitric oxide release, one aspect of the disclosure relates to a method of modulating nitric oxide in living mammalian tissue, the method comprising: impinging light on the tissue, wherein the light impinged on the tissue comprises incoherent light emissions including a first peak wavelength in a range of from 410 nm to 440 nm and a first radiant flux, and wherein the first peak wavelength and the first radiant flux are selected to stimulate at least one of (i) enzymatic generation of nitric oxide to increase endogenous stores of nitric oxide or (ii) release of nitric oxide from endogenous stores of nitric oxide; wherein the light impinged on the tissue is substantially devoid of light emissions having a peak wavelength in a range of from 600 nm to 900 nm (e.g., encompassing red visible light as well as a portion of the infrared range). An absence of red and/or infrared light contradicts various references describing the desirability of red and/or infrared light as primary wavelengths for skin penetration and to provide phototherapeutic benefit.

In certain embodiments, the light impinged on the tissue is devoid of emissions of any wavelength conversion material (e.g., a phosphor, a quantum dot, or another lumiphoric material) stimulated by incoherent light emissions having a peak wavelength in a range of from 410 nm to 440 nm. In certain embodiments, the tissue on which light is impinged is devoid of an applied or received photosensitive therapeutic compound or agent (e.g., a pharmaceutical composition or the like, which may be administered topically, orally, or via injection). In certain embodiments, at least 65%, at least 75%, at least 80%, at least 85%, or at least 95% of a fluence of light impinged on the tissue consists of the incoherent light emissions including a first peak wavelength in a range of from 410 to 440 nm. In certain embodiments, the light impinged on the tissue is substantially devoid of light emissions having a peak wavelength in a range of from 441 nm to 490 nm. In certain embodiments, the incoherent light emissions including a first peak wavelength in a range of from 410 nm to 440 nm are provided as a plurality of discrete pulses.

In certain embodiments, the light impinged on the tissue further comprises incoherent light emissions including a second peak wavelength in a range of from 500 nm to 540 nm. This is consistent with Applicant's finding that light having a peak wavelength of 530 nm appears to be more effective than certain other wavelengths (including longer wavelength red) at triggering NO release from GSNO. In certain embodiments, the incoherent light emissions including a first peak wavelength in a range of from 410 nm to 440 nm are impinged on the tissue during a first time window, the incoherent light emissions including a second peak wavelength in a range of from 500 nm to 540 nm are impinged on the tissue during a second time window, and at least a portion of the second time window is non-overlapping with the first time window.

In certain embodiments, the first peak wavelength and the first radiant flux are selected to stimulate enzymatic generation of nitric oxide to increase endogenous stores of nitric oxide. In certain embodiments, the first peak wavelength and the first radiant flux are selected to release nitric oxide from the endogenous stores of nitric oxide.

In certain embodiments, the tissue comprises at least one of epithelial tissue, mucosal tissue, connective tissue, muscle tissue, or cervical tissue. In certain embodiments, the tissue comprises dermal tissue. In certain embodiments, a method further comprises sensing a temperature condition on or proximate to (a) a therapeutic device arranged to impinge light on the tissue, or (b) the tissue; generating at least one signal indicative of the temperature condition; and controlling impingement of light on the tissue responsive to the at least one signal. In certain embodiments, the light impinged on the tissue comprises a fluence in a range of from about 0.5 J/cm$^2$ to about 100 J/cm$^2$, or from about 2 J/cm$^2$ to about 80 J/cm$^2$, or from about 5 J/cm$^2$ to about 50 J/cm$^2$.

In another aspect, the disclosure relates to a device for modulating nitric oxide in living mammalian tissue, the device comprising: an ambient light blocking element; and at least one first light emitting element positioned between the ambient light blocking element and the tissue, wherein the at least one first light emitting element is configured to impinge incoherent light on the tissue, said incoherent light having a first peak wavelength and a first radiant flux, wherein the first peak wavelength and the first radiant flux are selected to stimulate at least one of (i) enzymatic generation of nitric oxide to increase endogenous stores of nitric oxide or (ii) release of nitric oxide from endogenous stores of nitric oxide; wherein the device is substantially devoid of any light emitting element configured to impinge on the tissue light having a peak wavelength in a range of from 600 nm to 900 nm.

In certain embodiments, the device is substantially devoid of any light emitting element configured to impinge light having a peak wavelength in a range of from 441 nm to 490 nm on the tissue. In certain embodiments, the device is devoid of any wavelength conversion material configured to be stimulated by the at least one first light emitting element. In certain embodiments, the device further comprises a flexible substrate supporting the at least one first light emitting element. In certain embodiments, the device is configured to conform to the tissue with a light-transmissive material arranged in contact with the tissue. In certain embodiments, the light impinged on the tissue is substantially devoid of light emissions having a peak wavelength in a range of from 441 nm to 490 nm. In certain embodiments, the device further comprises driver circuitry configured to generate the incoherent light emissions including the first peak wavelength, wherein the first peak wavelength is in a range of from 410 nm to 440 nm, and said incoherent light emissions comprise a plurality of discrete pulses.

In certain embodiments, the device further comprises at least one second light emitting element configured to impinge incoherent light on the tissue, said incoherent light having a second peak wavelength and a second radiant flux, wherein the second peak wavelength is in a range of from 500 nm to 540 nm. In certain embodiments, the device is configured to impinge incoherent light emissions including the first peak wavelength during a first time window, wherein the first peak wavelength is in a range of from 410 nm to 440 nm, and being configured to impinge incoherent light emissions including the second peak wavelength in a range of from 500 nm to 530 nm during a second time window, wherein at least a portion of the second time window is non-overlapping with the first time window. In certain embodiments, the device further comprises a probe configured for insertion into a mammalian body cavity or opening (e.g., incision) defined in a mammalian body, wherein the at least one first light emitting element is supported by the probe.

Figure 65:
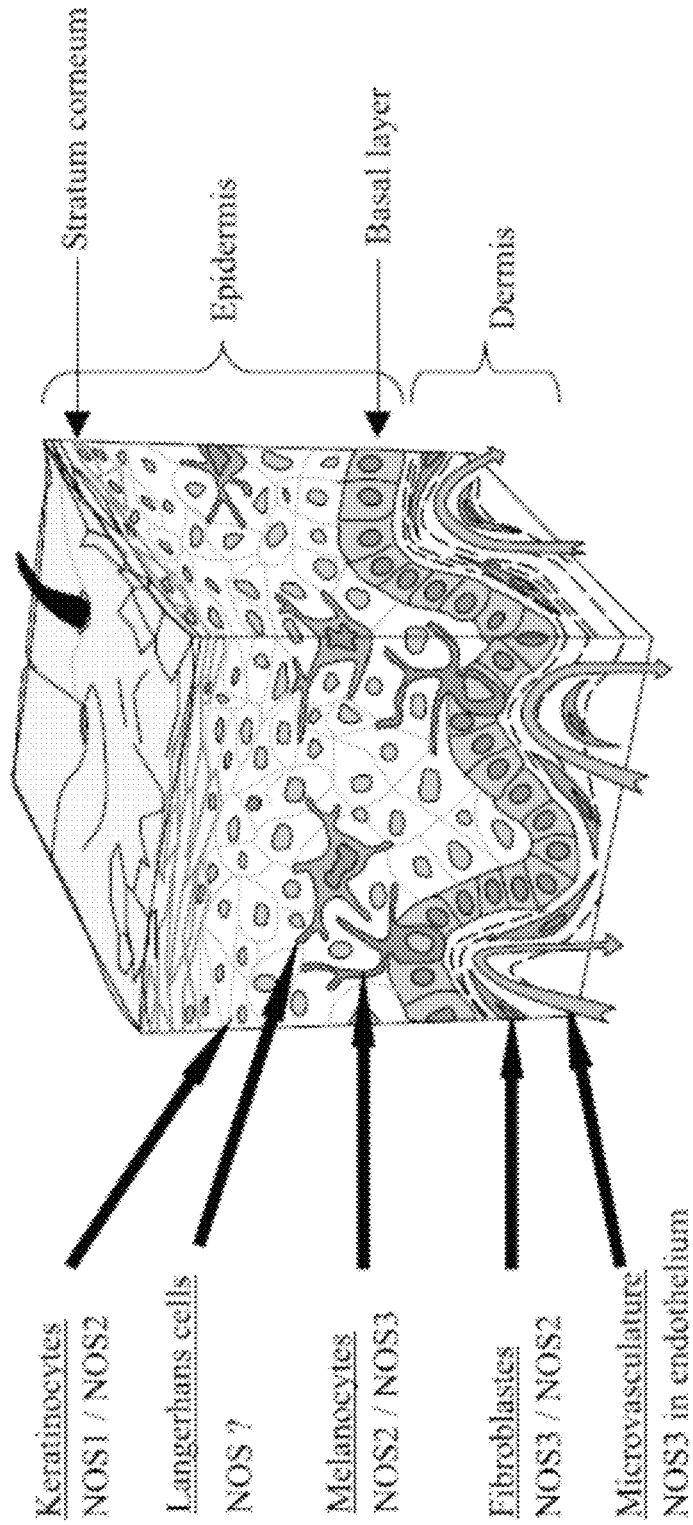
FIG. 65 is a related art perspective view illustration of a cross-section of dermis and epidermis layers of human skin showing various types of cells containing nitric oxide compounds.

FIG. 65 is a perspective view illustration of a cross-section of dermis and epidermis layers of human skin showing various types of cells containing nitric oxide synthases or enzymes. Such image is reproduced from Cals-Grierson, M. M and Ormerod, A. D. Nitric Oxide 10 (2004) 179-193. As shown, the epidermis (extending from the stratum corneum to and including the basal layer) includes keratinocytes, Langerhans cells, and melanocytes, whereas the dermis (under the basal layer) includes fibroblasts and microvasculature. Different NOS enzymes occur in different layers of the skin. nNOS (or NOS1) is present in keratinocytes; eNOS (or NOS3) is present in fibroblasts, melanocytes, and the endothelium; and iNOS (or NOS2) is present throughout. Both nNOS and eNOS are calcium dependent enzymes. iNOS is inducible and therefore increases in response to the immune system.

Figure 66:
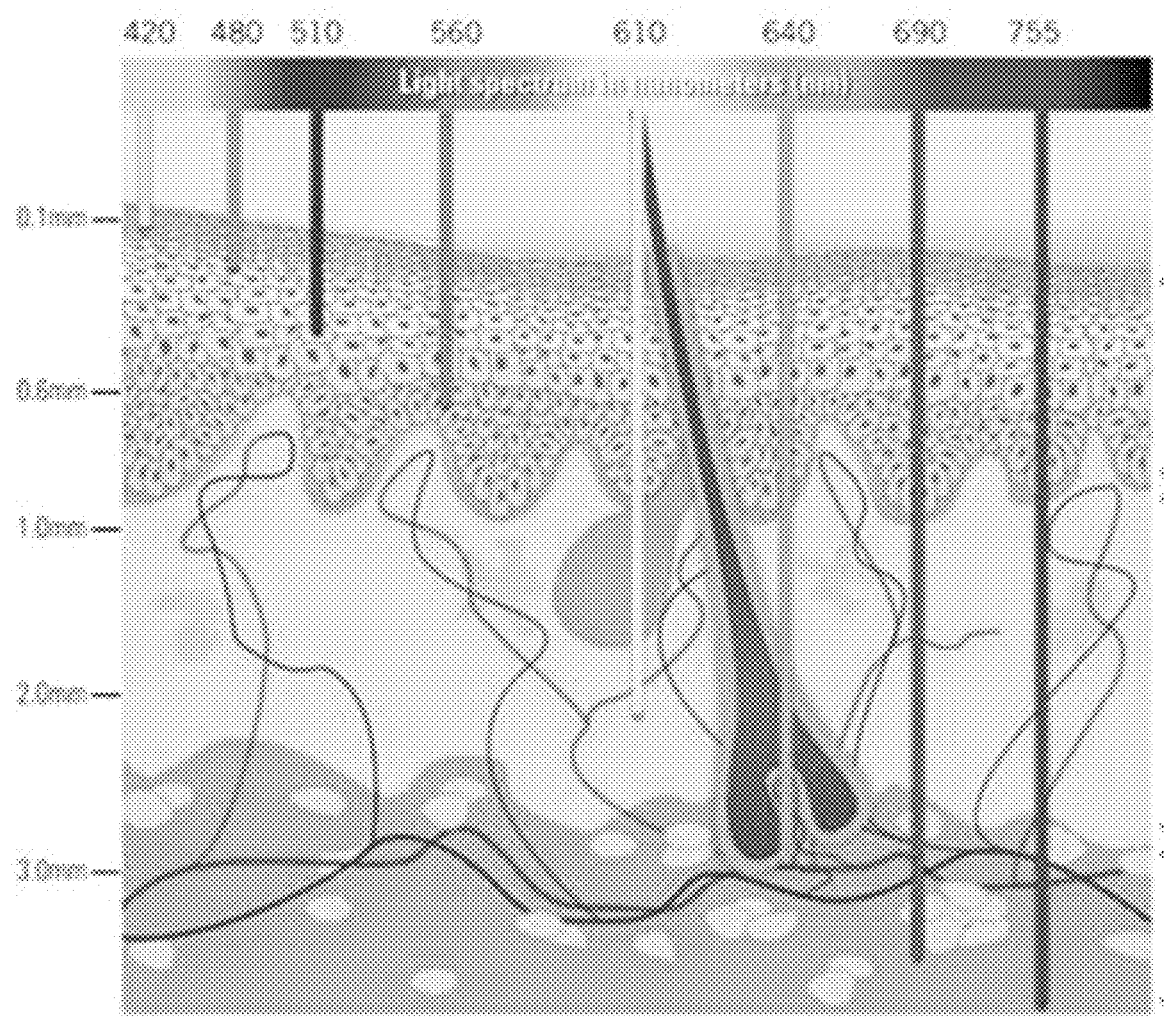
FIG. 66 is a related art cross-sectional illustration of human skin with a superimposed representation of depth penetration of coherent light of eight different wavelengths ranging from 420 nm to 755 nm.

FIG. 66 is a related art cross-sectional illustration of human skin with a superimposed representation of depth penetration of coherent (e.g., laser) light of eight different wavelengths ranging from 420 nm to 755 nm. Such image is sourced from www.spectrumsciencebeauty.com/au/2014/09/16/ipl-hair-removal/#prettyPhoto/0/. FIG. 66 shows a single hair follicle (below the value of "640 nm", at a depth of between 2 and 3 mm). As shown, the conclusion in the art is that blue light (e.g., 420 nm, 480 nm) is incapable of penetrating human skin to a sufficient depth to reach a hair follicle.

Figure 67A:
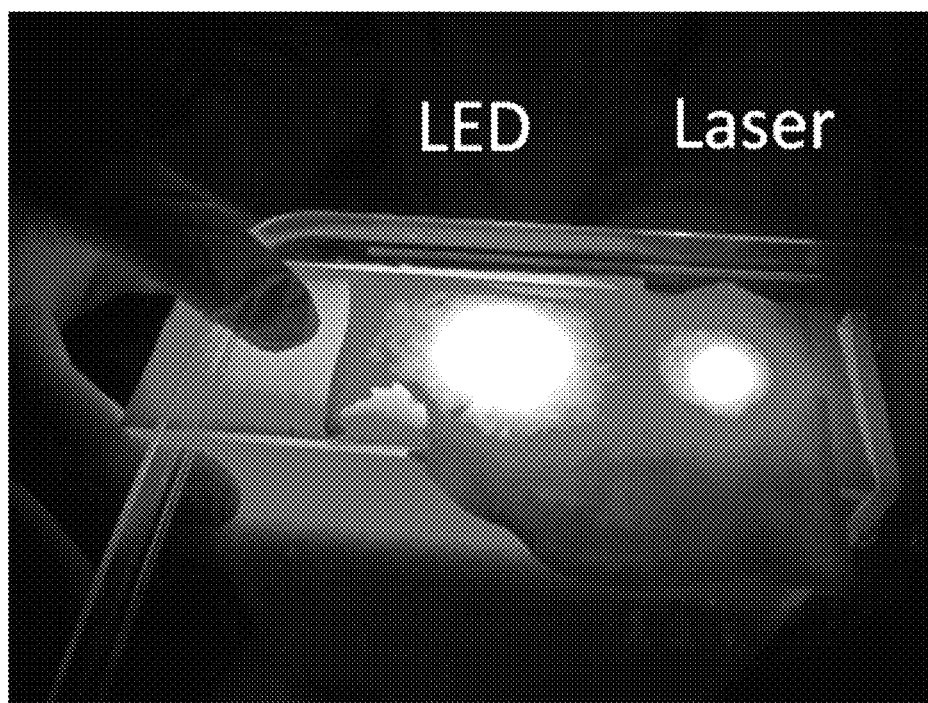
FIG. 67A is an upper perspective view photograph comparing the transmittance of red (660 nm peak wavelength) incoherent (LED) light and a red (660 nm) coherent (laser) light through a human skin sample.
Figure 67B:
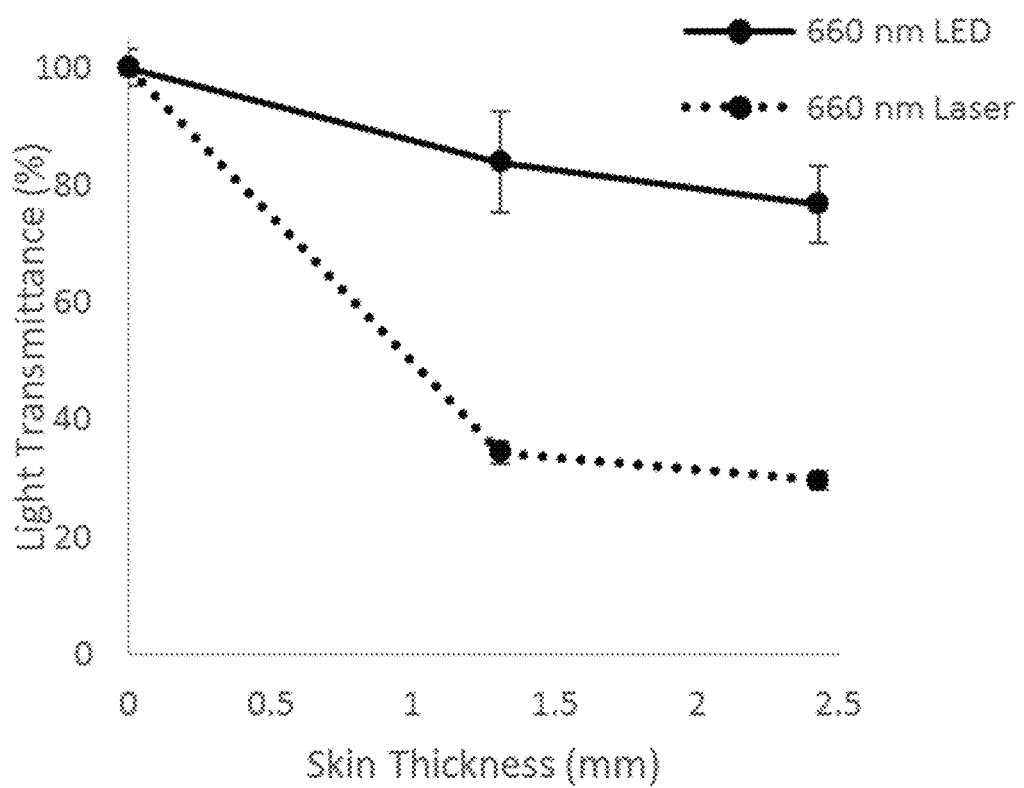
FIG. 67B is a plot of light transmittance percentage as a function of skin thickness (mm) for transmittance of red (660 nm peak wavelength) incoherent (LED) light and a red (660 nm) coherent (laser) light through human skin samples of two different thicknesses at equivalent irradiance.
Figure 68A:
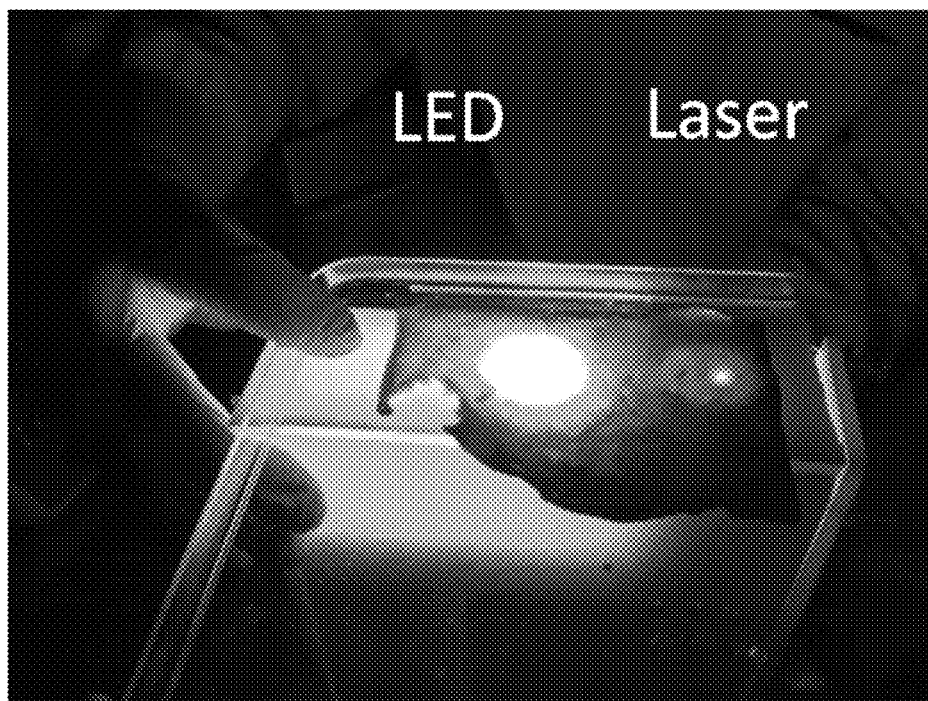
FIG. 68A is an upper perspective view photograph comparing the transmittance of a green (530 nm peak wavelength) incoherent (LED) light and a green (530 nm) coherent (laser) light through a human skin sample.
Figure 68B:
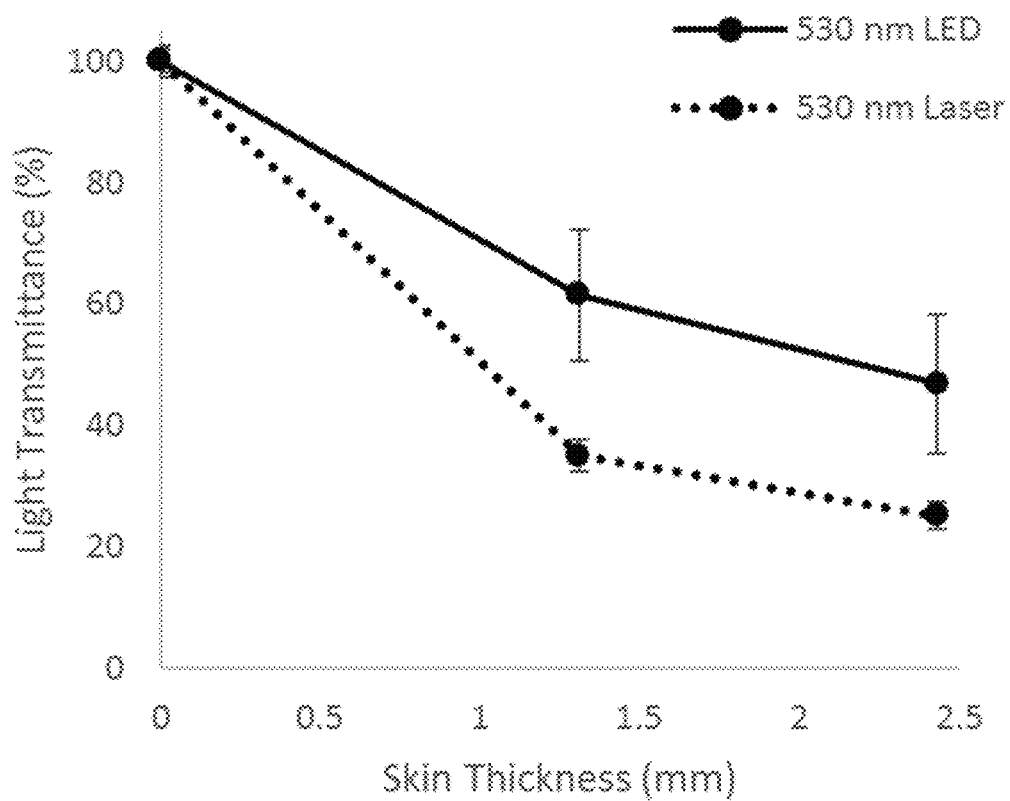
FIG. 68B is a plot of light transmittance percentage as a function of skin thickness (mm) for transmittance of green (530 nm peak wavelength) incoherent (LED) light and a green (530 nm) coherent (laser) light through human skin samples of two different thicknesses at equivalent irradiance.
Figure 69A:
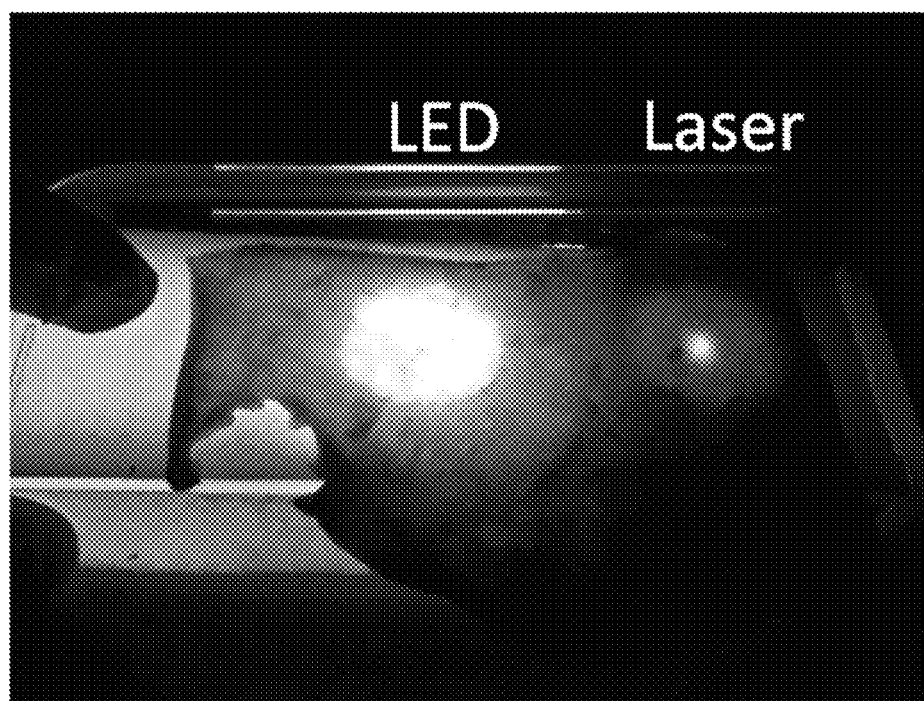
FIG. 69A is an upper perspective view photograph comparing the transmittance of a blue (420 nm peak wavelength) incoherent (LED) light and a blue (420 nm) coherent (laser) light through a human skin sample.
Figure 69B:
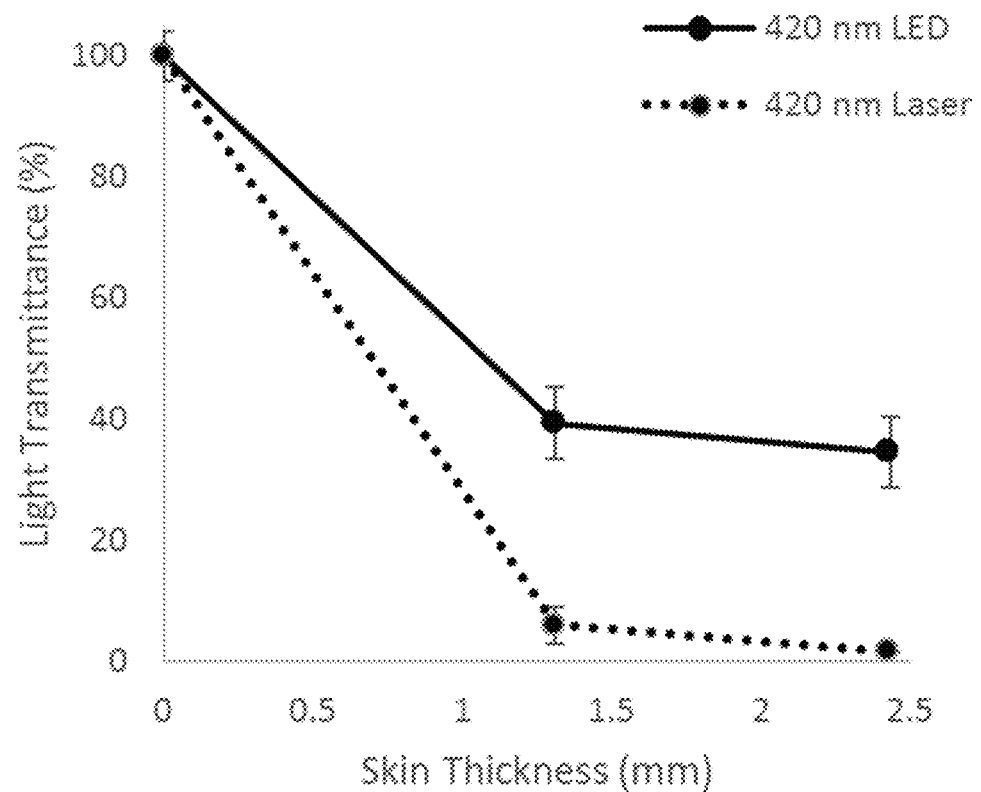
FIG. 69B is a plot of light transmittance percentage as a function of skin thickness (mm) for transmittance of blue (420 nm peak wavelength) incoherent (LED) light and a blue (420 nm) coherent (laser) light through human skin samples of two different thicknesses at equivalent irradiance.

Applicant performed various experiments to contradict this conclusion—instead confirming that coherent blue light is capable of penetrating human skin to a depth sufficient to reach hair follicles. Irradiance transmitted through full thickness skin was measured as a function of wavelength for laser and LED light sources. Light sources were matched to have equivalent irradiance as measured by a common photodiode. Wavelength was also matched between laser and LED light sources. FIGS. 67A, 68A, and 69A embody upper perspective view photographs of transmittance of incoherent (LED) light and coherent (laser) light through Caucasian (Fitzpatrick Skin Type II) human skin samples, with the respective figures separately corresponding to red (660 nm peak wavelength), green (530 nm peak wavelength), and blue (420 nm peak wavelength) sources. Human skin samples of different thicknesses (1.3 mm and 2.5 mm) were used in each instance. FIGS. 67B, 68B, and 69B embody plots of light transmittance percentage as a function of skin thickness (mm) for transmittance of incoherent (LED) light and coherent (laser) light through the human skin samples of two different thicknesses. In each of FIGS. 67B, 68B, and 69B, a significantly greater percentage of incoherent (LED) light was transmitted through skin than coherent (laser) light. Notably, referring to FIG. 69B, nearly 40% of the incoherent (420 nm peak) blue light was transmitted through a Caucasian skin sample having a thickness of 2.5 mm, whereas a low single digit percentage of coherent blue light was transmitted through the same sample.

Figure 70:
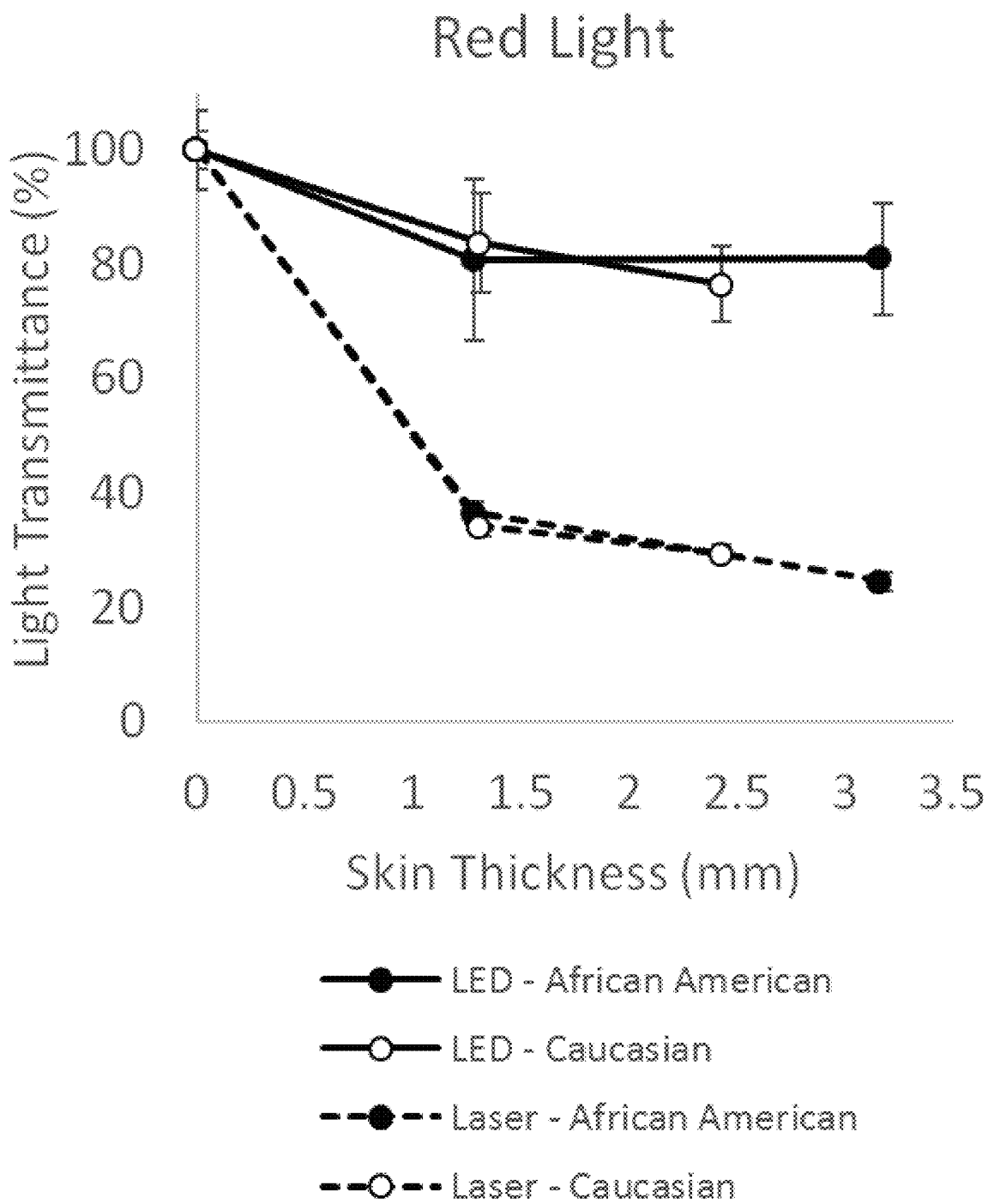
FIG. 70 is a plot of light transmittance percentage as a function of skin thickness (mm) for transmittance of red (660 nm peak wavelength) incoherent (LED) light and red (660 nm) coherent (laser) light through human skin samples of two different pigmentations and three different thicknesses.
Figure 71:
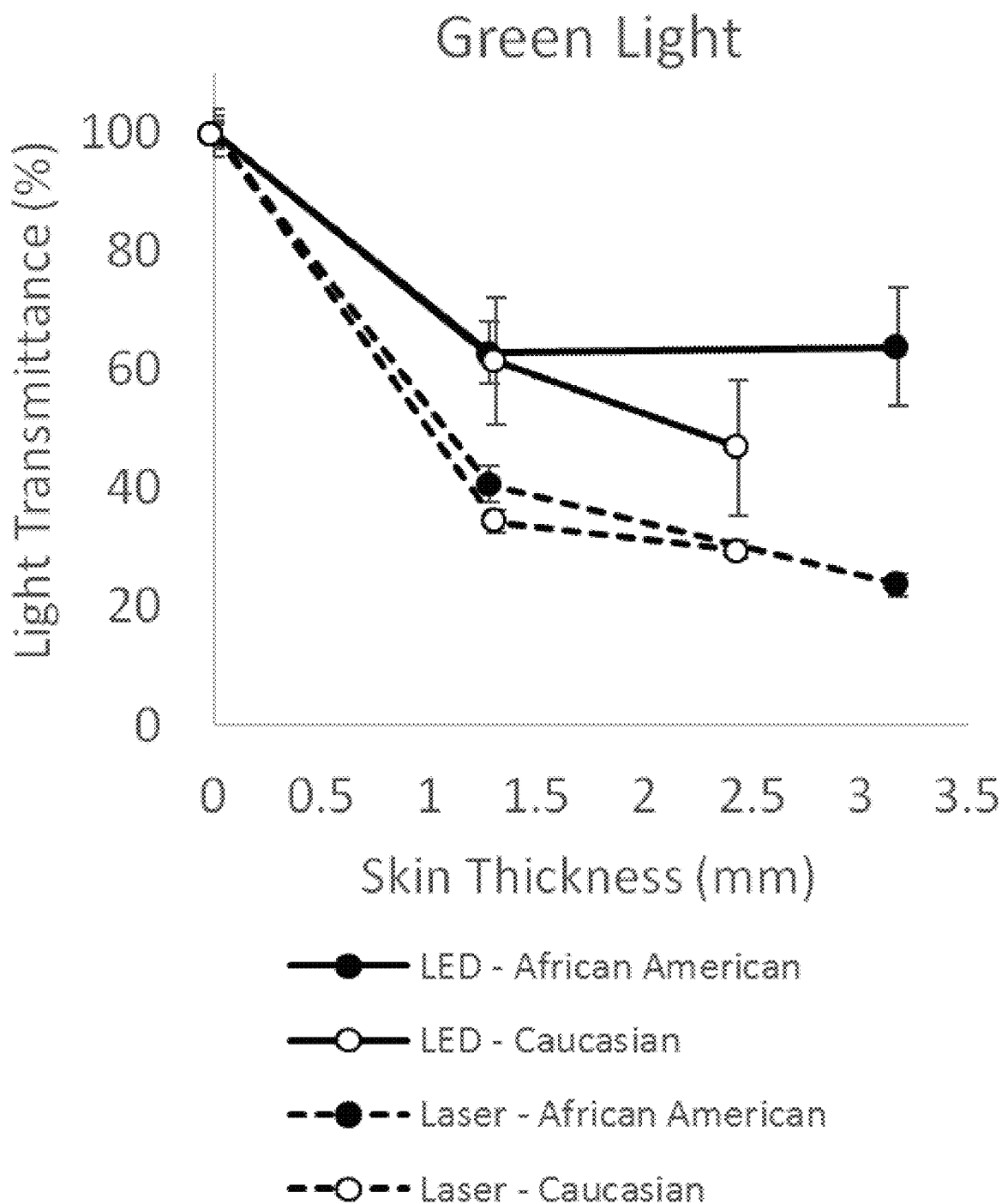
FIG. 71 is a plot of light transmittance percentage as a function of skin thickness (mm) for transmittance of green (530 nm peak wavelength) incoherent (LED) light and green (530 nm) coherent (laser) light through human skin samples of two different pigmentations and three different thicknesses.
Figure 72:
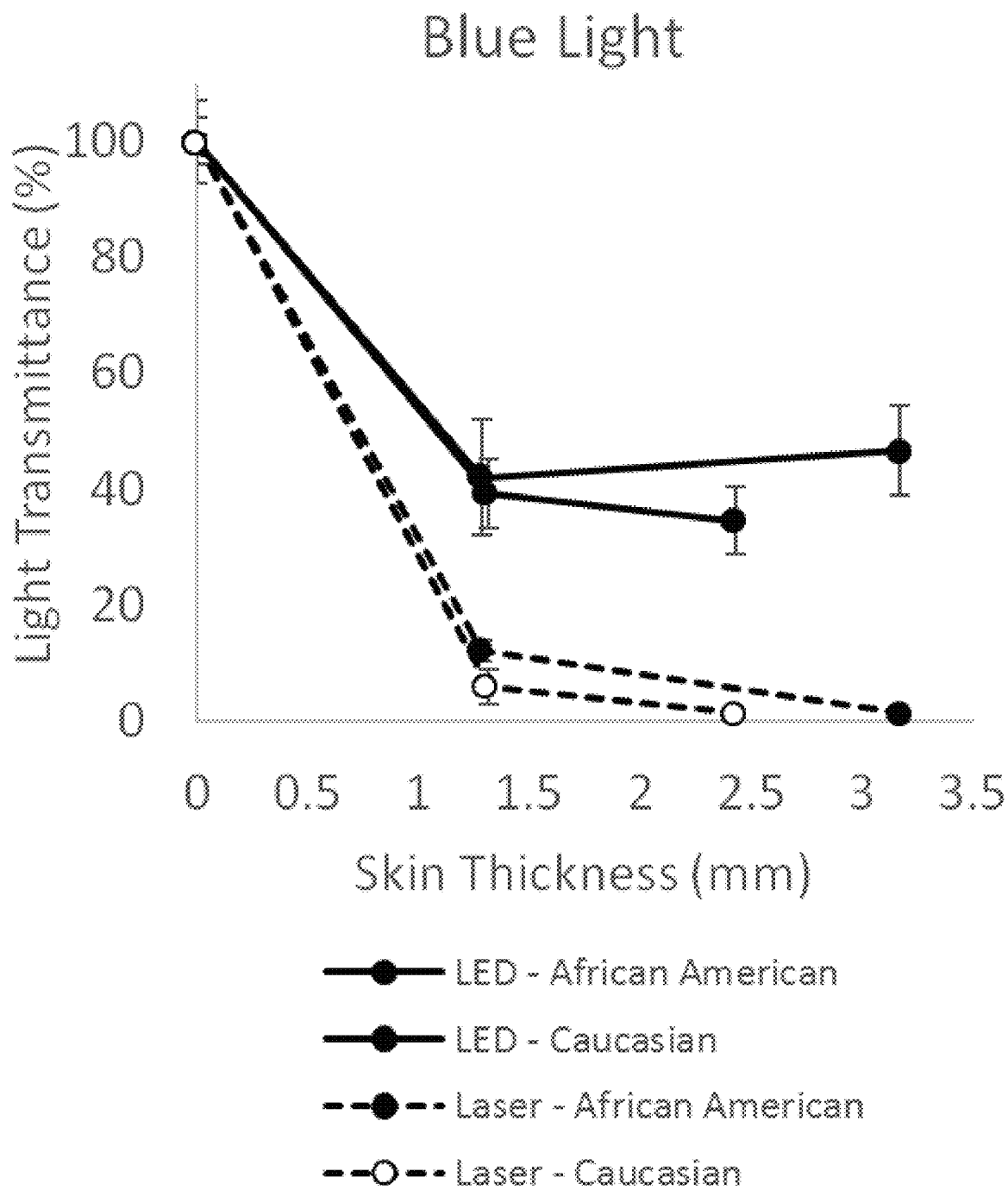
FIG. 72 is a plot of light transmittance percentage as a function of skin thickness (mm) for transmittance of blue (420 nm peak wavelength) incoherent (LED) light and blue (420 nm) coherent (laser) light through human skin samples of two different pigmentations and three different thicknesses.

To determine whether red, green, and blue coherent and incoherent light can penetrate skin of racially diverse types, experiments were performed using the apparatuses of FIGS. 67A, 68A, and 69A using human skin samples of three different thicknesses for each of two different pigmentations (i.e., African American skin of Fitzpatrick Skin Type V, and Caucasian skin of Fitzpatrick Skin Type II). Results of these experiments for red (660 nm peak wavelength), green (530 nm peak wavelength), and blue (420 nm peak wavelength) sources are shown in FIGS. 70 to 72, respectively. As shown, despite the different skin pigmentation, the samples of African American skin of Fitzpatrick Skin Type V and samples of Caucasian skin of Fitzpatrick Skin Type II skin samples performed similarly with respect to light transmittance properties. As shown in FIG. 70, red incoherent (LED) light was transmitted through each sample at more than twice the percentage of red coherent (laser) light. As shown in FIGS. 71 and 72, green and blue incoherent (LED) light were transmitted through each sample at more than twice the percentage of green and blue coherent (laser) light, respectively. Conclusions to be gleaned from the foregoing experiments are that LEDs appear to be at least as effective as lasers (for wavelengths of 420-660 nm) at penetrating skin of different types; and that a high percentage of blue LED light is capable of penetrating Caucasian and African American skin at depths of 2.5 mm or more.

In certain embodiments, methods and devices disclosed herein may be used to enhance nitric oxide production and/or release to provide a hair loss solution (e.g., for treating androgenic alopecia and/or similar conditions). Hair loss is caused by an increase in DHT produced by the enzyme 5α-reductase. In particular, 5α-reductase reacts with testosterone and NADPH to produce dihydrotestosterone (DHT), which leads to shrinkage of hair follicles and hair loss. Applicant performed experiments to determine whether nitric oxide inhibits 5α-reductase, to thereby provide a potential for decreasing DHT concentration in the scalp and inhibit (or reverse) hair loss. S-Nitrosoglutathione (GSNO) was used as a NO donor. Nitric oxide is released from GSNO by NADPH, which is a necessary cofactor for the 5α-reductase enzyme.

Figure 73:
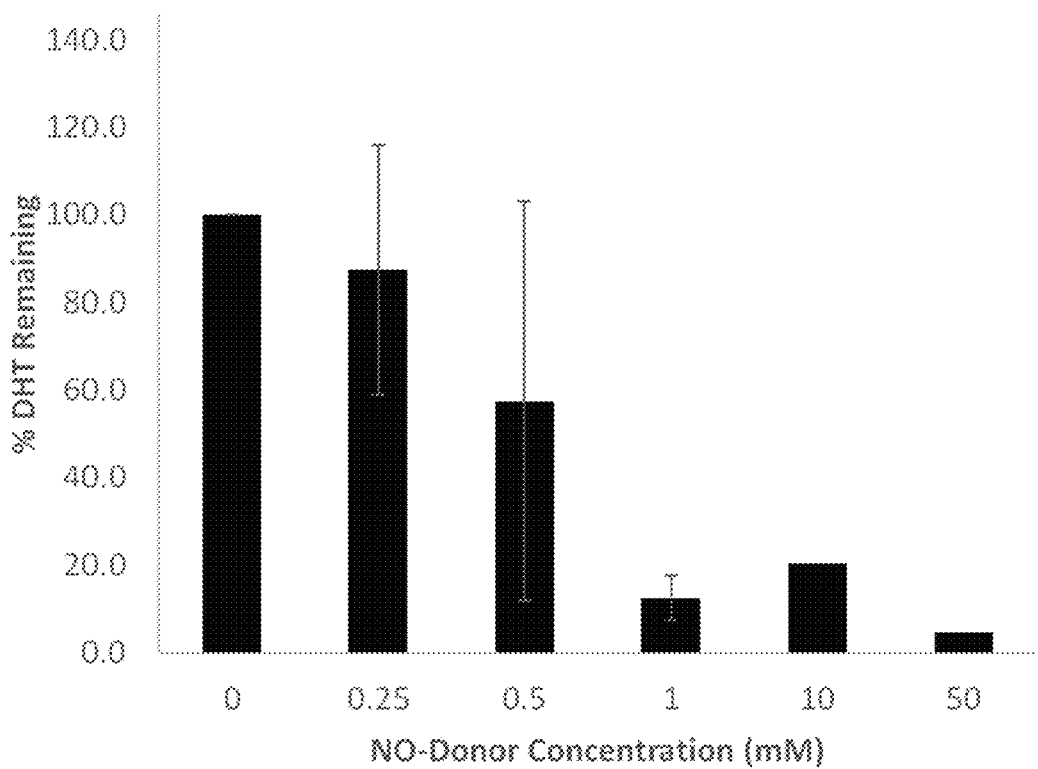
FIG. 73 is a plot of percentage of DHT remaining as a function of NO-donor concentration (mM) for six values ranging from 0 to 50 mM, showing that lower percentages of DHT remaining are correlated with increased NO-donor concentrations.
Figure 74:
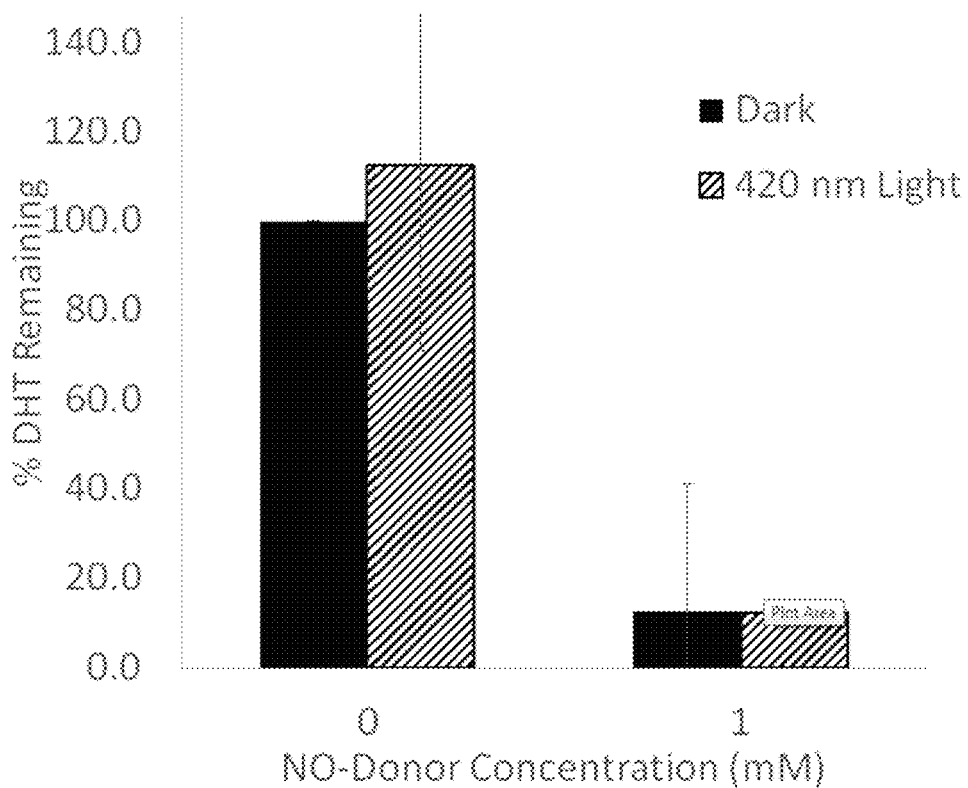
FIG. 74 is a plot of percentage of DHT remaining as a function of NO-donor concentration (mM) for dark conditions and 420 nm light exposure conditions for NO-donor concentrations of 0 and 1 mM.

FIG. 73 is a plot of percentage of DHT remaining as a function of NO-donor concentration (mM) for six values ranging from 0 to 50 mM, showing that lower percentages of DHT remaining are correlated with increased nitric oxide donor (e.g., GSNO) concentrations. FIG. 74 is a plot of percentage of DHT remaining as a function of NO-donor concentration (mM) for dark conditions and 420 nm light exposure conditions for NO-donor concentrations of 0 and 1 mM. Inhibition was still observed in the dark because the nitric oxide donor releases nitric oxide under the conditions of the assay. FIG. 74 shows that light does not have a detrimental effect on NO-induced inhibition. As demonstrated previously herein, modulated light therapy releases nitric oxide, which can then inhibit 5α-reductase and thereby provide a therapeutic benefit in terms of reduced (or reversed) hair loss for suffers of androgenic alopecia and/or similar conditions.

Phototherapy has been shown to be effective in treating various conditions, including alopecia, acne, seasonal affective disorder, psoriasis, excess bilirubin, atopic dermatitis, and a broad range of aesthetic indications. While there may not be a single universally accepted mechanism for the biological activity of light, there may be multiple biological mechanisms that are relevant depending on the intensity and wavelength of the therapeutic light. UV light may be configured to provide ultraviolet germicidal irradiation for disinfecting of surfaces, food, air, and water. In such applications, the peak wavelength of light used may be in one or more wavelength ranges of the ultraviolet spectrum, for example 260 to 270 nm, which is understood to break bonds in DNA of microorganisms, thereby damaging genetic material with fatal effect. While UV light is highly effective against microorganisms, it is non-selective and is known to also cause damage to human cells. In this regard, UV light provides some undesirable attributes that render it not universally suitable for all phototherapy applications. For visible light, such as in a range from 400 nm to 700 nm, phototherapy has been suggested to provide therapeutic benefits which include increasing circulation (e.g., by increasing formation of new capillaries); stimulating the production of collagen; stimulating the release of adenosine triphosphate (ATP); enhancing porphyrin production; reducing excitability of nervous system tissues; modulating fibroblast activity; increasing phagocytosis; inducing thermal effects; stimulating tissue granulation and connective tissue projections; reducing inflammation; and stimulating acetylcholine release.

As previously described, phototherapy has also been suggested to stimulate cells to generate nitric oxide. Various biological functions attributed to nitric oxide include roles as signaling messenger, cytotoxin, antiapoptotic agent, antioxidant, and regulator of microcirculation. Nitric oxide is recognized to relax vascular smooth muscles, dilate blood vessels, inhibit aggregation of platelets, and modulate T cell-mediated immune response. Nitric oxide is produced by multiple cell types in tissue and may be formed by the conversion of the amino acid L-arginine to L-citrulline and nitric oxide, mediated by the enzymatic action of nitric oxide synthases (NOSs).

Certain aspects of the present disclosure relate to phototherapeutic delivery of light to mammalian tissue, including use of light having a single peak wavelength and a single radiant flux or light having multiple peak wavelengths and/or multiple radiant fluxes to inhibit the progression of a viral disease and/or to eradicate a viral infection.

In mammals, three distinct genes encode NOS isozymes: neuronal (nNOS or NOS-I), cytokine-inducible (iNOS or NOS-II), and endothelial (eNOS or NOS-III). iNOS and nNOS are soluble and found predominantly in the cytosol, while eNOS is membrane associated. Many cells in mammals synthesize iNOS in response to inflammatory conditions. Systems and methods for phototherapeutic modulation of nitric oxide has been described in US Patent Application Publication No. 2017/0028216, now U.S. Pat. No. 10,688, 315, which is hereby incorporated by reference herein in its entirety.

In illustrative embodiments, provided are methods and exemplary devices for inactivating viruses in contact with tissue and/or treating a viral-infected tissue. In certain aspects, methods and corresponding devices may include irradiating target tissue with a therapeutic dose (J/cm$^2$) from a light source for a period of time, and repeating the irradiating step for a number (N) of iterations to constitute a duration, wherein N is an integer greater than 1. Irradiances of light (mW/cm$^2$) have been proposed at specific wavelengths of visible light for a threshold time over a given duration to yield therapeutic dosages (J/cm$^2$) which are effective for inactivating virus or treating viral infections while maintaining the viability of epithelial tissues. These treatments can be tailored to the particular tissue being treated, as well as to the various fluids in the media, such as blood, sputum, saliva, cervical fluid, and mucous. The total dosage (J/cm$^2$) to treat an infection can be spread out over multiple administrations, with each dose applied over seconds or minutes, and with multiple doses over days or weeks, at individual doses that treat the infection while minimizing damage to the particular tissue. Exemplary and nonlimiting RNA and DNA viruses that may be treated according to the principles of the present disclosure are summarized below.

There are currently 5 recognized orders and 47 families of RNA viruses, and there are also many unassigned species and genera. Related to but distinct from the RNA viruses are the viroids and the RNA satellite viruses.

There are several main taxa: levivirus and related viruses, picornaviruses, alphaviruses, flaviviruses, dsRNA viruses, and the -ve strand viruses (Wolf et al., "Origins and Evolution of the Global RNA Virome," mBio, 9(6) (November 2018)).

Positive strand RNA viruses are the single largest group of RNA viruses, with 30 families. Of these, there are three recognized groups. The picorna group (Picornavirata) includes bymoviruses, comoviruses, nepoviruses, nodaviruses, picornaviruses, potyviruses, obemoviruses and a subset of luteoviruses (beet western yellows virus and potato leafroll virus). The flavi-like group (Flavivirata) includes carmoviruses, dianthoviruses, flaviviruses, pestiviruses, statoviruses, tombusviruses, single-stranded RNA bacteriophages, hepatitis C virus and a subset of luteoviruses (barley yellow dwarf virus). The alpha-like group (Rubivirata) includes alphaviruses, carlaviruses, furoviruses, hordeiviruses, potexviruses, rubiviruses, tobraviruses, tricornaviruses, tymoviruses, apple chlorotic leaf spot virus, beet yellows virus and hepatitis E virus.

A division of the alpha-like (Sindbis-like) supergroup has been proposed, with two proposed groups. The 'altovirus' group includes alphaviruses, furoviruses, hepatitis E virus, hordeiviruses, tobamoviruses, tobraviruses, tricornaviruses and rubiviruses, and the 'typovirus' group includes apple chlorotic leaf spot virus, carlaviruses, potexviruses and tymoviruses.

There are five groups of positive-stranded RNA viruses containing four, three, three, three, and one order(s), respectively. These fourteen orders contain 31 virus families (including 17 families of plant viruses) and 48 genera (including 30 genera of plant viruses). Alphaviruses and flaviviruses can be separated into two families, the Togaviridae and Flaviridae.

This analysis also suggests that the dsRNA viruses are not closely related to each other but instead belong to four additional classes, Birnaviridae, Cystoviridae, Partitiviridae, and Reoviridae, and one additional order (Totiviridae) of one of the classes of positive ssRNA viruses in the same subphylum as the positive-strand RNA viruses.

There are two large clades: One includes the families Caliciviridae, Flaviviridae, and Picornaviridae and a second that includes the families Alphatetraviridae, Birnaviridae, Cystoviridae, Nodaviridae, and Permutotretraviridae.

Satellite viruses include Albetovirus, Aumaivirus, Papanivirus, Virtovirus, and Sarthroviridae, which includes the genus Macronovirus.

Double-stranded RNA viruses (dsRNA viruses) include twelve families and a number of unassigned genera and species recognized in this group. The families include Amalgaviridae, Birnaviridae, Chrysoviridae, Cystoviridae, Endornaviridae, Hypoviridae, Megabirnaviridae, Partitiviridae, Picobirnaviridae, Reoviridae, which includes Rotavirus, Totiviridae, Quadriviridae. Botybirnavirus is one genus, and unassigned species include *Botrytis porri* RNA virus 1, *Circulifer tenellus* virus 1, *Colletotrichum camelliae* filamentous virus 1, Cucurbit yellows associated virus, *Sclerotinia sclerotiorum* debilitation-associated virus, and *Spissistilus festinus* virus 1.

Positive-sense ssRNA viruses (Positive-sense single-stranded RNA viruses) include three orders and 34 families, as well as a number of unclassified species and genera. The order Nidovirales includes the families Arteriviridae, Coronaviridae, which includes Coronaviruses, such as SARS-CoV and SARS-CoV-2, Mesoniviridae and Roniviridae. The order Picornavirales includes families Dicistroviridae, Iflaviridae, Marnaviridae, Picornaviridae, which includes Poliovirus, Rhinovirus (a common cold virus), and Hepatitis A virus, Secoviridae, which includes the subfamily Comovirinae, as well as the genus Bacillariornavirus and the species Kelp fly virus. The order Tymovirales includes the families Alphaflexiviridae, Betaflexiviridae, Gammaflexiviridae, and Tymoviridae. A number of families are not assigned to any of these orders, and these include Alphatetraviridae, Alvernaviridae, Astroviridae, Barnaviridae, Benyviridae, Botourmiaviridae, Bromoviridae, Caliciviridae, which includes the Norwalk virus (i.e., norovirus), Carmotetraviridae, Closteroviridae, Flaviviridae, which includes Yellow fever virus, West Nile virus, Hepatitis C virus, Dengue fever virus, and Zika virus, Fusariviridae, Hepeviridae, Hypoviridae, Leviviridae, Luteoviridae, which includes Barley yellow dwarf virus, Polycipiviridae, Narnaviridae, Nodaviridae, Permutotetraviridae, Potyviridae, Sarthroviridae, Statovirus, Togaviridae, which includes Rubella virus, Ross River virus, Sindbis virus, and Chikungunya virus, Tombusviridae, and Virgaviridae. Unassigned genuses include Blunervirus, Cilevirus, Higrevirus, Idaeovirus, Negevirus, Ourmiavirus, Polemovirus, Sinaivirus, and Sobemovirus. Unassigned species include *Acyrthosiphon pisum* virus, Bastrovirus, Blackford virus, Blueberry necrotic ring blotch virus, Cadicistrovirus, *Chara australis* virus, Extra small virus, Goji berry chlorosis virus, *Harmonia axyridis* virus 1, Hepelivirus, Jingmen tick virus, Le Blanc virus, Nedicistrovirus, *Nesidiocoris tenuis* virus 1, Niflavirus, *Nylanderia fulva* virus 1, Orsay virus, *Osedax japonicus* RNA virus 1, Picalivirus, Planarian secretory cell nidovirus, *Plasmopara halstedii* virus, *Rosellinia necatrix* fusarivirus 1, Santeuil virus. Secalivirus, *Solenopsis invicta* virus 3, and Wuhan large pig roundworm virus.

Satellite viruses include the family Sarthroviridae and the genuses Albetovirus, Aumaivirus, Papanivirus, Virtovirus, and the Chronic bee paralysis virus. Six classes, seven orders and twenty four families are currently recognized in this group. A number of unassigned species and genera are yet to be classified.

Negative-sense ssRNA viruses (Negative-sense single-stranded RNA viruses) are, with the exception of the Hepatitis D virus, within a single phylum, Negarnaviricota, with two subphyla, Haploviricotina and Polyploviricotina, with four classes, Chunqiuviricetes, Milneviricetes, Monjiviricetes and Yunchangviricetes. The subphylum Polyploviricotina has two classes, Ellioviricetes and Insthoviricetes.

There are also a number of unassigned species and genera. The Phylum Negarnaviricota includes Subphylum Haploviricotina, Class Chunqiuviricetes, Order Muvirales, Family Qinviridae. The Class Milneviricetes includes Order Serpentovirales and Family Aspiviridae. The Class Monjiviricetes includes Order Jingchuvirales and Family Chuviridae. The order Mononegavirales includes families Bornaviridae, which includes the Borna disease virus, Filoviridae, which includes the Ebola virus and the Marburg virus, Mymonaviridae, Nyamiviridae, Paramyxoviridae, which includes Measles, Mumps, Nipah, Hendra, and NDV, Pneumoviridae, which RSV and Metapneumovirus, Rhabdoviridae, which Rabies, and Sunviridae, as well as genuses Anphevirus, Arlivirus, Chengtivirus, Crustavirus, and Wastrivirus. Class Yunchangviricetes includes order Goujianvirales and family Yueviridae. Subphylum Polyploviricotina includes class Ellioviricetes, order Bunyavirales, and the families Arenaviridae, which includes Lassa virus, Cruliviridae, Feraviridae, Fimoviridae, Hantaviridae, Jonviridae, Nairoviridae, Peribunyaviridae, Phasmaviridae, Phenuiviridae, Tospoviridae, as well as genus Tilapineviridae.

Class Insthoviricetes includes order Articulavirales and family Amnoonviridae, which includes the Taastrup virus, and family Orthomyxoviridae, which includes Influenza viruses.

The genus Deltavirus includes the Hepatitis D virus.

Specific viruses include those associated with infection of mucosal surfaces of the respiratory tract, including Betacoronavirus (SARS-CoV-2 and MERS-CoV), rhinoviruses, influenza virus (including influenza A and B, parainfluenza). Generally, orthomyxoviruses and paramyxoviruses can be treated.

A DNA virus is a virus that has DNA as its genetic material and replicates using a DNA-dependent DNA polymerase. The nucleic acid is usually double-stranded DNA (dsDNA) but may also be single-stranded DNA (ssDNA). DNA viruses belong to either Group I or Group II of the Baltimore classification system for viruses. Single-stranded DNA is usually expanded to double-stranded in infected cells. Although Group VII viruses such as hepatitis B contain a DNA genome, they are not considered DNA viruses according to the Baltimore classification, but rather reverse transcribing viruses because they replicate through an RNA intermediate. Notable diseases like smallpox, herpes, and the chickenpox are caused by such DNA viruses.

Some DNA viruses have circular genomes (Baculoviridae, Papovaviridae and Polydnaviridae) while others have linear genomes (Adenoviridae, Herpesviridae and some phages). Some families have circularly permuted linear genomes (phage T4 and some Iridoviridae). Others have linear genomes with covalently closed ends (Poxviridae and Phycodnaviridae).

Fifteen DNS virus families are enveloped, including all three families in the order Herpesvirales and the following families: Ascoviridae, Ampullaviridae, Asfarviridae, Baculoviridae, Fuselloviridae, Globuloviridae, Guttaviridae, Hytrosaviridae, Iridoviridae, Lipothrixviridae, Nimaviridae and Poxviridae.

Of these, species of the order Herpesvirales, which includes the familes Alloherpesviridae, Herpesviridae, which includes human herpesviruses and the Varicella Zoster, and the families Adenoviridae, which includes viruses which cause human adenovirus infection, and Malacoherpesviridae, infect vertebrates.

Asfarviridae, which includes African swine fever virus, Iridoviridae, Papillomaviridae, Polyomaviridae, which includes Simian virus 40, JC virus, and BK virus, and Poxviridae, which includes Cowpox virus and smallpox, infect vertebrates. Anelloviridae and Circoviridae also infect animals (mammals and birds respectively).

The family Smacoviridae includes a number of single-stranded DNA viruses isolated from the feces of various mammals, and there are 43 species in this family, which includes six genera, namely, Bovismacovirus, Cosmacovirus, Dragsmacovirus, Drosmacovirus, Huchismacovirus and Porprismacovirus. Circo-like virus Brazil hs1 and hs2 have also been isolated from human feces. An unrelated group of ssDNA viruses includes the species bovine stool associated circular virus and chimpanzee stool associated circular virus.

Animal viruses include parvovirus-like viruses, which have linear single-stranded DNA genomes, but unlike the parvoviruses, the genome is bipartate. This group includes Hepatopancreatic parvo-like virus and Lymphoidal parvo-like virus. Parvoviruses have frequently invaded the germ lines of diverse animal species including mammals.

The human respiratory-associated PSCV-5-like virus has been isolated from the respiratory tract. The PSCV-50-like virus may also be subject to phototherapy principles of the present disclosure.

According to certain embodiments, provided herein are methods of treating and/or preventing a viral infection. A method of treating and/or preventing a viral infection may comprise administering light to the skin of a subject, thereby treating and/or preventing the viral infection in the subject. In some embodiments, aspects of the present invention may provide suppression and/or inhibition of viral replication and/or enhancement of local immune responses of a subject.

According to certain embodiments of the present disclosure, provided herein are methods and devices of treating and/or preventing virus-related cutaneous conditions. A method of treating and/or preventing a virus-related cutaneous condition may comprise administering light to the skin of a subject, thereby treating and/or preventing the virus-related cutaneous condition in the subject. Virus-related cutaneous conditions that may be treated and/or prevented include, but are not limited to, cutaneous conditions associated with bowenoid papulosis, buffalopox, butcher's wart, condylomata acuminate, cowpox, cytomegalovirus, disseminated herpes zoster, eczema herpeticum (Kaposi's varicelliform eruption), eczema vaccinatum, epidermodysplasia verruciformis, erythema infectiosum (fifth disease, slapped cheek disease), farmyard pox, generalized vaccinia, genital herpes (herpes genitalis, herpes progenitalis), Buschke-Löwenstein tumor, hand-foot-and-mouth disease (Coxsackie), Heck's disease (focal epithelial hyperplasia), herpangina, herpes gladiatorum (scrum pox), herpes simplex, herpetic keratoconjunctivitis, herpetic sycosis, herpetic whitlow, human monkeypox, human T-lymphotropic virus 1 infection, human tanapox, intrauterine herpes simplex, Kaposi sarcoma, Lipschtltz ulcer (ulcus vulvae acutum), Milker's nodule, molluscum contagiosum, neonatal herpes simplex, ophthalmic zoster, orf (contagious pustular dermatosis, ecthyma contagiosum, infectious labial dermatitis, sheep pox), oral florid papillomatosis, oral hairy leukoplakia (EBV), orolabial herpes (herpes labialis), progressive vaccinia (vaccinia gangrenosum, vaccinia necrosum), pseudocowpox, recurrent respiratory papillomatosis (laryngeal papillomatosis), sealpox, varicella (chickenpox), variola major (smallpox), verruca plana (flat warts), verruca plantaris (plantar wart), verruca vulgaris (wart), verrucae palmares et plantares, and/or zoster (herpes zoster, shingles). In some embodiments, the viral infection may be caused by a papillomavirus, such as a human papillomavirus. The human papillomavirus (HPV) may be HPV type 1, 2, 3, 4, 6, 10, 11, 16, 18, 31, 33, 35, 39, 45, 51, 52, 56, 58, and/or 59.

In certain embodiments, methods and/or devices for treating and/or preventing a virus-related gastrointestinal (GI) condition may comprise administering light via colorectal administration via a probe inserted into the body cavity of a subject, thereby treating and/or preventing the virus-related colorectal or intestinal condition in the subject. Viruses in the GI tract include rotavirus, picornavirus, and coronavirus. In one embodiment the condition is caused by Enterovirus D68 known to cause severe illness in children and acute flacid myelitis.

In other embodiments, methods and/or devices for treating and/or preventing a virus-related central nervous system (CNS) infection may comprise administering light transcranially, through the nose of a patient, or upon implantation of a light source into the tissue of a subject, thereby treating and/or preventing the virus-related CNS condition in the subject. CNS infections are frequently caused by viruses, such as the enteroviruses, which cause the majority of cases of aseptic meningitis and meningoencephalitis as well as other neurotropic viruses including but not limited to human cytomegalovirus, herpes simplex viruses, varicella-zoster virus, and the emerging viruses West Nile virus, Murray Valley encephalitis virus, henipaviruses, Japanese encephalitis virus, chikungunya virus, Ebola virus, and rabies virus.

In specific embodiments, intranasal administration to the nasal mucosa can be used as a method of treating and/or preventing a virus-related infection. Data from animal studies and human cases have demonstrated that the olfactory and/or trigeminal nerve pathway represents a major route of CNS entry for several groups of viruses. It is known that herpes simplex virus type 1, bovine herpesvirus 5, and equine herpesvirus 9 spread from the nasal mucosa to the CNS via the olfactory nerves in animal models of infection. Orthomyxoviridae, including influenza virus, is also spread from the nasal cavity to the olfactory bulb and the rest of the CNS. Paramyxoviruses, including Nipah virus, Hendra virus, and parainfluenza virus, may enter the CNS directly from the nasal mucosa.

According to other embodiments of the present disclosure, methods and/or devices for treating and/or preventing a virus-related bloodstream infection may comprise transdermal administration of light to superficial vasculature, administering light to blood passed through an extra-corporeal loop, shining light on a blood product derived from the patient for use on other patients, and other methods for illumination of biological fluids of a subject, thereby treating and/or preventing the virus-related blood stream infection in the subject. In some embodiments, the biological fluid is treated to help treat or prevent viremia, which is when viruses are present in the blood at abnormal levels. Viremia can be classified into primary viremia, the spread of the virus into the blood from the initial site of infection or secondary viremia, the spread of the virus to other organs that come into contact with the blood where the virus replicates and then enters the bloodstream once more. In some methods, the viremia may be active. In other embodiments, the viremia may be passive. In some embodiments, the viremia is caused by West Nile virus, dengue, rubella, measles, cytomegalovirus, Epstein-Barr virus, HIV, hepatitis B virus, poliovirus, yellow fever virus, or varicella-zoster virus.

In other embodiments, the light is applied external to the body to the joints including those in the feet and hands, as well as the ankles, elbows, knees, and shoulders as a method of treating and/or preventing a joint arthritis related to side effects caused by autoimmune reactions to viruses including but not limited to chikungunya and ross river virus.

The terms phototherapy and phototherapeutic relate to the therapeutic use of light. As used herein, phototherapy is used to treat or prevent microbial infections, including viral infections of the body including mucosal epithelial tissues in the vaginal cavity, anal canal, oral cavity, the auditory canal, the upper respiratory tract and esophagus.

The mechanisms by which the wavelengths of light are effective can vary, depending on the wavelength that is administered. Biological effects, including antimicrobial effects, can be provided over a wide range of wavelengths, including UV ranges, visible light ranges, and infrared ranges. The effects vary depending on the mechanism by which the light is antimicrobial, and the wavelengths that bring about these mechanisms. Phot A handful of photoacceptors for blue light have been identified in non-pigmented cells, including cytochrome c oxidase, flavins, porphyrins, opsins, and nitrosated proteins. Light absorption by photoreceptors can lead to release of reactive oxygen species (ROS) and/or nitric oxide (NO) that may function to inactivate viruses in a cell-free or cell-associated environment. Reactive oxygen species and/or bioactive NO may elicit activation of transcription factors involved in immune signaling, such as nuclear factor kappa-light-chain-enhancer of activated B cells (NF-κB) and mitogen activated protein kinase (MAPK) signaling. NFκB and MAPK pathways can lead to transcriptional activation of innate and inflammatory immune response molecules that may interfere with viral replication. Nitric oxide may also mediate inactivation of cell-associated virus through S-nitrosylation of cysteine residues in the active site of viral encoded enzymatic proteins. Reactive oxygen species and/or NO may also function to inactivate cell-free virions. Photosensitizers present in cell media may facilitate generation of ROS and/or NO that directly impact virion proteins and/or viral RNA to prevent infection and replication. Evidence demonstrating that SARS-CoV can be inactivated by exogenous addition of NO donor molecules substantiate the potential for SARS-CoV-2 inactivation by nitric oxide.

In some embodiments, the wavelengths of light activate immune cells of the innate and/or adaptive immune responses, including macrophages.

When administering light to arrive at a suitable total dose (J/cm$^2$), it can be important to provide the therapeutic dosage of light at a suitable combination of a wavelength, and irradiance (W/cm$^2$) to the target tissue, and exposure time, and multiple exposures, at these conditions to yield total dose in J/cm$^2$.

The wavelength should be safe to the tissue being irradiated, and the irradiance should be safe to the tissue as well, ideally not heating the tissue to a temperature that is unsafe, and the cumulative exposure time should be matched with the desired clinical application. In some embodiments, the device used to administer the light can include a means for controlling the amount of light that is administered, such as a timer, actuator, dosimeter, and the like, such that the light does not exceed safe limits.

For example, light is ideally administered at a dosage that is safe and at a dosage that is effective at killing viruses or other microbes. In this regard, aspects of the present disclosure provide a ratio of the IC$_{25}$ (the concentration or dose required to reduce living tissue viability by 25% when compared to control-treated tissues) to the EC$_{50}$ (dose required to kill 50% of the virus or other microbe for the specific tissue being treated as quantified at a cellular level) is greater than or equal to 2. As disclosed herein, the IC$_{25}$/EC$_{50}$ ratio or fraction may be referred to as a light therapeutic index (LTI) that quantifies safe and effective light dosages. In another context, one can consider, in an in vitro setting, the ratio of the CC$_{50}$ (concentration of a therapeutic to reduce cell viability by 50%) to the EC$_{50}$ for treated cells (i.e., the Selectivity Index, or "SI"). This ratio will vary depending on the type of cells or tissue that are exposed, for example, with some cells having differential tolerance to oxidative damage than other cells.

Figure 75:
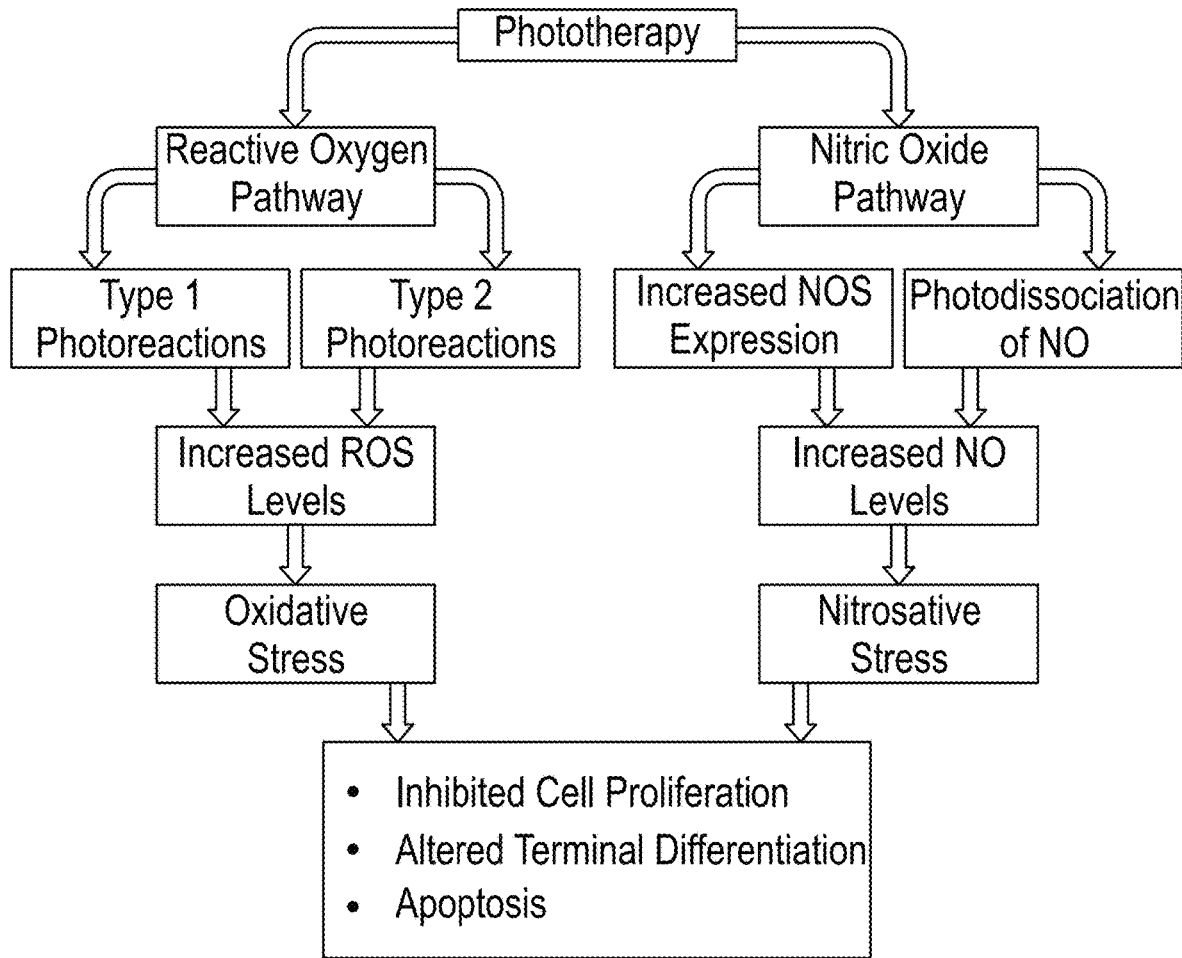
FIG. 75 is a diagrammatic drawing showing two potential mechanisms of action by which phototherapy may inhibit or eradicate viral infections.

Phototherapeutic light can induce oxidative and nitrosative stresses within cells or the tissues comprised therefrom. Referring now to FIG. 75, shown is a diagrammatic illustration of proposed mechanisms of action whereby phototherapy leads to inhibited cell proliferation, altered terminal differentiation, and apoptosis. Illustratively, the Reactive Oxygen Species (ROS) or Reactive Oxygen Pathway causes oxidative stress through either Type 1 or Type 2 Photoreactions. Type 1 reactions involve the excitation of an endogenous photosensitizer (most likely an endogenous porphyrin). This excited photosensitizer reacts with another cellular component to form a free radical directly (e.g. superoxide and hydroxyl groups). Type 2 reactions involve the excitation of an endogenous photosensitizer (again, most likely a porphyrin) with oxygen to form singlet oxygen (102). It is understood that phototherapy causes increased ROS levels which can create oxidative stress in the subject tissue. Virus-infected tissues are known to already be under considerable oxidative stress due to their viral infections. The increase in oxidative stress through phototherapy thus exacerbates the oxidative environment and depending on phototherapy dosage, can inhibit cell proliferation, alter terminal differentiation, and cause apoptosis.

Referring back to FIG. 75, phototherapy can also induce a nitric oxide pathway which can create nitrosative stress. The nitrosative stress is induced by the increase in the enzymatic generation of nitric oxide and the photodissociation of endogenous nitric oxide. Both enhancing the enzymatic generation of nitric oxide and the photodissociation of nitric oxide from the Endogenous Stores (ES), result in increased NO levels. It is understood that this nitrosative stress likewise can inhibit cell proliferation, alter terminal differentiation, and cause apoptosis.

As disclosed herein, high doses of blue light are shown to increase the expression of nitric oxide synthase enzymes. Furthermore, the photodissociation of NO from endogenous stores is well known. The release of NO from nitrosated/nitrosylated proteins is possible through a wavelength dependent process as described in U.S. Patent Application Publication No. 2017/0028215, now U.S. Pat. No. 10,569,097, which is incorporated by reference herein in its entirety for disclosure associated with phototherapy.

The photoinitiated release of endogenous stores of nitric oxide effectively regenerates "gaseous" (or unbound) nitric oxide that may be autooxidized into nitrosative intermediates and bound covalently in the body in a "bound" state. By stimulating release of nitric oxide from endogenous stores, nitric oxide may be maintained in a gaseous state for an extended duration and/or a spatial zone of nitric oxide release may be expanded.

Another aspect of the present disclosure is that one or more viruses can be inactivated pre-infection and one or more viral infections can be inhibited and/or eradicated by light-induced nitrosative or oxidative stress.

An illumination device for the treatment of pathogen infected tissues and/or for the inducing one or more biological effects, may take any form suitable for delivering light to the infected tissue. The device will contain a light source capable of emitting a suitable light profile that can provide one or more direct or indirect biological effects. A light profile can be represented with a graph of emission intensity versus wavelength of light for any particular light source. Disclosed herein are light sources with light profiles in the visible spectrum, for example with light emissions with peak wavelengths primarily in a range from 400 nm to 700 nm. Depending on the target application, light profiles may also include infrared or near-infrared peak wavelengths at or above 700 nm including up to 900 nm, or ultraviolet peak wavelengths at or below 400 nm including as low as 200 nm. In certain embodiments, light emissions may have a single peak wavelength in a range from 200 nm to 900 nm, or in a range from 400 nm to 490 nm, or in a range from 400 nm to 450 nm, or in a range from 400 nm to 435 nm, or in a range from 400 nm to 420 nm, or in a range from 410 nm to 440 nm, or in a range from 420 nm to 440 nm, or in a range from 450 nm to 490 nm, or in a range from 500 nm to 900 nm, or in a range from 490 nm to 570 nm, or in a range from 510 nm to 550 nm, or in a range from 520 nm to 540 nm, or in a range from 525 nm to 535 nm, or in a range from 528 nm to 532 nm, or in a range from 320 nm to 400 nm, or in a range from 350 nm to 395 nm, or in a range from 280 nm to 320 nm, or in a range from 320 nm to 350 nm, or in a range from 200 nm to 280 nm, or in a range from 260 nm to 270 nm, or in a range from 240 nm to 250 nm, or in a range from 200 nm to 225 nm. In further embodiments, light emissions may include multiple peak wavelengths selected from any of the above listed ranges, depending on the target application and desired biological effects. Depending on the target application, full width half maximum (FWHM) values for any of the above-described peak wavelength ranges may be less than or equal to 100 nm, or less than or equal to 90 nm, or less than or equal to 40 nm, or less than or equal to 20 nm. In certain aspects, lower FWHM values are typically associated with single emission color LEDs in any of the above-described wavelength bands. Larger FWHM values (e.g., from 40 nm to 100 nm) may be associated with phosphor-converted LEDs where spectral bandwidths are a combination of LED emissions and phosphor-converted emissions. Exemplary phosphor-converted LEDs that may be applicable to the present disclosure are phosphor-converted amber LEDs having peak wavelengths in a range from 585 nm to 600 nm and FWHM values in a range from 70 nm to 100 nm, and phosphor-converted mint and/or lime LEDs having peak wavelengths in a range from 520 nm to 560 nm. Additional embodiments of the present disclosure may also be applicable to broad spectrum white LEDs that may include an LED with a peak wavelength in a range from 400 nm to 470 nm, and one or more phosphors to provide the broad emission spectrum. In such embodiments, a broad spectrum LED may provide certain wavelengths that induce one or more biological effects while also providing broad spectrum emissions to the target area for illumination. In this regard, light impingement on tissue for single and/or multiple microorganism and/or multiple pathogenic biological effects may be provided with light of a single peak wavelength or a combination of light with more than one peak wavelength.

Doses of light to induce one or more biological effects may be administered with one or more light characteristics, including peak wavelengths as described above, radiant flux, and irradiance to target tissues. Irradiances to target tissues may be provided in a range from 0.1 mW/cm$^2$ to 200 mW/cm$^2$, or in a range from 5 mW/cm$^2$ to 200 mW/cm$^2$, or in a range from 5 mW/cm$^2$ to 100 mW/cm$^2$, or in a range from 5 mW/cm$^2$ to 60 mW/cm$^2$, or in a range from 60 mW/cm$^2$ to 100 mW/cm$^2$, or in a range from 100 mW/cm$^2$ to 200 mW/cm$^2$. Such irradiance ranges may be administered in one or more of continuous wave and pulsed configurations, including LED-based photonic devices that are configured with suitable power (radiant flux) to irradiate a target tissue with any of the above-described ranges. A light source for providing such irradiance ranges may be configured to provide radiant flux values from the light source of at least 5 mW, or at least 10 mW, or at least 15 mW, or at least 20 mW, or at least 30 mW, or at least 40 mW, or at least 50 mW, or at least 100 mW, or at least 200 mW, or in a range of from 5 mW to 200 mW, or at least 500 mW, or at least 2500 mW, or at least 5000 mw, or in a range of from 5 mW to 100 mW, or in a range of from 5 mW to 60 mW, or in a range of from 5 mW to 30 mW, or in a range of from 5 mW to 20 mW, or in a range of from 5 mW to 10 mW, or in a range of from 10 mW to 60 mW, or in a range of from 20 mW to 60 mW, or in a range of from 30 mW to 60 mW, or in a range of from 40 mW to 60 mW, or in a range of from 60 mW to 100 mW, or in a range of from 100 mW to 200 mW, or in a range of from 200 mW to 500 mW, or in a range of from 5 mW to 5000 mW, or in a range of from 5 mW to 2500 mW, or in another range specified herein. Depending on the configuration of one or more of the light source, the corresponding illumination device, and the distance away from a target tissue, the radiant flux value for the light source may be higher than the irradiance value at the tissue. In certain embodiments, the radiant flux value may be configured with a value that is greater than the irradiance value to the tissue. For example, the radiant flux may be in a range from 5 to 20 times greater than the irradiance, or in a range from 5 to 15 times greater than the irradiance, among other ranges and depending on the embodiments.

While certain peak wavelengths for certain target tissue types may be administered with irradiances up to 1 W/cm$^2$ without causing significant tissue damage, safety considerations for other peak wavelengths and corresponding tissue types may require lower irradiances, particularly in continuous wave applications. In certain embodiments, pulsed irradiances of light may be administered, thereby allowing safe application of significantly higher irradiances. Pulsed irradiances may be characterized as average irradiances that fall within safe ranges, thereby providing no or minimal damage to the applied tissue. In certain embodiments, irradiances in a range from 0.1 W/cm$^2$ to 10 W/cm$^2$ may be safely pulsed to target tissue.

Administered doses of light, or light doses, may be referred to as therapeutic doses of light in certain aspects. Doses of light may include various suitable combinations of the peak wavelength, the irradiance to the target tissue, and the exposure time period. Particular doses of light are disclosed that are tailored to provide safe and effective light for inducing one or more biological effects for various types of pathogens and corresponding tissue types. In certain aspects, the dose of light may be administered within a single time period in a continuous or a pulsed manner. In further aspects, a dose of light may be repeatably administered over a number of times to provide a cumulative or total dose over a cumulative time period. By way of example, a single dose of light as disclosed herein may be provided over a single time period, such as in a range from 10 microseconds to no more than an hour, or in a range from 10 seconds to no more than an hour, while the single dose may be repeated at least twice to provide a cumulative dose over a cumulative time period, such as a 24-hour time period. In certain embodiments, doses of light are described that may be provided in a range from 0.5 joules per square centimeter (J/cm$^2$) to 100 J/cm$^2$, or in a range from 0.5 J/cm$^2$ to 50 J/cm$^2$, or in a range from 2 J/cm$^2$ to 80 J/cm$^2$, or in a range from 5 J/cm$^2$ to 50 J/cm$^2$, while corresponding cumulative doses may be provided in a range from 1 J/cm$^2$ to 1000 J/cm$^2$, or in a range from 1 J/cm$^2$ to 500 J/cm$^2$, or in a range from 1 J/cm$^2$ to 200 J/cm$^2$, or in a range from 1 J/cm$^2$ to 100 J/cm$^2$, or in a range from 4 J/cm$^2$ to 160 J/cm$^2$, or in a range from 10 J/cm$^2$ to 100 J/cm$^2$, among other discloses ranges. In a specific example, a single dose may be administered in a range from 10 J/cm$^2$ to 20 J/cm$^2$, and the single dose may be repeated twice a day for four consecutive days to provide a cumulative dose in a range from 80 J/cm$^2$ to 160 J/cm$^2$. In another specific example, a single dose may be administered at about 30 J/cm$^2$, and the single dose may be repeated twice a day for seven consecutive days to provide a cumulative dose of 420 J/cm$^2$.

In still further aspects, light for inducing one or more biological effects may include administering different doses of light to a target tissue to induce one or more biological effects for different target pathogens. As disclosed herein, a biological effect may include altering a concentration of one or more pathogens within the body and altering growth of the one or more pathogens within the body. The biological effect may include at least one of inactivating the first pathogen in a cell-free environment, inhibiting replication of the first pathogen in a cell-associated environment, upregulating a local immune response in the mammalian tissue, stimulating enzymatic generation of nitric oxide to increase endogenous stores of nitric oxide in the mammalian tissue, releasing nitric oxide from endogenous stores of nitric oxide in the mammalian tissue, and inducing an anti-inflammatory effect in the mammalian tissue. As further disclosed herein, a pathogen may include a virus, a bacteria, and a fungus, or any other types of microorganisms that can cause infections. Notably, light doses as disclosed herein may provide non-systemic and durable effects to targeted tissues. Light can be applied locally and without off-target tissue effects or overall systemic effects associated with conventional drug therapies which can spread throughout the body. In this regard, phototherapy may induce a biological effect and/or response in a target tissue without triggering the same or other biological responses in other parts of the body. Phototherapy as described herein may be administered with safe and effective doses that are durable. For example, a dose may be applied for minutes at time, one to a few times a day, and the beneficial effect of the phototherapy may continue in between treatments.

Light sources may include one or more of LEDs, OLEDs, lasers and other lamps according to aspects of the present disclosure. Lasers may be used for irradiation in combination with optical fibers or other delivery mechanisms. A disadvantage of using a laser is that it may require sophisticated equipment operated by highly skilled professionals to ensure proper laser radiation protection, thereby increasing costs and reducing accessibility. LEDs are solid state electronic devices capable of emitting light when electrically activated. LEDs may be configured across many different targeted emission spectrum bands with high efficiency and relatively low costs. In this regard, LEDs are comparatively simpler devices that operate over much wider ranges of current and temperature, thereby providing an effective alternative to expensive laser systems. Accordingly, LEDs may be used as light sources in photonic devices for phototherapy applications. Light from an LED is administered using a device capable of delivering the requisite power to a targeted treatment area or tissue. High power LED-based devices can be employed to fulfill various spectral and power needs for a variety of different medical applications. LED-based photonic devices described herein may be configured with suitable power to reach power densities as high as 100 mW/cm$^2$ or 200 mW/cm$^2$ in the desired wavelength range. An LED array in this device can be incorporated into an irradiation head, hand piece and or as an external unit. When incorporated into hand piece or irradiation head, risk of eye or other organs being exposed to harmful radiation may be avoided.

According to aspects of the present disclosure, exemplary target tissues and cells light treatments may include one or more of epithelial tissue, mucosal tissue, connective tissue, muscle tissue, cervical tissue, dermal tissue, mucosal epithelial tissues in the vaginal cavity, anal canal, oral cavity, the auditory canal, the upper respiratory tract and esophagus, keratinocytes, fibroblasts, blood, sputum, saliva, cervical fluid, and mucous. Light treatments may also be applied to and/or within organs, to external body surfaces, and within any mammalian body and/or body cavity, for example the oral cavity, esophageal cavity, throat, and vaginal cavity, among others.

Figure 76:
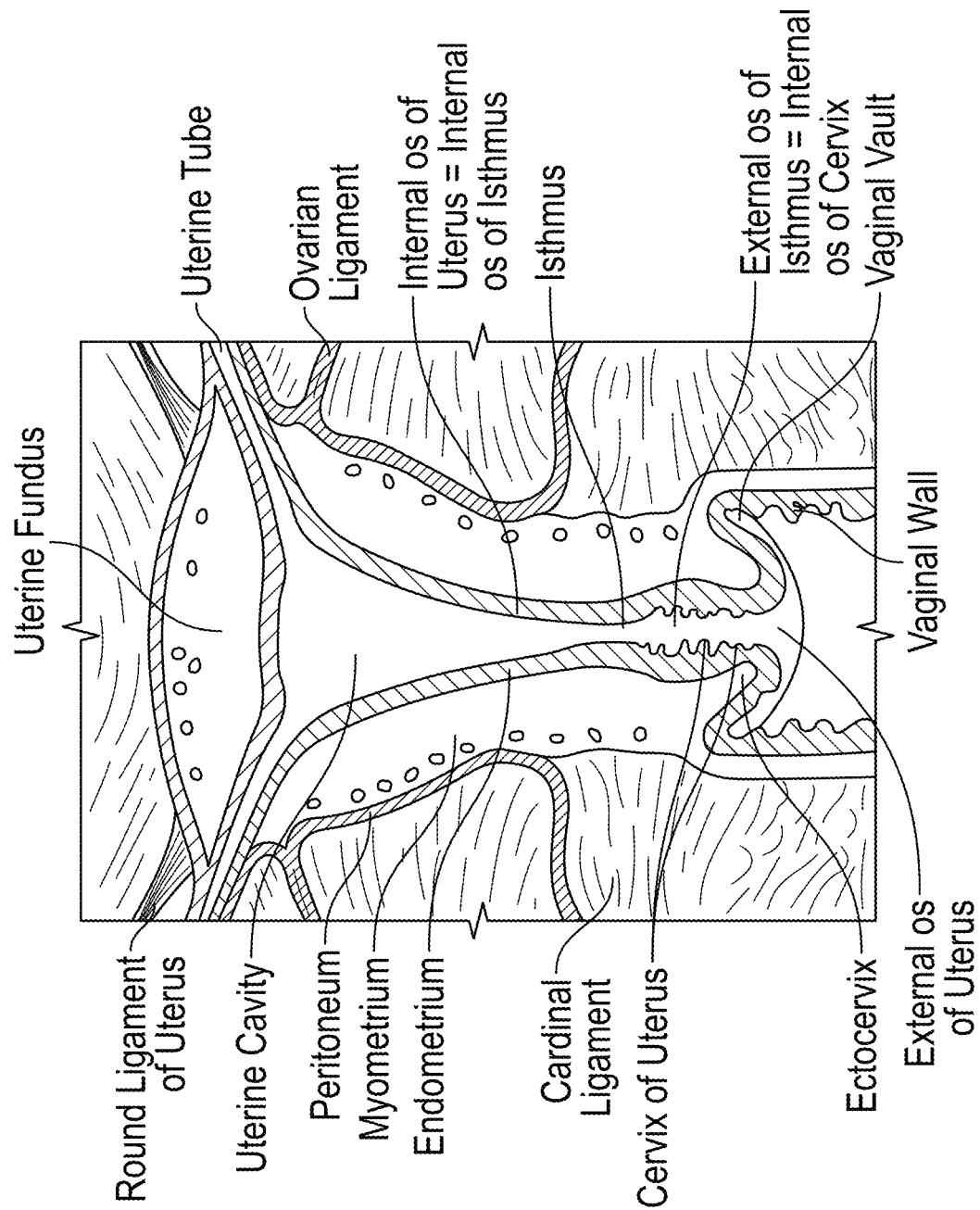
FIG. 76 is a schematic illustration of the female reproductive system.

In certain aspects, effective phototherapy-based treatment modalities are provided for precancerous and cancerous conditions of portio and cervical regions of a female anatomy, as well as tissues in the anus, throat and mouth of both sexes. By way of illustration, an illustration of the female reproductive system is shown in FIG. 76. Certain oncogenic human papilloma virus (HPV) can infect the cells in the cervix and portio region inducing dysplasias that can develop into cancerous conditions when left untreated. In the US alone, there are around half a million patients surgically treated per year for colonization of the portio. This virus can also cause mouth, throat and anal cancers. The region of the cervix where the columnar epithelium has been replaced by the new metaplastic squamous epithelium is referred to as the transformation zone. Identifying the transformation zone is important as almost all manifestations of cervical carcinogenesis occur in this zone.

Exemplary devices for delivering phototherapy within body cavities are described below with regard to FIGS. 77A, 77B, 78A, and 78B. While various aspects of such exemplary devices are provided, it is understood that phototherapy and light treatments according to the principles of the present disclosure may be administered by many different types of devices beyond the examples provided below. Devices for administering phototherapy and light treatments as described herein may embody hand-held devices, disposable devices, and devices that are incorporated or attached with larger medical equipment, among other device types. Additionally, such devices may be configured for partial or complete insertion within one or more body cavities. The phototherapy devices as described below for FIGS. 77A-78B may include any of the components as described for FIG. 40, including the microcontroller, the battery, the boost circuits, the charging integrated circuit, the microUSB connector, the user input buttons, the temperature and/or proximity sensor as previously described.

Figure 77A:
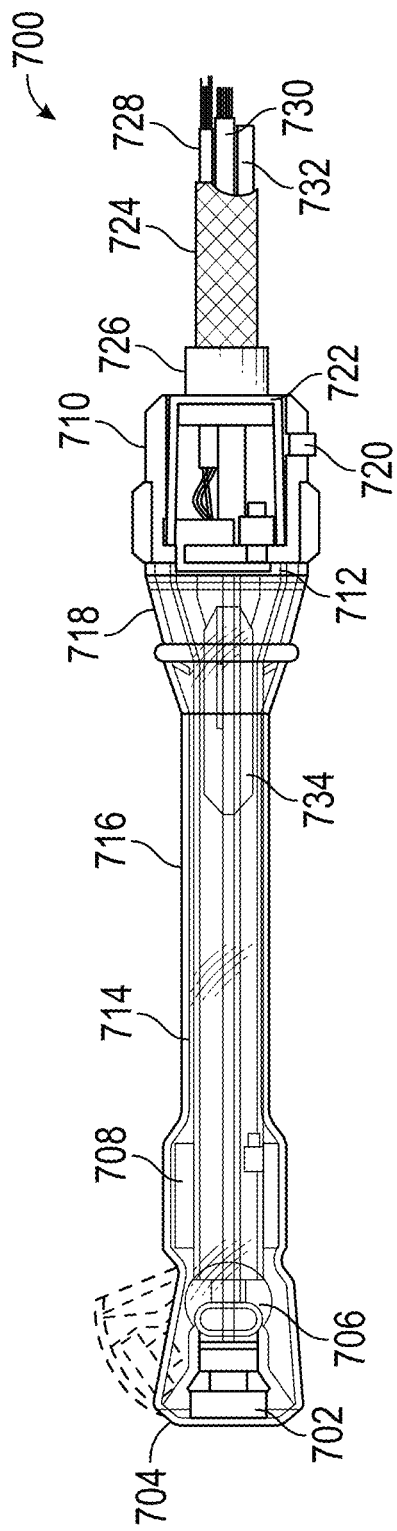
FIG. 77A is a schematic illustration of the inside of one embodiment of an illumination device for delivering light energy to tissue.

FIG. 77A illustrates an internal view of an exemplary illumination device 700 as described herein. As illustrated, the illumination device 700 may include a structure, such as a wand, that can be at least partially inserted into one or more body cavities, including intravaginally, intra-anally, orally, or within the nasal cavity. At one end, the illumination device 700 may include a lens optic 702 that is arranged within an illumination head 704. The lens optic 702 may be configured to pass light toward a target tissue and in certain embodiments, the lens optic 702 may be provided in optical communication with a camera for viewing the target tissue. The illumination head 704 may be coupled to a rotation yoke 706, thereby allowing the illumination head 704 to be adjustable to a number of tilt and/or rotation angles relative to the remainder of the illumination device 700. In certain embodiments, the illumination head 704 may be configured to tilt, angle, and/or rotate as much as 60 degrees from a lengthwise direction of the illumination device 700. The illumination device 700 may include an inflation bladder 708 that may be inflated for holding the illumination device 700 in place after insertion into a body cavity. A light source housing 710 may be provided at an opposite end of the illumination device 700 to the illumination head 704. For LED embodiments, the light source housing 710 may include an LED board 712 that is populated with one or more LEDs that are configured to provide any of the wavelength ranges described above. In particular, the LED board 712 may be configured to provide a single target peak wavelength or a plurality of different target peak wavelengths, depending on the application. A light guide housing 714 that includes at least one light guide is arranged between the illumination head 704 and the light source housing 710 to direct light from the LEDs to the illumination head 704. The light guide may include one or more of a waveguide and a fiber optic material. A sheath 716 may form a protective covering over the illumination head 704 and the light guide housing 714 along areas of the illumination device 700 that may be inserted within a body cavity. In certain embodiments, the sheath 716 may comprise silicone. In this regard, the LEDs (e.g., on the LED board 712) may be positioned outside of a body cavity and light from the LEDs may be delivered through the illumination head 704 that resides within the body cavity. The LED board 712 may further comprise driver circuitry for driving the LEDs. In certain embodiments, a screw-on locking cap 718 may be provided between the light guide housing 714 and the light source housing 710. The screw-on locking cap 718 may be configured to allow the light guide housing 714 and illumination head 704 to be removably attached to the light source housing 710. The illumination device 700 may further include a set screw 720, an insulation/wiring chamber 722, a flex cable 724 (e.g., braided polyvinyl chloride (PVC)) and corresponding strain relief 726, electrical wiring 728 (e.g., DC wiring), a video cable 730, and an air line 732 for inflating the inflation bladder 708. Circuitry for the camera, such as a camera printed circuit board 734, may be arranged within one or more of the light guide housing 714 and the light source housing 710.

Figure 77B:
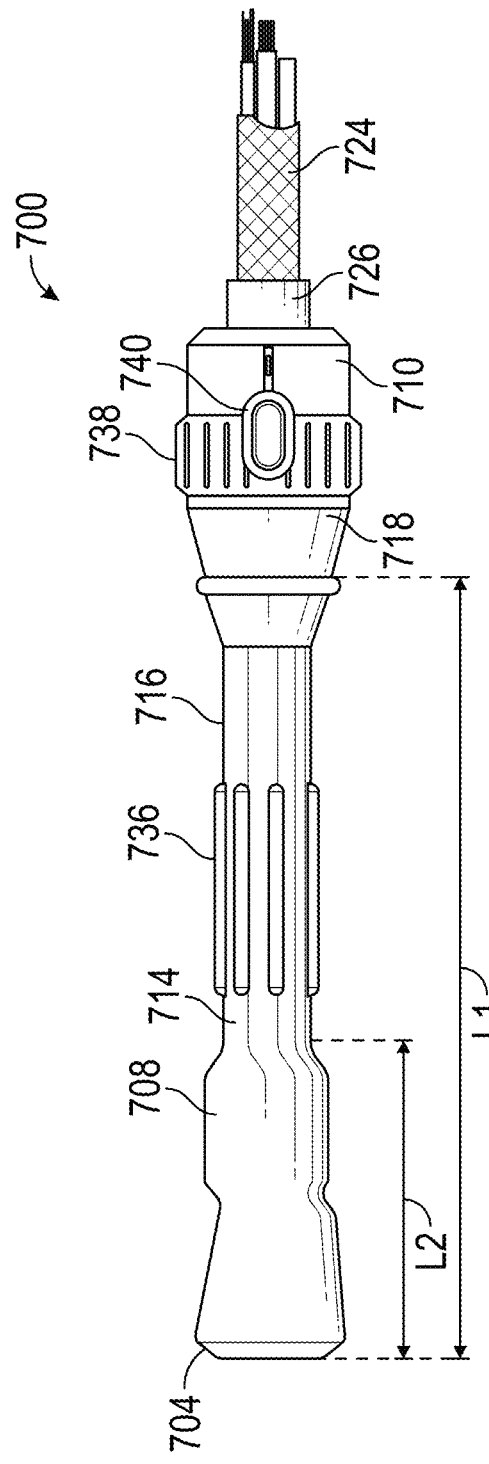
FIG. 77B is a schematic illustration of the device shown in FIG. 77A.

FIG. 77B illustrates an external view of the illumination device 700 of FIG. 77A. As illustrated, the inflation bladder 708 may be inflated and hold the illumination device 700 in place within a body cavity, for example within the vaginal canal, the anus, the oral cavity, and/or the nasal cavity. In certain embodiments, grip ridges 736 may be formed in the sheath 716 so that the sheath 716 may be rolled back from the light source housing 710, for ease of cleaning between uses. As describe above, the light guide housing 714 and illumination head 704 may form a detachable shaft that can be removably attached to the light source housing 710 by way of the locking cap 718. Dimensions of the detachable shaft may be determined based on the target body cavity. By way of example, for use in the vaginal canal, the detachable shaft may include a length L1 in a range from 75 mm to 160 mm, or in a range from 140 mm to 160 mm as measured by a length of the sheath 716 from the locking cap 718 to an end of the illumination device 700 at the illumination head 704. In certain embodiments, a combination of the inflation bladder 708 and the illumination head 704 may encompass a sub-dimension or sub-length L2 of the length L1 of the detachable shaft that is in a range from 25 mm to 55 mm. A grip ring 738, such as a polycarbonate ring, may be attached to the locking cap 718. The illumination device 700 may further include an adjustment control 740, such as a button or slide switch, that allows a user to adjust an angle of the illumination head 704 during operation so that the direction of light emissions and/or the direction of the camera are adjustable. The adjustment control 740 may further be lockable once a desired angle of the illumination head 704 is achieved.

Figure 78A:
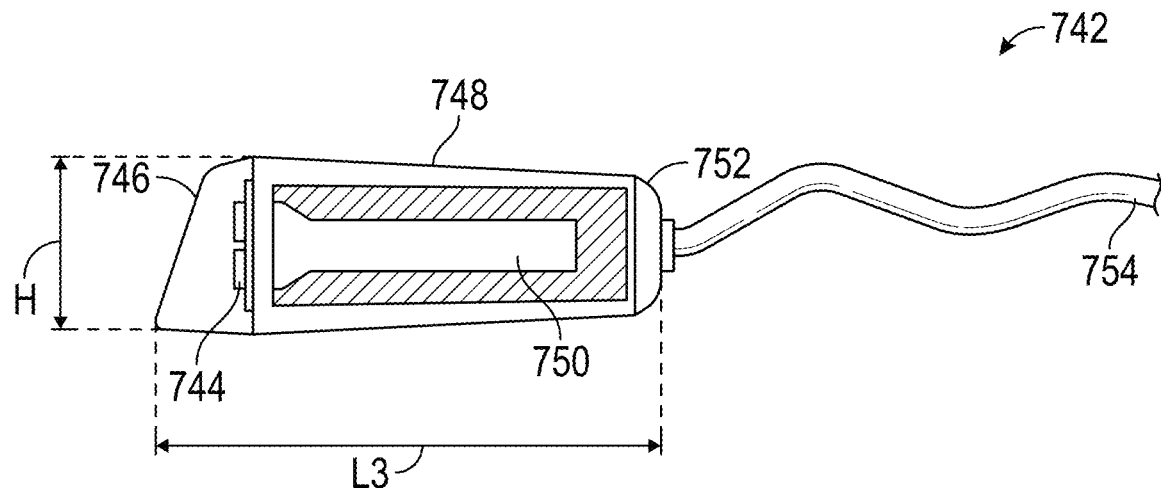
FIG. 78A is a schematic illustration of another device for delivering light energy to tissue.

FIG. 78A illustrates an internal view of an illumination device 742 that may be disposable according to principles of the present disclosure. The illumination device 742 may include a light source 744 that is covered by an optic 746. The light source 744 may include one or more single or multiple-LED packages that are configured to provide a single target peak wavelength or a plurality of different target peak wavelengths, depending on the application. While not shown, the single or multiple-LED packages may optionally include one or more lenses. The optic 746 may comprise silicone, e.g., a liquid silicone rubber and the like, and the optic 746 may form any shape for directing emissions from the light source 744 in a desired direction and/or pattern. By way of example, the optic 746 in FIG. 78A forms an angled shape that may preferentially direct emissions in a non-perpendicular direction from a mounting plane of the light source 744. The light source 744 may be at least partially encased in a protective covering 748 that together with the optic 746 seals the light source 744 within the illumination device 742. In certain embodiments, the protective covering 748 may comprise clear or light-transmissive material, such as silicone. In certain embodiments, the optic 746 is an integral single piece with the protective covering 748. Stated differently, a portion of the protective covering 748 may form the optic 746 in such embodiments. A heat sink 750 may be provided within the protective covering 748 and in thermal communication with the light source 744. The heat sink 750 may comprise any material with high thermal conductivity relative to other elements of the illumination device 742. In certain embodiments, the light source 744 may generate heat during operation and the heat sink 750 may accordingly form a heat pipe that provides a heat dissipation path away from the light source 744. A thermal sensor 752 and corresponding circuitry may also be provided within the protective covering 748 that is configured to electrically deactivate the light source 744 if a safe predetermined operating temperate range is exceeded. A cable 754 may also be arranged to power and control the light source 744. Additionally, the cable 754 may be used to retrieve the illumination device 742 from a body cavity after completion of phototherapy. In this regard, the illumination device 742 may be configured to be fully inserted within a body cavity, but for a portion of the cable 754. In certain embodiments, the protective covering 748 may also encase one or more portions of the cable 754. The illumination device 742 as described herein may be configured as a disposable device with a form factor that is suitable for single use and/or a limited number of uses. Dimensions of the illumination device 742 may be determined based on the target body cavity. By way of example, in certain embodiments, a length L3 as measured from an end of the optic 746 to the cable 754 may be provided in a range from 20 mm to 100 mm, or in a range from 20 mm to 80 mm, or in a range from 30 mm to 70 mm, or in a range from 40 mm to 60 mm. In certain embodiments, a height H or diameter of the illumination device 742 may be provided in a range from 1 mm to 20 mm, or in a range from 1 mm to 15 mm, or in a range from 5 mm to 15 mm.

Figure 78B:
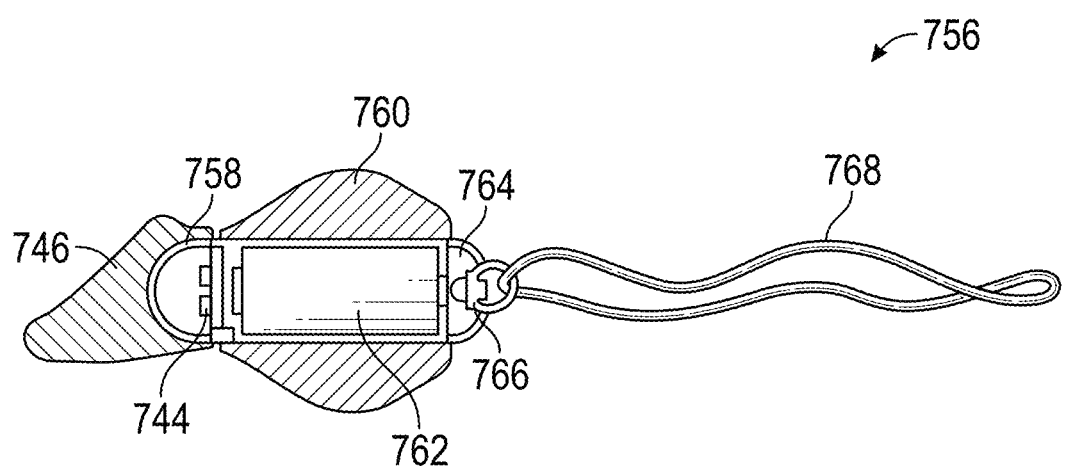
FIG. 78B is a schematic illustration of another device for delivering light energy to tissue.

FIG. 78B illustrates an internal view of another illumination device 756 that may be disposable according to principles of the present disclosure. The illumination device 756 may include the light source 744 and the optic 746 as described for the illumination device 742 of FIG. 78A. The light source 744 may comprise a packaged LED that optionally includes a lens 758. The lens 758, when present, and the optic 746 may together direct emissions from LEDs in a desired emission direction and/or pattern. One or more placement structures 760, such as placement wings of foam and/or silicone, may be provided for ensuring proper positioning within a particular body cavity. The illumination device 756 may configured with a power source 762, such as a battery, so that the illumination device 756 may embody a wireless device that does not require external electrical connections during use. A circuit element 764, such as a flexible circuit, may be provided within the illumination device 756 and an activation baffle 766 may be in communication with the circuit element 764. A cord 768 may be coupled with the activation baffle 766 so that when the illumination device 756 is positioned within a body cavity, the cord 768 may be used to activate the activation baffle 766 and to electrically activate the light source 744. The cord 768 may further allow retrieval of the illumination device 756 after phototherapy is complete. In certain embodiments, the activation baffle 766 may comprise silicone. Additionally, the entire device from the activation baffle 766 to the optic 746 may comprise the protective covering 748 as described for FIG. 78A. In other embodiments, the placement structures 760 may be separately formed around the illumination device 756. The illumination device 756 as described herein may be configured as a disposable device with a form factor that is suitable for single use and/or a limited number of uses.

A number of experiments are provided below that demonstrate various aspects of phototherapy according to principles of the present disclosure. The aspects include treatment of human papilloma virus (HPV)-infected tissues for FIGS. 79-81, inhibition of infection and/or replication of severe acute respiratory syndrome coronavirus 2 (SARS-CoV-2) for FIGS. 82A-95, and the efficacy of certain light against wild-type and Tamiflu-resistant influenza A viruses for FIGS. 96A-97D.

Figure 79B:
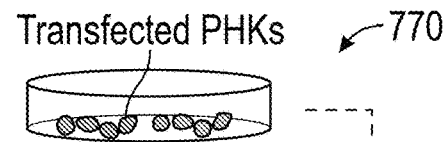
Figure 79C:
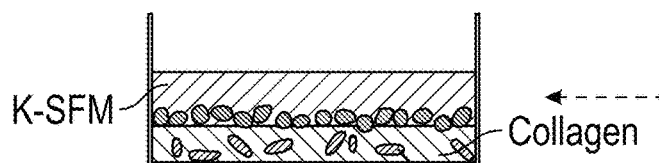
Figure 79D:
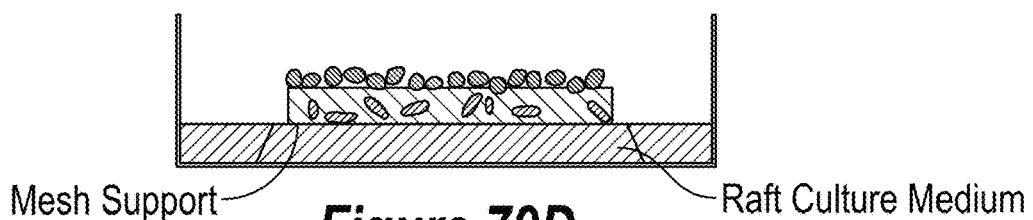
Figure 79E:
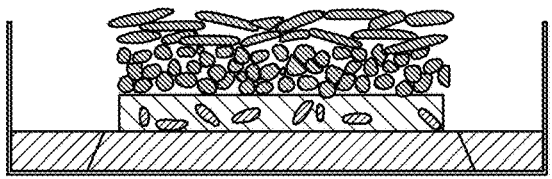
Figure 79F:
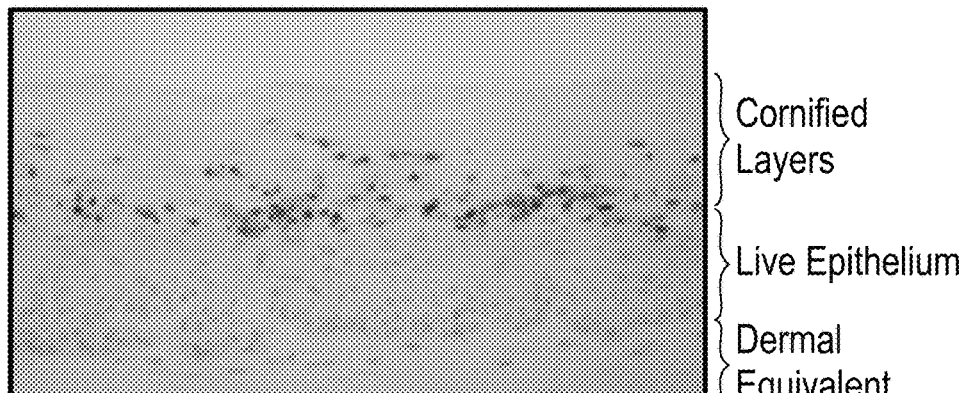

FIG. 79A-79F is an illustration of an experimental design 770 for treatment of HPV-infected tissues where an HPV-infected organotypic epithelial raft culture model was used to prepare HPV-infected tissue for performing anti-viral experiments. For the experiment, HPV-infected and non-infected organotypic epithelial cultures were provided. As shown in FIG. 79A, primary human keratinocytes (PHKs) that were isolated from circumcised neonatal foreskin are subjected to plasmid cotransfection. In FIG. 79B, transfected PHKs are selected based on drug selection and resistance. In FIG. 79C, the transfected PHKs are placed in a dish and cultured with Keratinocyte-Serum Free Medium (K-SFM) on a bed of a dermal equivalent. In this case, the dermal equivalent included a collagen support embedded with fibroblasts and held at a medium-air interface. In FIG. 79D, the transfected PHKs, collagen, and fibroblasts are then transferred to another dish with a mesh support and a raft culture medium. In step FIG. 79E, after greater than 9 days (in this case 10 days), the result is a collection of epithelial cells transfected with HPV-18 that are useful for performing antiviral experiments. FIG. 79F is a photograph showing HPV-IL L1 viral capsids as darker image features that are accumulated in the upper live cell strata and cornified layers by D16 in an organotypic raft culture prepared according to FIGS. 79A-79F. As shown in the photograph, there are cornified layers, live epithelium, and a dermal equivalent.

As provided by FIGS. 79A-79F, PHKs were isolated from circumcised neonatal foreskin and grown on a dermal equivalent. After 10 days, the keratinocytes were stratified and differentiated to form a squamous epithelium HPV-infected cultures transfected with HPV-18 genomic plasmid. HPV-infected and non-infected (or healthy) organotypic epithelial cultures were grown in the dark for six days. Certain cultures were exposed to phototherapy with LED light treatments on days 7-12 and harvested on day 13 for characterization. The phototherapy involved application of 428 nm light at the following daily-dosages for different culture samples: 12.5 J/cm$^2$, or 25 J/cm$^2$, or 50 J/cm$^2$, or 75 J/cm$^2$, or 100 J/cm$^2$, or 150 J/cm2 daily in either a 10-minute treatment period or with lower irradiance levels over a 7-hour treatment period. Control cultures for both HPV-infected and healthy samples were not exposed to phototherapy. For other cultures, the above daily dosages were repeated for 7-hour treatment periods.

The following assays were or may be performed on the above-prepared cultures: Histology by Hematoxylin and Eosin, indirect immunofluorescence detection of BrdU incorporation, Fluorescence In Situ Hybridization (FISH) to visualize HPV-18 DNA amplification, Immunofluorescence for γ-H2AX, a marker for double-stranded DNA breaks, TUNEL assay to evaluate apoptosis, Quantitative real-time PCR for HPV-18 DNA copy number, Immunofluorescence for PCNA, Immunoblot assays: E6, E7, E6AP, Tp53, pRB, p130, g-H2AX. HPV-18 E7-induced host DNA replication was abrogated following exposure to 50 J/cm$^2$ as indicated by a loss in BrdU positive nuclei. Similar trends were observed following either the 10-minute or 7-hour exposures. Similarly, host DNA replication in the basal strata was abolished following exposure to fluences of 50 J/cm$^2$ concluded to be due to the local heating of tissue samples >40° C. from drive currents exceeding 2.0 Amps required to deliver the 50 and 75 J/cm$^2$ doses in a 10-minute window.

One aspect of the present disclosure is that healthy cells and virus infected cells respond differently to various phototherapy treatments. Particularly, phototherapy differentially impacts the viability of healthy and infected cells; the viability of infected cells is retarded more strongly than the viability of healthy cells. In this regard, FIGS. 80A-80J and FIGS. 81A-81J are photomicrographs representing phototherapy experiments using light units with improved temperature control for HPV-infected and healthy cultures as described above and stained with Hematoxylin and Eosin.

Figure 80A:
FIGS. 80A-80J are photomicrographs of organotypic epithelial cultures which were either healthy (FIGS. 80A-80E) or infected with HPV-18 (FIGS. 80F-80J) where certain cultures were exposed to phototherapy over a 10-minute time period.
Figure 80F:
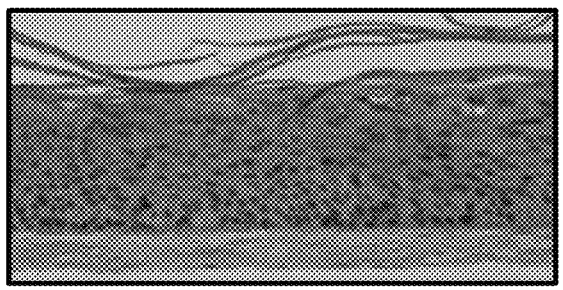
Figure 80B:
Figure 80G:
Figure 80C:
Figure 80H:
Figure 80D:
Figure 80I:
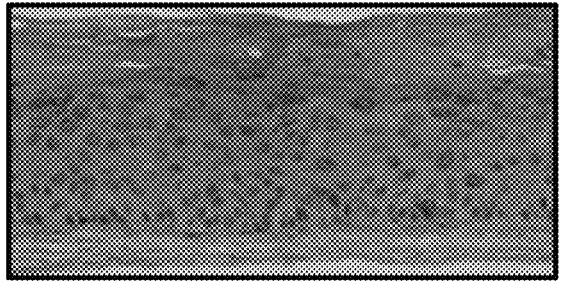
Figure 80E:
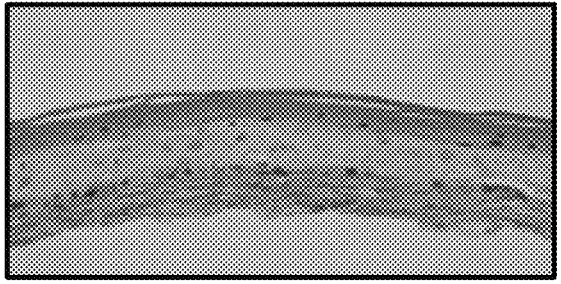
Figure 80J:
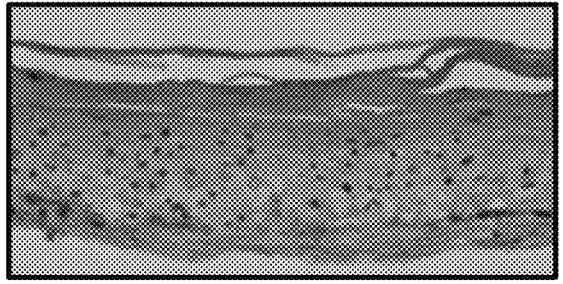

FIGS. 80A-80J are photomicrographs of organotypic epithelial cultures which were either healthy (FIGS. 80A-80E) or infected with HPV-18 (FIGS. 80F-80J) where certain cultures were exposed to phototherapy over a 10-minute time period. FIGS. 80A and 80F are healthy and infected control cultures respectively that were not subjected to phototherapy. FIGS. 80B and 80G were subjected to phototherapy at a dosage of 12.5 J/cm$^2$, FIGS. 80C and 80H were subjected to phototherapy at a dosage of 25 J/cm$^2$, FIGS. 80D and 80I were subjected to phototherapy at a dosage of 50 J/cm$^2$, and FIGS. 80E and 80J were subjected to phototherapy at a dosage of 75 J/cm$^2$. It was observed that altered terminal differentiation was affected by the phototherapy at 50 J/cm$^2$ for infected cultures (as evidenced by the overlap of keratinized and non-keratinized cells in FIG. 80I), while this was not observed in the correspondingly treated healthy cultures. Highly condensed nuclei, as shown by small dark features in FIGS. 80E and 80J, were evident in both infected and healthy cultures at 75 J/cm$^2$, indicative of apoptosis. It was observed that in healthy cultures, terminal differentiation appeared normal at 50 J/cm$^2$ (FIG. 80D) but was negatively affected by the phototherapy at a dose of 75 J/cm$^2$ (FIG. 80E) which again led to local tissue heating above 40° C.

Figure 81A:
FIGS. 81A-81J are additional photomicrographs of organotypic epithelial cultures which were either healthy (FIGS. 81A-81E) or infected with HPV-18 (FIGS. 81F-81J).
Figure 81F:
Figure 81B:
Figure 81G:
Figure 81C:
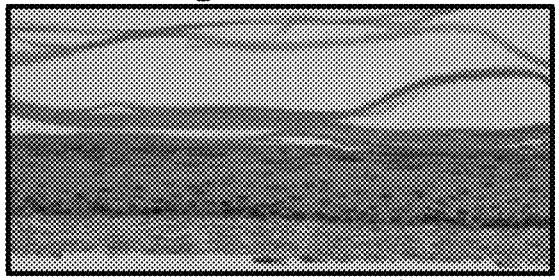
Figure 81H:
Figure 81D:
Figure 81I:
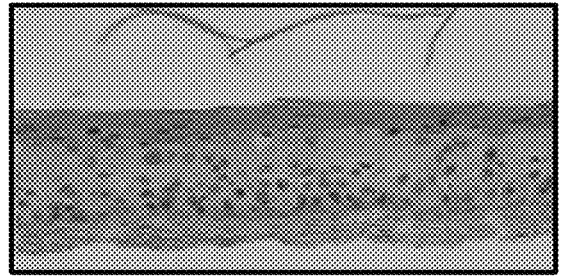
Figure 81E:
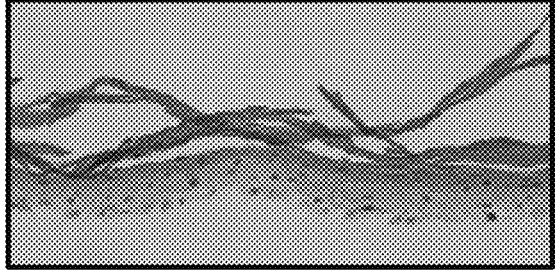
Figure 81J:
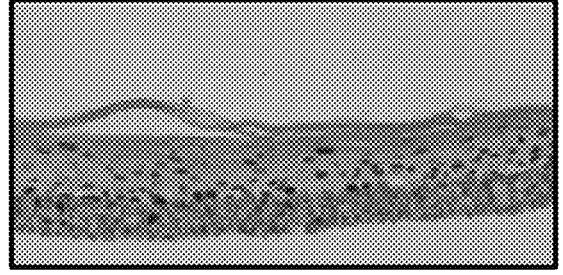
Figure 82A:
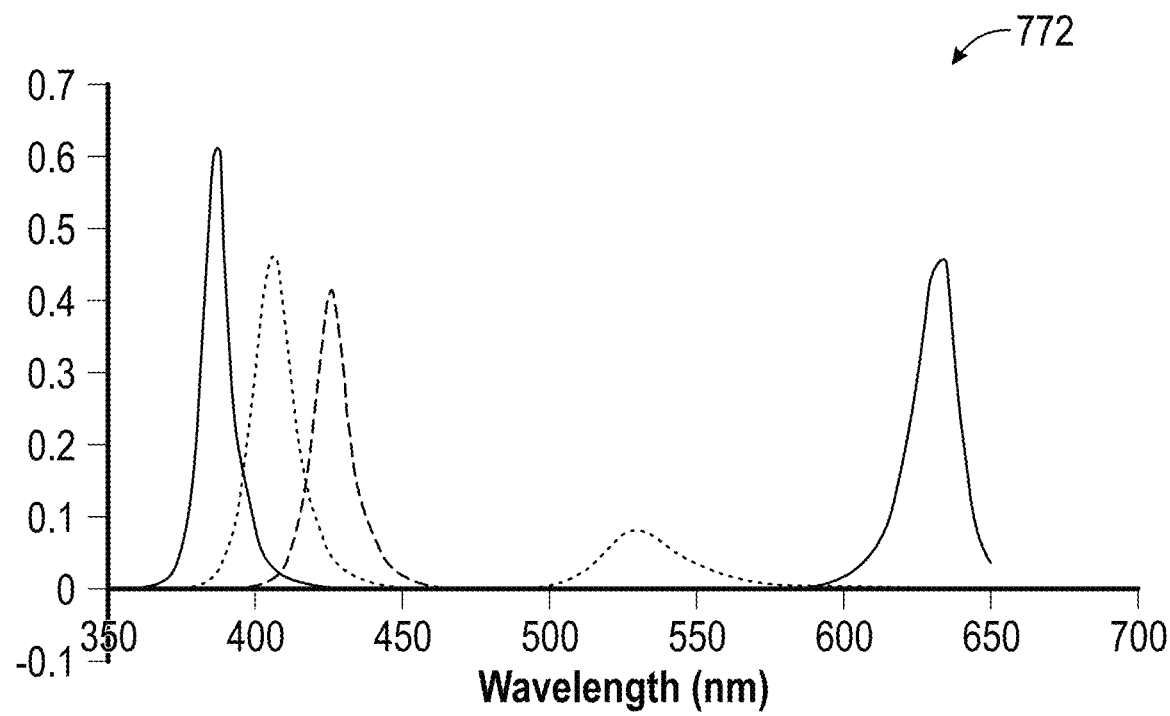
FIG. 82A is a chart illustrating measured spectral flux relative to wavelength for different exemplary LED arrays.
Figure 82B:
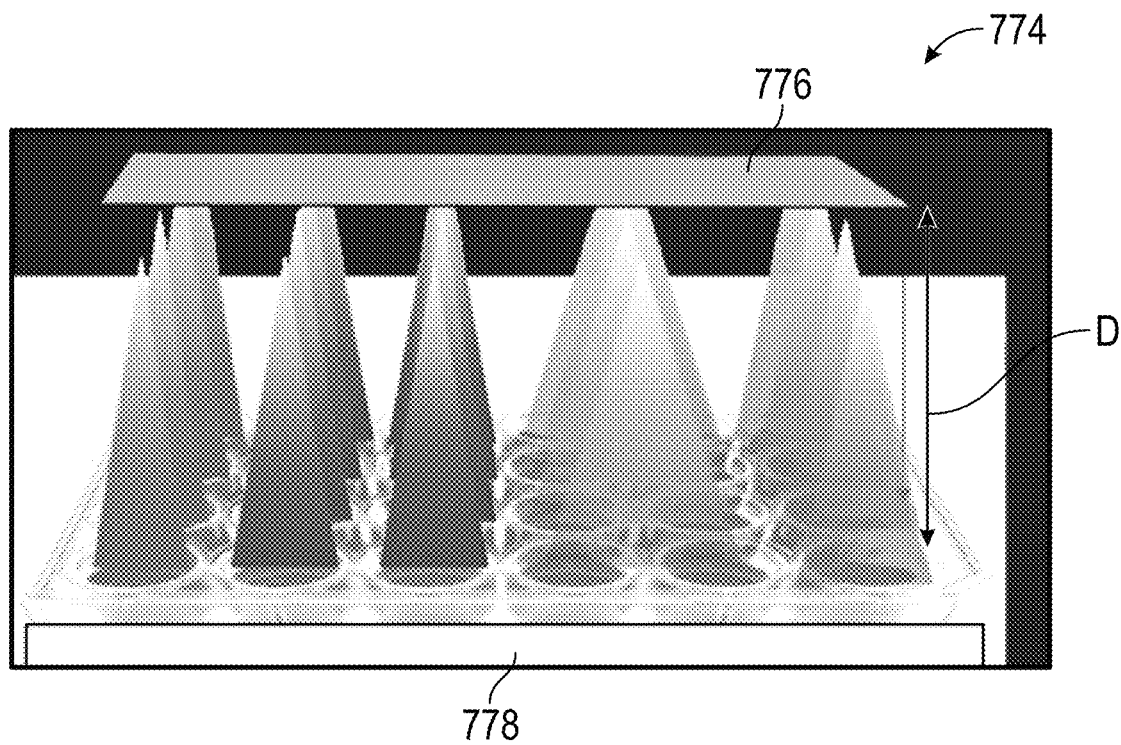
FIG. 82B illustrates a perspective view of a testing set-up for providing light from one or more LED arrays to a biological test article.

FIGS. 81A-81J are photomicrographs of organotypic epithelial cultures (described below in greater detail) which were either healthy (FIGS. 81A-81E) or infected with HPV-18 (FIGS. 81F-81J). The respective cultures illustrated in FIGS. 81A-81E were exposed to the same cumulative dosages as described for FIGS. 80A-80F of phototherapy, but over a 7-hour time frame. For the 7-hour exposure, terminal differentiation was observed by the phototherapy starting at 25 J/cm$^2$ (FIGS. 81C and 81H) for HPV-18 infected cultures. It was observed that in healthy cultures, terminal differentiation appeared normal at 50 J/cm$^2$ (FIG. 81D) but was affected by the phototherapy at 75 J/cm$^2$ (FIG. 81E). Highly condensed nuclei were evident in both cultures at 75 J/cm$^2$ (FIGS. 81E and 81J), indicative of apoptosis. Altered terminal differentiation, with overlap of keratinized and non-keratinized cells, is shown in FIG. 81H.

As demonstrated in the photomicrographs of FIGS. 80A-80J and FIGS. 81A-81J, altered terminal differentiation may be achieved in infected cultures before apoptosis of uninfected cultures. This may be evidenced by the observed terminal differentiation starting at 50 J/cm$^2$ for the 10-minute treatments and at 25 J/cm$^2$ for the 7-hour treatments. In both the 10-minute and 7-hour treatments, apoptosis is indicated at 75 J/cm$^2$. In the samples above, host cell DNA replication and proliferation was detected with Bromodeoxyuridine (BrdU) immunohistochemistry staining and DNA amplification was detected by HPV-18 fluorescence in situ hybridization. The 7-hour and 10-minute exposures were both effective in reducing or abolishing viral activity, with a percent reduction of HPV-18 DNA copy number/cell of approximately 40% for both 50 J/cm$^2$ dosing schedules. In the uninfected PHK cultures, only host cell replication was observed in the basal or bottom layer of cells. This normal replication was inhibited at 75 J/cm² at both 10-minute and 7-hour treatments histologically and confirmed via abundant TUNEL positivity. Based on this, it is observed that some DNA damage may occur as phototherapy dosages increase before apoptosis is realized, the physiological effects of which are not determined. Cell proliferation in layers above the basal layer was abnormal, driven by HPV infection. The 7-hour exposure at 50 J/cm² was effective in reducing both E6 and E7 activities, returning levels similar to normal uninfected raft cultures. Viral protein E7 reactivates cell cycle genes including Cyclin B1 and DNA damage response genes. The DNA damage response proteins stabilize p53, which in HPV-positive cells is normally destabilizing by high risk E6 protein. In these studies, 428 nm blue light results in stabilization of p53 and reduction of Cyclin B1. Abnormal cell proliferation was eliminated at 75 J/cm², a dose which caused apoptosis in uninfected cultures. Abnormal cell proliferation was reduced at 25 J/cm² and eliminated at 50 J/cm² for the longer 7-hour treatments. In this regard, potential phototherapy treatment protocols may be realized by inducing a biological effect in infected tissues, e.g., terminal differentiation in the example of HPV cultures, with applied dosages that provide reduced impact on healthy tissues.

While not wishing to be bound to a particular theory regarding action mechanisms, it is believed that blue light may induce oxidative and nitrosative stresses. Referring back to FIG. 75, oxidative stress may be caused by Type 1 and Type 2 reactions. Type 1 reactions can involve the excitation of an endogenous photosensitizer (most likely an endogenous porphyrin). This excited photosensitizer reacts with another cellular component to form a free radical directly (e.g. superoxide and hydroxyl groups). Type 2 reactions can involve the excitation of an endogenous photosensitizer (again, most likely a porphyrin) with oxygen to form singlet oxygen ($^1O_2$). Nitrosative stress may be induced by the increase in the enzymatic generation of nitric oxide and the photodissociation of endogenous nitric oxide. Experiments have been performed to show that high doses of blue light can increase the expression of nitric oxide synthase enzymes. The photodissociation of NO from endogenous stores is well known, with wavelength dependent release of NO from nitrosated/nitrosylated proteins. HPV infections may be inhibited by nitric oxide and NO-releasing serums may inhibit viral activity and can reduce HPV warts. Literature reports that NO from exogenous sources (e.g., sodium nitroprusside) can inhibit the proliferation and induce apoptosis in high risk HPV cell lines. The more progressed cervical carcinomas and HPV-positive dysplastic lesions become, the less inducible nitric oxide synthase (iNOS) is produced in the tissue. This means that pro-apoptotic concentrations of NO cannot be produced. Low concentrations of NO may enhance mutagenesis and increase VEGF-mediated angiogenesis.

While not wishing to be bound to a particular theory, it is believed that the phototherapy according to the present disclosure may proceed by one or two different pathways: 1) a nitric oxide pathway, where increased NOS expression and photodissociation of NO leads to increased NO levels, and thus nitrosative stress, and 2) an ROS pathway, where Type I and Type II photoreactions lead to increased ROS levels, which leads to oxidative stress. In either pathway, inhibited cell proliferation, altered terminal differentiation, DNA damage to host cells, DNA damage to virus, and apoptosis can be observed. It is proposed that a mechanism of action is that, at increasing phototherapy light doses, infected cultures have DNA damage to host cells, reduced cell proliferation, and altered terminal differentiation. At higher dosages, infected cultures see an inhibition of virus, an eradication of virus, and apoptosis of host cells. In non-infected cultures, reduced cell proliferation is observed. At still higher dosages, non-infected cultures undergo apoptosis. Accordingly, by using phototherapy to increase NO levels to apoptotic concentrations by increasing free NO and iNOS, one can treat HPV infection. Cells infected with HPV are more sensitive to reactive oxygen species. HPV infected cells are in a state of chronic oxidative stress. This makes them more susceptible to ROS generated by blue light. HPV upregulates E6 protein. The E6 onco-protein increases ROS levels in cells and decreases the expression of superoxide dismutase (an enzyme used to mitigate superoxide and convert it to $O_2$ or $H_2O_2$).

In another example, aspects are provided in relation to phototherapy with blue light for the inhibition of infection and replication of SARS-CoV-2. The delivery of safe, visible wavelengths of light can be an effective, pathogen-agnostic, antiviral therapeutic countermeasure that would expand the current portfolio of intervention strategies for SARS-CoV-2 and other respiratory viral infections beyond the conventional approaches of vaccine, antibody, and drug therapeutics. Employing LED arrays, specific wavelengths of visible light may be harnessed for uniform delivery across various targeted biological surfaces. In certain aspects of the present disclosure, it is demonstrated that primary 3D human tracheal/bronchial-derived epithelial tissues exhibited differential tolerance to light in a wavelength and dose-dependent manner. Primary 3D human tracheal/bronchial tissues tolerated high doses of 425 nm peak wavelength blue light. These studies were extended to Vero E6 cells to provide understanding of how light may influence viability of a mammalian cell line conventionally used for assaying SARS-CoV-2. Exposure of single-cell monolayers of Vero E6 cells to similar doses of 425 nm blue light resulted in viabilities that were dependent on dose and cell density. Doses of 425 nm blue light that are well-tolerated by Vero E6 cells also inhibited SARS-CoV-2 replication by greater than 99% at 24 hours post-infection after a single five-minute light exposure. Red light at 625 nm had no effect on SARS-CoV-2 replication, or cell viability, indicating that inhibition of SARS-CoV-2 replication is specific to the antiviral environment elicited by blue light. Moreover, 425 nm visible light inactivated up to 99.99% of cell-free SARS-CoV-2 in a dose-dependent manner. Importantly, doses of 425 nm light that dramatically interfere with SARS-CoV-2 infection and replication are also well-tolerated by primary human 3D tracheal/bronchial tissue. In this regard, safe, deliverable doses of visible light may be considered part of a strategic portfolio for development of SARS-CoV-2 therapeutic countermeasures to prevent coronavirus disease 2019 (COVID-19).

Among other approaches for treating SARS-CoV-2 infection, there are nucleoside analogs such as Remdesivir, and convalescent plasma, both separately demonstrated to shorten time to recovery for Covid-19 patients. The glucocorticoid dexamethasone was demonstrated to lower the mortality rate in individuals receiving oxygen alone or mechanical ventilation support. To curb the long timelines associated with clinical safety and efficacy trials for traditional drug therapeutics, researchers are briskly working to evaluate FDA-approved drug therapeutics against SARS-CoV-2. Although encouraging, many of the current strategies are SARS-CoV-2 specific and target the virus either outside (cell-free virus), or inside the cell (cell-associated, replicating virus). Expanding the therapeutic armory beyond conventional strategies may expedite the availability of therapeutic countermeasures with non-specific antiviral properties that can inactivate cell-free and cell-associated virus.

Light therapy has the potential to inactivate both cell-free and cell-associated virus. Mitigating SARS-CoV-2 infection with light therapy requires knowledge of which wavelengths of light most effectively interfere with viral infection and replication, while minimizing damage to host tissues and cells. A large body of literature demonstrates that ultraviolet light, predominantly UVC at the 254 nm wavelength, is highly effective at inactivating cell-free coronaviruses on surfaces, aerosolized, or in liquid. UVC inactivates coronaviruses, as well as many other RNA and DNA viruses, through absorption of UVC photons by pyrimidines in the RNA backbone, leading to the formation of pyrimidine dimers that preclude replication of the coronavirus genome. UVC is also highly damaging to replicating mammalian cells, causing perturbations in genomic DNA that can increase the risk of mutagenic events. As such, viral inactivation with UV light is primarily limited to cell-free environmental applications. In the present disclosure, inactivating coronaviridae, including coronaviruses, with safe, visible light (e.g., above 400 nm) is presented as a new approach to interfering with SARS-CoV-2 infection and replication.

Photobiomodulation (PBM), or light therapy, is an approach to mitigate outcomes of viral infection in mammals, such as humans. PBM may also refer to phototherapy as disclosed herein. PBM is the safe, low-power, illumination of cells and tissues using light-emitting diodes (LEDs) or low-level laser therapy (LLLT) within the visible/near-infrared spectrum (400 nm-1050 nm). Importantly, the therapeutic effect is driven by light's interaction with photoacceptors within the biological system, and is not to be confused with photodynamic therapy (PDT), which employs the exogenous addition of photosensitizers or chemicals to induce reactive oxygen species (though the addition of photosensitizers or other chemicals to induce reactive oxygen species is another embodiment within the scope of the methods described herein).

The safe and effective use of blue light PBM in the 450-490 nm range was adopted for mainstream clinical use in the late 1960's to treat jaundice in neonates caused by hyperbilirubinemia, and continues to be employed in hospitals today as a primary treatment for hyperbilirubinemia. According to aspects of the present disclosure, changing the wavelengths of visible light based on targeted applications can broaden the scope of therapeutic applications. Studies also indicate that PBM with visible light may function to inactivate replication of RNA and DNA viruses in vitro. Importantly, several studies demonstrate that PBM therapy can be safely applied to the oral and nasal cavities to treat a spectrum of illnesses. As disclosed herein, PBM therapy in the oral and nasal cavities, as well as in the lungs or endothelial tissues, may be an effective means of mitigating replication of SARS-CoV-2 in the upper respiratory tract, so long as it can be done at doses which do not significantly affect the viability of the tissues being treated. A deeper exploration of the precise selection of optical irradiance (e.g., in $mW/cm^2$) combined with one or more monochromatic wavelengths of visible light can broaden the scope of therapeutic applications in respiratory medicine.

In order to evaluate the safety of visible light on cells and tissues in vitro and the efficacy of visible light in SARS-CoV-2 infectious assays, careful designs of LED arrays having narrow band emission spectra with peak wavelengths at 385 nm, 405 nm, 425 nm, and 625 nm wavelengths are provided and summarized in FIGS. 82A and 82B. In this manner, LED arrays may be properly calibrated to provide repeatable and uniform doses of light so that illumination may occur reliably across many assays and in multiple laboratories. Measuring the full emission spectrum around the peak emission wavelength is necessary to confirm proper function for each LED array and the photon density per nanometer. In this regard, such measurements are recommended as an important characterization step to help harmonize the variability of results published in literature. FIG. 82A is a chart 772 illustrating measured spectral flux relative to wavelength for different exemplary LED arrays. Each LED array was independently characterized by measuring the spectral flux, which may be measured in W/nm, relative to the wavelength (nm). In FIG. 82A, an LED array with a peak wavelength of 385 nm is clearly within the upper bounds of the UVA spectrum (315-400 nm), whereas only a small amount (e.g., about 10%) of an LED array with a peak wavelength of 405 nm light extends into the UVA spectrum, and an LED array with a peak wavelength of 425 nm light is 99% within the visible light spectrum (400-700 nm). FIG. 82B illustrates a perspective view of a testing set-up 774 for providing light from one or more LED arrays 776 to a biological test article 778. In addition to the design of the LED arrays 776, including the emission spectrums, other important experimental conditions including a distance D of the LED arrays 776 from the biological test article 778 (e.g., 90 mm) an illumination power (e.g., 25 $mW/cm^2$ or 50 $mW/cm^2$ depending on the wavelength), and indicated doses ($J/cm^2$) were carefully calibrated to reduce any effects of temperature on the biological test articles 778. Moreover, each LED array 776 is validated to ensure that light is evenly distributed across multi-well tissue culture plates, such that the biological test articles 778 in each replicate well receive uniform doses of light.

Understanding how target tissues in the upper airway tolerate blue light is central to the development of a light-derived antiviral approach for SARS-CoV-2. Initial evaluation of LED arrays was conducted on 3D tissue models developed from cells isolated from bronchial/tracheal region of a single donor. The 3D EpiAirway tissue models are 3-4 cell layers thick comprising a mucociliary epithelium layer with a ciliated apical surface. To assess the wavelength and doses of light most tolerated by these tissues, replicate tissue samples were exposed to 385 nm, 405 nm, or 425 nm light at various doses. Viability was assayed at 3 hours post-exposure using the indicated doses and wavelengths of light, and data is represented as +/−standard deviation. The percent viability of tissue was assessed using a well-established MTT cytotoxicity assay optimized for the 3D EpiAirway tissue models. FIG. 83A is a chart 780 illustrating a percent viability for a peak wavelength of 385 nm for doses in a range from 0 to 120 $J/cm^2$. FIG. 83B is a chart 782 illustrating a percent viability for a peak wavelength of 405 nm for the same doses of FIG. 83A. FIG. 83C is a chart 784 illustrating a percent viability for a peak wavelength of 425 nm for the same doses of FIG. 83A. As illustrated in FIGS. 83A-83C, the percent viability of tissue was clearly impacted in a wavelength-dependent and a dose-dependent manner. Illumination with 385 nm light exhibited the most dramatic loss in viability with nearly a 50% decrease at a dose of 60 $J/cm^2$ (FIG. 83A). Light at 385 nm actually showed increased cell viability at doses of 15 $J/cm^2$. Although less dramatic, 405 nm light exhibited a dose-dependent decrease in viability with greater than 25% loss at 60 $J/cm^2$ and about a 50% loss at 120 $J/cm^2$ (FIG. 83B).

Notably, the 425 nm light was well tolerated at doses of light out to 120 J/cm² (FIG. 83C). Using 75% viability as a threshold level of acceptable cytotoxicity, 385 nm light may be safely administered to these tissues at power levels of up to 30 J/cm², and 405 nm light may be safely administered to these tissues at power levels of up to 45 J/cm², and 425 nm light may be safely administered to these tissues at power levels up to 120 J/cm² with only negligible loss of viability between 90 and 120 J/cm², and 425 nm doses up to around 75 J/cm² actually showed increased cell viability.

In this regard, 425 nm blue light is shown to have little or no impact on human upper airway-derived 3D tissue models. As such, longer wavelengths of visible light such as 425 nm and greater that do not bleed into the UVA spectrum may have reduced impact on tissue viability of primary human tissue derived from the upper respiratory tract. In particular, less than 20% tissue loss may be realized at higher doses with such longer wavelengths. Based on these studies, visible blue light at 425 nm was chosen for subsequent evaluation in the widely available Vero E6 cell line, conventionally used to evaluate SARS-CoV-2 infection and replication.

Vero E6 cells are commonly used for preparing stocks, performing growth curves, and evaluating therapeutic countermeasures for SARS-CoV-2. Depending on the type of assay being performed it could be necessary to vary the seeding cell density and multi-well tissue culture plate format. Often, cell viability is evaluated to determine if the antiviral properties of a therapeutic can be parsed from potential therapeutic-induced cytotoxic effects. Experiments were performed to determine if cell density and multi-well plate format can influence cell viability upon exposure to 425 nm blue light. To effectively evaluate the cell viability, the cytotoxicity assay was optimized for use with Vero E6 cell densities up to $1 \times 10^6$ cells.

Figure 84A:
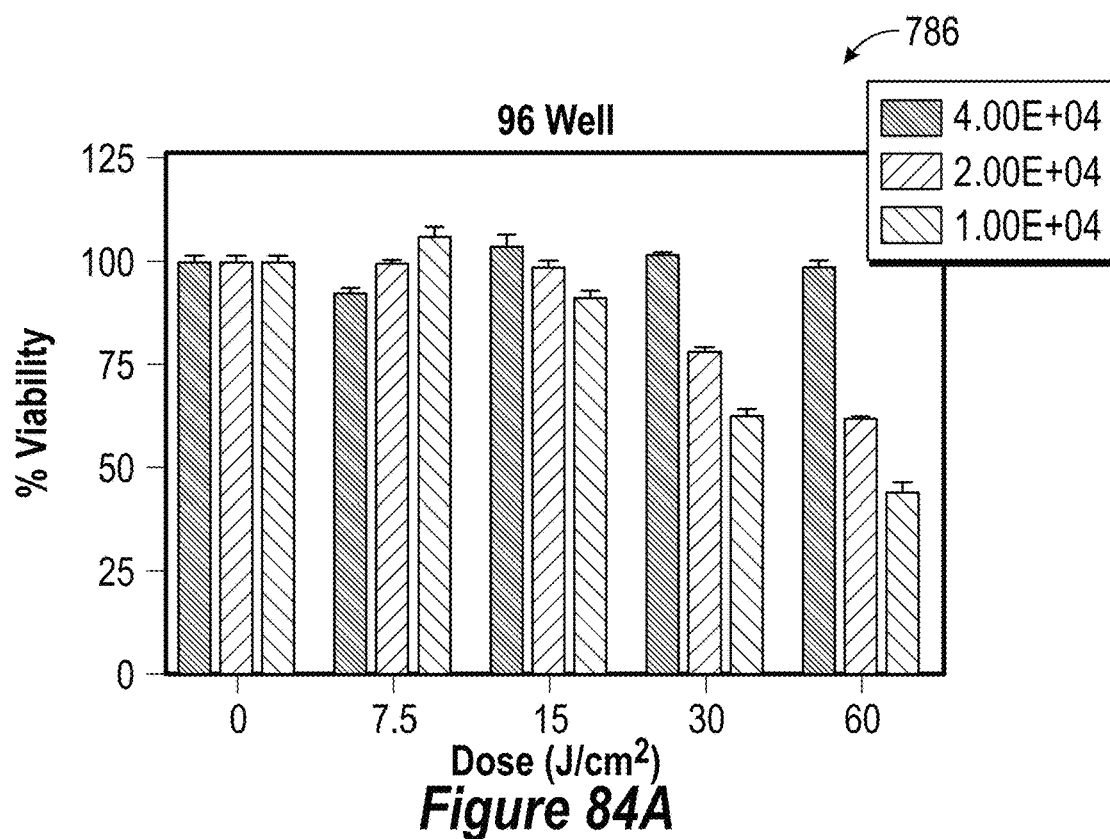
FIG. 84A is a chart illustrating percent viability for Vero E6 cells for antiviral assays performed on ninety-six well plates at various cell seeding densities.
Figure 84B:
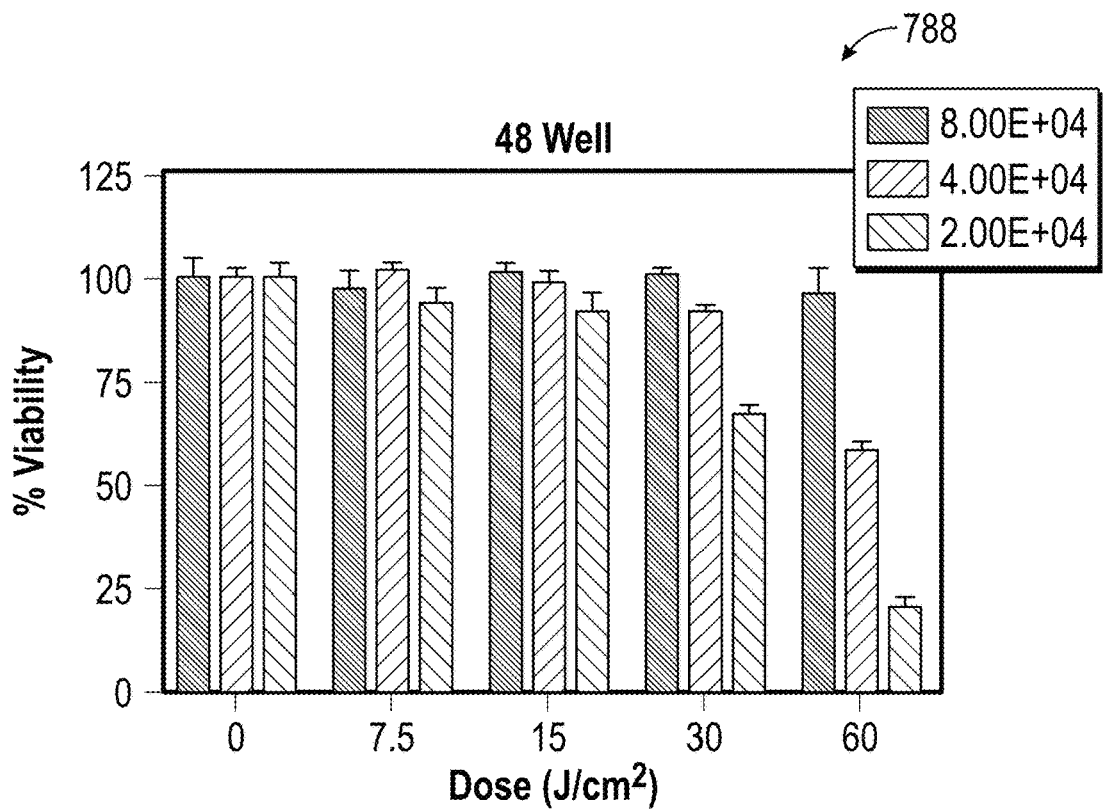
FIG. 84B is a chart illustrating percent viability for Vero E6 cells for antiviral assays performed on forty-eight well plates at various cell seeding densities.
Figure 84C:
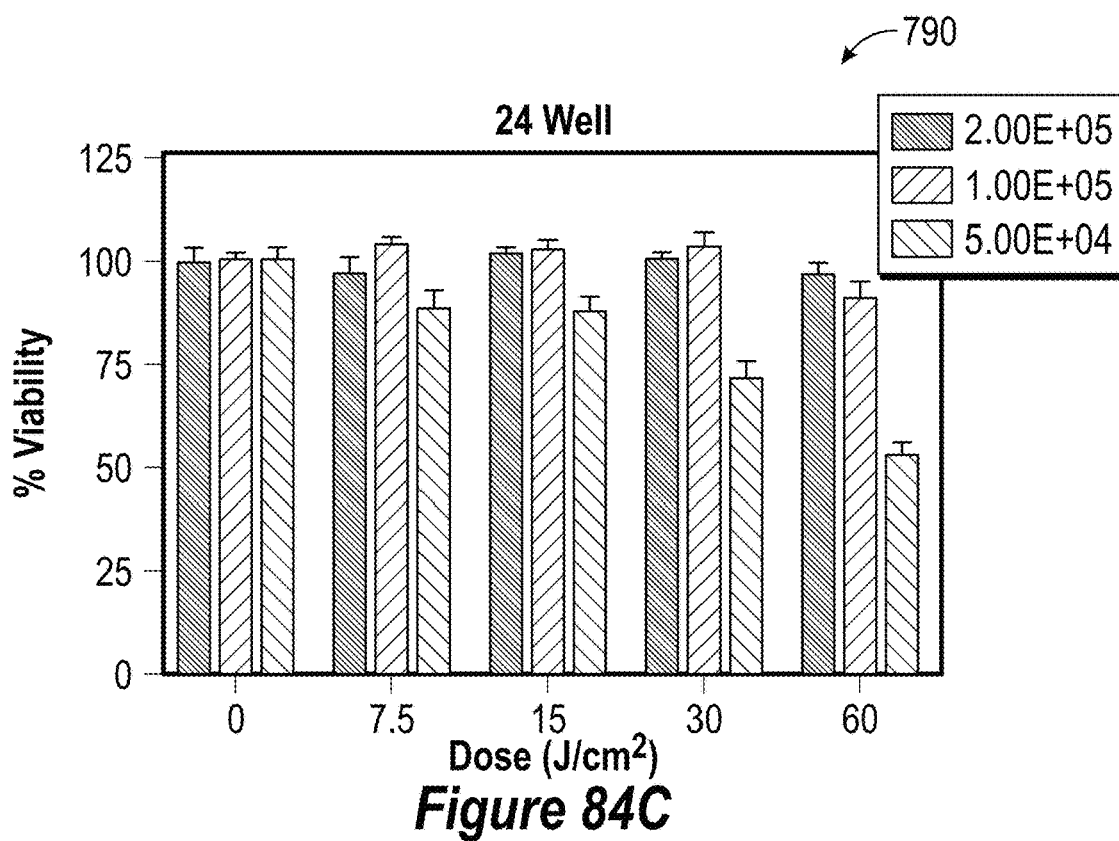
FIG. 84C is a chart illustrating percent viability for Vero E6 cells for antiviral assays performed on twenty-four well plates at various cell seeding densities.

FIG. 84A is a chart 786 illustrating percent viability for Vero E6 cells for antiviral assays performed on 96 well plates at cell seeding densities of $1 \times 10^4$, $2 \times 10^4$, and $4 \times 10^4$ cells. Under these conditions, it is illustrated that 425 nm blue light may result in decreased cell viability (e.g., 25-50%) at doses of 30 J/cm² and 60 J/cm² by 24 hours post-illumination, whereas a seeding density of $4 \times 10^4$ cells tolerates high doses of light exposure. FIG. 84B is a chart 788 illustrating percent viability for Vero E6 cells for antiviral assays performed on 48 well plates at cell seeding densities of $2 \times 10^4$, $4 \times 10^4$, and $8 \times 10^4$ cells. Unexpectedly, $4 \times 10^4$ cells seeded on a 48-well plate were not well tolerated, showing about a 50% reduction in cell viability at a dose of 60 J/cm² compared to $8 \times 10^4$ cells. These results demonstrated that the cell seeding density relative to the surface area of the culture well influences the susceptibility to 425 nm light. FIG. 84C is a chart 790 illustrating percent viability for Vero E6 cells for antiviral assays performed on 24 well plates at cell seeding densities of $5 \times 10^4$, $1 \times 10^5$, and $2 \times 10^5$ cells. As illustrated, the 24 well plate format of FIG. 84C with cell seeding densities of $1 \times 10^5$ and $2 \times 10^5$ demonstrated acceptable viability at all doses tested. In contrast, illumination of Vero E6 cells to high doses of 625 nm light may have no impact on cell viability; thereby, indicating that cell density-dependent susceptibility of Vero E6 cells to 425 nm light appears to be characteristic of shorter wavelengths of light. Higher Vero E6 seeding densities resulted in 100% cell confluence prior to illumination, exhibiting cell-to-cell contact that mimics the 3D EpiAirway models. Thus, high confluence Vero E6 cell monolayers readily tolerate 425 nm blue light as well as 3D EpiAirway tissue models.

Figure 85A:
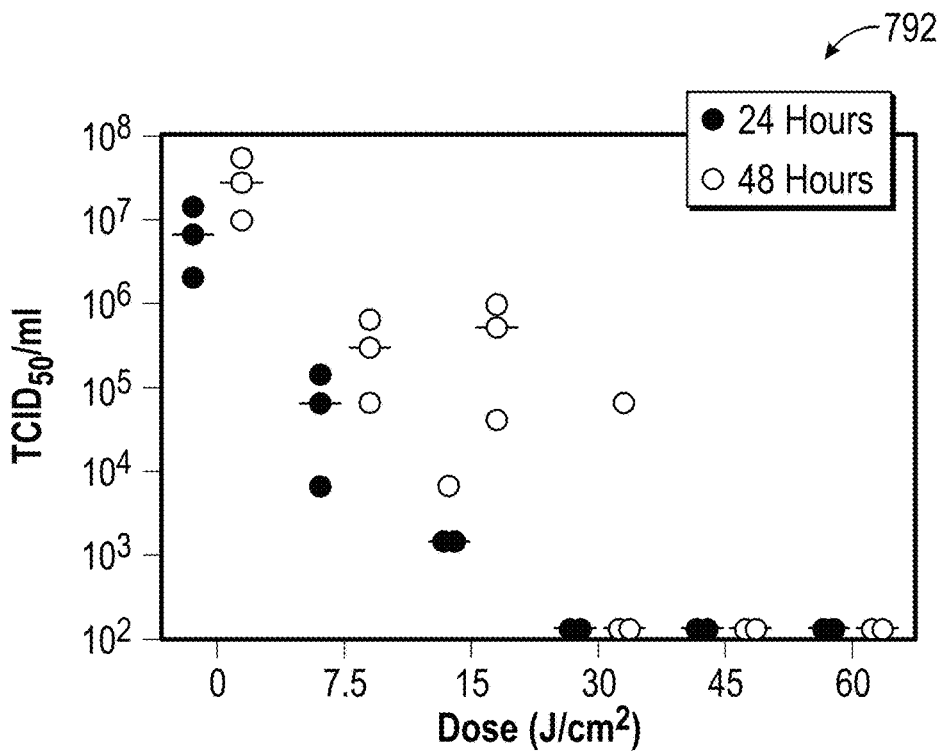
FIG. 85A is a chart illustrating tissue culture infectious dose ($TCID_{50}$) per milliliter (ml) for the 425 nm light at the various dose ranges for Vero E6 cells infected with a multiplicity of infection (MOI) of 0.001 SARS-CoV-2 isolate USA-WA1/2020 for 1 hour.
Figure 85B:
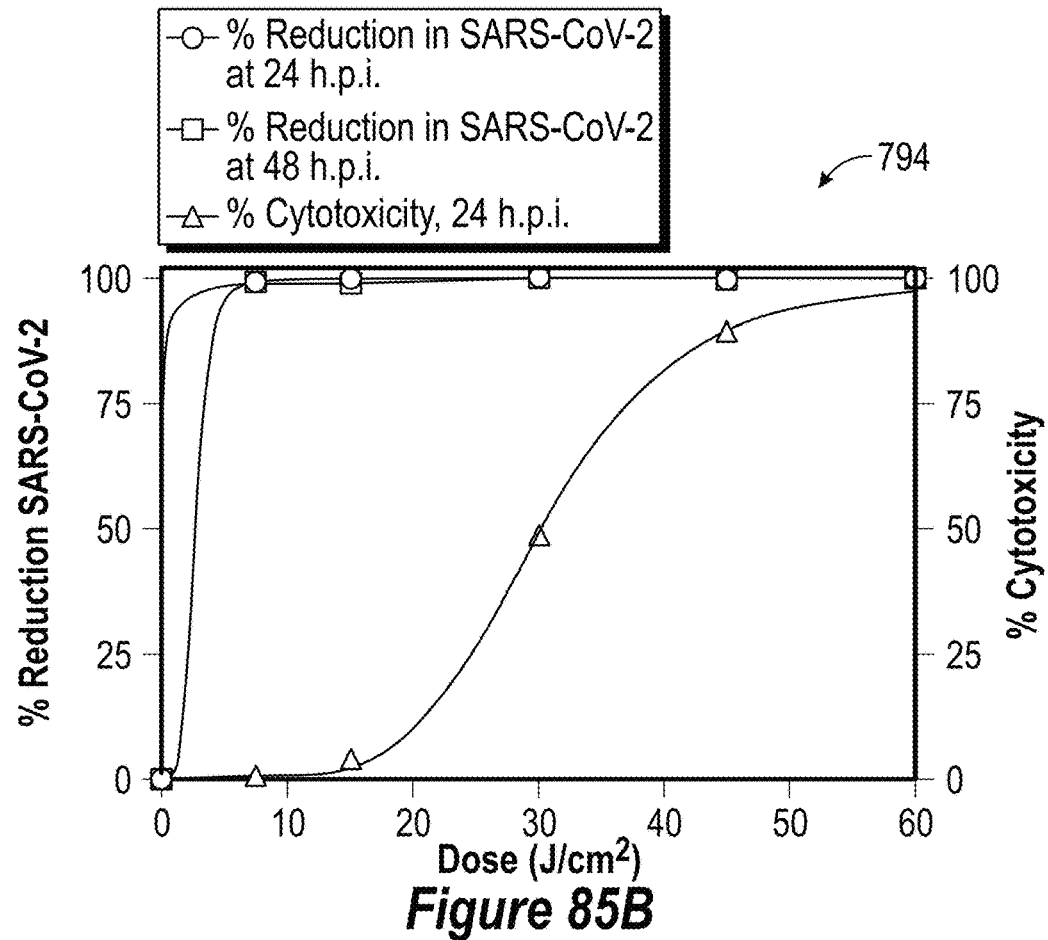
FIG. 85B is a chart illustrating percent reduction in SARS-CoV-2 replication versus percent cell cytotoxicity for the doses of light as illustrated in FIG. 62A.

The use of visible light to inactivate cell-free and cell-associated coronaviridae, including coronaviruses, is unprecedented. To assess the capability of 425 nm blue light to inactivate SARS-CoV-2, Vero E6 cells were infected with a multiplicity of infection (MOI) of 0.001 SARS-CoV-2 isolate USA-WA1/2020 for 1 hour. At 1 hour post-infection (h.p.i.) the cell-associated virus was treated with a single illumination of 425 nm blue light at doses ranging from 7.5 to 60 J/cm². FIG. 85A is a chart 792 illustrating tissue culture infectious dose ($TCID_{50}$) per milliliter (ml) for the 425 nm light at the doses ranging from 7.5 to 60 J/cm² for the Vero E6 cells infected with a MOI of 0.001 SARS-CoV-2 isolate USA-WA1/2020 for 1 hour. At 24 h.p.i, there was a clear dose-dependent decrease in SARS-CoV-2 $TCID_{50}$/ml. Low doses of 425 nm light were sufficient to reduce SARS-CoV-2 by at least 2 logs for 7.5 J/cm², at least 3 logs for 15 J/cm², and at least a 5 log reduction for 30 J/cm². A similar trend was observed at 48 h.p.i., although continued viral replication may account for the similarity in $TCID_{50}$/ml observed at low doses between 7.5 J/cm² and 15 J/cm². This data demonstrates that 425 nm blue light interferes with SARS-CoV-2 replication in a dose-dependent manner. Specific $TCID_{50}$/ml values are presented to demonstrate data trends and data values relative to on another, the actual values may vary from lab to lab are not meant to be limiting. FIG. 85B is a chart 794 illustrating percent reduction in SARS-CoV-2 replication versus percent cell cytotoxicity for the doses of light as illustrated in FIG. 85A. At doses of light that have little impact on the viability of Vero E6 cells (e.g., 7.5, 15, and 30 J/cm²), up to a 99.99% reduction in SARS-CoV-2 replication was observed. Notably, cell viability was a bit lower at 45 J/cm² and 60 J/cm² than the data shown in FIGS. 83A-83C; however, slight variations in the cytotoxicity assay are anticipated since the SARS-CoV-2 experiments were executed in independent laboratories with differences in cell seeding, cell passage, and cell media.

Figure 86A:
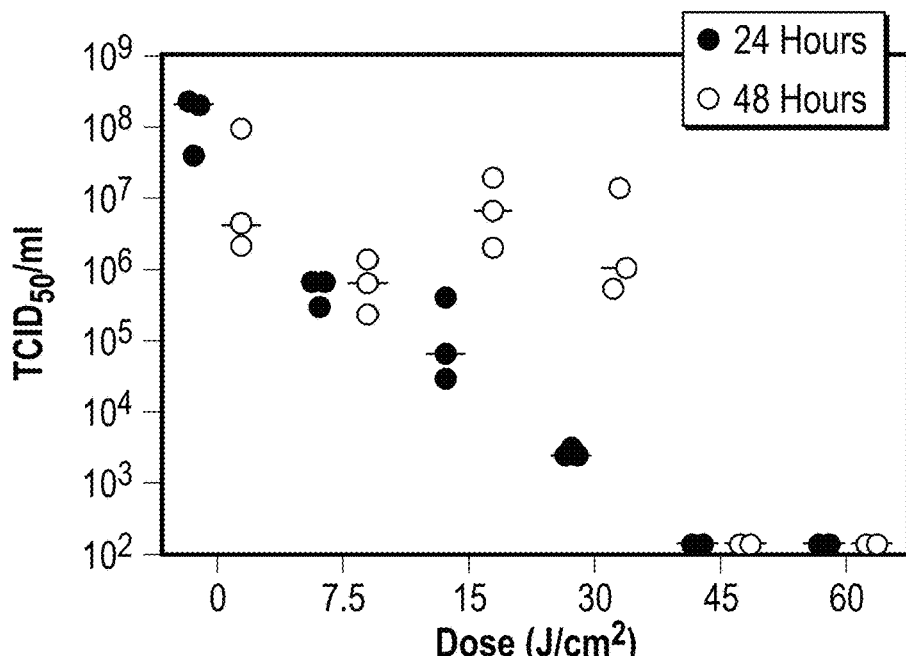
FIG. 86A is a chart illustrating $TCID_{50}$/ml for 425 nm light at various dose ranges for Vero E6 cells infected with a MOI of 0.01 SARS-CoV-2 isolate USA-WA1/2020 for 1 hour.
Figure 86B:
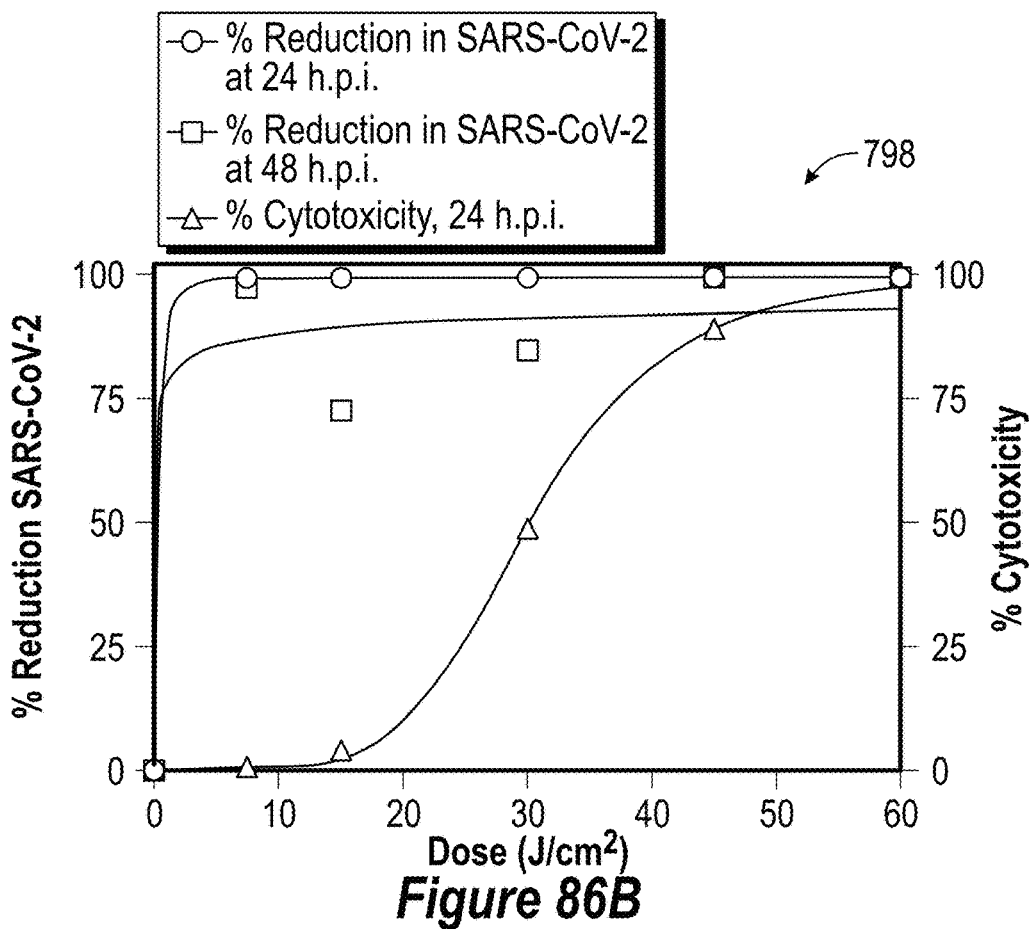
FIG. 86B is a chart illustrating percent reduction in SARS-CoV-2 replication versus percent cell cytotoxicity for the doses of light as illustrated in FIG. 63A.

FIGS. 86A and 86B represent experimental data similar to FIGS. 85A and 85B, but with the MOI increased to 0.01. FIG. 86A is a chart 796 illustrating $TCID_{50}$/ml for 425 nm light at doses ranging from 7.5 to 60 J/cm² for Vero E6 cells infected with a MOI of 0.01 SARS-CoV-2 isolate USA-WA1/2020 for 1 hour. Specific $TCID_{50}$/ml values are presented to demonstrate data trends and data values relative to on another, the actual values may vary from lab to lab and are not meant to be limiting. FIG. 86B is a chart 798 illustrating percent reduction in SARS-CoV-2 replication versus percent cell cytotoxicity for the doses of light as illustrated in FIG. 86A. As illustrated, increasing the MOI to 0.01 yielded a similar dose-dependent reduction in SARS-CoV-2 replication as previously illustrated for the MOI of 0.001 of FIGS. 85A and 85B. Despite increasing the amount of input virus 10-fold (e.g., from MOI 0.001 to MOI 0.01), a short, 2.5 minute dose of 7.5 J/cm² with 425 nm blue light still demonstrated reduction in SARS-CoV-2 replication by at least 2-logs at 24 h.p.i.

FIG. 86C is a table 800 showing an evaluation of SARS-CoV-2 RNA with reverse transcription polymerase chain reaction (rRT-PCR) for samples collected for the $TCID_{50}$ assays of FIGS. 86A-86B. The cycle number for detection is the basic test result and may be referred to as a quantification cycle (Cq) where low Cq values represent higher initial amount of the target. As shown, there is a dose-dependent reduction in SARS-CoV-2 genomic RNA further substantiating the impact of 425 nm light on SARS-CoV-2. The fold reduction between doses of 425 nm light with rRT-PCR test detection is lower than those observed for replication competent virus ($TCID_{50}$ detection), indicating that SARS- CoV-2 viral RNA is readily detectable despite decreases in infectious virions. These data imply that 425 nm blue light may have less of an impact on viral RNA replication and RNA packaging relative to the inactivation of virus particles.

Figure 87A:
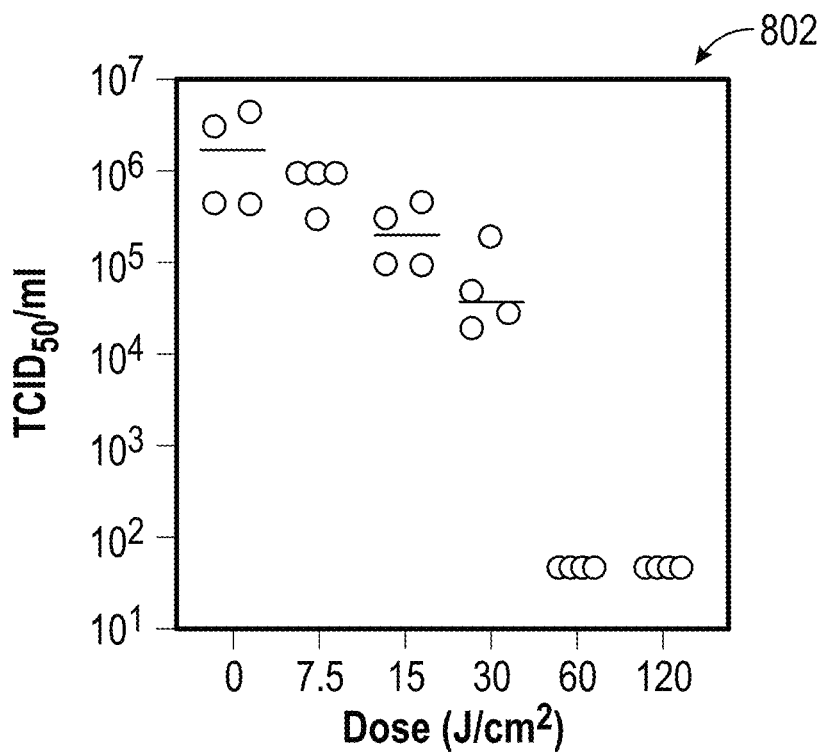
FIG. 87A is a chart illustrating $TCID_{50}$/ml for 425 nm light at various dose ranges for Vero 76 cells infected with a MOI of 0.01 SARS-CoV-2.
Figure 87B:
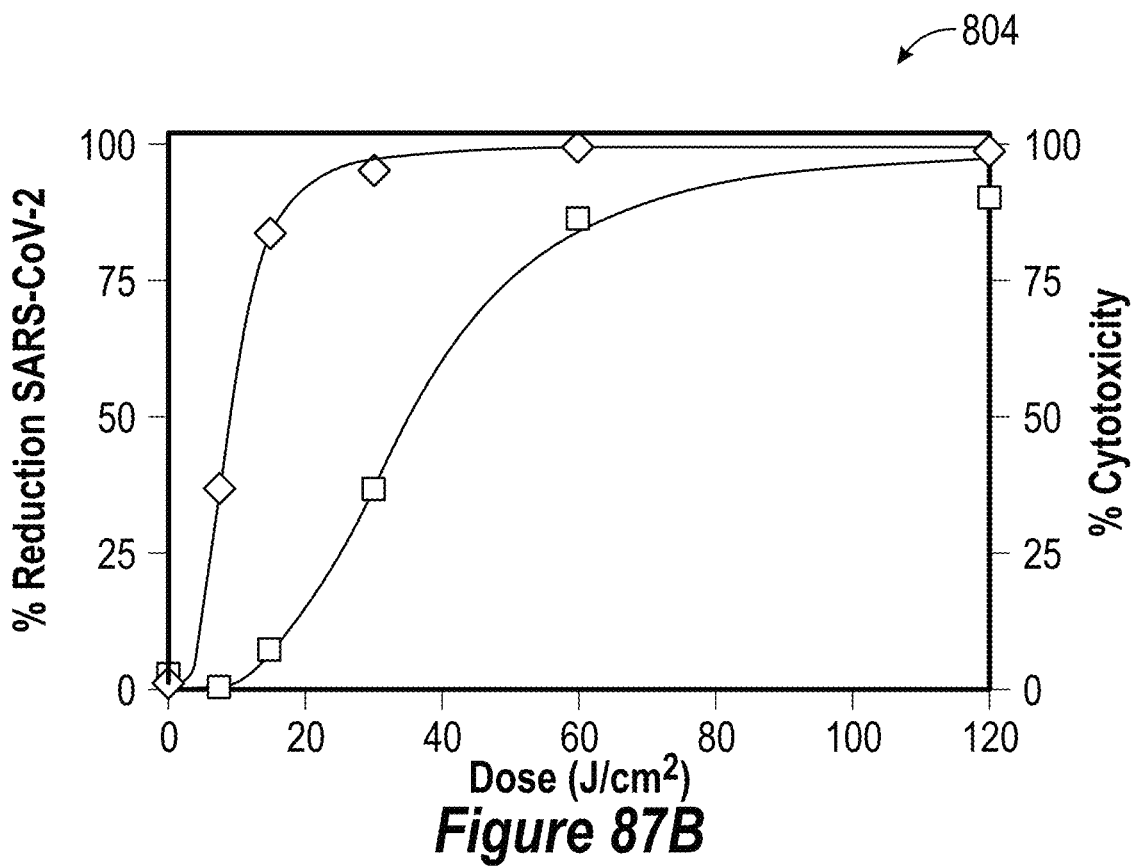
FIG. 87B is a chart illustrating percent reduction in SARS-CoV-2 replication versus percent cell cytotoxicity for the doses of light as illustrated in FIG. 87A.

FIGS. 87A and 87B represent experimental data similar to FIGS. 86A and 86B that was obtained by a second, independent laboratory evaluation using Vero 76 cells infected with a MOI of 0.01 at 48 h.p.i. FIG. 87A is a chart 802 illustrating $TCID_{50}$/ml for 425 nm light at doses ranging from 7.5 to 60 $J/cm^2$ for Vero 76 cells infected with a MOI of 0.01 SARS-CoV-2. Specific $TCID_{50}$/ml values are presented to demonstrate data trends and data values relative to on another, the actual values may vary from lab to lab and are not meant to be limiting. FIG. 87B is a chart 804 illustrating percent reduction in SARS-CoV-2 replication versus percent cell cytotoxicity for the doses of light as illustrated in FIG. 87A. Consistent with FIGS. 86A and 86B, a similar trend in the dose-dependent effects of 425 nm blue light on SARS-CoV-2 replication is observed in FIGS. 87A and 87B. Importantly, the dose-dependent trend showed similar log reductions despite differences in cell type (Vero 76), SARS-CoV-2 virus stock preparation, cell culture media, and viability assay.

Figure 88:
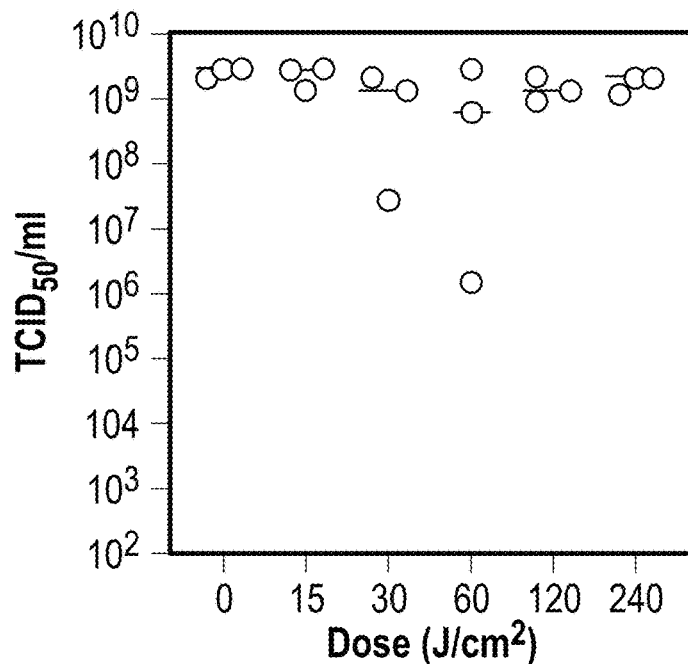
FIG. 88 is a chart illustrating $TCID_{50}$/ml versus various doses of 625 nm red light for Vero E6 cells infected with a MOI of 0.01.

To understand if the antiviral activity of light against SARS-CoV-2 is specific to 425 nm blue light, Vero E6 cells infected with a MOI of 0.01 were exposed to high doses red light. In this regard, FIG. 88 is a chart 806 illustrating $TCID_{50}$/ml versus various doses of 625 nm red light for Vero E6 cells infected with a MOI of 0.01. Specific $TCID_{50}$/ml values are presented to demonstrate data trends and data values relative to on another, the actual values may vary from lab to lab and are not meant to be limiting. Extensive illumination times with doses ranging from 15 $J/cm^2$ to 240 $J/cm^2$ showed no reduction in $TCID_{50}$/ml at 24 h.p.i. demonstrating that 425 nm blue light elicits a unique antiviral environment that results in SARS-CoV-2 inactivation. In this regard, light at 425 nm can be administered at effective virucidal doses, which are relatively safe (e.g., less than 25% cytotoxicity) in Vero E6 cell lines, and at even higher doses in endothelial cells, like those found in the respiratory tract and all blood vessels. Red light may have little to no effect on SARS-CoV-2 replication, and/or enhances viral load, as measured by $TCID_{50}$ over 24/48 hours. However, red light may decrease inflammation resulting from exposure to blue light, which may positively impact cell viability, thereby lowering cytotoxicity. A decrease in severe inflammatory response can be beneficial when treating viral infections, particularly when a virus can elicit a cytokine storm and/or inflammation can result in secondary bacterial infections. Accordingly, the combination of blue light, such as light at around 425 nm, and red light at one or more anti-inflammatory wavelengths, can provide a desirable combination of biological effects.

Figure 89A:
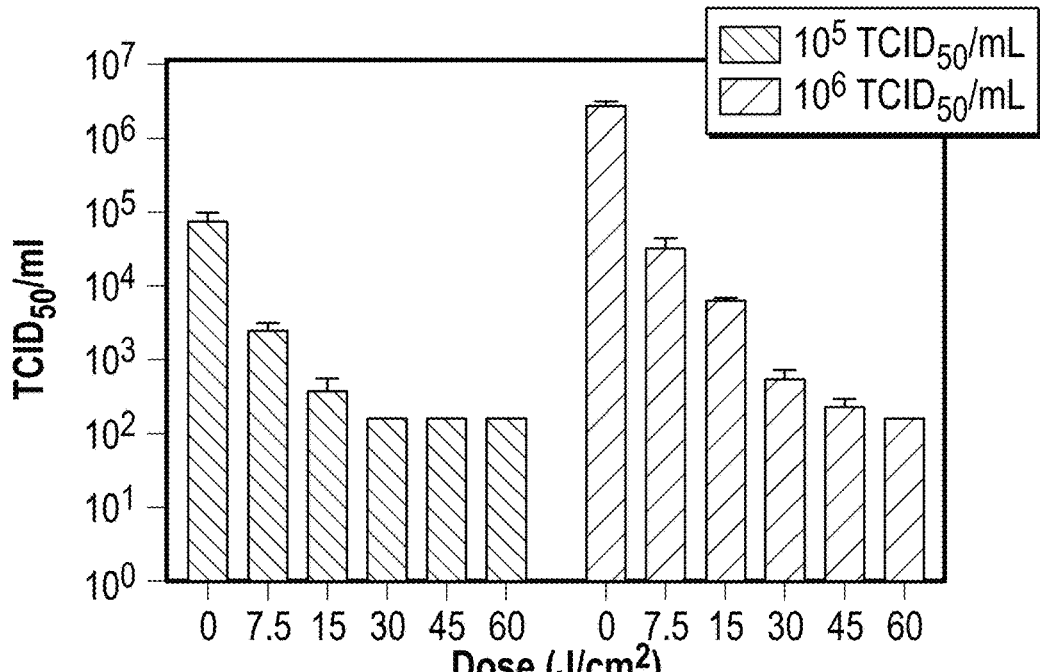
FIG. 89A is a chart illustrating a virus assay by $TCID_{50}$ on Vero E6 cells for SARS-CoV-2 from a first laboratory.
Figure 89B:
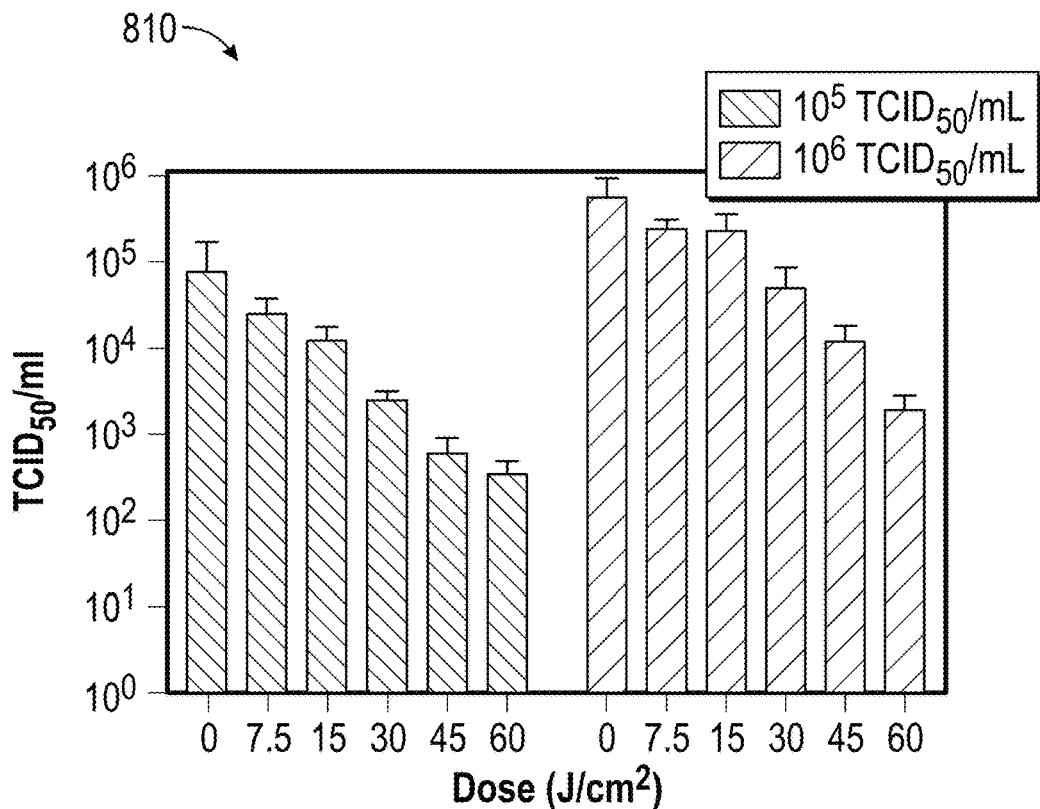
FIG. 89B is a chart illustrating a virus assay by $TCID_{50}$ on Vero E6 cells for SARS-CoV-2 from a first laboratory.

Efficacy of 425 nm blue light against cell-associated SARS-CoV-2 can be a combination of blue light eliciting an antiviral environment in the cells and inactivating cell-free virions. To distinguish between these, FIGS. 89A and 89B represent cell-free SARS-CoV-2 inactivation that was evaluated by two independent laboratories. Two different virus suspensions containing the equivalent of ~$10^5$ and ~$10^6$ $TCID_{50}$/ml were illuminated with the indicated doses of 425 nm blue light. Following illumination, virus was assayed by $TCID_{50}$ on Vero E6 cells in a first laboratory as illustrated in a chart 808 of FIG. 89A and on Vero 76 cells in a second laboratory as illustrated in a chart 810 of FIG. 89B. As illustrated in FIG. 89A, in the first laboratory, low doses of 425 nm light were sufficient to inactivate $10^6$ $TCID_{50}$/ml SARS-CoV-2 with at least 1 log reduction at 7.5 $J/cm^2$ (or greater than 90%), with at least 2 log reduction at 15 $J/cm^2$ (or greater than 99%), with at least 3 log reduction at 30 $J/cm^2$ (or greater than 99.9%), and at least 4 log reduction at 60 $J/cm^2$ (or greater than 99.99%). A similar trend in the data was observed in the second laboratory for the Vero 76 cells as illustrated in FIG. 89B. Despite a less dramatic reduction in SARS-CoV-2 inactivation, at least a 2 log reduction was still observed at 60 $J/cm^2$ (or at least 99%). Technical differences between laboratories including SARS-CoV-2 virus stock preparation, cell culture media, and cell types used for assaying virus may be factors that influenced the magnitude of susceptibility. Overall, the results from two independent laboratories demonstrated that low doses of 425 nm blue light (e.g., 15 $J/cm^2$) effectively inhibits the infection and replication of cell-free and cell-associated SARS-CoV-2, with minimal impact on cell viability. Specific $TCID_{50}$/ml values are presented to demonstrate data trends and data values relative to on another, the actual values may vary from lab to lab and are not meant to be limiting.

Figure 90A:
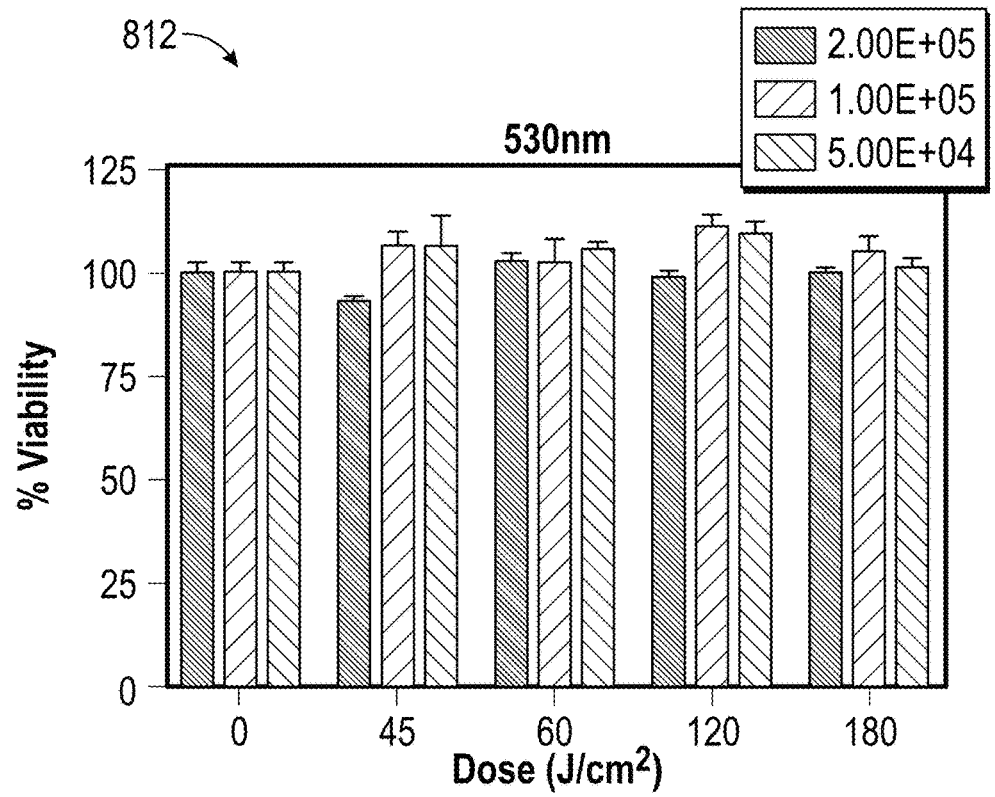
FIG. 90A is a chart indicating that Vero E6 cells do not show decreased viability under 530 nm light at doses ranging from 0-180 $J/cm^2$.
Figure 90B:
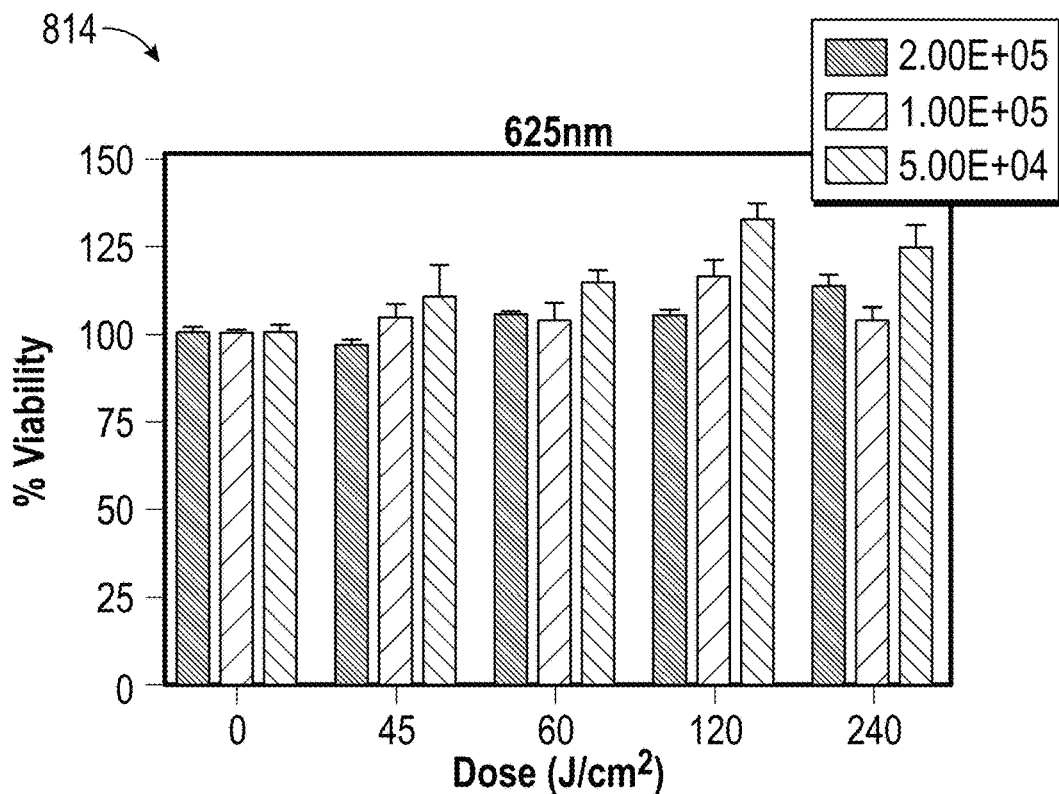
FIG. 90B is a chart indicating that Vero E6 cells do not show decreased viability under 625 nm light at doses ranging from 0-240 $J/cm^2$.

For completeness of collected data, FIGS. 90A and 90B are provided to show that Vero E6 cells do not exhibit decreased percent viability when exposed to doses of green light or doses of red light. In both FIGS. 90A and 90B, a number of cells was provided at $2 \times 10^5$ cells, $1 \times 10^5$ cells, and $5 \times 10^4$ cells. FIG. 90A is a chart 812 indicating that Vero E6 cells do not show decreased viability under 530 nm light at doses ranging from 0-180 $J/cm^2$. FIG. 90B is a chart 814 indicating that Vero E6 cells do not show decreased viability under 625 nm light at doses ranging from 0-240 $J/cm^2$.

The expedited need for therapeutic countermeasures against SARS-CoV-2 and other respiratory viral pathogens beckons the rapid development of novel approaches that may complement existing public health measures. As disclosed herein, LED arrays were carefully designed to demonstrate for the first time that safe, visible blue 425 nm light can inhibit both cell-free and cell-associated SARS-CoV-2 infection and replication in a dose-dependent manner. Results from two independent laboratories demonstrate that low doses of 425 nm blue light (e.g., 15 $J/cm^2$) effectively inhibit infection and replication of SARS-CoV-2 (e.g., >99%), with minimal impact on Vero E6 cell viability. Importantly, doses of 425 nm light 60 $J/cm^2$ were well tolerated in the 3D EpiAirway tissue models established from human tracheal/bronchial tissues.

The EpiAirway model is a commercially available in vitro organotypic model of human mucociliary airway epithelium cultured at the air/liquid interface to provide a differentiated in vivo-like epithelial structure with barrier properties and metabolic functions. There is strong global momentum to replace animal model testing with relevant in vitro human-derived test systems to reduce the number of animals used in preclinical testing. Current testing guidelines (TG403, TG433, and TG436), established by the Organization for Economic Co-operation and Development (OECD), for inhalation toxicity outline the use of animals to determine $LC_{50}$ (e.g., a concentration required to cause death of 50% of the test animals). The EpiAirway in vitro tissue model can be used to determine the $IC_{25}$ value (concentration required to reduce tissue viability by 25% of vehicle control-treated tissues) of a test article. Following 3 hours of exposure, the model have been shown to predict respiratory tissue viability using chemicals with the Globally Harmonized System (GHS) Acute Inhalation Toxicity Category 1 and 2, and Environmental Protection Agency (EPA) Acute Inhalation Toxicity Category I-II classifications. Extended exposure times (e.g., 24 and 72 hours) with toxic chemicals also reflect in vivo responses and have demonstrated the predictive value of the EpiAirway models for respiratory toxins in humans. Furthermore, such a uniform in vitro model is ideally suited to evaluate the safety doses of light applied to a fixed surface area (e.g., in $J/cm^2$), rather than attempting to scale the optical delivery of light to the appropriate small rodent anatomy.

Figure 83A:
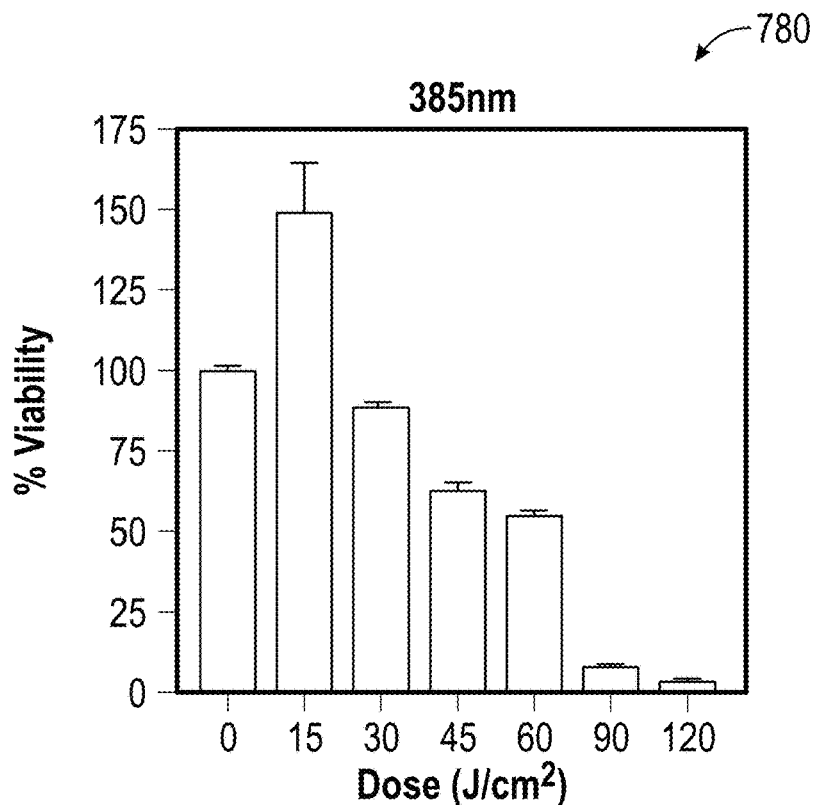
FIG. 83A is a chart illustrating a percent viability for a peak wavelength of 385 nm for a range of doses.
Figure 83B:
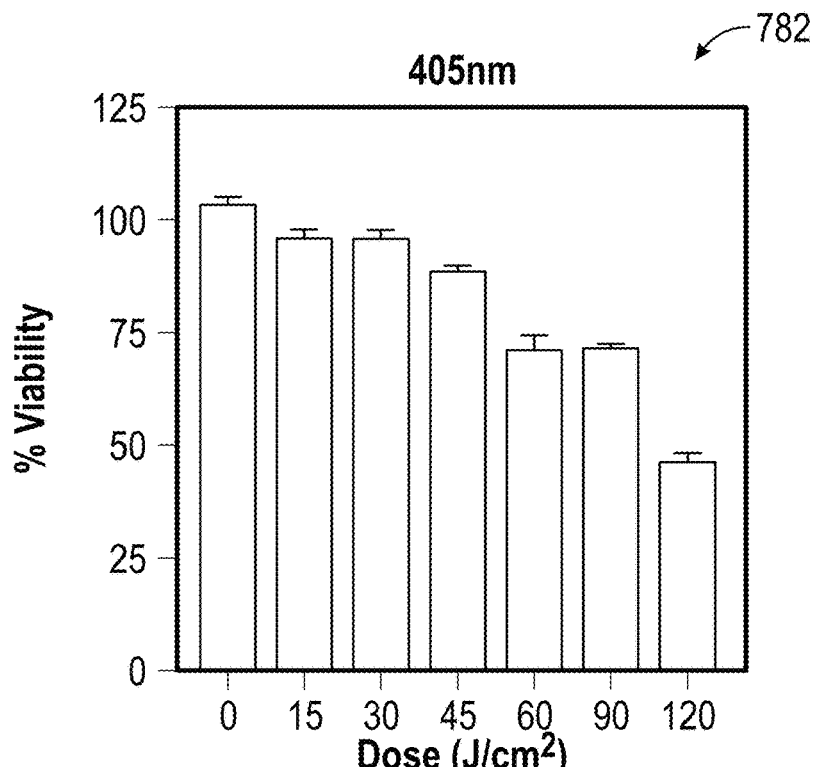
FIG. 83B is a chart illustrating a percent viability for a peak wavelength of 405 nm for the same doses of FIG. 83A.
Figure 83C:
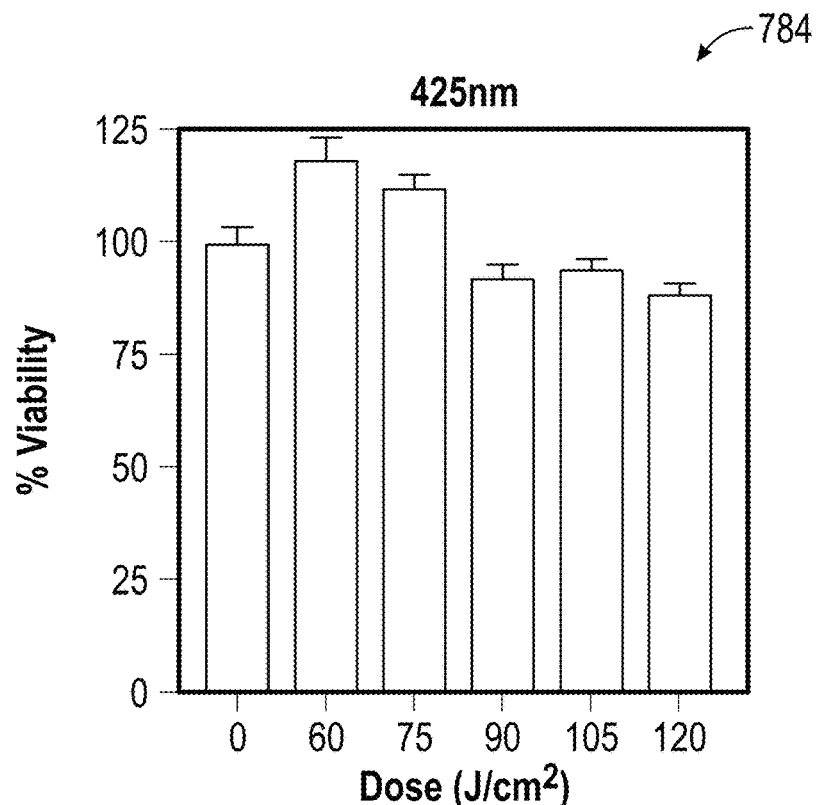
FIG. 83C is a chart illustrating a percent viability for a peak wavelength of 425 nm for the same doses of FIG. 83A.

As previously shown in FIGS. 83A-83C, the EpiAirway model was exposed to various dose ranges at light with wavelengths of 385 nm, 405 nm, and 425 nm. Exposure to UVA light at 385 nm exhibited greater than 25% loss in viability at greater than 45 $J/cm^2$, identifying a dose that breaches the $IC_{25}$ threshold established for acute cytotoxicity in the EpiAirway model. In contrast, higher doses of the 425 nm blue light reached the $IC_{25}$ threshold for validated acute airway irritation. Greater than 100% tissue viability was observed following illumination with antiviral (e.g., >99.99% reduction in SARS-CoV-2) 425 nm blue light doses of 60 $J/cm^2$. The distinct viability profiles observed at 385 nm, 405 nm, and 425 nm demonstrate that the 3D EpiAirway tissue models are amenable for identifying acute respiratory effects associated with light therapy in a dose- and wavelength-dependent manner. Minimal loss in viability out to 120 $J/cm^2$ at 425 nm indicates that the 3D human respiratory tissue models are highly tolerant to this wavelength. In FIGS. 84A to 84C, 2D Vero E6 cell cultures exhibited a cell density-dependent viability response to 425 nm doses at greater than or equal to 15 $J/cm^2$, wherein low seeding densities per surface area were more susceptible to light-induced cytotoxic effects. The enhanced tolerance of the 3D EpiAirway tissue models to 425 nm blue light compared to 2D Vero E6 cell cultures is not surprising, given that cells in 3D culture are often more resistant to drug treatment, drug metabolism is more effective, and there is increased resistance to drug-induced apoptosis. The characteristics of 3D tissue models more closely reflect cellular attributes observed in the context of tissues in vivo. Developing optimal conditions for SARS-CoV-2 infection and replication in 3D respiratory tissue models will help elucidate mechanisms that govern the ability of 425 nm blue light to inactivate SARS-CoV-2.

The mechanisms underlying 425 nm blue light to inactivate SARS-CoV-2 are still being developed; however, a brief introduction to putative molecular contributors is relevant. The molecular mechanisms governing the impact of blue light on non-pigmented cells are only beginning to be revealed. The effects of blue light should follow the first law of photochemistry, which states that light must be absorbed to have an effect. A handful of photoacceptors for blue light have been identified in non-pigmented cells, including cytochrome c oxidase, flavins, porphyrins, opsins, and nitrosated proteins. Light absorption by photoreceptors can lead to release of reactive oxygen species (ROS) and/or nitric oxide (NO) that may function to inactivate SARS-CoV-2 in a cell-free or cell-associated environment. Reactive oxygen species and/or bioactive NO may elicit activation of transcription factors involved in immune signaling, such as nuclear factor kappa-light-chain-enhancer of activated B cells (NF-κB) and mitogen activated protein kinase (MAPK) signaling. NFκB and MAPK pathways can lead to transcriptional activation of innate and inflammatory immune response molecules that may interfere with SARS-CoV-2 replication. Nitric oxide may also mediate inactivation of cell-associated SARS-CoV-2 through S-nitrosylation of cysteine residues in the active site of viral encoded enzymatic proteins. Reactive oxygen species and/or NO may also function to inactivate cell-free virions. Photosensitizers present in cell media may facilitate generation of ROS and/or NO that directly impact virion proteins and/or viral RNA to prevent infection and replication. It has also been demonstrated that inactivation of cell-free feline calicivirus (FCV) by 405 nm light was dependent on naturally occurring photosensitizers in media. Importantly, FCV was inactivated by 4 logs in artificial saliva and blood plasma, indicating that light-induced inactivation of cell-free virus is obtainable under biologically-relevant conditions. Evidence demonstrating that SARS-CoV-2 can be inactivated by exogenous addition of NO donor molecules, or possibly by single oxygen, substantiates the potential for SARS-CoV-2 inactivation by nitric oxide.

In the above described experiments, materials and methods are provided in more detail below for reference. With regard to cells, tissues, and viruses, Vero E6 cells were purchased from ATCC and maintained in DMEM (Sigma-Aldrich) supplemented with 10% FetalClonell (HyClone) and 1% Antibiotic-Antimycotic (Gibco). Vero 76 cells (ATCC CRL-1587) were maintained in MEM supplemented with 2 mM L-glutamine and 5% FBS. Primary human airway epithelium (EpiAirway AIR-100, MatTek Corporation) were cultured for 28 days in transwell inserts by MatTek Corporation. The cultured tissues were shipped in 24 well plates with agarose embedded in the basal compartment. Upon arrival, the transwell inserts were removed and placed in 6-well plates with cold Maintenance Media in the basal compartment; no media added to the apical surface. Cells were incubated at 37° C. and 5% $CO_2$ overnight prior to experimental use. All work with live virus was conducted in two independent Biosafety Level-3 (BSL-3) laboratories, MRI Global's Kansas City facility and the Institute for Antiviral Research at Utah State University, with adherence to established safety guidelines. At both laboratories, SARS-CoV-2 (USA-WA1/2020) was obtained from the World Reference Center for Emerging Viruses and Arboviruses (WRCEVA) and propagated with slight modifications. At MRI Global, Vero E6 cells were cultured overnight with DMEM (Gibco; 12320-032) supplemented with 10% FBS (Avantor, 97068-085), 1% nonessential amino acids (Corning 25-025-CI), and 1% penicillin/streptomycin (VWR 97063-708). To generate master stocks, cells were infected prior to infection with an approximate MOI of 0.08 in infection media (as above with 5% FBS). Cells were monitored for cytopathic effects daily and harvested at 4 days post-infection as CPE approached 100%. Working stocks were cultured in Vero E6 cells with DMEM/F12 media (Gibco; 11330-032) supplemented with 10% FBS and 1% penicillin/streptomycin at an MOI of 0.005. Cells were monitored for CPE and harvested two days post-infection as CPE approached 70%. Cell culture debris was pelleted by centrifugation at 500×g for 5 min and viral stocks were stored at −80° C. Infectivity of viral stocks was determined by $TCID_{50}$ assay. At Utah State University, SARS-CoV-2 (USA-WA1/2020) was propagated in Vero 76 cells. Infection media was Minimal Essential Media supplemented with 2 mM I-glutamine, 2% FBS, and 50 μg/mL gentamicin.

For cytotoxicity assays for human tissues, prior to illumination, the maintenance media was changed on the human tissue transwell inserts. Tissues were illuminated with 385 nm, 405 nm, or 425 nm light and incubated at 37° C. and 5% $CO_2$ for 3 hours. Cytotoxicity was determined using the EpiAirway MTT assay following manufacturer's instructions. Briefly, tissues were rinsed with TEER buffer and placed into pre-warmed MTT reagent and incubated at 37° C. and 5% $CO_2$ for 90 minutes. The MTT solution was extracted with MTT extractant solution by shaking for 2 hours. The tissue inserts were discarded and the extractant solution was added to a 96 well plate to be read at 570 nm. Extractant solution served as the experimental blank and cell viabilities were calculated against plates that were not illuminated.

For cytotoxicity assays for cell lines, Vero E6 cells were incubated in clear 24-well, 48-well, and 96-well plates (Corning) at varying seeding densities and incubated at 37° C. and 5% $CO_2$ overnight. Cells were illuminated with 385 nm, 405 nm, or 425 nm light and incubated at 37° C. and 5% $CO_2$ for 24 hours post-illumination. After 24 hours, cytotoxicity was determined using the CellTiterGlo One Solution (Promega) with modifications. The amount of CellTiterGlo One Solution ("CTG") was optimized in a preliminary experiment. For 24-well plates, 100 µl solution was used and 60 µl solution was used for 48- and 96-well plates. The cells were placed on an orbital shaker for 2 minutes and the chemiluminescent signal was stabilized for 10 minutes before 50 µl of the solution was added to a black well, black bottom 96-well plates and read using the CellTiterGlo program on the GloMax (Promega). CellTiterGlo One solution served as a blank and cell viabilities were calculated against plates that were not illuminated.

Cytotoxicity analysis was conducted at 48 hours post-illumination. Cells were treated for 2 hours with 0.01% neutral red for cytotoxicity. Excess dye was rinsed from cells with PBS. Absorbed dye was eluted from the cells with 50% Sorensen's citrate buffer/50% ethanol for 30 minutes. Buffer was added to 10 wells per replicate. Optical density was measured at 560 nm and cell viabilities were calculated against cells that were not illuminated.

Antiviral assays were conducted in separate laboratories with modifications. At MRI Global, cells were infected with SARS-CoV-2 at MOIs of 0.01 and 0.001 in triplicate. At one hour post-infection, infected cells were illuminated with 425 nm light at the specified doses. Cell culture supernatants were harvested at 24 hours and 48 hours post-infection for $TCID_{50}$ determination and qPCR analysis. No illumination controls and no virus controls were included as a positive control for viral growth and for cytotoxicity, respectively. Cytotoxicity analysis was conducted at 24 hours post-illumination as above.

Vero 76 cells were infected with SARS-CoV-2 at MOIs of 0.01 and 0.001. At one hour post-infection, infected cells were illuminated with 425 nm light at the specified doses. Cell culture supernatants were harvested at 48 hours post-infection for $TCID_{50}$ determination. No illumination controls and no virus controls served as a positive control for viral growth and for cytotoxicity, respectively. Cytotoxicity analysis was conducted at 48 hours post-illumination.

Virucidal assays were conducted in parallel in separate laboratories. At one laboratory, 1 mL solutions containing $10^5$ and $10^6$ $TCID_{50}$/ml were illuminated with varying doses of light. The viruses were then tittered on Vero E6 cells in triplicate via $TCID_{50}$ assay. No illumination controls served as a positive control for viral growth.

At a second laboratory, 1 mL solutions containing $10^5$ and $10^6$ $TCID_{50}$/ml were illuminated with varying doses of light. The viruses were then tittered on Vero 76 cells in triplicate via $TCID_{50}$ assay. No illumination controls served as a positive control for viral growth.

Viral RNA levels for SARS-CoV-2 samples were determined by quantitative RT-PCR using the CDC N1 assay. Samples for the RT-PCR reactions were live virus in culture supernatants without nucleic acid extraction. Primers and probes for the N1 nucleocapsid gene target region were sourced from Integrated DNA Technologies (2019-nCoV CDC RUO Kit, No. 10006713). TaqPath 1-step RT-qPCR Master Mix, CG was sourced from ThermoFisher (No. A15299). Reaction volumes and thermal cycling parameters followed those published in the CDC 2019-Novel Coronavirus (2019-nCoV) Real-Time RT-PCR Diagnostic Panel: Instructions for Use. For the RT-PCR reaction, 15 mL of prepared master mix was added to each well followed by 5 mL of each sample, for a final total volume of 20 mL per reaction well. Reactions were run on a Bio-rad CFX real-time PCR instrument.

$TCID_{50}$ assays were conducted as follows at both laboratories with slight modifications. At one laboratory, Vero E6 cells were plated in 96-well plates at 10,000 cells/well in 0.1 ml/well of complete medium (DMEM/F12 with 10% fetal bovine serum and 1× Penicillin/Streptomycin) and incubated overnight in a 37° C., 5% $CO_2$ humidified incubator. The next day virus samples were serially diluted into un-supplemented DMEM/F12 media at 1:10 dilutions by adding 0.1 ml virus to 0.9 ml diluent, vortexing briefly and repeating until the desired number of dilutions was achieved. Media was decanted from 96-well plates and 0.1 ml of each virus dilution aliquoted into 5 or 8 wells. After 4 days of incubation at 37° C., 5% $CO_2$, plates were scored for presence of cytopathic effect. $TCID_{50}$/ml were made using the Reed & Muench method. At the second laboratory, cell culture samples were serially diluted and plated on fresh Vero 76 cells in quadruplicate. Plates were visually examined for CPE at 6 days post-infection. Wells were indicated as positive or negative and virus titers were calculated using the Reed-Muench endpoint dilution method.

Figure 91A:
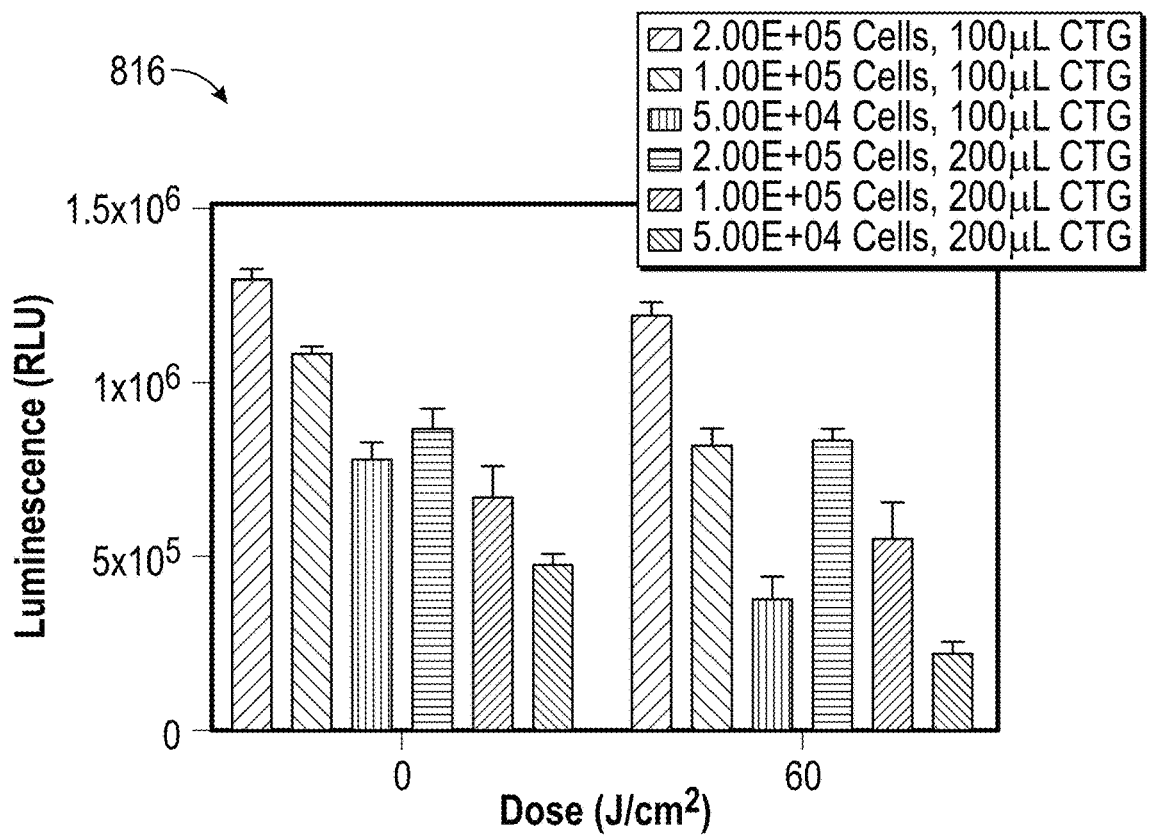
Figure 91B:
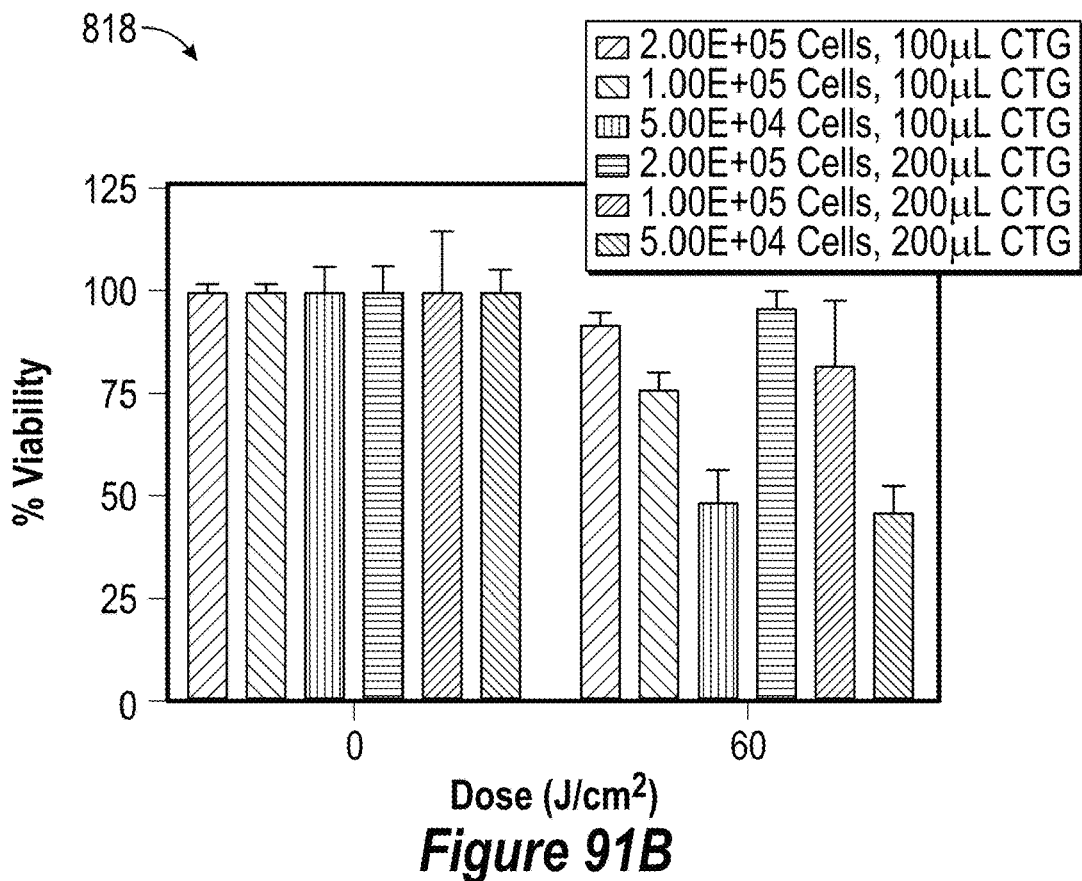
Figure 91C:
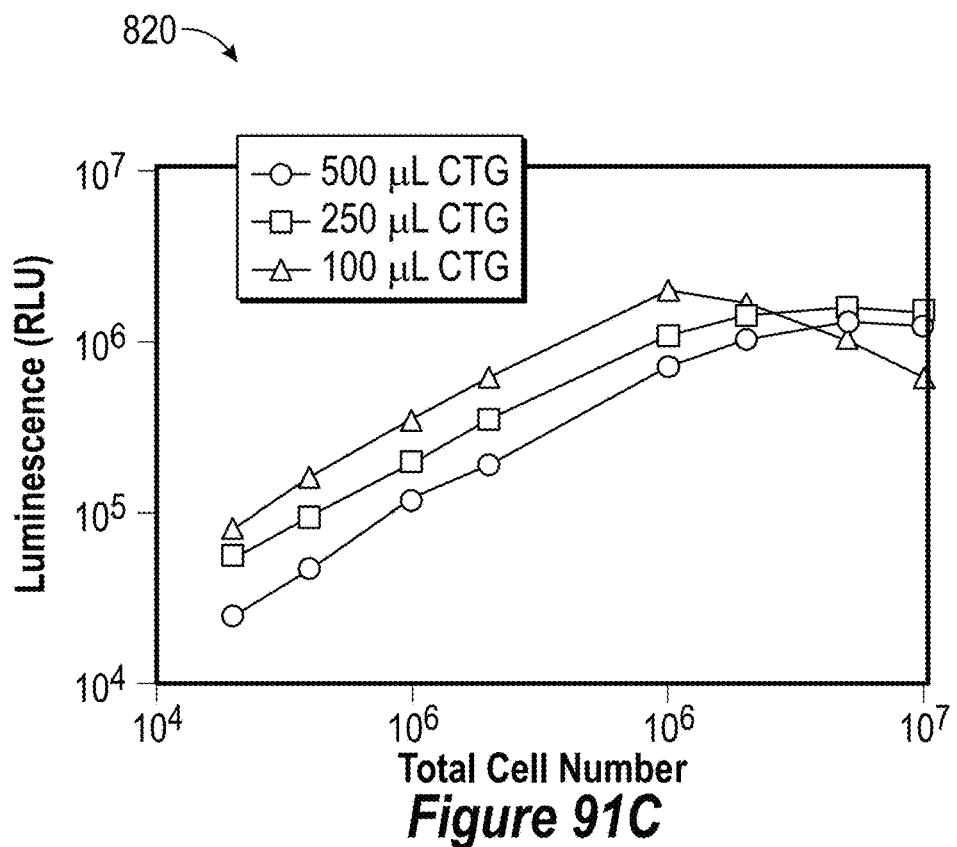

FIG. 91A is a chart 816 showing raw luminescence values (RLU) for different seedings of Vero E6 cell densities and various doses of light ($J/cm^2$). FIG. 91B is a chart 818 showing percent viability for the different seedings of Vero E6 cell densities and various doses of light of FIG. 91A. FIG. 91B indicates the viability of Vero E6 cells may not reach saturation until cell densities are above $10^6$ cells. RLU and percent viability based on the various doses of light demonstrate that both 100 µL and 200 µL of CellTiter-Glo (CTG) are effective volumes for measuring cell viability after seeding different Vero E6 cell densities. For FIGS. 91A and 91B, cell densities of $2×10^5$ cells with 100 µL CTG, $1×10^5$ cells with 100 µL CTG, $5×10^4$ cells with 100 µL CTG, $2×10^5$ cells with 200 µL CTG, $1×10^5$ cells with 200 µL CTG, and $5×10^4$ cells with 200 µL CTG are represented. FIG. 91C is a chart 820 comparing RLU versus total cell number to show that CTG is an effective reagent for measuring cell densities of above $10^6$ Vero E6 cells. RLU values versus total cell number are provided for 500 µL CTG, 250 µL CTG, and 100 µL CTG and data is represented as +/−standard deviation.

Figure 92A:
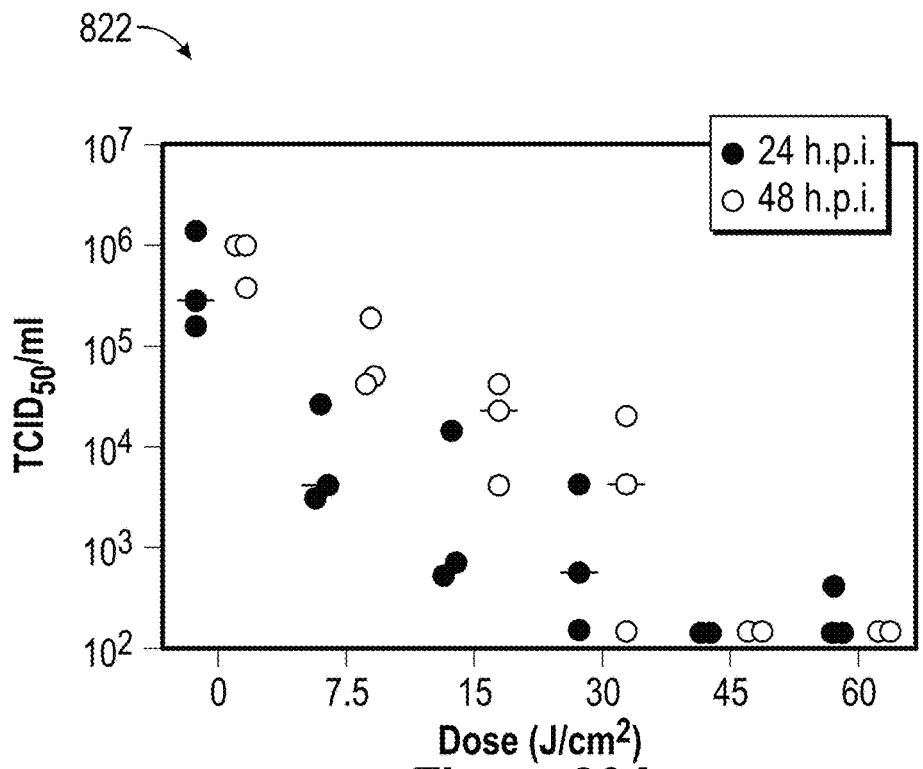
Figure 92B:
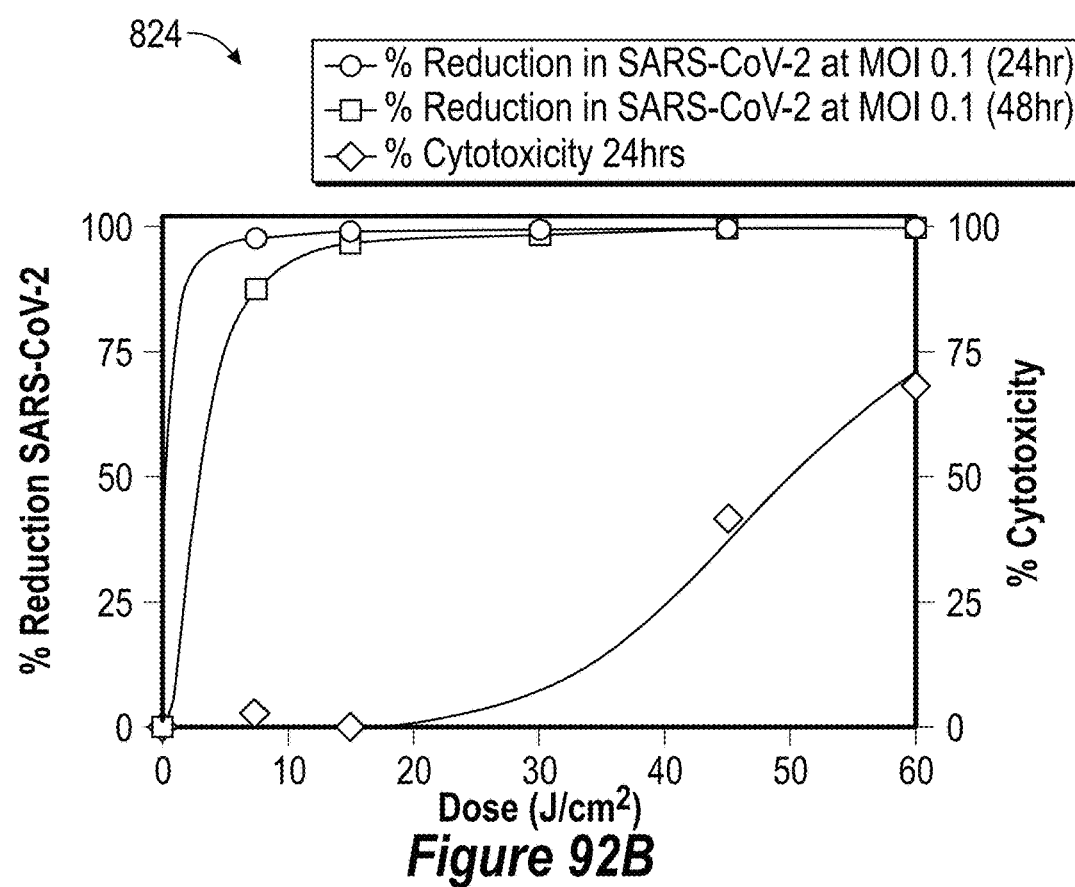

FIG. 92A is a chart 822 of $TCID_{50}$/ml versus dose at 24 hours and 48 hours post infection for Calu-3 cells infected with SARS-CoV-2. Specific $TCID_{50}$/ml values are presented to demonstrate data trends and data values relative to on another, the actual values may vary from lab to lab and are not meant to be limiting. FIG. 92B is a chart 824 showing the percent reduction in SARS-Cov-2 compared with percent cytotoxicity, for the Calu-3 cells of FIG. 92A. For FIG. 92B, the chart lines for percent reduction in SARS-Cov-2 and percent cytotoxicity are provided as nonlinear regression curves based on the doses illustrated in FIG. 92A. As shown, visible light at 425 nm inhibits viral replication of SARS-CoV-2 in the human respiratory cell line, Calu-3. The Calu-3 cells were infected with SARS-CoV-2 at an MOI of 0.1 and exposed to the indicated doses of 425 nm light at 1 hour post-infection. SARS-CoV-2 samples were harvested for TCID$_{50}$ assays at 24 hours and 48 hours post-infection. Greater than a 99% reduction in virus was observed following a single treatment for doses of 15 J/cm$^2$. Percent reduction in SARS-CoV-2 virus as shown in FIG. 92B was calculated for each dose and timepoint. As previously described, the selectivity index (SI) may be defined as a ratio of the CC$_{50}$ to the EC$_{50}$ for treated cells. As shown in FIG. 92B, 50% percent reduction in SARS-CoV-2 at 24 hours and 48 hours post infection are indicated at relatively low dose values. In this regard, the doses of light that inhibit viral replication have desirable SI values of greater than 100 24 hours post infection and greater than 25 when factoring in the cell viability of Calu-3 cells not infected with virus.

Figure 93A:
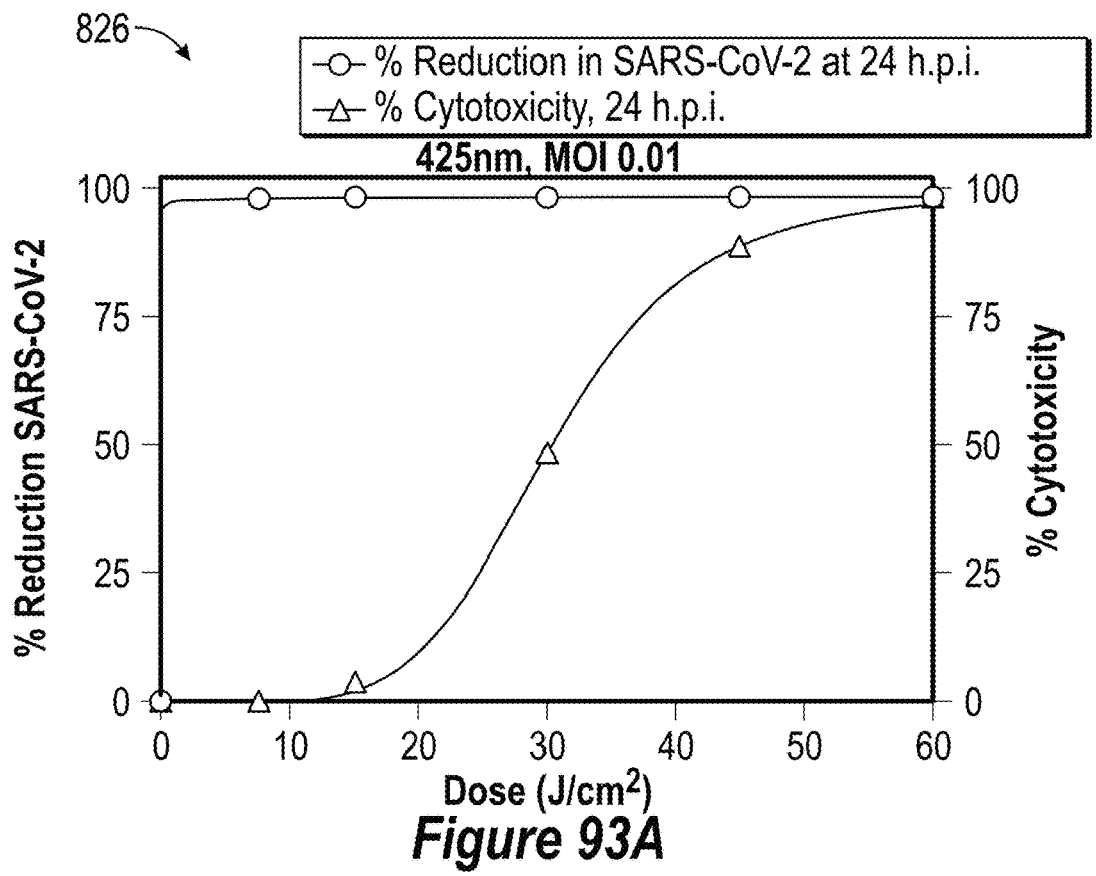
Figure 93B:
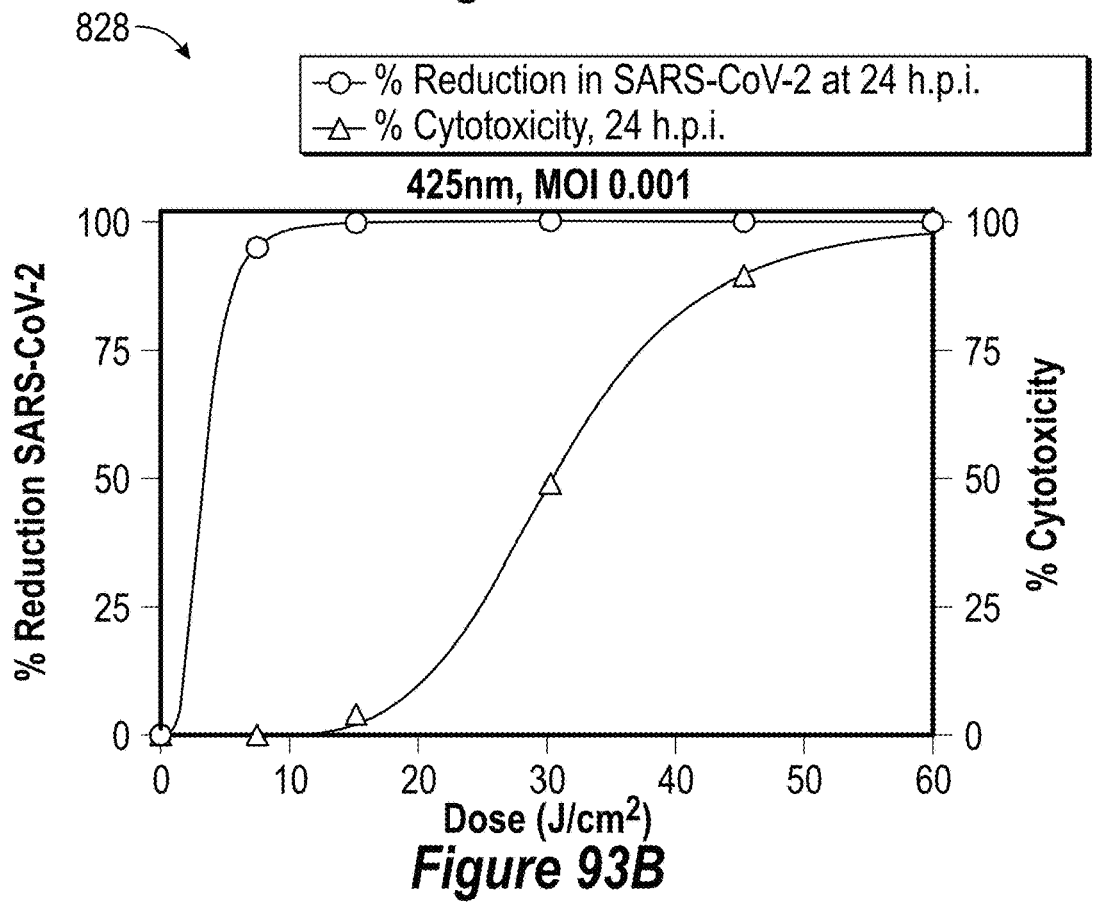

FIG. 93A is a chart 826 illustrating percent reduction in SARS-CoV-2 replication versus percent cell cytotoxicity for Vero E6 cells infected with a MOI of 0.01. FIG. 93B is a chart 828 illustrating percent reduction in SARS-CoV-2 replication versus percent cell cytotoxicity for Vero E6 cells infected with a MOI of 0.001. In both FIGS. 93A and 93B, the indicated doses were applied at 1 hour post infection and dose responses were determined at 24 hours post infection. The doses were administered by application of 425 nm light with an irradiance of 50 mW/cm$^2$ for times of 2.5 minutes (for 7.5 J/cm$^2$), 5 minutes (for 15 J/cm$^2$), 10 minutes (for 30 J/cm$^2$), 15 minutes (for 45 J/cm$^2$), and 20 mins (for 60 J/cm$^2$). Consistent with previously presented charts, similar trends are observed for dose-dependent effects of 425 nm blue light on SARS-CoV-2 replication for both MOI values. The cytotoxicity curve indicates a CC$_{50}$ of about 30.2. In FIG. 93A, the percent reduction in SARS-CoV-2 is close to 100% for doses as low as 7.5 J/cm$^2$ and the corresponding nonlinear regression curve has a sharp decrease at or near the 0 J/cm$^2$ dose. For the purposes of SI calculations, a conservative value of 1 was selected for the EC$_{50}$ value to give a SI value (e.g., CC$_{50}$/EC$_{50}$) of about 30. In FIG. 93B, the percent reduction in SARS-CoV-2 is farther away from 100% for the 7.5 J/cm$^2$ dose, thereby providing the corresponding nonlinear regression curve with a decrease toward 0% at a dose slightly above the 0 J/cm$^2$ dose. In this manner, a value of about 3.4 may be indicated for the EC$_{50}$ value to give a SI value (e.g., CC$_{50}$/EC$_{50}$) of about 9. Due to variability in experiments, slight differences in data sets may be expected. In this regard, the results illustrated in FIGS. 93A and 93B may be considered as similar and within normal experimental variations.

Figure 93C:
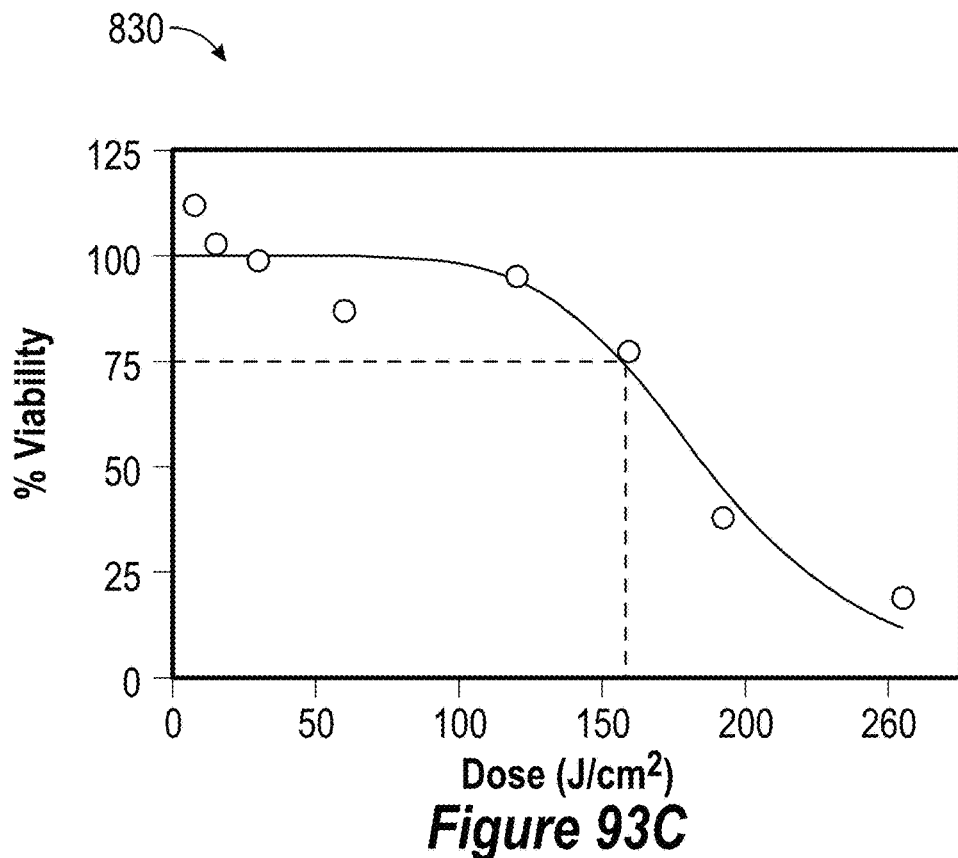

While FIGS. 93A and 93B provide percent reduction in SARS-CoV-2 at the cellular level for determining EC$_{50}$ values, IC$_{25}$ values for target tissues are needed to determine suitable LTI treatment values. FIG. 93C is a chart 830 representing percent viability at various doses for primary human tracheal/bronchial tissue from a single donor. Tissue viability is determined at 3 hours post-exposure by MTT assay, a measure of cell viability by assessing enzymatic activity of NAD(P)H-dependent cellular oxidoreductase ability to reduce MTT dye to formazan. From the chart 830, the IC$_{25}$ value corresponds to the dose where the viability curve is at 75% (e.g., 25% reduction in tissue viability). In FIG. 93C, the IC$_{25}$ value is about 157, as indicated by the superimposed dashed lines. In combination with the EC$_{50}$ values of FIGS. 93A and 93B, the corresponding LTI values may be determined as about 157 for FIG. 93A and about 46 for FIG. 93B.

Figure 94A:
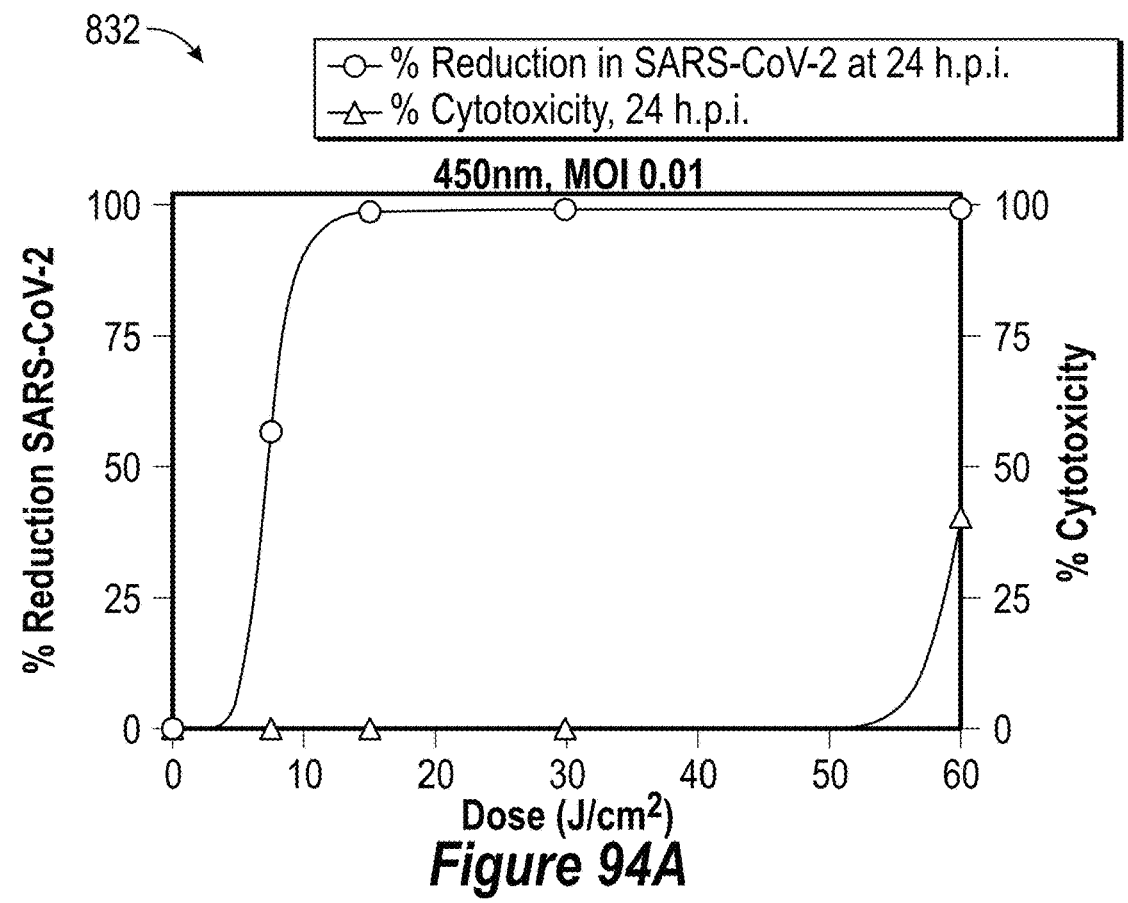
Figure 94B:
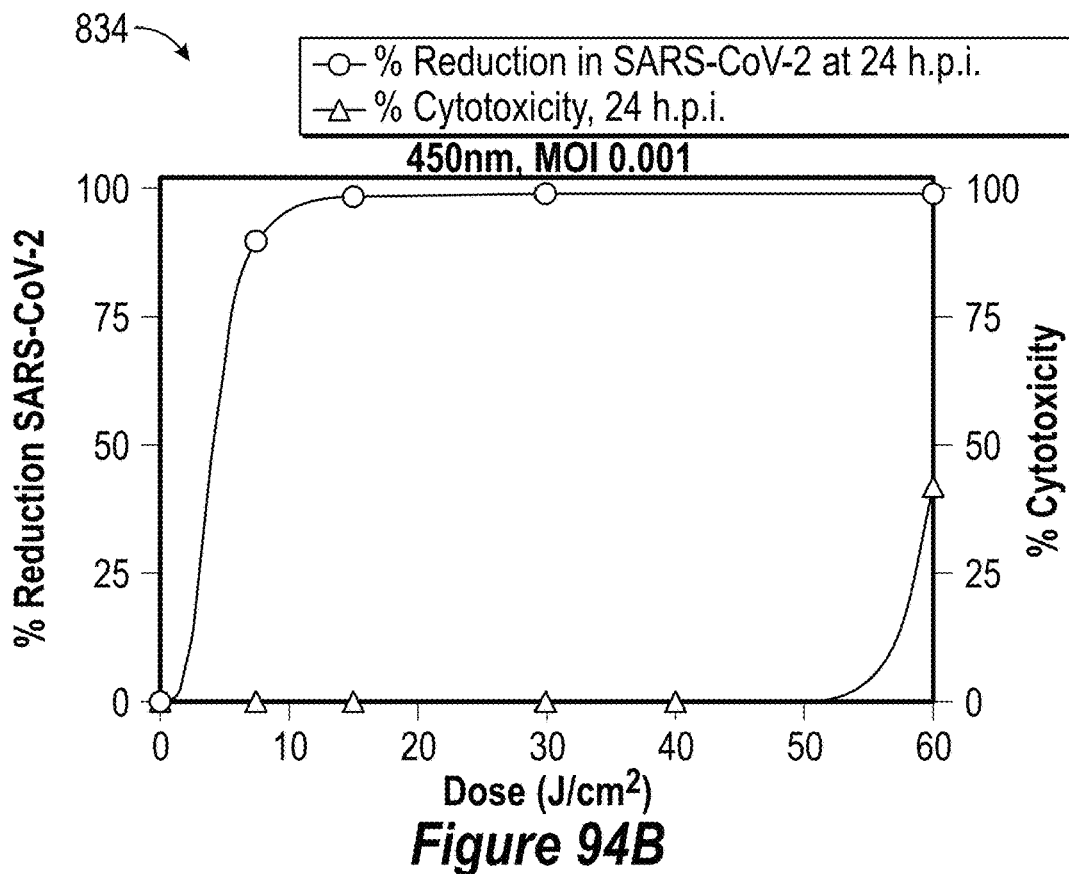
Figure 94C:
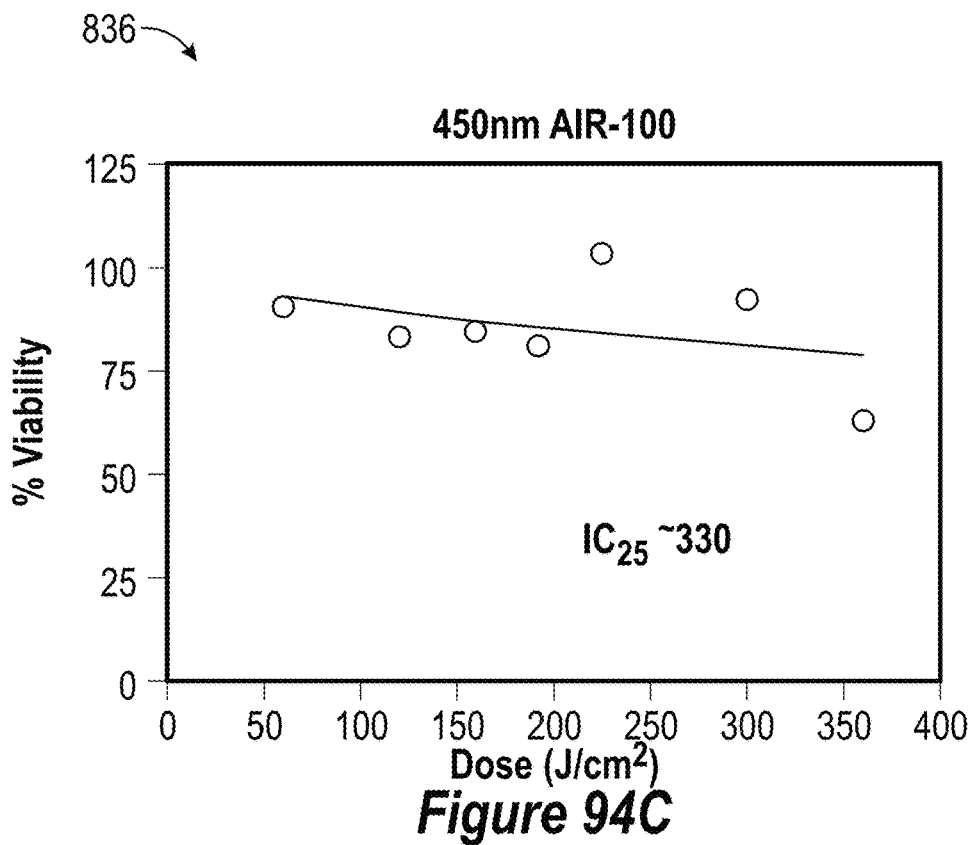

FIGS. 94A-94C repeat the experiments of FIGS. 93A-93C, but with light having a peak wavelength of 450 nm. FIG. 94A is a chart 832 illustrating percent reduction in SARS-CoV-2 replication versus percent cell cytotoxicity for Vero E6 cells infected with a MOI of 0.01. FIG. 94B is a chart 834 illustrating percent reduction in SARS-CoV-2 replication versus percent cell cytotoxicity for Vero E6 cells infected with a MOI of 0.001. Consistent with previously presented charts, similar trends are observed for dose-dependent effects of 450 nm blue light on SARS-CoV-2 replication for both MOI values. The cytotoxicity curves indicate a CC$_{50}$ of greater than 60 since the curve does not extend to 50% cytotoxicity. In turn, SI values based on CC$_{50}$ value of greater than 60 may also be considered as greater than the particular SI values. In FIG. 94A, a value of about 7.2 may be indicated for the EC$_{50}$ value to give a SI value (e.g., CC$_{50}$/EC$_{50}$) of greater than 8. In FIG. 94B, a value of about 4.1 may be indicated for the EC$_{50}$ value to give a SI value (e.g., CC$_{50}$/EC$_{50}$) of about greater than 15. As before, due to variability in experiments, slight differences in data sets may be expected. In this regard, the results illustrated in FIGS. 94A and 94B may be considered as similar and within normal experimental variations. Notably, Vero E6 cells receiving similar doses of 450 nm blue light exhibit less cytotoxicity than that observed for 425 nm blue light, demonstrating a wavelength-dependent biological effect.

FIG. 94C is a chart 836 representing percent viability at various doses for primary human tracheal/bronchial tissue from a single donor. As with FIG. 93C, tissue viability is determined at 3 hours post-exposure by MTT assay. From the chart 836, the IC$_{25}$ value may be determined at about 330. In combination with the EC$_{50}$ values of FIGS. 94A and 94B, the corresponding LTI values may be determined as about 46 for FIG. 94A and about 80 for FIG. 94B. While FIG. 94C shows about 63% viability at a dose of 360 J/cm$^2$, variability between biological replicates was high at this dose. In this regard, the IC$_{25}$ values may be even greater than the approximated value of 330, indicating very high doses may be administered before significant toxicity is observed. Consistent with data in Vero E6 cells, primary human respiratory tissues receiving 450 nm blue light exhibit an increased tolerance to higher doses compared to 425 nm blue light, demonstrating a wavelength-dependent biological effect.

FIG. 95 is a table 838 summarizing the experiments of FIGS. 93A-93C and 94A-94C. The higher SI and LTI values for 450 nm light are predominantly a consequence of lower cytotoxicity relative to 425 nm light. Lower EC$_{50}$ values demonstrate more effective virus inhibition at 425 nm, but this can be associated with higher cytotoxicity values at lower light doses than at 450 nm. Ideally, light therapy may include lower EC$_{50}$ values with CC$_{50}$ values as high as possible. Different targeted pathogens and tissue types may provide different LTI values. In this regard, LTI values according to the present disclosure may be provided at values of greater than or equal to 2, or in a range from 2 to 100,000, or in a range from 2 to 1000, or in a range from 2 to 250, depending on the application. Considering experimental variances, the exemplary data provided for treatment of SARS-CoV-2 with light in a range from 425 nm to 450 nm indicates LTI values in any of the above ranges may be achieved.

Using techniques analogous to those used above to measure the antiviral activity of 425 nm to 450 nm light against SARS-CoV-2, the antiviral activity of light at 405 nm to 425 nm against wild-type (WT) and Tamiflu-resistant influenza A was investigated. FIG. 96A is a chart 840 showing the titer of WT influenza A virus based on remaining viral loads for different initial viral doses after treatment with different doses of 405 nm light. The initial viral doses were set at 1×10$^4$ and 1×10$^5$, and the remaining viral load (e.g., TCID$_{50}$/ml) following treatment with light at 405 nm at dosages of 0 J/cm², 60 J/cm², and 120 J/cm² is shown. The data demonstrates significant reductions in wild-type influenza A viral loads when either 60 J/cm² or 120 J/cm² doses were administered, with an additional roughly 0.5-log reduction in viral loads observed at the higher dosage.

FIG. 96B is a chart 842 showing the titer of Tamiflu-resistant influenza A virus based on remaining viral load for a single initial viral dose after treatment of different doses of 425 nm light. The initial viral dose was set at $1\times10^4$, the remaining viral load (e.g., number of copies) following treatment with light at 425 nm at dosages of 0 J/cm², 60 J/cm², and 120 J/cm² is shown. The initial dose is provided at about $1\times10^4$, and the remaining viral load (e.g., number of copies) following treatment with light at 425 nm at dosed of 0 J/cm², 30 J/cm², 60 J/cm², 120 J/cm², 180 J/cm², and 240 J/cm² is shown. The data shows an increase in viral load when no light was administered, and dose-dependent reductions in viral loads up to about 180 J/cm², totaling a roughly 2-log reduction in viral load.

FIG. 97A is a chart 844 showing the $TCID_{50}$/ml versus energy dose for WT influenza A treated with light at 425 nm at various doses. The MOI for the WT influenza A was provided at 0.01. The selected doses were provided at 0 J/cm², 3 J/cm², 7.5 J/cm², 15 J/cm², 30 J/cm², 45 J/cm², 60 J/cm² and 90 J/cm². Results were collected after 24 hours and after 48 hours. When no light was applied (e.g., dose of 0 J/cm²), viral loads increased to $10^3$ copies at 24 hours, and to $10^5$ copies at 48 hours. At doses between about 7.5 J/cm² and 60 J/cm², a dose-dependent decrease in viral loads was observed at 24 hours, though the virus significantly rebounded by 48 hours. However, at doses of 90 J/cm², the viral loads significantly decreased by 24 hours, and did not significantly increase at 48 hours. Specific $TCID_{50}$/ml values are presented to demonstrate data trends and data values relative to on another, the actual values may vary from lab to lab and are not meant to be limiting.

FIG. 97B is a chart 846 showing the percent reduction in viral loads of WT influenza A and percent cytotoxicity against the treated cells when influenza A-infected Madin-Darby Canine Kidney (MDCK) cells were exposed to 425 nm light at various doses. The MOI for the WT influenza A was provided at 0.01. As illustrated, the doses were provided at 0 J/cm², 7.5 J/cm², 15 J/cm², 30 J/cm², 45 J/cm², 60 J/cm² and 90 J/cm². The reduction in viral loads and the cytotoxicity were monitored at 24 and 48 hours post irradiation. Virtually no cytotoxicity was observed at any time period for any of the doses. The reduction in viral loads was dose dependent, with doses of 45 J/cm², 60 J/cm², and 90 J/cm² demonstrating a nearly complete reduction in viral loads.

FIG. 97C is a chart 848 that is similar to FIG. 97A, but with a starting MOI of 0.1. In this regard, FIG. 97C illustrates the $TCID_{50}$ of cells infected with WT influenza A and treated with 425 nm light at doses of 0 J/cm², 3 J/cm², 7.5 J/cm², 15 J/cm², 30 J/cm², 45 J/cm², 60 J/cm² and 90 J/cm². Results were collected after 24 hours and after 48 hours. Viral loads stayed fairly constant at 24 hours for doses from 0 to 15 J/cm² and decreased in a dose dependent manner as the doses increased to 90 J/cm². Over the next 24 hours (i.e., a total of 48 hours post-exposure), the viral loads significantly rebounded at all dosages other than 90 J/cm².

FIG. 97D is a chart 850 that is similar to FIG. 97B, but with a starting MOI of 0.1. In this regard, FIG. 97D illustrates the percent reduction in viral loads of WT influenza A and percent cytotoxicity against the treated cells when influenza A-infected Madin-Darby Canine Kidney (MDCK) cells were exposed to 425 nm light at various doses. The MOI for the WT influenza A was provided at 0.1. As illustrated, the doses were provided at 0 J/cm², 7.5 J/cm², 15 J/cm², 30 J/cm², 45 J/cm², 60 J/cm² and 90 J/cm². The reduction in viral loads and the cytotoxicity were monitored at 24 and 48 hours post irradiation. As with FIG. 97B, virtually no cytotoxicity was observed at any time period for any of the doses and the reduction in viral loads was dose dependent, with doses of 45 J/cm², 60 J/cm² and 90 J/cm² demonstrating a high or nearly complete reduction in viral loads. Specific $TCID_{50}$/ml values are presented to demonstrate data trends and data values relative to on another, the actual values may vary from lab to lab and are not meant to be limiting.

As a summary of the findings, therapeutic light treatments can be selected from optimal doses including various combinations of wavelengths, irradiance, and treatment times as discussed above for various viruses, including coronaviridae (e.g., coronavirus, SARS-CoV-2, etc.) and Orthomyxoviridae (e.g., influenza), among others. Ideally, the phototherapy may induce a dual mechanism of action on the virus, including damaging the lipid membrane using single oxygen and/or nitric oxide. The treatments demonstrate efficacy both extracellular in the absence of cells pre-infection, as well as intracellular in the presence of cells post infection. The antiviral effect can be remarkably fast. For example, inactivation of the SARS-CoV-2 virus was demonstrated within 24 to 48 hours, compared to the course of viral load reduction observed clinically as the SARS-CoV-2 virus clears the body in untreated patients, or even in patients treated with Remdesivir.

It is important to consider the "Light Therapeutic Index," or "LTI," a ratio of the $IC_{25}$ and the $EC_{50}$ values for light that is used on cells and tissues. Ideally, the light treatment will be effective at killing one or more target viruses at power levels that are not overly cytotoxic. Preferably, the ratio of $IC_{25}/EC_{50}$ is as high as possible, including greater than 2. Cell systems for each virus have a number of variables (e.g., cell density, different cell types for productive infection, media, etc.), which makes it hard to have a single LTI for all viruses. Important aspects for evaluating LTI across all viruses, particularly for respiratory viruses, include evaluating the types of human tissue these viruses are likely to infect, such as EpiAirway from both large airway (AIR-100) and nasal (NAS-100) tissues. EpiAirway is a ready-to-use, 3D mucociliary tissue model consisting of normal, human-derived tracheal/bronchial epithelial cells, also available as a co-culture system with normal human stromal fibroblasts (EpiAirwayFT). A reduction as large as 75-fold is observed after a 2.5-minute treatment dose at 50 mW/cm². The light therapy shows significant antiviral activity post infection, inhibiting about 50% of viral replication. Additionally, this treatment shows a full log inactivation of virus on WT influenza A at doses of greater than 8.5 J/cm². A dose of 8.5 J/cm² was a dose that provided an $EC_{50}$ against influenza post infection. In this regard, doses of less than 10 J/cm² can provide a multi-pathogenic treatment that can eliminate different viruses via one or more separate mechanisms. In a particular example, a multi-pathogenic treatment of 425 nm light for 5 minutes and an irradiance of 50 mW/cm² may be effective for treating both SARS-CoV-2 and influenza A. Additionally, at doses of around 60 J/cm², a greater than 2-log reduction in virucidal activity was observed using 425 nm light with a 20-minute exposure at 50 mW/cm².

Considering LTI calculations (e.g., the ratio of $IC_{25}/EC_{50}$) in antiviral assays for specific tissues for SARS-CoV-2 and influenza at just 425 nm, it is observed that there are safe and effective doses of light that can be administered. Because the viral lipid membranes are similar for other respiratory viruses, it is believed (based on successful results with SARS-CoV-2 and influenza A) that such treatments can be effective against other respiratory viruses. When comparing the results with light at 425 nm with the results at 405 nm or 385 nm, the LTI may be smaller, though it will be expected to vary depending on tissue types. Extrapolating the data obtained herein, the relatively high-powered light (e.g., dosed at hundreds of $J/cm^2$) used in the past to disinfect surfaces cannot safely be used in vivo. Importantly, the dosage of light ($J/cm^2$) had to be sufficiently non-cytotoxic (i.e., would not reduce viability by more than 25% at a dose that resulted in an $EC_{50}$). The resulting LTI is expected to vary depending on the type of cell exposed to the phototherapy, but for a given cell type, ideally there is an effective therapeutic window, such as an LTI of at least 2, or in a range from 2 to 100,000, or in a range from 2 to 1000, or in a range from 2 to 250, depending on the application. Because SARS-CoV-2, influenza and other viruses have lipid membranes, and part of the method by which the light kills the viruses is believed to be oxidative damage to these membranes, it is believed that this treatment will also work equally well on other respiratory viruses. Further, the treatments described herein may also work on viruses that do not have lipid membranes (e.g., rhinoviruses that cause most common colds).

While the above-described examples are provided in the context of viral applications, the principles of the present disclosure may also be applicable for treatment of bacterial infections. There is a current problem when treating bacterial respiratory infections, namely, AMR and recalcitrant lung infections. Antimicrobial resistance has led to many patients having their lungs infected with bacteria that are resistant to many common antibiotics. As new antibiotics become developed, bacterial resistance soon follows. One potential solution to this problem would be to use visible light as described herein, at an effective antimicrobial wavelength and dosage, alone or in combination with conventional antibiotic therapy. While bacteria can develop resistance against antibiotics, it is more difficult for them to develop resistance to antimicrobial therapy using visible light. The potential uses are far-reaching; so long as the light is delivered in a safe, therapeutic dosage, patients can be effectively treated for a number of respiratory microbial infections, such as tuberculosis, *Mycobacterium avium* complex, and the like, and specifically including those caused by spore-forming bacteria. Bacterial infections caused by spore-forming bacteria can be particularly difficult to treat with conventional antibiotics, because the antibiotics only kill bacteria when they are not in spore form. As disclosed herein, certain wavelengths of light are effective at killing spore-forming microbes not only in their active form, but also in their spore form.

As discussed below, not all light at blue wavelengths are equivalent. Some have higher cytotoxicity to the infected tissues, and some have higher antimicrobial efficacy. It is useful to consider light therapeutic index (LTI), which is a combination of antimicrobial activity and safety to the exposed tissues. Accordingly, a series of experiments were performed to identify suitable wavelengths and dosage levels to provide safe and effective antibacterial treatments.

For the experiments, bacterial cultures were prepared in 1× phosphate buffered saline (PBS) or CAMHB at 106 CFU/ml, and 200 µl were aliquoted into wells of a 96-well microtiter plate. Plates with lids were placed under a white illumination box, with an LED array placed on top such that the light shines down onto bacteria. A fan blew across the device though vents in the illumination box to minimize the heat generated by the LED lights. All setups were done inside a Class II biosafety cabinet. Lights were turned on for a given time, then bacteria were sampled, serially diluted, and plated on MHA for enumeration.

The bacterial strains used in this study were obtained from the American Type Culture Collection (ATCC), the CDC-FDA's Antimicrobial Resistance Bank (AR-BANK), from Dr. John LiPuma at the *Burkholderia cepacia* Research Laboratory and Repository (BcRLR) at the University of Michigan, or from the laboratory of Dr. Mark Schoenfisch at the University of North Carolina Chapel Hill. Strains from the BcRLR were confirmed to be *Pseudomonas aeruginosa* by 16S sequencing, and the other strains were confirmed to be *P. aeruginosa* by growth on *Pseudomonas* isolation agar. Strains were stored in 20% glycerol stocks at −80° C. Strains were cultured on tryptic soy agar (TSA) at 30° C. or 37° C. for 1-2 days, or in cation-adjusted Mueller-Hinton Broth. *Streptococcus pyogenes* and *Haemophilus influenzae* were grown using Brain Heart Infusion in a chamber with 5% $CO_2$ packets. All bacteria were incubated at 37° C. Cytoxicity was measured as described above with respect to the antiviral data.

FIG. 98A is a chart 852 showing the effectiveness of light at 405, 425, 450, and 470 nm and administered with a dose of 58.5 $J/cm^2$, in terms of hours post-exposure, at killing *P. aeruginosa* (CFU/ml). The data show that, at a wavelength of 405 nm or 425 nm, a 5-log reduction in concentration was observed almost instantaneously, and the effect was maintained for four hours post-exposure.

FIG. 98B is a chart 854 showing the effectiveness of light at 405, 425, 450, and 470 nm, and administered with a dose of 58.5 $J/cm^2$, in terms of hours post-exposure, at killing *S. aureus* (CFU/ml). The data show that, at a wavelength of 405 nm, a 3-log reduction was observed within a half hour post-exposure, and this increased to a 4-log reduction by 2 hours post-exposure. At 425 nm, a 2-log reduction in concentration was observed within two hours, and this increased to a 4-log reduction by 4 hours post-exposure. At 450 nm, a 2-log reduction in concentration was observed within three hours, and this increased to a 4-log reduction by 4 hours post-exposure. Light at 470 nm was virtually ineffective.

FIG. 99A is a chart 856 showing the effectiveness of light at 425 nm and administered with doses ranging from 1 to 1000 $J/cm^2$ at killing *P. aeruginosa* (CFU/ml). The data show that, at a wavelength of 425 nm, at doses of around 60 $J/cm^2$, a 4-log reduction in concentration was observed, whereas at doses of 100 $J/cm^2$ or higher, a 5-log reduction was observed.

FIG. 99B is a chart 858 showing the effectiveness of light at 425 nm and administered with doses ranging from 1 to 1000 $J/cm^2$ at killing *S. aureus* (CFU/ml). The data show that, at a wavelength of 425 nm, at doses of around 100 $J/cm^2$ or more, a 4-log or even a 5-log reduction in concentration was observed.

FIG. 100A is a chart 860 showing the effectiveness of light at 405 nm and administered with doses ranging from 1 to 1000 $J/cm^2$ at killing *P. aeruginosa* (CFU/ml). The data show that, at a wavelength of 405 nm, at doses of around 60 $J/cm^2$, a 4-log reduction in concentration was observed, whereas at doses of 100 $J/cm^2$ or higher, a 5-log reduction was observed.

FIG. 100B is a chart 862 showing the effectiveness of light at 405 nm and administered with doses ranging from 1 to 1000 $J/cm^2$ at killing *S. aureus* (CFU/ml). The data show that, at a wavelength of 405 nm, at doses of around 100 $J/cm^2$ or more, a 5-log reduction in concentration was observed.

FIG. 101 is a chart 864 showing the toxicity of 405 nm and 425 nm light in primary human aortic endothelial cells (HAEC). Data is provided showing the effect of light at 405 nm and at 425 nm for a variety of indicated doses. Even at dosages up to 99 J/cm$^2$, the viability of the cells never dropped below 75%, which is a useful threshold for determining the safety of a treatment.

FIG. 102A is a chart 866 showing the bacterial $\log_{10}$ reduction and the % loss of viability of infected AIR-100 tissues following exposure of the tissue to doses of light ranging from 4 to 512 J/cm$^2$ at 405 nm. FIG. 102B is a chart 868 showing the bacterial $\log_{10}$ reduction and the % loss of viability of infected AIR-100 tissues following exposure of the tissue to doses of light ranging from 4 to 512 J/cm$^2$ at 425 nm. At both wavelengths (405 nm and 425 nm), notable bacterial $\log_{10}$ reductions are realized before dose levels reach 25% loss in tissue viability.

In a similar manner, additional data as described above for FIGS. 102A and 102B were collected and provided as shown in FIGS. 102C-102F. This data demonstrates similar results, thereby confirming identification of safe and effective operating windows. FIG. 102C is a chart 870 showing the bacterial $\log_{10}$ reduction and the % loss of viability of infected AIR-100 tissues with gram negative bacteria (e.g., *P. aeruginosa*) following exposure of the tissue to doses of light ranging from 4 to 512 J/cm$^2$ at 405 nm. FIG. 102D is a chart 872 showing the bacterial $\log_{10}$ reduction and the % loss of viability of infected AIR-100 tissues with gram negative bacteria (e.g., *P. aeruginosa*) following exposure of the tissue to doses of light ranging from 4 to 512 J/cm$^2$ at 425 nm. FIG. 102E is a chart 874 showing the bacterial $\log_{10}$ reduction and the % loss of viability of infected AIR-100 tissues with gram positive bacteria (e.g., *S. aureus*) following exposure of the tissue to doses of light ranging from 4 to 512 J/cm$^2$ at 405 nm, in a similar manner to FIGS. 102A and 102C. FIG. 102F is a chart 876 showing the bacterial $\log_{10}$ reduction and the % loss of viability of infected AIR-100 tissues with gram positive bacteria (e.g., *S. aureus*) following exposure of the tissue to doses of light ranging from 4 to 512 J/cm$^2$ at 425 nm, in a similar manner to FIGS. 102B and 102D.

Most in-vitro assays against bacteria are conducted in a cell-free system. There are two classic or industry standard measurements for anti-bacterial activity. The first is related to inhibition of growth and may be quantified in terms of a minimum inhibitory concentration (MIC). The MIC refers to the dose required to completely inhibit growth of bacteria over a 24-hour period in a broth/growth medium. Given the rapidly dividing nature of bacteria, any growth leads to high concentration of microorganism. Stated differently a 50% reduction is not sufficient for bacterial infections. A second standard is related to bactericidal results and may be quantified in terms of a minimum bactericidal concentration (MBC). The MBC refers to the dose required to result in a 3-log reduction (e.g., 99.9%) of bacteria. Assays can be run in PBS or broth/growth media and lead to different results and time is also a variable. In general, for the bacterial experiments described above, the MIC dose for a given organism has typically been greater than the MBC determined in phosphate buffered saline.

FIGS. 103A-103J are a series of charts showing the effect of light at 405 nm and 425 nm, at differing dosage levels, in terms of bacterial survival (CFU/ml) vs. dose (J/cm$^2$). The data is provided for both *P. aeruginosa* and *S. aureus* bacteria. As illustrated, light at 405 nm is particularly effective at killing these bacteria, and that light at 425 nm is also effective, though either not as effective, or not effective at higher doses. MBC values are indicated on the charts of FIGS. 103A-103J to show 3-log reductions in bacteria.

For the purposes of the present bacterial experiments, LTI calculations may be realized from the above-referenced data for providing safe and effective phototherapeutic treatments. As previously described, LTI may be determined from the relationship of $IC_{25}$ divided by the $EC_{50}$ in the context of viruses. For the bacterial data presented in FIGS. 102A-103J, the $EC_{50}$ values may be replaced or substituted with MBC values as illustrated in FIGS. 103A-103J. The $IC_{25}$ values may be determined by the horizontal dashed lines indicating 25% loss of tissue viability in FIGS. 102A-102D.

FIG. 104 is a table 878 summarizing the LTI calculations and corresponding bactericidal doses for the bacterial experiments illustrated in FIGS. 102A-103J. Notably, the bacterial pathogens are selected as those that are commonly associated with bacterial pneumonia. As illustrated, safe and effective phototherapy treatments for gram negative *P. aeruginosa* strains according to this experiment may have LTI values in a range from 1.5 to 2.5, thereby indicating LTI values for such strains may be provided with values of at least 1.5 or higher. For gram positive *S. aureus* strains, the LTI values for this experiment are lower for some of the doses than the *P. aeruginosa* strains.

FIG. 105 is a chart 880 showing the effect of 425 nm light at various doses at killing *P. aeruginosa* (CFU/ml) over a period of time from 0 hours, 2 hours, 4 hours, and 22.5 hours. At higher doses of light, such as 120 J/cm$^2$, the bacterial concentration actually decreases over time. Importantly, it is largely irrelevant whether the entire dosage of light (J/cm$^2$) is administered in one dose, or in a combination of smaller doses, so long as the same amount of light is administered before the bacteria rebound.

FIG. 106 is a chart 882 showing that whether all of the light (J/cm$^2$) is administered in one dose or in a series of smaller doses, the antimicrobial effect (average CFU/ml) vs. dose (J/cm2×number of treatments) is largely the same, at 8 hours and 48 hours post-administration.

FIG. 107A is a chart 884 showing the treatment of a variety of drug-resistant bacteria (Average CFU/ml) vs. dose (J/cm$^2$) at 24 hours post-exposure. At doses of 80-120 J/cm$^2$ (a combination of two treatments of 40, 50, or 60 J/cm$^2$), all of the different drug-resistant bacterial strains were effectively killed. In this regard, the treatments described herein offer advantages over antibiotic treatments, in that a) drug resistance is not observed following treatment, and b) the treatment can be effective against drug-resistant bacteria. As shown in FIG. 107A, when the treatment was applied to a variety of drug-resistant bacteria, at doses of 80-120 J/cm$^2$ in a combination of two treatments of 40, 50, or 60 J/cm$^2$, all of the different drug-resistant bacterial strains were effectively killed.

FIG. 107B is a table 886 summarizing the bacteria species and strains that were tested. ATCC refers to American Type Culture Collection. BcRLR refers to *Burkholderia cepacia* Research Laboratory and Repository provided by Dr. John LiPuma of the University of Michigan. MDR refers to multidrug resistant, e.g., resistant to 3 classes of antibiotics. XDR refers to extremely drug resistant, e.g., resistant to 5 classes of antibiotics, such as amikacin (AMK), aztreonam (ATM), cefepime (FEP), ceftazidime (CAZ), ceftazidime-avibactam (CZA), ceftolozane-tazobactam (C/T), ciprofloxacin (CIP), colistin (CST), doripenem (DOR), gentamicin (GEN), imipenem (IPM), levofloxacin (LVX), meropenem (MEM), piperacillin-tazobactam (TZP), or tobramycin (TOB).

FIG. 107C is a table 888 that summarizes the efficacy of twice daily dosing of 425 nm light against difficult-to-treat clinical lung pathogens. Bactericidal doses are in PBS and for a 3-log reduction relative to dark control samples. MIC doses are in broth with no change in CFU/ml relative to starting CFU/ml. MBC doses are in broth and for a 3-log reduction in CFU/ml relative to dark control samples. Accordingly, one can use the treatments described herein to deliver safe and effective antimicrobial treatments to a number of different bacterial infections, including those caused by drug-resistant bacteria. Additionally, illumination devices and treatments as disclosed herein may provide multiple pathogenic benefits (e.g., for viruses, bacteria, and fungi) with single wavelength and/or multiple wavelength light treatments.

Light therapies as disclosed herein may be combined with conventional pharmaceutical agents, such as antivirals, anticoagulants, anti-inflammatories, and the like, and the antiviral wavelengths can be combined with anti-inflammatory wavelengths to reduce the inflammatory damage caused by the virus, by the cytokine storm induced by the virus, and/or by the phototherapy at the antiviral NO-producing/NO-releasing/singlet oxygen producing wavelengths.

It is contemplated that any of the foregoing aspects, and/or various separate aspects and features as described herein, may be combined for additional advantage. Any of the various embodiments as disclosed herein may be combined with one or more other disclosed embodiments unless indicated to the contrary herein.

Those skilled in the art will recognize improvements and modifications to the preferred embodiments of the present disclosure. All such improvements and modifications are considered within the scope of the concepts disclosed herein and the claims that follow.

What is claimed is:

1. A method comprising:
    providing a light source configured to emit light comprising a first light characteristic including a first peak wavelength in a range from 400 nanometers (nm) to 450 nm; and
    irradiating mammalian tissue within a body with the light to induce a biological effect by administering a dose of light of no more than 50 joules per square centimeter ($J/cm^2$) during a time period of no more than 10 minutes, and repeatably administering the dose of light a number of times to provide a cumulative dose in a range from greater than 50 $J/cm^2$ to 1000 $J/cm^2$ over a cumulative time period in a range from 1 day to 7 consecutive days, wherein the biological effect comprises altering a concentration of one or more pathogens within the body and altering growth of the one or more pathogens within the body.

2. The method of claim 1, wherein the first peak wavelength is in a range from 400 nm to 435 nm.

3. The method of claim 1, wherein less than 5% of the light is in a wavelength range that is less than 400 nm.

4. The method of claim 1, wherein the first peak wavelength is a range from 410 nm to 440 nm.

5. The method of claim 1, wherein a full width half maximum of the first peak wavelength is less than or equal to 100 nm.

6. The method of claim 1, wherein a full width half maximum of the first peak wavelength is less than or equal to 40 nm.

7. The method of claim 1, wherein the first light characteristic includes a radiant flux in a range from 5 milliwatts (mW) to 5000 mW.

8. The method of claim 7, wherein the radiant flux is configured to provide an irradiance to the tissue in a range from 5 $mW/cm^2$ to 200 $mW/cm^2$.

9. The method of claim 1, wherein the biological effect comprises inactivating the one or more pathogens that are in a cell-free environment in the body and inhibiting replication of the one or more pathogens that are in a cell-associated environment in the body within the body.

10. The method of claim 1, wherein the biological effect further comprises upregulating a local immune response within the body.

11. The method of claim 1, wherein the biological effect comprises stimulating at least one of enzymatic generation of nitric oxide to increase endogenous stores of nitric oxide and releasing nitric oxide from endogenous stores of nitric oxide.

12. The method of claim 1, wherein the dose of light is in a range from 0.5 $J/cm^2$ to 50 $J/cm^2$.

13. The method of claim 12, wherein the dose of light is in a range from 2 $J/cm^2$ to 50 $J/cm^2$.

14. The method of claim 12, wherein administering the dose of light comprises providing light with an irradiance to the mammalian tissue that is in a range from 5 milliwatts per square centimeter ($mW/cm^2$) to 200 $mW/cm^2$ over the time period that is in a range from 10 seconds to 10 minutes.

15. The method of claim 14, wherein the irradiance is delivered in a continuous manner.

16. The method of claim 14, wherein the irradiance is delivered in a plurality of discrete pulses.

17. The method of claim 16, wherein the plurality of discrete pulses comprises a plurality of equal pulses that is delivered during the time period.

18. The method of claim 16, wherein the plurality of discrete pulses comprises a plurality of dissimilar pulses that is delivered during the time period.

19. The method of claim 1, wherein the cumulative dose is up to 420 $J/cm^2$ over the cumulative time period.

20. The method of claim 1, wherein the dose of light is in a range from 0.5 $J/cm^2$ to 50 $J/cm^2$ and the dose of light is repeatably administered at least two times over the cumulative time period.

21. The method of claim 12, wherein administering the dose of light comprises providing light with an irradiance in a range from 0.1 milliwatts per square centimeter ($mW/cm^2$) to 10 watts per square centimeter ($W/cm^2$), wherein the irradiance is delivered in a plurality of discrete pulses.

22. The method of claim 1, wherein impinging light to the mammalian tissue within the body comprises administering a dose of light with a light therapeutic index of greater than or equal to 2, the light therapeutic index being defined as a dose concentration that reduces tissue viability by 25% divided by a dose concentration that reduces cellular percentage of the pathogens by 50%.

23. The method of claim 22, wherein the light therapeutic index is in a range from 2 to 250.

24. The method of claim 1, wherein the one or more pathogens comprise at least one of a virus, a bacteria, and a fungus.

25. The method of claim 1, wherein the one or more pathogens comprise coronaviridae.

26. The method of claim 1, wherein the one or more pathogens comprise orthomyxoviridae.

27. The method of claim 1, wherein the one or more pathogens comprise at least two types of viruses.

28. The method of claim 27, wherein the one or more pathogens comprise coronaviridae and orthomyxoviridae.

29. The method of claim 1, wherein the light is provided by at least one of a light-emitting diode, an organic light-emitting diode, and a laser.

30. The method of claim 1, wherein the mammalian tissue comprises mucosal epithelial tissue.

31. The method of claim 1, wherein the light is provided at a tissue depth of less than or equal to 2.5 mm.

32. The method of claim 1, wherein the light further comprises a second peak wavelength that is in a range from 400 nm to 900 nm, wherein the second peak wavelength differs from the first peak wavelength by at least 10 nm.

33. The method of claim 32, wherein a full width half maximum of the second peak wavelength is less than or equal to 100 nm.

34. The method of claim 1, wherein impinging light to the mammalian tissue within the body comprises administering a first dose of light and a second dose of light for a single type of microorganism.

* * * * *

UNITED STATES PATENT AND TRADEMARK OFFICE
CERTIFICATE OF CORRECTION

PATENT NO. : 12,109,429 B2
APPLICATION NO. : 17/117858
DATED : October 8, 2024
INVENTOR(S) : Nathan Stasko et al.

It is certified that error appears in the above-identified patent and that said Letters Patent is hereby corrected as shown below:

In the Specification
Column 9, Line 14, replace "5a-reductase" with --5α-reductase--.
Column 26, Line 46, replace "FIG. 1078" with --FIG. 107B--.
Column 82, Line 40, replace "(e.g., 15 J/cm$^2$)" with --(e.g., $\leq$ 15 J/cm$^2$)--.
Column 94, Line 59, replace "resistant to 3 classes of antibiotics" with --resistant to $\geq$ 3 classes of antibiotics--.
Column 94, Lines 60-61, replace "resistant to 5 classes of antibiotics" with --resistant to $\geq$ 5 classes of antibiotics--.

Signed and Sealed this
Third Day of December, 2024

Katherine Kelly Vidal
*Director of the United States Patent and Trademark Office*